(12) United States Patent
Okada

(10) Patent No.: US 8,147,986 B2
(45) Date of Patent: Apr. 3, 2012

(54) ORGANIC ELECTROLUMINESCENT DEVICE

(75) Inventor: Hisashi Okada, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 1262 days.

(21) Appl. No.: 11/529,595

(22) Filed: Sep. 29, 2006

(65) Prior Publication Data
US 2007/0075311 A1    Apr. 5, 2007

(30) Foreign Application Priority Data
Sep. 30, 2005    (JP) .................................. 2005-288831

(51) Int. Cl.
*H01L 51/54* (2006.01)
(52) U.S. Cl. ........ 428/690; 428/917; 313/504; 313/506; 257/E51.036; 257/E51.044
(58) Field of Classification Search .......................... None
See application file for complete search history.

(56) References Cited

U.S. PATENT DOCUMENTS

| 6,303,238 | B1 | 10/2001 | Thompson et al. | |
| 6,399,224 | B1 * | 6/2002 | Li .................................. | 428/690 |
| 6,653,564 | B2 | 11/2003 | Scheidle | |
| 6,905,784 | B2 * | 6/2005 | Seo ................................. | 428/690 |
| 2003/0091862 | A1 * | 5/2003 | Tokito et al. ................... | 428/690 |
| 2004/0086744 | A1 * | 5/2004 | Che et al. ....................... | 428/690 |
| 2006/0134461 | A1 * | 6/2006 | Huo et al. ...................... | 428/690 |

FOREIGN PATENT DOCUMENTS

| JP | 2003-77675 A | 3/2003 |
| WO | WO-00/70655 A2 | 11/2000 |

* cited by examiner

*Primary Examiner* — Marie R. Yamnitzky
(74) *Attorney, Agent, or Firm* — Birch, Stewart, Kolasch & Birch, LLP

(57) ABSTRACT

The invention provides an organic electroluminescent device having at least an organic compound layer provided between a pair of electrodes. The organic electroluminescent device has at least a polymer comprising a metal complex containing a tri- or higher-dentate ligand in the polymer molecule. The metal complex preferably contains a tetra- or higher-dentate ligand in the polymer molecule. At least one of the ligands is preferably a chain. The metal complex preferably contains a transition metal ion or a rare earth metal ion. The metal complex preferably contains a nitrogen atom in its complex structure. Further, the polymer preferably contains the metal complex in its main chain or its side chain.

1 Claim, No Drawings

ORGANIC ELECTROLUMINESCENT DEVICE

CROSS-REFERENCE TO RELATED APPLICATION

This application claims priority under 35 USC 119 from Japanese Patent Application No. 2005-288831, the disclosure of which is incorporated by reference herein.

BACKGROUND OF THE INVENTION

The present invention relates to an organic electroluminescent device (hereinafter, also referred to as "organic EL device" or "luminescent device") which can emit light by the conversion of electric energy to light.

DESCRIPTION OF THE RELATED ART

Recently, research and development on various display devices have been conducted. In particular, organic electroluminescent devices (organic EL devices) have attracted attention because emission can be obtained with high luminance by driving at low voltage.

Luminescence efficiency improvements, savings in energy consumption, and improvements in driving durability by the use of organic EL devices have become of interest.

Various research and development for improving the external quantum efficiency have been conducted recently, and devices which include trisphenylpyridine iridium complex (see, for example, WO00/070655), and octaethylporphine platinum complexes (see, for example U.S. Pat. Nos. 6,303,238 B1 and 6,653,564 B1) have become of interest. However, the devices disclosed in these patents do not have sufficient durability, and further improvement is demanded.

As to a method of mass-producing panels, vacuum deposition methods that use low molecular weight materials, ink-jet methods that use polymer materials and printing methods can be cited. Among these, as methods that can readily be scaled up to large area panels, method using polymer materials are being studied.

As mentioned above, in order to obtain organic luminescent elements having high luminescence efficiency and large area, phosphorescent polymer materials are necessary. As such a phosphorescent polymer material, a polymer incorporating an iridium complex is disclosed (JP-A Nos. 2003-77675 and 2003-342325). However, in practice, regarding luminescence efficiency and driving durability, further improvement is desired. Furthermore, when manufacturing, polymers used in organic electroluminescent elements are normally used by dissolving in a solvent. However, in known phosphorescent polymers, owing to changes in the storage conditions of the solutions when manufacturing, performance variation is likely to occur. Accordingly, there is a need to overcome these problems.

SUMMARY OF THE INVENTION

The current invention provides an organic EL device that is capable of producing superior emission characteristics and driving durability at a low driving voltage.

Namely, the present invention provides an organic electroluminescent device comprising an organic compound layer provided between a pair of electrodes, which comprises a polymer comprising a metal complex containing a tri- or higher-dentate ligand in the polymer molecule.

In one embodiment of the present invention, the metal complex contains a tetra- or higher-dentate ligand in the polymer molecule.

In another embodiment of the present invention, the metal complex is represented by the following Formula (I).

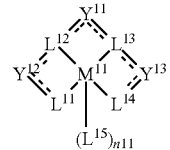

Formula (I)

In Formula (I), $M^{11}$ represents a metal ion; $L^{11}$ to $L^{15}$ each independently represent a ligand coordinated to $M^{11}$; an additional atomic group may connect $L^{11}$ and $L^{14}$ to form a cyclic ligand; $L^{15}$ may be bonded to both $L^{11}$ and $L^{14}$ to form a cyclic ligand; $Y^{11}$ to $Y^{13}$ each independently represent a connecting group, a single bond, or a double bond; when $Y^{11}$, $Y^{12}$, or $Y^{13}$ represent a connecting group, the bond between $L^{11}$ and $Y^{12}$, the bond between $Y^{12}$ and $L^{12}$, the bond between $L^{12}$ and $Y^{11}$, the bond between $Y^{11}$ and $L^{13}$, the bond between $L^{13}$ and $Y^{13}$, and the bond between $Y^{13}$ and $L^{14}$ are each independently a single bond or a double bond; and $n^{11}$ represents an integer of 0 to 4; and each of the bonds between $M^{11}$ and each of $L^{11}$ to $L^{15}$ is independently a coordination bond, an ionic bond or a covalent bond.

In another embodiment of the present invention, at least one of the ligands is a chain.

In another embodiment of the present invention, the metal complex is represented by the following Formula (II):

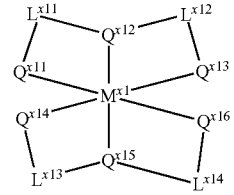

Formula (II)

In Formula (II), $M^{X11}$ represents a metal ion; $Q^{X11}$ to $Q^{X16}$ each independently represent an atom coordinating to $M^{X1}$ or an atomic group containing an atom coordinating to $M^{X1}$; $L^{X11}$ to $L^{X14}$ each independently represent a single bond, a double bond or a connecting group; the atomic group comprising $Q^{X11}$-$L^{X11}$-$Q^{X12}$-$L^{X12}$-$Q^{X13}$ and the atomic group comprising $Q^{X14}$-$L^{X13}$-$Q^{X15}$-$L^{X14}$-$Q^{X16}$ each independently form a tridentate ligand; and each of the bonds between $M^{X1}$ and each of $Q^{X11}$ to $Q^{X16}$ is independently a coordination bond, an ionic bond or a covalent bond.

In another embodiment of the present invention, the metal complex is represented by the following Formula (III).

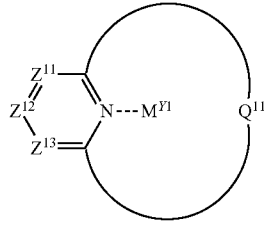

Formula (III)

In Formula (III), $Q^{11}$ represents an atomic group forming a nitrogen-containing heterocycle; $Z^{11}$, $Z^{12}$, and $Z^{13}$ each independently represent a substituted carbon atom, an unsubstituted carbon atom, a substituted nitrogen atom, or an unsubstituted nitrogen atom; and $M^{y1}$ represents a metal ion that may have an additional ligand.

In another embodiment of the present invention, a metal ion in the metal complex is a transition metal ion.

In another embodiment of the present invention, the metal complex comprises at least one metal ion selected from the group consisting of an iridium ion, a platinum ion, a gold ion, a rhenium ion, a tungsten ion, a rhodium ion, a ruthenium ion, an osmium ion, a palladium ion, a silver ion, a copper ion, a cobalt ion, a zinc ion, a nickel ion, a lead ion, an aluminum ion, and a gallium ion.

In another embodiment of the present invention, a metal ion in the metal complex is a rare earth metal ion.

In another embodiment of the present invention, the metal complex comprises a nitrogen atom in its complex structure.

In another embodiment of the present invention, the metal complex comprises a pyridine skeleton, a pyrimidine skeleton, a pyrazine skeleton, an imidazole skeleton, and a pyrazole skeleton, any of which may form a condensed ring by condensing with a ring in another skeleton in the metal complex.

In another embodiment of the present invention, the polymer comprises the metal complex in a side chain thereof.

In another embodiment of the present invention, the polymer comprises the metal complex in its main chain.

In another embodiment of the present invention, the polymer is an unconjugated polymer.

In another embodiment of the present invention, the polymer comprises a phosphorescent luminescent compound portion.

In another embodiment of the present invention, the polymer comprises a hole transporting portion.

In still another embodiment of the present invention, the polymer comprises a portion with an electron transporting ability.

According to the present invention, an organic electroluminescent device that provides emission with high luminance and efficiency, excellent driving durability, and suppression of a variation of the performance due to variations in manufacturing factors can be provided.

DETAILED DESCRIPTION OF THE INVENTION

Organic Electroluminescent Device

The organic electroluminescent device of the invention is characterized by having an anode and a cathode provided on a substrate and an organic compound layer provided between the electrodes. The organic compound layer has at least one luminescent layer. In view of the property of the luminescent layer, it is preferable that at least one of the anode and the cathode is transparent.

An organic compound layer in the invention may be either a single layer or multiple layers. In laminate embodiments, layering, from the positive electrode side, a positive hole transport layer, a luminescent layer and an electron transport layer in this order is preferable. Furthermore, a charge blocking layer or the like may be disposed between the positive hole transport layer and the luminescent layer, or between the luminescent layer and the electron transport layer. A positive hole injection layer may be disposed between the positive electrode and the positive hole transport layer, and an electron injection layer may be disposed between the negative electrode and the electron transport layer. Each of these layers may also be divided into plural secondary layers.

Next, details are provided regarding the polymer material used in the organic electroluminescent device of the invention.

The polymer used in the invention contains a metal complex having a tri- or higher-dentate ligand.

Hereinafter, the metal complex having a tri- or higher-dentate ligand and the polymer containing the metal complex used in the invention will be described in detail.

Metal Complex Having Tri- or Higher-Dentate Ligand

The atom in the metal complex coordinating to the metal ion is not particularly limited. Preferable examples thereof include an oxygen atom, a nitrogen atom, a carbon atom, a sulfur atom or a phosphorus atom, more preferably an oxygen atom, a nitrogen atom or carbon atom, and still more preferable examples thereof include a nitrogen atom and a carbon atom. Particularly preferably, the metal complex includes a nitrogen atom in its complex structure. The "complex structure" used herein means the portion of ligands which constitute the metal complex.

The metal ion in the metal complex is not particularly limited. In view of improving emission efficiency and driving durability and reducing of driving voltage, the metal is preferably a transition metal ion or a rare earth metal ion. Examples thereof include an iridium ion, a platinum ion, a gold ion, a rhenium ion, a tungsten ion, a rhodium ion, a ruthenium ion, an osmium ion, a palladium ion, a silver ion, a copper ion, a cobalt ion, a zinc ion, a nickel ion, a lead ion, an aluminum ion, a gallium ion, a rare-earth metal ion (such as an europium ion, a gadolinium ion, or a terbium ion). More preferable examples thereof include an iridium ion, a platinum ion, a gold ion, a rhenium ion, a tungsten ion, a palladium ion, a zinc ion, an aluminum ion, a gallium ion, a europium ion, a gadolinium ion, and a terbium ion. When the metal complex is used as a luminescent material, preferable examples of the metal ion include an iridium ion, a platinum ion, a rhenium ion, a tungsten ion, a europium ion, a gadolinium ion, and a terbium ion. When the metal complex is used as a charge transfer material or a host material in a luminescent layer, preferable examples of the metal ion include an iridium ion, a platinum ion, a palladium ion, a zinc ion, an aluminum ion, and a gallium ion.

In view of improving emission efficiency and driving durability, the metal complex having a tri- or higher-dentate ligand used in the invention is preferably a metal complex having a tri- to hexa-dentate ligand. When a metal ion in the metal complex is selected from those which tend to form a six-coordinated complex (such as an iridium ion), the metal complex is more preferably one that has a tri-, tetra- or hexa-dentate ligand. When a metal ion in the metal complex is selected from those which tend to form a four-coordinated complex (such as a platinum ion), the metal complex is more preferably one that has a tri- or tetra-dentate ligand, and is still more preferably one that has a tetra-dentate ligand.

In view of improving emission efficiency and driving durability, at least one of the ligands contained in the metal complex used in the invention is preferably a chained or cyclic, and preferably at least one thereof is nitrogen-containing heterocycle (e.g., a pyridine ring, a quinoline ring, a pyrimidine ring, a pyrazine ring, a pyrrole ring, an imidazole ring, a pyrazole ring, an oxazole ring, an thiazole ring, an oxadiazole ring, a thiadiazole ring, a triazole ring, and the like) that coordinates to the central metal (e.g., $M^{11}$ in the compound represented by Formula (I) described below) via the nitrogen. More preferably, the metal complex used in the invention includes a pyridine skeleton, a pyrimidine skeleton, a pyrazine skeleton, an imidazole skeleton, and a pyrazole skeleton. The nitrogen-containing heterocycle is more preferably a nitrogen-containing six-membered heterocycle or a nitrogen-containing five-membered heterocycle. Any of these heterocycles (skeletons) may condense with another ring in another heterocycle (skeleton) to form a condensed ring.

The term "chained" used herein for the ligand contained in the metal complex described above refers to a structure of the ligand which does not encircling the central metal completely (e.g., terpyridyl ligand). The chained ligand contained in the metal complex used in the invention preferably has 12 to 60 carbon atoms, more preferably has 12 to 50 carbon atoms, and still more preferably has 12 to 40 carbon atoms. The term "cyclic" used for the ligand contained in the metal complex refers to a closed structure of the ligand encircling the central metal (e.g., phthalocyanine or crown ether ligand).

The metal complex is preferably a compound represented by Formula (I), (II) or (III) described in detail below.

The compound represented by Formula (I) will be described first.

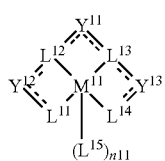

Formula (I)

In Formula (I), $M^{11}$ represents a metal ion; $L^{11}$ to $L^{15}$ each independently represent a ligand coordinated to $M^{11}$; an additional atomic group may connect $L^{11}$ and $L^{14}$ to form a cyclic ligand; $L^{15}$ may be bonded to both $L^{11}$ and $L^{14}$ to form a cyclic ligand; $Y^{11}$ to $Y^{13}$ each independently represent a connecting group, a single bond, or a double bond; when $Y^{11}$, $Y^{12}$, or $Y^{13}$ represent a connecting group, the bond between $L^{11}$ and $Y^{12}$, the bond between $Y^{12}$ and $L^{12}$, the bond between $L^{12}$ and $Y^{11}$, the bond between $Y^{11}$ and $L^{13}$, the bond between $L^{13}$ and $Y^{13}$, and the bond between $Y^{13}$ and $L^{14}$ are each independently a single bond or a double bond; and $n^{11}$ represents an integer of 0 to 4. Each of the bonds connecting $M^{11}$ and each of $L^{11}$ to $L^{15}$ may be selected from a coordinate bond, an ionic bond and a covalent bond.

Hereinafter, details of the compound represented by Formula (I) will be described.

In Formula (I), $M^{11}$ represents a metal ion. While the metal ion is not particularly limited, it is preferably a divalent- or trivalent-metal ion. Preferable examples of the divalent- or trivalent-metal ion include a platinum ion, an iridium ion, a rhenium ion, a palladium ion, a rhodium ion, a ruthenium ion, a copper ion, a europium ion, a gadolinium ion, and a terbium ion. More preferable examples thereof include a platinum ion, an iridium ion, and a europium ion. Still more preferable examples thereof include a platinum ion and an iridium ion. Particularly preferable examples thereof include a platinum ion.

In Formula (I), $L^{11}$, $L^{12}$, $L^{13}$, and $L^{14}$ each independently represent a moiety coordinating to $M^{11}$. Preferable examples of the atom coordinating to $M^{11}$ contained in $L^{11}$, $L^{12}$, $L^{13}$, or $L^{14}$ include preferably a nitrogen atom, an oxygen atom, a sulfur atom, a carbon atom, and a phosphorus atom. More preferable examples thereof include a nitrogen atom, an oxygen atom, a sulfur atom, and a carbon atom. Still more preferable examples thereof include a nitrogen atom, an oxygen atom, and a carbon atom.

The bonds between $M^{11}$ and $L^{11}$, between $M^{11}$ and $L^{12}$, between $M^{11}$ and $L^{13}$, between $M^{11}$ and $L^{14}$ each may be independently selected from a covalent bond, an ionic bond, and a coordination bond. In this specification, the term "ligand" is used also when the bond between the central metal and the ligand is a bond (such as an ionic bond or a covalent bond) other than a coordination bond, as well as when the bond between the central metal and the ligand is a coordination bond.

The entire ligand comprising $L^{11}$, $Y^{12}$, $L^{12}$, $Y^{11}$, $L^{13}$, $Y^{13}$, and $L^{14}$ is preferably an anionic ligand. The number of anions in the anionic ligand is preferably 1 to 3, more preferably 1 or 2, and still more preferably 2.

When the moiety represented by any of $L^{11}$, $L^{12}$, $L^{13}$, and $L^{14}$ coordinates to $M^{11}$ via a carbon atom, the moiety is not particularly limited, and examples thereof include imino ligands, aromatic carbon ring ligands (e.g., a benzene ligand, a naphthalene ligand, an anthracene ligand, and a phenanthrene ligand), and heterocyclic ligands [e.g., a thiophene ligand, a pyridine ligand, a pyrazine ligand, a pyrimidine ligand, a thiazole ligand, an oxazole ligand, a pyrrole ligand, an imidazole ligand, and a pyrazole ligand, ring-condensation products thereof (e.g., a quinoline ligand and a benzothiazole ligand), and tautomers thereof].

When the moiety represented by any of $L^{11}$, $L^{12}$, $L^{13}$, and $L^{14}$ coordinates to $M^{11}$ via a nitrogen atom, the moiety is not particularly limited, and examples thereof include nitrogen-containing heterocyclic ligands such as a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand, an oxadiazole ligand, and a thiadiazole ligand, and ring-condensation products thereof (e.g., a quinoline ligand, a benzoxazole ligand, and a benzimidazole ligand), and tautomers thereof [in the invention, the following ligands (pyrrole tautomers) are also included in tautomers, in addition to normal isomers: the five-membered heterocyclic ligand of compound (24), the terminal five-membered heterocyclic ligand of compound (64), and the five-membered heterocycle ligand of compound (145), the compounds (24), (64), (145) being shown below as typical examples of the compound represented by formula (I)]; amino ligands such as alkylamino ligands (preferably having 2 to 30 carbon atoms, more preferably 2 to 20 carbon atoms, and particularly preferably 2 to 10 carbon atoms, such as methylamino), arylamino ligands (preferably having 6 to 30 carbon atoms, more preferably 6 to 20 carbon atoms, and particularly preferably 6 to 12 carbon atoms, such as phenylamino), acylamino ligands (preferably having 2 to 30 carbon atoms, more preferably 2 to 20 carbon atoms, and particularly preferably 2 to 10 carbon atoms, such as acetylamino and benzoylamino), alkoxycarbonylamino ligands (preferably having 2 to 30 carbon atoms, more preferably 2 to 20 carbon atoms, and particularly preferably 2 to 12 carbon atoms, such as methoxycarbonylamino), aryloxycarbonylamino ligands (preferably having 7 to 30 carbon atoms, more preferably 7 to 20 carbon atoms, and particularly preferably 7 to 12 carbon atoms, such as phenyloxycarbonylamino), sulfonylamino ligands (preferably having 1 to 30 carbon atoms, more preferably 1 to 20 carbon atoms, and particularly preferably 1 to 12 carbon atoms, such as methanesulfonylamino and benzenesulfonylamino), and imino ligands. These ligands may be substituted.

When the moiety represented by any of $L^{11}$, $L^{12}$, $L^{13}$, and $L^{14}$ coordinates to $M^{11}$ via an oxygen atom, the moiety is not particularly limited, and examples thereof include alkoxy ligands (preferably having 1 to 30 carbon atoms, more preferably 1 to 20 carbon atoms, and particularly preferably 1 to 10 carbon atoms, such as methoxy, ethoxy, butoxy, and 2-ethylhexyloxy), aryloxy ligands (preferably having 6 to 30 carbon atoms, more preferably 6 to 20 carbon atoms, and particularly preferably 6 to 12 carbon atoms, such as phenyloxy, 1-naphthyloxy, and 2-naphthyloxy), heterocyclic oxy ligands (preferably having 1 to 30 carbon atoms, more preferably 1 to 20 carbon atoms, and particularly preferably 1 to 12 carbon atoms, such as pyridyloxy, pyrazyloxy, pyrimidyloxy, and quinolyloxy), acyloxy ligands (preferably having 2 to 30 carbon atoms, more preferably 2 to 20 carbon atoms, and particularly preferably 2 to 10 carbon atoms, such as acetoxy and benzoyloxy), silyloxy ligands (preferably having 3 to 40 carbon atoms, more preferably 3 to 30 carbon atoms, and particularly preferably 3 to 24 carbon atoms, such as trimethylsilyloxy and triphenylsilyloxy), carbonyl ligands (e.g., ketone ligands, ester ligands, and amido ligands), and ether ligands (e.g., dialkylether ligands, diarylether ligands, and furyl ligands).

When the moiety represented by any of $L^{11}$, $L^{12}$, $L^{13}$, and $L^{14}$ coordinates to $M^{11}$ via a sulfur atom, the moiety is not particularly limited, and examples thereof include alkylthio ligands (preferably having 1 to 30 carbon atoms, more preferably 1 to 20 carbon atoms, and particularly preferably 1 to 12 carbon atoms, such as methylthio and ethylthio), arylthio ligands (preferably having 6 to 30 carbon atoms, more preferably 6 to 20 carbon atoms, and particularly preferably 6 to 12 carbon atoms, such as phenylthio), heterocyclic thio ligands (preferably having 1 to 30 carbon atoms, more preferably 1 to 20 carbon atoms, and particularly preferably 1 to 12 carbon atoms, such as pyridylthio, 2-benzimidazolylthio, 2-benzoxazolylthio, and 2-benzothiazolylthio), thiocarbonyl ligands (e.g., thioketone ligands and thioester ligands), and thioether ligands (e.g., dialkylthioether ligands, diarylthioether ligands, and thiofuryl ligands). These substitution ligands may respectively have a substitutent.

When the moiety represented by any of $L^{11}$, $L^{12}$, $L^{13}$, and $L^{14}$ coordinates to $M^{11}$ via a phosphorus atom, the moiety is not particularly limited, and examples thereof include dialkylphosphino groups (preferably having 2 to 30 carbon atoms, more preferably 2 to 20 carbon atoms, and particularly preferably 2 to 12 carbon atoms, such as dicyclohexylphosphino), diarylphosphino groups (preferably having 12 to 40 carbon atoms, more preferably 12 to 30 carbon atoms, and particularly preferably 12 to 20 carbon atoms, such as diphenylphosphino), trialkylphosphine groups (preferably having 3 to 30 carbon atoms, more preferably 3 to 20 carbon atoms, and particularly preferably 3 to 12 carbon atoms, such as tributylphosphine, tri-tert-butylphosphine, or tricyclohexylphosphine), triarylphosphine groups (preferably having 18 to 40 carbon atoms, more preferably 18 to 30 carbon atoms, and particularly preferably 18 to 20 carbon atoms, such as triphenylphosphine, diphenyl(p-tolyl)phosphine, tri-p-tolylphosphine, (R)-(+)-2,2'-bis(diphenylphosphino)-1,1'-binaphthyl, or (S)-(−)-2,2'-bis(diphenylphosphino)-1,1'-binaphthyl), alkylarylphosphinine groups (preferably having 8 to 40 carbon atoms, more preferably 8 to 30 carbon atoms, and particularly preferably 13 to 30 carbon atoms, such as dicyclophenylphosphine, bis(diphenylphosphino)methane, 1,2-bis(diphenylphosphino)ethane, or 3-bis(diphenylphosphino)propane), phosphinine groups and the like. These groups may respectively have a substituent.

In a preferable embodiment, $L^{11}$ and $L^{14}$ each independently represent a moiety selected from an aromatic carbon ring ligand, an alkyloxy ligand, an aryloxy ligand, an ether ligand, an alkylthio ligand, an arylthio ligand, an alkylamino ligand, an arylamino ligand, an acylamino ligand, or a nitrogen-containing heterocyclic ligand [e.g., a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand, an oxadiazole ligand, a thiadiazole ligand, or a condensed ring containing one or more of the above ligands (e.g., a quinoline ligand, a benzoxazole ligand, or a benzimidazole ligand), or a tautomer of any of the above ligands]; more preferably, an aromatic carbon ring ligand, an aryloxy ligand, an arylthio ligand, an arylamino ligand, a pyridine ligand, a pyrazine ligand, an imidazole ligand, a condensed ring ligand containing one or more of the above ligands (e.g., a quinoline ligand, a quinoxaline ligand, or a benzimidazole ligand), or a tautomer of any of the above ligands; still more preferably, an aromatic carbon ring ligand or an aryloxy ligand, an arylthio ligand, or an arylamino ligand; and particularly preferably, an aromatic carbon ring ligand or an aryloxy ligand.

In a preferable embodiment, $L^{12}$ and $L^{13}$ each independently represent a moiety forming a coordination bond with $M^{11}$. The moiety forming a coordination bond with $M^{11}$ is preferably a pyridine, pyrazine, pyrimidine, triazine, thiazole, oxazole, pyrrole or triazole ring, a condensed ring containing one or more of the above rings (e.g., a quinoline ring, a benzoxazole ring, a benzimidazole ring, an indolenine ring), or a tautomer of any of the above rings; more preferably a pyridine, pyrazine, pyrimidine, or pyrrole ring, a condensed ring containing one or more of the above rings (e.g., a quinoline ring, a benzopyrrole ring), or a tautomer of any of the above rings; still more preferably a pyridine, pyrazine or pyrimidine ring, or a condensed ring containing one or more of the above rings (e.g., quinoline ring); particularly preferably a pyridine ring or a condensed ring containing a pyridine ring (e.g., a quinoline ring).

In Formula (I), $L^{15}$ represents a ligand coordinating to $M^{11}$. $L^{15}$ is preferably a monodentate- to tetradentate-ligand and more preferably a monodentate to tetradentate anionic ligand. While the monodentate- to tetradentate-anionic ligand is not particularly limited, it is preferably a halogen ligand, a 1,3-diketone ligand (e.g., an acetylacetone ligand), a monoanionic bidentate ligand containing a pyridine ligand [e.g., a picolinic acid ligand or a 2-(2-hydroxyphenyl)-pyridine ligand], or a tetradentate ligand $L^{11}$, $Y^{12}$, $L^{12}$, $Y^{11}$, $L^{13}$, $Y^{13}$, and $L^{14}$ can form; more preferably, a 1,3-diketone ligand (e.g., an acetylacetone ligand), a monoanionic bidentate ligand containing a pyridine ligand [e.g., a picolinic acid ligand or a 2-(2-hydroxyphenyl)-pyridine ligand], or a tetradentate ligand $L^{11}$, $Y^{12}$, $L^{12}$, $Y^{11}$, $L^{13}$, $Y^{13}$, and $L^{14}$ can form; still more preferably, a 1,3-diketone ligand (e.g., an acetylacetone ligand) or a monoanionic bidentate ligand containing a pyridine ligand [e.g., a picolinic acid ligand or a 2-(2-hydroxyphenyl)-pyridine ligand]; and particularly preferably, a 1,3-diketone ligand (e.g., an acetylacetone ligand). The number of coordination sites and the number of ligands do not exceed the valency of the metal. $L^{15}$ does not bind to both $L^{11}$ and $L^{14}$ to form a cyclic ligand.

In Formula (I), $Y^{11}$, $Y^{12}$ and $Y^{13}$ each independently represent a connecting group or a single or double bond. The connecting group is not particularly limited, and examples thereof include those which comprise a carbon atom, a nitrogen atom, an oxygen atom, a sulfur atom, a silicon atom or phosphorus atom.

Specific examples of the connecting group include the following connecting groups.

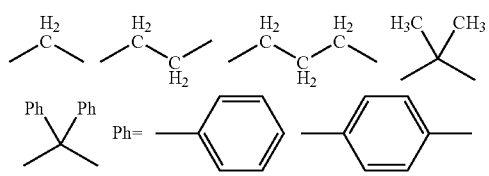

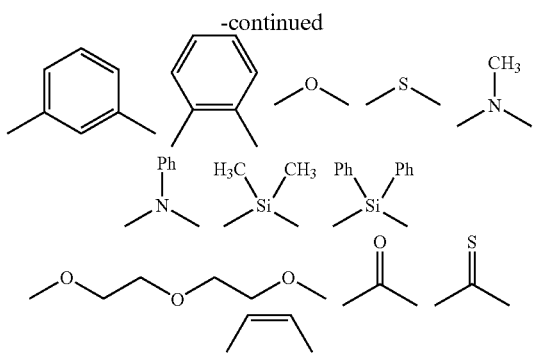

When each of $Y^{11}$, $Y^{12}$, or $Y^{13}$ represents a connecting group, the bond between $L^{11}$ and $Y^{12}$ the bond between $Y^{12}$ and $L^{12}$, the bond between $L^{12}$ and $Y^{11}$, the bond between $Y^{11}$ and $L^{13}$, the bond between $L^{13}$ and $Y^{13}$ and the bond between $Y^{13}$ and $L^{14}$ are each independently a single bond or a double bond.

Preferably, $Y^{11}$, $Y^{12}$, and $Y^{13}$ each independently represent a single bond, a double bond, a carbonyl connecting group, an alkylene connecting group, or an alkenylene group. $Y^{11}$ is more preferably a single bond or an alkylene group, and still more preferably an alkylene group. Each of $Y^{12}$ and $Y^{13}$ is more preferably a single bond or an alkenylene group and still more preferably a single bond.

The ring formed by $Y^{12}$, $L^{11}$, $L^{12}$, and $M^{11}$, the ring formed by $Y^{11}$, $L^{12}$, $L^{13}$, and $M^{11}$, and the ring formed by $Y^{13}$, $L^{13}$, $L^{14}$, and $M^{11}$ are each preferably a four- to ten-membered ring, more preferably a five- to seven-membered ring, and still more preferably a five- to six-membered ring.

In Formula (I), $n^{11}$ represents an integer of 0 to 4. When $M^{11}$ is a tetravalent metal, $n^{11}$ is 0. When $M^{11}$ is a hexavalent metal, $n^{11}$ is preferably 1 or 2 and more preferably 1. When $M^{11}$ is a hexavalent metal and $n^{11}$ is 1, $L^{15}$ represents a bidentate ligand. When $M^{11}$ is a hexavalent metal and $n^{11}$ is 2, $L^{15}$ represents a monodentate ligand. When $M^{11}$ is an octavalent metal, $n^{11}$ is preferably 1 to 4, more preferably, 1 or 2, and still more preferably 1. When $M^{11}$ is an octavalent metal and $n^{11}$ is 1, $L^{15}$ represents a tetradentate ligand. When $M^{11}$ is an octavalent metal and $n^{11}$ is 2, $L^{15}$ represents a bidentate ligand. When $n^{11}$ is 2 or larger, there are plural $L^{15}$'s, and the $L^{15}$'s may be the same as or different from each other.

Preferable embodiments of the compound represented by Formula (I) include compounds represented by the following Formulae (1), (2), (3) or (4).

Firstly, explanation of the compound represented by Formula (1) is provided.

Formula (1)

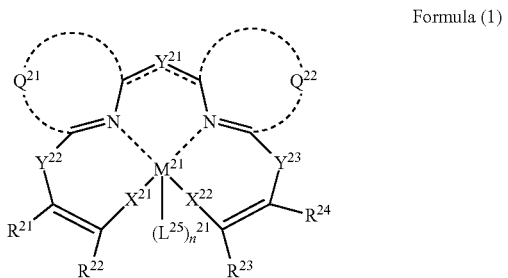

In Formula (1), $M^{21}$ represents a metal ion; and $Y^{21}$ represents a connecting group, a single group, or a double bond. $Y^{23}$ and $Y^{23}$ each represent a single bond or a connecting group. $Q^{21}$ and $Q^{22}$ each represent an atomic group forming a nitrogen-containing heterocycle, and the bond between $Y^{21}$ and the ring containing $Q^{21}$ and the bond between $Y^{21}$ and the ring containing $Q^{22}$ are each a single or double bond. $X^{21}$ and $X^{22}$ each independently represent an oxygen atom, a sulfur atom, or a substituted or unsubstituted nitrogen atom. $R^{21}$, $R^{22}$, $R^{23}$, and $R^{24}$ each independently represent a hydrogen atom or a substituent. $R^{21}$ and $R^{22}$ may be bound to each other to form a ring, and $R^{23}$ and $R^{24}$ may bind to each other to form a ring. $L^{25}$ represents a ligand coordinating to $M^{21}$, and $n^{21}$ represents an integer of 0 to 4.

The compound represented by formula (1) will be described in detail.

In Formula (1), the definition of $M^{21}$ is the same as the definition of $M^{11}$ in Formula (I), and their preferable ranges are also similar.

$Q^{21}$ and $Q^{22}$ each independently represent an atomic group forming a nitrogen-containing heterocycle (ring containing a nitrogen atom coordinating to $M^{21}$). The nitrogen-containing heterocycles formed by $Q^{21}$ and $Q^{22}$ are not particularly limited, and may be selected, for example, from a pyridine ring, a pyrazine ring, a pyrimidine ring, a triazine ring, a thiazole ring, an oxazole ring, a pyrrole ring, a triazole ring, and condensed rings containing one or more of the above rings (e.g., a quinoline ring, a benzoxazole ring, a benzimidazole ring, and an indolenine ring), and tautomers thereof.

Preferable examples of the nitrogen-containing heterocycle formed by $Q^{21}$ and $Q^{22}$ include a pyridine ring, a pyrazine ring, a pyrimidine ring, a pyridazine ring, a triazine ring, a pyrazole ring, an imidazole ring, an oxazole ring, a pyrrole ring, a benzazole ring, and condensed rings containing the above rings (e.g., a quinoline ring), and tautomers thereof. More preferable examples thereof include a pyridine ring and condensed rings containing the above rings (e.g., a quinoline ring), and particularly preferable examples thereof include a pyridine ring.

$X^{21}$ and $X^{22}$ each independently represent an oxygen atom, a sulfur atom, or a substituted or unsubstituted nitrogen atom. $X^{21}$ and $X^{22}$ are each preferably an oxygen atom, a sulfur atom, or a substituted nitrogen atom, more preferably an oxygen atom or a sulfur atom, and particularly preferably an oxygen atom.

The definition of $Y^{21}$ is the same as that of $Y^{11}$ in Formula (I), and their preferable ranges are also similar.

$Y^{22}$ and $Y^{23}$ each independently represent a single bond or a connecting group, preferably a single bond. The connecting group is not particularly limited, and examples thereof include a carbonyl connecting group, a thiocarbonyl connecting group, an alkylene group, an alkenylene group, an arylene group, a heteroarylene group, connecting groups which connects moieties via an oxygen atom or a nitrogen atom, and connecting groups comprising combinations of connecting groups selected from the above.

The connecting group represented by $Y^{22}$ or $Y^{23}$ is preferably a carbonyl connecting group, an alkylene connecting group, or an alkenylene connecting group, more preferably a carbonyl connecting group or an alkenylene connecting group, and still more preferably a carbonyl connecting group.

$R^{21}$, $R^{22}$, $R^{23}$, and $R^{24}$ each independently represent a hydrogen atom or a substituent. The substituent is not particularly limited, and examples thereof include alkyl groups (preferably having 1 to 30 carbon atoms, more preferably 1 to 20 carbon atoms, and particularly preferably 1 to 10 carbon atoms, and examples thereof include a methyl group, an ethyl group, an iso-propyl group, a tert-butyl group, a n-octyl group, a n-decyl group, a n-hexadecyl group, a cyclopropyl group, a cyclopentyl group, and a cyclohexyl group), alkenyl groups (preferably having 2 to 30 carbon atoms, more preferably 2 to 20 carbon atoms, and particularly preferably 2 to 10 carbon atoms, and examples thereof include a vinyl group, an allyl group, a 2-butenyl group, and a 3-pentenyl group), alkynyl groups (preferably having 2 to 30 carbon atoms, more preferably 2 to 20 carbon atoms, and particularly preferably 2 to 10 carbon atoms, and examples thereof include a propargyl group and a 3-pentynyl group), aryl groups (preferably having 6 to 30 carbon atoms, more preferably 6 to 20 carbon atoms, and particularly preferably 6 to 12 carbon atoms, and examples thereof include a phenyl group, a p-methylphenyl group, a naphthyl group, and an anthranyl group), amino groups (preferably having 0 to 30 carbon atoms, more preferably 0 to 20 carbon atoms, and particularly preferably 0 to 10 carbon atoms, and examples thereof include an amino group, a, methylamino group, a dimethylamino group, a diethylamino group, a dibenzylamino group, a diphenylamino group, and a ditolylamino group), alkoxy groups (preferably having 1 to 30 carbon atoms, more preferably 1 to 20 carbon atoms, and particularly preferably 1 to 10 carbon atoms, and examples thereof include a methoxy group, a ethoxy group, a butoxy group, and a 2-ethylhexyloxy group), aryloxy groups (preferably having 6 to 30 carbon atoms, more preferably 6 to 20 carbon atoms, and particularly preferably 6 to 12 carbon atoms, and examples thereof include a phenyloxy group, a 1-naphthyloxy group, and a 2-naphthyloxy group), heterocyclic oxy groups (preferably having 1 to 30 carbon atoms, more preferably 1 to 20 carbon atoms, and particularly preferably 1 to 12 carbon atoms, and examples thereof include a pyridyloxy group, a pyrazyloxy group, a pyrimidyloxy group, and a quinolyloxy group), acyl groups (preferably having 1 to 30 carbon atoms, more preferably 1 to 20 carbon atoms, and particularly preferably 1 to 12 carbon atoms, and examples thereof include a acetyl group, a benzoyl group, a formyl group, and a pivaloyl group), alkoxycarbonyl groups (preferably having 2 to 30 carbon atoms, more preferably 2 to 20 carbon atoms, and particularly preferably 2 to 12 carbon atoms, and examples thereof include a methoxycarbonyl group and an ethoxycarbonyl group), aryloxycarbonyl groups (preferably having 7 to 30 carbon atoms, more preferably 7 to 20 carbon atoms, and particularly preferably 7 to 12 carbon atoms, and examples thereof include a phenyloxycarbonyl group), acyloxy groups (preferably having 2 to 30 carbon atoms, more preferably 2 to 20 carbon atoms, and particularly preferably 2 to 10 carbon atoms, and examples thereof include an acetoxy group and a benzoyloxy group), acylamino groups (preferably having 2 to 30 carbon atoms, more preferably 2 to 20 carbon atoms, and particularly preferably 2 to 10 carbon atoms, and examples thereof include an acetylamino group and a benzoylamino group), alkoxycarbonylamino groups (preferably having 2 to 30 carbon atoms, more preferably 2 to 20 carbon atoms, and particularly preferably 2 to 12 carbon atoms, and examples thereof include a methoxycarbonylamino group), aryloxycarbonylamino groups (preferably having 7 to 30 carbon atoms, more preferably 7 to 20 carbon atoms, and particularly preferably 7 to 12 carbon atoms, and examples thereof include a phenyloxycarbonylamino group), sulfonylamino groups (preferably having 1 to 30 carbon atoms, more preferably 1 to 20 carbon atoms, and particularly preferably 1 to 12 carbon atoms, and examples thereof include a methanesulfonylamino group and a benzenesulfonylamino group), sulfamoyl groups (preferably having 0 to 30 carbon atoms, more preferably 0 to 20 carbon atoms, and particularly preferably 0 to 12 carbon atoms, and examples thereof include a sulfamoyl group, a methylsulfamoyl group, a dimethylsulfamoyl group, and a phenylsulfamoyl group), carbamoyl groups (preferably having 1 to 30 carbon atoms, more preferably 1 to 20 carbon atoms, and particularly preferably 1 to 12 carbon atoms, and examples thereof include a carbamoyl group, a methylcarbamoyl group, a diethylcarbamoyl group, and a phenylcarbamoyl group), alkylthio groups (preferably having 1 to 30 carbon atoms, more preferably 1 to 20 carbon atoms, and particularly preferably 1 to 12 carbon atoms, and examples thereof include a methylthio group and an ethylthio group), arylthio groups (preferably having 6 to 30 carbon atoms, more preferably 6 to 20 carbon atoms, and particularly preferably 6 to 12 carbon atoms, and examples thereof include a phenylthio group), heterocyclic thio groups (preferably having 1 to 30 carbon atoms, more preferably 1 to 20 carbon atoms, and particularly preferably 1 to 12 carbon atoms, and examples thereof include a pyridylthio group, a 2-benzimidazolylthio group, a 2-benzoxazolylthio group, and a 2-benzothiazolylthio group), sulfonyl groups (preferably having 1 to 30 carbon atoms, more preferably 1 to 20 carbon atoms, and particularly preferably 1 to 12 carbon atoms, and examples thereof include a mesyl group and a tosyl group), sulfinyl groups (preferably having 1 to 30 carbon atoms, more preferably 1 to 20 carbon atoms, and particularly preferably 1 to 12 carbon atoms, and examples thereof include a methanesulfinyl group and a benzenesulfinyl group), ureido groups (preferably having 1 to 30 carbon atoms, more preferably 1 to 20 carbon atoms, and particularly preferably 1 to 12 carbon atoms, and examples thereof include a ureido group, a methylureido group, and a phenylureido group), phosphoric amide groups (preferably having 1 to 30 carbon atoms, more preferably 1 to 20 carbon atoms, and particularly preferably 1 to 12 carbon atoms, and examples thereof include a diethylphosphoric amide group and a phenylphosphoric amide group), a hydroxy group, a mercapto group, halogen atoms (such as fluorine, chlorine, bromine, or iodine), a cyano group, a sulfo group, a carboxyl group, a nitro group, a hydroxamic acid group, sulfino groups, hydrazino groups, imino groups, heterocyclic groups (preferably having 1 to 30 carbon atoms and more preferably 1 to 12 carbon atoms; the heteroatom(s) may be selected from nitrogen, oxygen, and sulfur atoms), and examples thereof include an imidazolyl group, a pyridyl group, a quinolyl group, a furyl group, a thienyl group, a piperidyl group, a morpholino group, a benzoxazolyl group, a benzimidazolyl group, a benzothiazolyl group, a carbazolyl group, and an azepinyl group), silyl groups (preferably having 3 to 40 carbon atoms, more preferably 3 to 30 carbon atoms, and particularly preferably 3 to 24 carbon atoms, and examples thereof include a trimethylsilyl group and a triphenylsilyl group), and silyloxy groups (preferably having 3 to 40 carbon atoms, more preferably 3 to 30 carbon atoms, and particularly preferably 3 to 24 carbon atoms, and examples thereof include a trimethylsilyloxy group and a triphenylsilyloxy group). These substituents may have a substitutent(s).

In a preferable embodiment, $R^{21}$, $R^{22}$, $R^{23}$, and $R^{24}$ are each independently selected from alkyl groups or aryl groups. In another preferable embodiment, $R^{21}$ and $R^{22}$ are groups that bind to each other to form a ring structure (e.g., a benzo-condensed ring or a pyridine-condensed ring), and/or $R^{23}$ and $R^{24}$ are groups that bind to each other to form a ring structure or ring structures (e.g., a benzo-condensed ring or a pyridine-condensed ring). In a more preferable embodiment, $R^{21}$ and $R^{22}$ are groups that bind to each other to form a ring structure (e.g., a benzo-condensed ring or a pyridine-condensed ring), and/or $R^{23}$ and $R^{24}$ are groups that bind to each other to form a ring structure or ring structures (e.g., a benzo-condensed ring or a pyridine-condensed ring).

The definition of $L^{25}$ is similar to that of $L^{15}$ in Formula (I), and their preferable ranges are also similar.

The definition of $n^{21}$ is similar to that of $n^{11}$ in Formula (I), and their preferable ranges are also similar.

In Formula (1), examples of preferable embodiments are described below:

(1) the rings formed by $Q^{21}$ and $Q^{22}$ are pyridine rings, and $Y^{21}$ is a connecting group;

(2) the rings formed by $Q^{21}$ and $Q^{22}$ are pyridine rings, $Y^{21}$ is a single or double bond, and $X^{21}$ and $X^{22}$ are selected from sulfur atoms, substituted nitrogen atoms, and unsubstituted nitrogen atom;

(3) the rings formed by $Q^{21}$ and $Q^{22}$ are each a five-membered nitrogen-containing heterocycle, or a nitrogen-containing six-membered ring containing two or more nitrogen atoms.

Preferable examples of compounds represented by Formula (1) are compounds represented by the following Formula (1-A).

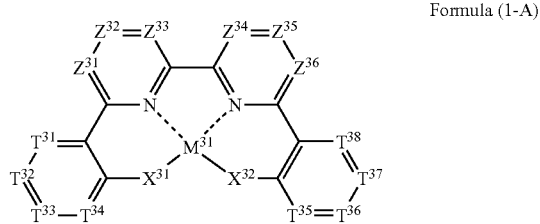

Formula (1-A)

The compound represented by Formula (1-A) will be described below.

In Formula (1-A), the definition of $M^{31}$ is similar to that of $M^{11}$ in Formula (I), and their preferable ranges are also similar.

$Z^{31}$, $Z^{32}$, $Z^{33}$, $Z^{34}$, $Z^{35}$, and $Z^{36}$ each independently represent a substituted carbon atom, an unsubstituted carbon atom, a substituted nitrogen atom, or an unsubstituted nitrogen atom, and preferably a substituted carbon atom or an unsubstituted carbon atom. The substituent on the carbon may be selected from the substituents described as examples of $R^{21}$ in Formula (1). $Z^{31}$ and $Z^{32}$ may be bonded to each other via a connecting group to form a condensed ring (e.g., a benzo-condensed ring or a pyridine-condensed ring). $Z^{32}$ and $Z^{33}$ may be bonded to each other via a connecting group to form a condensed ring (e.g., a benzo-condensed ring or a pyridine-condensed ring). $Z^{33}$ and $Z^{34}$ may be bonded to each other via a connecting group to form a condensed ring (e.g., a benzo-condensed ring or a pyridine-condensed ring). $Z^{34}$ and $Z^{35}$ may be bonded to each other via a connecting group to form a condensed ring (e.g., a benzo-condensed ring or a pyridine-condensed ring). $Z^{35}$ and $Z^{36}$ may be bonded to each other via a connecting group to form a condensed ring (e.g., a benzo-condensed ring or a pyridine-condensed ring). $Z^{31}$ and $T^{31}$ may be bonded to each other via a connecting group to form a condensed ring (e.g., a benzo-condensed ring or a pyridine-condensed ring). $Z^{36}$ and $T^{38}$ may be bonded to each other via a connecting group to form a condensed ring (e.g., a benzo-condensed ring or a pyridine-condensed ring).

The substituent on the carbon is preferably an alkyl group, an alkoxy group, an alkylamino group, an aryl group, a group capable of forming a condensed ring (e.g., a benzo-condensed ring or a pyridine-condensed ring), or a halogen atom, more preferably an alkylamino group, an aryl group, or a group capable of forming a condensed ring (e.g., a benzo-condensed ring or a pyridine-condensed ring), still more preferably an aryl group or a group capable of forming a condensed ring (e.g., a benzo-condensed ring or a pyridine-condensed ring), and particularly preferably a group capable of forming a condensed ring (e.g., a benzo-condensed ring or a pyridine-condensed ring).

$T^{31}$, $T^{32}$, $T^{33}$, $T^{34}$, $T^{35}$, $T^{36}$, $T^{37}$, and $T^{38}$ each independently represent a substituted carbon atom, an unsubstituted carbon atom, a substituted nitrogen atom, or an unsubstituted nitrogen atom, and more preferably a substituted carbon atom or an unsubstituted carbon atom. Examples of the substituents on the carbon include the groups described as examples of $R^{21}$ in Formula (1); $T^{31}$ and $T^{32}$ may be bonded to each other via a connecting group to form a condensed ring (e.g., a benzo-condensed ring or a pyridine-condensed ring). $T^{32}$ and $T^{33}$ may be bonded to each other via a connecting group to form a condensed ring (e.g., a benzo-condensed ring or a pyridine-condensed ring). $T^{33}$ and $T^{34}$ may be bonded to each other via a connecting group to form a condensed ring (e.g., a benzo-condensed ring or a pyridine-condensed ring). $T^{35}$ and $T^{36}$ may be bonded to each other via a connecting group to form a condensed ring (e.g., a benzo-condensed ring or a pyridine-condensed ring). $T^{36}$ and $T^{37}$ may be bonded to each other via a connecting group to form a condensed ring (e.g., a benzo-condensed ring or a pyridine-condensed ring). $T^{37}$ and $T^{38}$ may be bonded to each other via a connecting group to form a condensed ring (e.g., a benzo-condensed ring or a pyridine-condensed ring).

The substituent on the carbon is preferably an alkyl group, an alkoxy group, an alkylamino group, an aryl group, a group capable of forming a condensed ring (e.g., a benzo-condensed ring or a pyridine-condensed ring), or a halogen atom; more preferably an aryl group, a group capable of forming a condensed ring (e.g., a benzo-condensed ring or pyridine-condensed ring), or a halogen atom; still more preferably an aryl group or a halogen atom, and particularly preferably an aryl group.

The definitions and preferable ranges of $X^{31}$ and $X^{32}$ are similar to the definitions and preferable ranges of $X^{21}$ and $X^{22}$ in Formula (1), respectively.

The compound represented by Formula (2) will be described below.

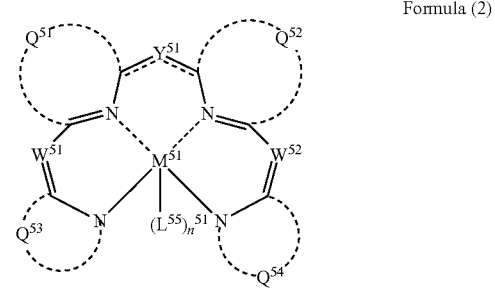

Formula (2)

In Formula (2), the definition of $M^{51}$ is similar to that of $M^{11}$ in Formula (I), and their preferable ranges are also similar.

The definitions of $Q^{51}$ and $Q^{52}$ are similar to the definitions of $Q^{21}$ and $Q^{22}$ in Formula (1), and their preferable ranges are also similar.

$Q^{53}$ and $Q^{54}$ each independently represent a group forming a nitrogen-containing heterocycle (ring containing a nitrogen atom coordinating to $M^{51}$). The nitrogen-containing heterocycles formed by $Q^{53}$ and $Q^{54}$ are not particularly limited, and are preferably selected from tautomers of pyrrole compounds, tautomers of imidazole compounds (e.g., the five-membered heterocyclic ligand contained in the compound (29) shown below as a specific example of the compound represented by Formula (I)), tautomers of thiazole compounds (e.g., the five-membered heterocyclic ligand contained in the compound (30) shown below as a specific example of the compound represented by Formula (I)), and tautomers of oxazole compounds (e.g., the five-membered heterocyclic ligand contained in the compound (31) shown below as a specific example of the compound represented by Formula (I)), more preferably selected from tautomers of pyrrole, imidazole, and thiazole compounds; still more preferably selected from tautomers of pyrrole and imidazole compounds; and particularly preferably selected from tautomers of pyrrole compounds.

The definition of $Y^{51}$ is similar to that of $Y^{11}$ in Formula (I), and their preferable range are also the same.

The definition of $L^{55}$ is similar to that of $L^{15}$ in Formula (I), and their preferable ranges are also similar.

The definition of $n^{51}$ is similar to that of $n^{11}$, and their preferable ranges are also similar.

$W^{51}$ and $W^{52}$ each independently represent a substituted carbon atom, an unsubstituted carbon atom, a substituted nitrogen atom, or an unsubstituted nitrogen atom, more preferably an unsubstituted carbon atom or an unsubstituted nitrogen atom, and still more preferably an unsubstituted carbon atom.

The compound represented by Formula (3) will be described below.

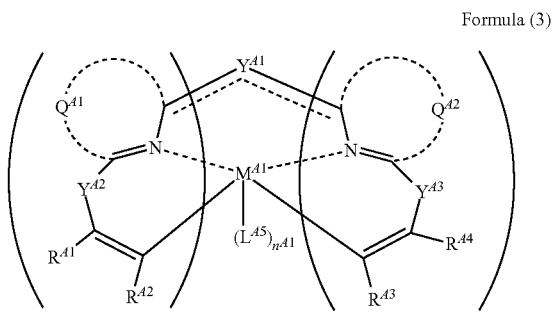

Formula (3)

In Formula (3), the definitions and preferable ranges of $M^{41}$, $Q^{41}$, $Q^{42}$, $Y^{41}$, $Y^{42}$, $Y^{43}$, $R^{41}$, $R^{42}$, $R^{43}$, $R^{44}$, $L^{45}$, and $n^{41}$ are similar to the definitions and preferable ranges of $M^{21}$, $Q^{21}$, $Q^{22}$, $Y^{21}$, $Y^{22}$, $Y^{23}$, $R^{21}$, $R^{22}$, $R^{23}$, $R^{24}$, $L^{25}$, and $n^{21}$ in Formula (1) respectively.

Preferable examples of compounds represented by Formula (3) are compounds represented by the following Formula (3-A) or (3-B).

The compound represented by Formula (3-A) will be described first.

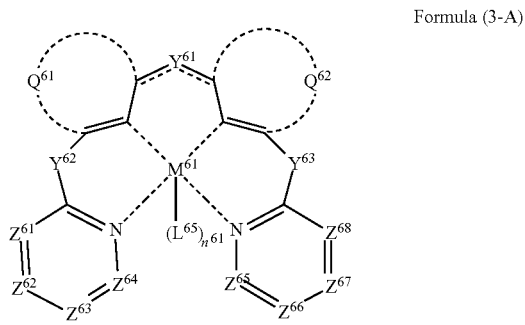

Formula (3-A)

In Formula (3-A), the definitions of $M^{61}$ is the same as that of $M^{11}$ in Formula (I), and their preferable ranges are also similar.

$Q^{61}$ and $Q^{62}$ each independently represent a ring-forming group. The rings formed by $Q^{61}$ and $Q^{62}$ are not particularly limited, and examples thereof include a benzene ring, a pyridine ring, a pyridazine ring, a pyrimidine ring, a thiophene ring, an isothiazole ring, a furan ring, an isoxazole ring, and condensed rings thereof.

Each of the rings formed by $Q^{61}$ and $Q^{62}$ is preferably a benzene ring, a pyridine ring, a thiophene ring, a thiazole ring, or a condensed ring containing one or more of the above rings; more preferably a benzene ring, a pyridine ring, or a condensed ring containing one or more of the above rings; and still more preferably a benzene ring or a condensed ring containing a benzene ring.

The definition of $Y^{61}$ is similar to that of $Y^{11}$ in Formula (I), and their preferable ranges are also similar.

$Y^{62}$ and $Y^{63}$ each independently represent a connecting group or a single bond. The connecting group is not particularly limited, and examples thereof include a carbonyl connecting group, a thiocarbonyl connecting group, alkylene groups, alkenylene groups, arylene groups, heteroarylene groups, a connecting group which connects moieties via an oxygen atom or a nitrogen atom, and connecting groups comprising combinations of connecting groups selected from the above.

$Y^{62}$ and $Y^{63}$ are each independently selected, preferably from a single bond, a carbonyl connecting group, an alkylene connecting group, and an alkenylene group, more preferably from a single bond and an alkenylene group, and still more preferably from a single bond.

The definition of $L^{65}$ is similar to that of $L^{15}$ in Formula (I), and their preferable ranges are also similar.

The definition of $n^{61}$ is the same as the definition of $n^{11}$ in Formula (I), and their preferable ranges are also similar.

$Z^{61}$, $Z^{62}$, $Z^{63}$, $Z^{64}$, $Z^{65}$, $Z^{66}$, $Z^{67}$, and $Z^{68}$ each independently represent a substituted carbon atom, an unsubstituted carbon atom, a substituted nitrogen atom, or an unsubstituted nitrogen atom, and preferably a substituted carbon atom or an unsubstituted carbon atom. Examples of the substituent on the carbon include the groups described as examples of $R^{21}$ in Formula (1). $Z^{61}$ and $Z^{62}$ may be bonded to each other via a connecting group to form a condensed ring (e.g., a benzo-condensed ring or a pyridine-condensed ring) $Z^{62}$ and $Z^{63}$ may be bonded to each other via a connecting group to form a condensed ring (e.g., a benzo-condensed ring or a pyridine-condensed ring). $Z^{63}$ and $Z^{64}$ may be bonded to each other via a connecting group to form a condensed ring (e.g., a benzo-condensed ring or a pyridine-condensed ring). $Z^{65}$ and $Z^{66}$ may be bonded to each other via a connecting group to form a condensed ring (e.g., a benzo-condensed ring or a pyridine-condensed ring). $Z^{66}$ and $Z^{67}$ may be bonded to each other via a connecting group to form a condensed ring (e.g., a benzo-condensed ring or a pyridine-condensed ring). $Z^{67}$ and $Z^{68}$ may be bonded to each other via a connecting group to form a condensed ring (e.g., a benzo-condensed ring or a pyridine-condensed ring). The ring formed by $Q^{61}$ may be bonded to $Z^{61}$ via a connecting group to form a ring. The ring formed by $Q^{62}$ may be bonded to $Z^{68}$ via a connecting group to form a ring.

The substituent on the carbon is preferably an alkyl group, an alkoxy group, an alkylamino group, an aryl group, a group capable of forming a condensed ring (e.g., benzo-condensed ring or pyridine-condensed ring), or a halogen atom, more preferably an alkylamino group, an aryl group, or a group capable of forming a condensed ring (e.g., benzo-condensed ring or pyridine-condensed ring), still more preferably an aryl group or a group capable of forming a condensed ring (e.g., benzo-condensed ring or pyridine-condensed ring), and particularly preferably a group capable of forming a condensed ring (e.g., benzo-condensed ring or pyridine-condensed ring).

The compound represented by Formula (3-B) will be described below.

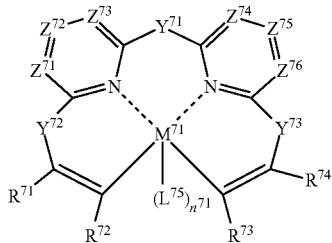

Formula (3-B)

In Formula (3-B), the definition of $M^{71}$ is similar to that of $M^{11}$ in Formula (I), and their preferable ranges are also similar.

The definitions and preferable ranges of $Y^{71}$, $Y^{72}$, and $Y^{73}$ are the same as the definition and preferable range of $Y^{62}$ in Formula (3-A).

The definition of $L^{75}$ is similar to that of $L^{15}$ in Formula (I), and their preferable ranges are also similar.

The definition of $n^{71}$ is similar to that of $n^{11}$ in Formula (I), and their preferable ranges are also similar.

$Z^{71}$, $Z^{72}$, $Z^{73}$, $Z^{74}$, $Z^{75}$, and $Z^{76}$ each independently represent a substituted carbon atom, an unsubstituted carbon atom, a substituted nitrogen atom, or an unsubstituted nitrogen atom, and more preferably a substituted carbon atom or an unsubstituted carbon atom. Examples of the substituent on the carbon include the groups described as examples of $R^{21}$ in Formula (1). In addition, $Z^{71}$ and $Z^{72}$ may be bonded to each other via a connecting group to form a ring (e.g., a benzene ring or a pyridine ring). $Z^{72}$ and $Z^{73}$ may be bonded to each other via a connecting group to form a ring (e.g., a benzene ring or a pyridine ring). $Z^{73}$ and $Z^{74}$ may be bonded to each other via a connecting group to form a ring (ring or a pyridine ring). $Z^{73}$ and $Z^{74}$ may be bonded to each other via a connecting (e.g., a benzene ring or a pyridine ring). $Z^{74}$ and $Z^{75}$ may be bonded to each other via a connecting group to form a ring (e.g., a benzene ring or a pyridine ring). $Z^{75}$ and $Z^{76}$ may be bonded to each other via a connecting group to form a ring (e.g., a benzene ring or a pyridine ring). The definitions and preferable ranges of $R^{71}$ to $R^{74}$ are similar to the definitions of $R^{21}$ to $R^{24}$ in Formula (1), respectively.

Preferable examples of compounds represented by Formula (3-B) include compounds represented by the following formula (3-C).

The compound represented by Formula (3-C) will be described below.

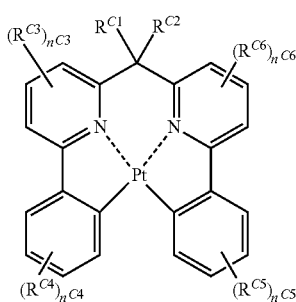

Formula (3-C)

In Formula (3-C), $R^{C1}$ and $R^{C2}$ each independently represent a hydrogen atom or a substituent, and the substituents may be selected from the alkyl groups and aryl groups described as examples of $R^{21}$ to $R^{24}$ in Formula (1). The definition of $R^{C3}$, $R^{C4}$, $R^{C5}$, and $R^{C6}$ is the same as the definition of $R^{21}$ to $R^{24}$ in Formula (1). Each of $n^{C3}$ and $n^{C6}$ represents an integer of 0 to 3; each of $n^{C4}$ and $n^{C5}$ represents an integer of 0 to 4; when there are plural $R^{C3}$s, $R^{C4}$s, $R^{C5}$s, or $R^{C6}$s, the plural $R^{C3}$s, $R^{C4}$s, $R^{C5}$s, or $R^{C6}$s may be the same as each other or different from each other, and may be bonded to each other to form a ring. $R^{C3}$, $R^{C4}$, $R^{C5}$, and $R^{C6}$ each preferably represent an alkyl group, an aryl group, a heteroaryl group, or a halogen atom.

The compound represented by Formula (4) will be described below.

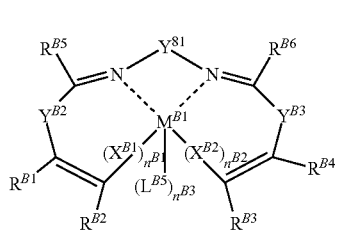

Formula (4)

In Formula (4), the definitions and preferable ranges of $M^{B1}$, $Y^{B2}$, $Y^{B3}$, $R^{B1}$, $R^{B2}$, $R^{B3}$, $R^{B4}$, $L^{B5}$, $n^{B3}$, $X^{B1}$, and $X^{B2}$ are similar to the definitions of $M^{21}$, $Y^{22}$, $Y^{23}$, $R^{21}$, $R^{22}$, $R^{23}$, $R^{24}$, $L^{25}$, $n^{21}$, $X^{21}$, $X^{22}$ in Formula (1), respectively.

$Y^{B1}$ represents a connecting group whose definition is similar to that of $Y^{21}$ in Formula (1). $Y^{B1}$ is preferably a vinyl group substituted at 1- or 2-position, a phenylene ring, a pyridine ring, a pyrazine ring, a pyrimidine ring, or an alkylene group having 2 to 8 carbons.

$R^{B5}$ and $R^{B6}$ each independently represent a hydrogen atom or a substituent, and the substituent may be selected from the alkyl groups, aryl groups, and heterocyclic groups described as examples of $R^{21}$ to $R^{24}$ in Formula (1). However, $Y^{B1}$ is not bonded to $R^{B5}$ or $R^{B6}$. $n^{B1}$ and $n^{B2}$ each independently represent an integer of 0 or 1.

Preferable examples of the compound represented by Formula (4) include compounds represented by the following Formula (4-A).

The compound represented by Formula (4-A) will be described below.

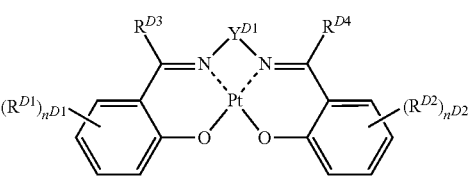

Formula (4-A)

In Formula (4-A), $R^{D3}$ and $R^{D4}$ each independently represent a hydrogen atom or a substituent, and $R^{D1}$ and $R^{D2}$ each represent a substituent. The substituents represented by $R^{D1}$, $R^{D2}$, $R^{D3}$, and $R^{D4}$ may be selected from the substituents described as examples of $R^{B5}$ and $R^{B6}$ in Formula (4), and have the same preferable range as $R^{B5}$ and $R^{B6}$ in Formula (4). $n^{D1}$ and $n^{D2}$ each represent an integer of 0 to 4. When there are plural $R^{D1}$s, the plural $R^{D2}$s may be the same as or different from each other or may be bonded to each other to form a ring. When there are plural $R^{D2}$s, the plural $R^{D2}$s may be the same as or different from each other or may be bonded to each other to form a ring. $Y^{D1}$ represents a vinyl group substituted at 1- or 2-position, a phenylene ring, a pyridine ring, a pyrazine ring, a pyrimidine ring, or an alkylene group having 1 to 8 carbon atoms.

Preferable examples of the metal complex having a tridentate ligand according to the invention include compounds represented by the following Formula (5).

The compound represented by Formula (5) will be described below.

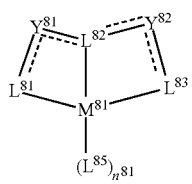

Formula (5)

In Formula (5), the definition of $M^{81}$ is similar to that of $M^{11}$ in Formula (I), and their preferable ranges are also similar.

The definitions and preferable ranges of $L^{81}$, $L^{82}$, and $L^{83}$ are similar to the definitions and preferable ranges of $L^{11}$, $L^{12}$, and $L^{13}$ in Formula (I), respectively.

The definitions and preferable ranges of $Y^{81}$ and $Y^{82}$ are similar to the definitions and preferable ranges of $Y^{11}$ and $Y^{12}$ in Formula (I), respectively.

$L^{85}$ represents a ligand coordinating to $M^{81}$. $L^{85}$ is preferably a mono- to tri-dentate ligand and more preferably a monodentate to tridentate anionic ligand. While the mono- to tri-dentate anionic ligand is not particularly limited, it is preferably a halogen ligand or a tridentate ligand formed by any of $L^{81}$, $Y^{81}$, $L^{82}$, $Y^{82}$, and $L^{83}$, and more preferably a tridentate ligand formed by any of $L^{81}$, $Y^{81}$, $L^{82}$, $Y^{82}$, and $L^{83}$. $L^{85}$ is not directly bonded to $L^{81}$ or $L^{83}$, and metal necessarily resides therebetween. The numbers of coordination sites and ligands do not exceed the valency of the metal.

$n^{81}$ represents an integer of 0 to 5. When $M^{81}$ is a tetravalent metal, $n^{81}$ is 1, and $L^{85}$ represents a monodentate ligand. When $M^{81}$ is a hexavalent metal, $n^{81}$ is preferably 1 to 3, more preferably 1 or 3, and still more preferably 1. When $M^{81}$ is hexavalent and $n^{81}$ is 1, $L^{85}$ represents a tridentate ligand. When $M^{81}$ is hexavalent and $n^{81}$ is 2, $L^{85}$ represents a monodentate ligand and a bidentate ligand. When $M^{81}$ is hexavalent and $n^{81}$ is 3, $L^{85}$ represents a monodentate ligand. When $M^{81}$ is an octavalent metal, $n^{81}$ is preferably 1 to 5, more preferably 1 or 2, and still more preferably 1. When $M^{81}$ is octavalent and $n^{81}$ is 1, $L^{85}$ represents a pentadentate ligand. When $M^{81}$ is octavalent and $n^{81}$ is 2, $L^{85}$ represents a tridentate ligand and a bidentate ligand. When $M^{81}$ is octavalent and $n^{81}$ is 3, $L^{85}$ represents a tridentate ligand and two monodentate ligands, or represents two bidentate ligands and one monodentate ligand. When $M^{81}$ is octavalent and $n^{81}$ is 4, $L^{85}$ represents one bidentate ligand and three monodentate ligands. When $M^{81}$ is octavalent and $n^{81}$ is 5, $L^{85}$ represents five monodentate ligands. When $n^{81}$ is 2 or larger, there are plural $L^{85}$'s, and the plural $L^{85}$'s may be the same as or different from each other.

In a preferable example of the compound represented by Formula (5), $L^{81}$, $L^{82}$, or $L^{83}$ each represent an aromatic carbon ring containing a carbon atom coordinating to $M^{81}$, a heterocycle containing a carbon atom coordinating to $M^{81}$, or a nitrogen-containing heterocycle containing a nitrogen atom coordinating to $M^{81}$, wherein at least one of $L^{81}$, $L^{82}$, and $L^{83}$ is a nitrogen-containing heterocycle. Examples of the aromatic carbon ring containing a carbon atom coordinating to $M^{81}$, heterocycle containing a carbon atom coordinating to $M^{81}$, or nitrogen-containing heterocycle containing a nitrogen atom coordinating to $M^{81}$ include the examples of ligands (moieties) each containing a nitrogen or carbon atom coordinating to $M^{11}$ in Formula (I) described in the explanation of formula (I). Preferable examples thereof are the same as in the description of ligands (moieties) each containing a nitrogen or carbon atom coordinating to $M^{11}$ in Formula (I). $Y^{81}$ and $Y^{82}$ each preferably represent a single bond or a methylene group.

Other preferable examples of compounds represented by Formula (5) include compounds represented by the following Formulae (5-A) and (5-B).

The compound represented by Formula (5-A) will be described below.

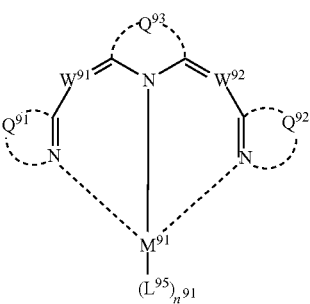

Formula (5-A)

In Formula (5-A), the definition of $M^{91}$ is similar to that of $M^{81}$ in Formula (5), and their preferable ranges are also similar.

$Q^{91}$ and $Q^{92}$ each represent a group forming a nitrogen-containing heterocycle (ring containing a nitrogen atom coordinating to $M^{91}$). The nitrogen-containing heterocycles formed by $Q^{91}$ and $Q^{92}$ are not particularly limited, and examples thereof include a pyridine ring, a pyrazine ring, a pyrimidine ring, a pyridazine ring, a triazine ring, a thiazole ring, an oxazole ring, a pyrrole ring, a pyrazole ring, a imidazole, a triazole ring, and condensed rings containing one or more of the above rings (e.g., a quinoline ring, a benzoxazole ring, a benzimidazole ring, and an indolenine ring), and tautomers thereof.

Each of the nitrogen-containing heterocycles formed by $Q^{91}$ and $Q^{92}$ is preferably a pyridine ring, a pyrazole ring, a thiazole ring, an imidazole ring, a pyrrole ring, a condensed ring containing one or more of the above ring (e.g., a quinoline ring, a benzothiazole ring, a benzimidazole ring, or an indolenine ring), or a tautomer of any of the above rings; more preferably a pyridine ring, a pyrrole ring, a condensed ring containing one or more of these rings (e.g., a quinoline ring), or a tautomer of any of the above rings; more preferably a pyridine ring or a condensed ring containing a pyridine ring (e.g., a quinoline ring); and particularly preferably a pyridine ring.

$Q^{93}$ represents a group forming a nitrogen-containing heterocycle (ring containing a nitrogen atom coordinating to $M^{91}$). The nitrogen-containing heterocycle formed by $Q^{93}$ is not particularly limited, but is preferably a pyrrole ring, an imidazole ring, a tautomer of a triazole ring, or a condensed ring containing one or more of the above rings (e.g., benzopyrrole), and more preferably a tautomer of a pyrrole ring or a tautomer of a condensed ring containing a pyrrole ring (e.g., benzopyrrole).

The definitions and preferable ranges of $W^{91}$ and $W^{92}$ are similar to the definitions and preferable ranges of $W^{51}$ and $W^{52}$ in Formula (2), respectively.

The definition of $L^{95}$ is similar to that of $L^{85}$ in Formula (5), and their preferable ranges are also similar.

The definition of $n^{91}$ is similar to that of $n^{81}$ in Formula (5), and their preferable ranges are also similar.

The compound represented by Formula (5-B) will be described next.

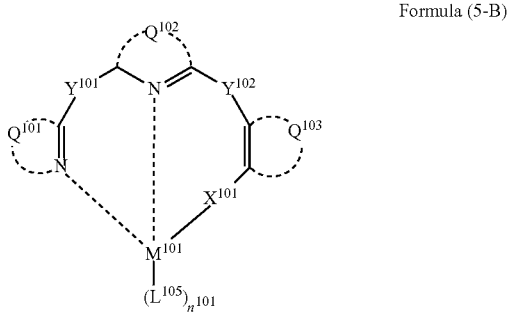

Formula (5-B)

In Formula (5-B), the definition of $M^{101}$ is similar to that of $M^{81}$ in Formula (5), and their preferable ranges are also similar.

The definition of $Q^{102}$ is similar to that of $Q^{21}$ in Formula (1), and their preferable ranges are also similar.

The definition of $Q^{101}$ is similar to that of $Q^{91}$ in Formula (5-A), and their preferable ranges are also similar.

Each of $Q^{102}$ and $Q^{103}$ represents a group forming an aromatic ring. While the aromatic ring formed by each of $Q^{102}$ and $Q^{103}$ is not particularly limited, it is preferably a benzene ring, a pyridine ring, a pyridazine ring, a pyrimidine ring, a furan ring, a thiophene ring, an isothiazole ring, a pyrrole ring, an isooxazole ring, or a condensed ring containing one or more of the above rings (e.g., a naphthalene ring), more preferably a benzene ring or a condensed ring containing a benzene ring (e.g., naphthalene ring), and particularly preferably a benzene ring.

The definitions and preferable ranges of $Y^{101}$ and $Y^{102}$ are similar to the definition and preferable range of $Y^{22}$ in Formula (1).

The definition of $L^{105}$ is similar to that of $L^{85}$ in Formula (5), and their preferable ranges are also similar.

The definition of $n^{101}$ is similar to that of $n^{81}$ in Formula (5), and their preferable ranges are also similar.

The definition of $X^{101}$ is similar to that of $X^{21}$ in Formula (1), and their preferable ranges are also similar.

The compound represented by Formula (II) will be described below.

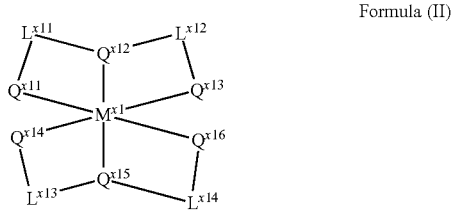

Formula (II)

In Formula (II), $M^{X1}$ represents a metal ion. $Q^{X11}$ to $Q^{X16}$ each independently represent an atom coordinating to $M^{X1}$ or an atomic group containing an atom coordinating to $M^{X1}$. $L^{X11}$ to $L^{X14}$ each independently represent a single bond, a double bond or a connecting group.

Namely, in Formula (II), the atomic group comprising $Q^{X11}$-$L^{X11}$-$Q^{X12}$-$L^{X12}$-$Q^{X13}$ and the atomic group comprising $Q^{X14}$-$L^{X13}$-$Q^{X15}$-$L^{X14}$-$Q^{X16}$ each form a tridentate ligand.

In addition, each of the bond between $M^{X1}$ and each of $Q^{X11}$ to $Q^{X16}$ may be a coordination bond, an ionic bond or a covalent bond.

The compound represented by Formula (II) will be described in detail below.

In Formula (II), $M^{X1}$ represents a metal ion. The metal ion is not particularly limited, but is preferably a monovalent to trivalent metal ion, more preferably a divalent or trivalent metal ion, and still more preferably a trivalent metal ion. Specifically, a platinum ion, an iridium ion, a rhenium ion, a palladium ion, a rhodium ion, a ruthenium ion, a copper ion, a europium ion, a gadolinium, and a terbium ion are preferable. Among these, an iridium ion and a europium ion are more preferable, and an iridium ion is still more preferable.

$Q^{X11}$ to $Q^{X16}$ each represent an atom coordinating to $M^{X1}$ or an atomic group containing an atom coordinating to $M^{X1}$.

When any of $Q^{X11}$ to $Q^{X16}$ is an atom coordinating to $M^{X1}$, specific examples of the atom include a carbon atom, a nitrogen atom, an oxygen atom, a silicon atom, a phosphorus atom, and a sulfur atom. Preferable specific examples of the atom include a nitrogen atom, an oxygen atom, a sulfur atom, and a phosphorus atom. More preferable specific examples of the atom include a nitrogen atom and an oxygen atom.

When any of $Q^{X11}$ to $Q^{X16}$ is an atomic group containing an atom coordinating to $M^{X1}$, examples of the atomic group coordinating to $M^{X1}$ via a carbon atom include imino groups, aromatic hydrocarbon ring groups (such as a benzene ring group or a naphthalene ring group), heterocyclic groups (such as a thiophene group, a pyridine group, a pyrazine group, a pyrimidine group, a pyridazine group, a triazine group, a thiazole group, an oxazole group, a pyrrole group, an imidazole group, a pyrazole group, or a triazole group), condensed rings containing one or more of the above rings, and tautomers thereof.

When any of $Q^{X11}$ to $Q^{X16}$ is an atomic group containing a nitrogen atom coordinating to $M^{X1}$, examples of the atomic group coordinating to $M^{X1}$ via a nitrogen atom include nitrogen-containing heterocyclic groups, amino groups, and imino groups. Examples of the nitrogen-containing heterocyclic groups include pyridine, pyrazine, pyrimidine, pyridazine, triazine, thiazole, oxazole, pyrrole, imidazole, pyrazole, or triazole. Examples of the amino groups include alkylamino groups (preferably having 2 to 30 carbon atoms, more preferably 2 to 20 carbon atoms, and particularly preferably 2 to 10 carbon atoms, and examples thereof include a methylamino group, a dimethylamino group, and a diethylamino group), arylamino groups (preferably having 6 to 40 carbon atoms, more preferably 6 to 30 carbon atoms, and particularly preferably 6 to 20 carbon atoms, and examples thereof include a phenylamino group, a diphenylamino group, and a phenyl-1-naphthylamino group), acylamino groups (preferably having 2 to 30 carbon atoms, more preferably 2 to 20 carbon atoms, and particularly preferably 2 to 10 carbon atoms, and examples thereof include an acetylamino group and a benzoylamino group), alkoxycarbonylamino groups (preferably having 2 to 30 carbon atoms, more preferably 2 to 20 carbon atoms, and particularly preferably 2 to 12 carbon atoms, and examples thereof include a methoxycarbonylamino group), aryloxycarbonylamino groups (preferably having 7 to 30 carbon atoms, more preferably 7 to 20 carbon atoms, and particularly preferably 7 to 12 carbon atoms, and examples thereof include a phenyloxycarbonylamino group), and sulfonylamino groups (preferably having 1 to 30 carbon atoms, more preferably 1 to 20 carbon atoms, and particularly preferably 1 to 12 carbon atoms, and examples thereof include a methanesulfonylamino and benzenesulfonylamino group). These groups may have a substituent(s).

When any of $Q^{X11}$ to $Q^{X16}$ is an atomic group containing an oxygen atom coordinating to $M^{X1}$, examples of the atomic groups coordinating to $M^{X1}$ via an oxygen atom include alkoxy groups (preferably having 1 to 30 carbon atoms, more preferably 1 to 20 carbon atoms, and particularly preferably 1 to 10 carbon atoms, and examples thereof include a methoxy group, an ethoxy group, a butoxy group, and a 2-ethylhexyloxy group), aryloxy groups (preferably having 6 to 30 carbon atoms, more preferably 6 to 20 carbon atoms, and particularly preferably 6 to 12 carbon atoms, and examples thereof include a phenyloxy group, a 1-naphthyloxy group, and a 2-naphthyloxy group), heterocyclic oxy groups (preferably having 1 to 30 carbon atoms, more preferably 1 to 20 carbon atoms, and particularly preferably 1 to 12 carbon atoms, and examples thereof include a pyridyloxy group, a pyrazyloxy group, a pyrimidyloxy group, and a quinolyloxy group), acyloxy groups (preferably having 2 to 30 carbon atoms, more preferably 2 to 20 carbon atoms, and particularly preferably 2 to 10 carbon atoms, and examples thereof include an acetoxy group and a benzoyloxy group), silyloxy groups (preferably having 3 to 40 carbon atoms, more preferably 3 to 30 carbon atoms, and particularly preferably 3 to 24 carbon atoms, and examples thereof include a trimethylsilyloxy group and a triphenylsilyloxy), carbonyl groups (e.g., ketone groups, ester groups, and amido groups), and ether groups (preferably having 2 to 30 carbon atoms, more preferably 2 to 20 carbon atoms, and particularly preferably 2 to 12 carbon atoms, and examples thereof include dialkylether groups, diarylether groups, and furyl groups).

When any of $Q^{X11}$ to $Q^{X16}$ is an atomic group containing a silicon atom coordinating to $M^{X1}$, examples of the atomic group coordinating to $M^{X1}$ via a silicon atom include alkylsilyl groups (preferably having 3 to 30 carbon atoms, and examples thereof include a trimethylsilyl group), and arylsilyl groups (preferably, having 18 to 30 carbon atoms, and examples thereof include a triphenylsilyl group). These groups may have a substituent(s).

When any of $Q^{X11}$ to $Q^{X16}$ is an atomic group containing a sulfur atom coordinating to $M^{X1}$, examples of the atomic group coordinating to $M^{X1}$ via a sulfur atom include alkylthio groups (preferably having 1 to 30 carbon atoms, more preferably 1 to 20 carbon atoms, and particularly preferably 1 to 12 carbon atoms, and examples thereof include a methylthio group and an ethylthio group), arylthio groups (preferably having 6 to 30 carbon atoms, more preferably 6 to 20 carbon atoms, and particularly preferably 6 to 12 carbon atoms, and examples thereof include a phenylthio group), heterocyclic thio groups (preferably having 1 to 30 carbon atoms, more preferably 1 to 20 carbon atoms, and particularly preferably 1 to 12 carbon atoms, and examples thereof include a pyridylthio group, a 2-benzimidazolylthio group, a 2-benzoxazolylthio group, and a 2-benzothiazolylthio group), thiocarbonyl groups (e.g., a thioketone group and a thioester group), and thioether groups (preferably having 2 to 30 carbon atoms, more preferably 2 to 20 carbon atoms, and particularly preferably 2 to 12 carbon atoms, and preferable examples thereof include a dialkylthioether group, a diarylthioether group, and a thiofuryl group).

When any of $Q^{X11}$ to $Q^{X16}$ is an atomic group containing a phosphorus atom coordinating to $M^{X1}$, examples of the atomic group coordinating to $M^{X1}$ via a phosphorus atom include dialkylphosphino groups (preferably having 2 to 30 carbon atoms, more preferably 2 to 20 carbon atoms, and particularly preferably 2 to 12 carbon atoms, and examples thereof include a dicyclohexylphosphino group), diarylphosphino groups (preferably having 12 to 40 carbon atoms, more preferably 12 to 30 carbon atoms, and particularly preferably 12 to 20 carbon atoms, and examples thereof include a diphenylphosphino group), trialkyl phosphines (preferably having 3 to 30 carbon atoms, more preferably 3 to 20 carbon atoms, and particularly preferably 3 to 12 carbon atoms, and examples thereof include a tributylphosphine group, tri-tert-butylphosphine, and tricyclohexylphosphine), triaryl phosphines (preferably having 18 to 40 carbon atoms, more preferably 18 to 30 carbon atoms, and particularly preferably 18 to 20 carbon atoms, and examples thereof include a triphenylphosphine group, a diphenyl(p-tolyl)phosphine group, a tri-p-tolylphosphine group, a (R)-(+)-2,2'-bis(diphenylphosphino)-1,1'-binaphthyl group, and a (S)-(−)-2,2'-bis(diphenylphosphino)-1,1'-binaphthyl group), and phosphinine groups. These groups may have a substituent(s).

The atomic groups represented by $Q^{X11}$ to $Q^{X16}$ are each preferably an aromatic hydrocarbon ring group containing a carbon atom coordinating to $M^{X1}$, an aromatic heterocyclic group containing a carbon atom coordinating to $M^{X1}$, a nitrogen-containing aromatic heterocyclic group containing a nitrogen atom coordinating to $M^{X1}$, an alkyloxy group, an aryloxy group, an alkylthio group, an arylthio group, or an dialkylphosphino group, and more preferably an aromatic hydrocarbon ring group containing a carbon atom coordinating to $M^{X1}$, an aromatic heterocyclic group containing a carbon atom coordinating to $M^{X1}$, or a nitrogen-containing aromatic heterocyclic group containing a nitrogen atom coordinating to $M^{X1}$.

The bond between $M^{X1}$ and each of $Q^{X11}$ to $Q^{X16}$ may be any one of a coordination bond, an ionic bond, and a covalent bond.

In Formula (II), $L^{X11}$ to $L^{X14}$ each represent a single or double bond or a connecting group. While the connecting group is not particularly limited, it is preferably a connecting group containing one or more atoms selected from carbon, nitrogen, oxygen, sulfur, and silicon. Examples of the connecting group are shown below, however, the scope of thereof is not limited by these.

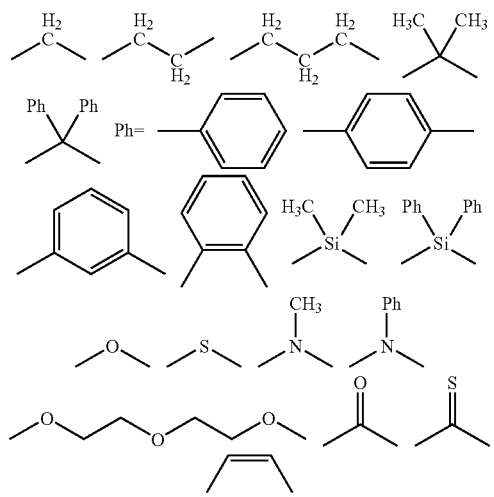

These connecting groups may have a substituent(s), and the substituent may be selected from the examples of the substituents represented by $R^{21}$ to $R^{24}$ in Formula (1), and the preferable range thereof is also the same as in Formula (1). $L^{X11}$ to $L^{X14}$ are each preferably a single bond, a dimethylmethylene group, or a dimethylsilylene group.

Among compounds represented by Formula (II), compounds represented by the following Formula (X2) are more preferable, and compounds represented by the following Formula (X3) are still more preferable.

The compound represented by Formula (X2) is described first.

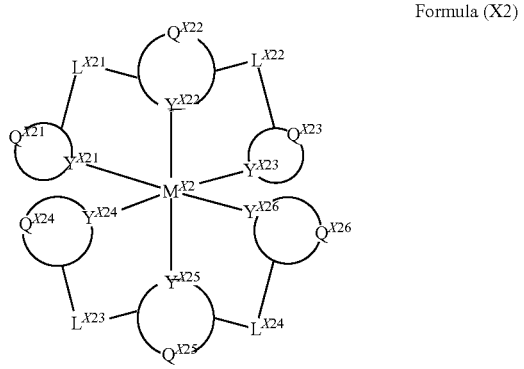

Formula (X2)

In Formula (X2), $M^{X2}$ represents a metal ion. $Y^{X21}$ to $Y^{X26}$ each represent an atom coordinating to $M^{X2}$; and $Q^{X21}$ to $Q^{X26}$ each represent an atomic group forming an aromatic ring or an aromatic heterocycle respectively with $Y^{X21}$ to $Y^{X26}$. $L^{X21}$ to $L^{X24}$ each represent a single or double bond or a connecting group. The bond between $M^{X2}$ and each of $Y^{X21}$ to $Y^{X26}$ may be any one of a coordination bond, an ionic bond, and a covalent bond.

The compound represented by Formula (X2) will be described below in detail.

In Formula (X2), the definition of $M^{X2}$ is similar to that of $M^{X1}$ in Formula (II), and their preferable ranges are also similar. $Y^{X21}$ to $Y^{X26}$ each represent an atom coordinating to $M^{X2}$. The bond between $M^{X2}$ and each of $Y^{X21}$ to $Y^{X26}$ may be any one of a coordination bond, an ionic bond, and a covalent bond. Each of $Y^{X21}$ to $Y^{X26}$ is a carbon atom, a nitrogen atom, an oxygen atom, a sulfur atom, a phosphorus atom, or a silicon atom, and preferably a carbon atom or a nitrogen atom. $Q^{X21}$ to $Q^{X26}$ represent atomic groups forming rings containing $Y^{X21}$ to $Y^{X26}$ respectively, and the rings are each independently selected from aromatic hydrocarbon rings and aromatic heterocycles. The aromatic hydrocarbon rings and aromatic heterocycles may be selected from a benzene ring, a pyridine ring, a pyrazine ring, a pyrimidine ring, a pyridazine ring, a triazine ring, a pyrrole ring, a pyrazole ring, an imidazole ring, a triazole ring, an oxazole ring, a thiazole ring, an oxadiazole ring, a thiadiazole ring, a thiophene ring, and a furan ring; preferably selected from a benzene ring, a pyridine ring, a pyrazine ring, a pyrimidine ring, a pyrazole ring, an imidazole ring, and a triazole ring; more preferably selected from a benzene ring, a pyridine ring, a pyrazine ring, a pyrazole ring, and a triazole ring; and particularly preferably selected from a benzene ring and a pyridine ring. The aromatic rings may have a condensed ring or a substituent.

The definitions and preferable ranges of $L^{X21}$ to $L^{X24}$ are similar to the definitions and preferable ranges of $L^{X11}$ to $L^{X14}$ in Formula (II), respectively.

Compounds represented by the following Formula (X3) are more preferable examples of the compounds represented by Formula (II).

The compound represented by Formula (X3) will be described below.

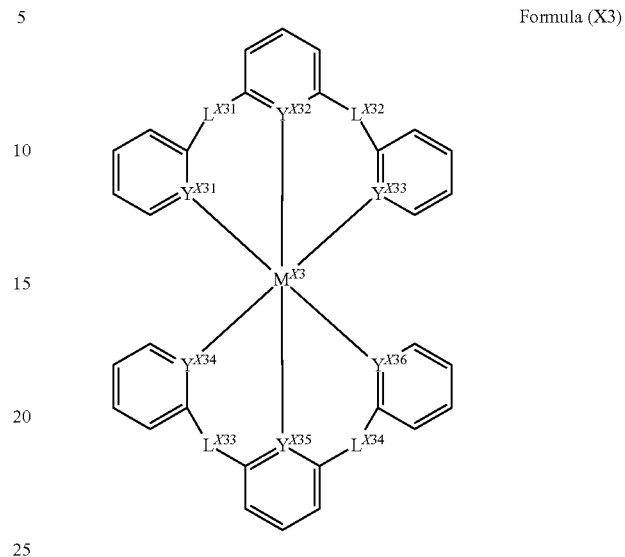

Formula (X3)

In Formula (X3), $M^{X3}$ represents a metal ion. $Y^{X31}$ to $Y^{X36}$ each represent a carbon atom, a nitrogen atom, or a phosphorus atom. $L^{X31}$ to $L^{X34}$ each represent a single bond, a double bond or a connecting group. The bond between $M^{X3}$ and each of $Y^{X31}$ to $Y^{X36}$ may be a coordination bond, an ionic bond or a covalent bond.

The definition of $M^{X3}$ is similar to that of $M^{X1}$ in Formula (II) above, and their preferable ranges are also similar. $Y^{X31}$ to $Y^{X36}$ each represent an atom coordinating to $M^{X3}$. The bond between $M^{X3}$ and each of $Y^{X31}$ to $Y^{X36}$ may be any one of a coordination bond, an ionic bond, and a covalent bond. $Y^{X31}$ to $Y^{X36}$ each represent a carbon atom, a nitrogen atom, or a phosphorus atom, and preferably a carbon atom or a nitrogen atom. The definitions and preferable ranges of $L^{X31}$ to $L^{X34}$ are similar to the definitions and preferable ranges of $L^{X11}$ to $L^{X14}$ in Formula (II), respectively.

Specific examples of compounds represented by the Formula (I), (II) or (5) include the exemplary compounds (1) to (242) described in Japanese Patent Application No. 2004-162849 and the exemplary compounds (243) to (245) (their structures being shown below). The invention is not limited thereto.

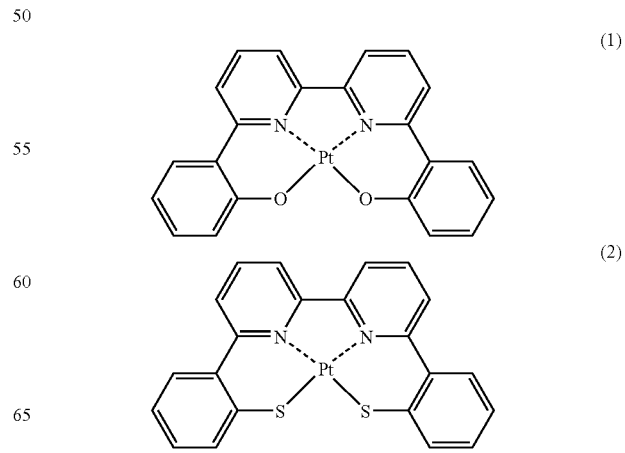

-continued
(3)
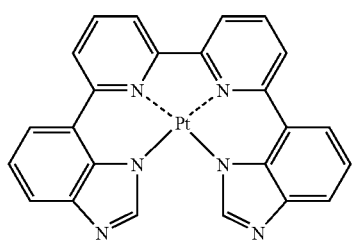
(4)
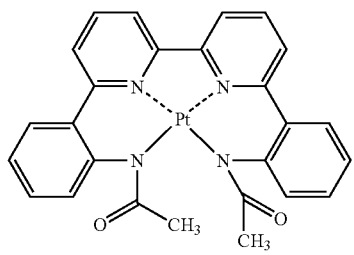
(5)
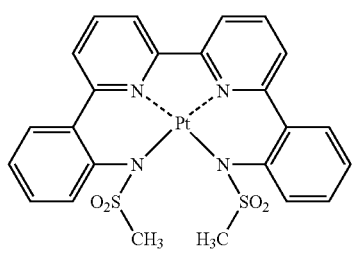
(6)
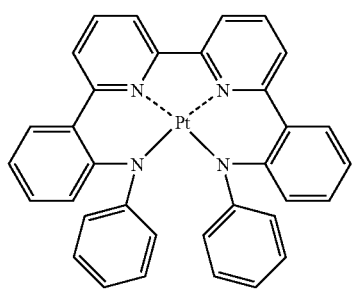
(7)
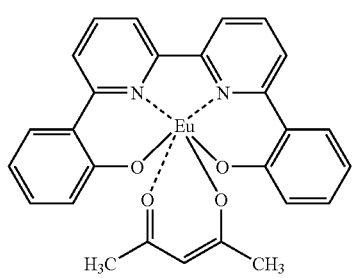
(8)
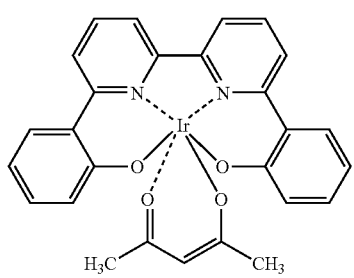
-continued
(9)
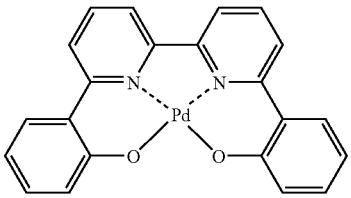
(10)
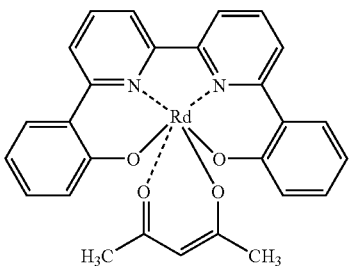
(11)
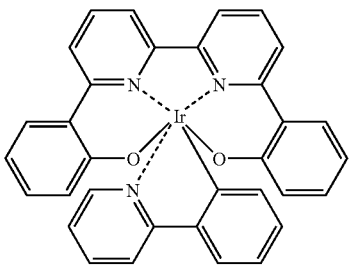
(12)
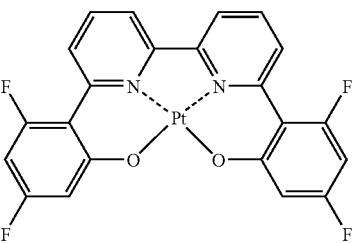
(13)
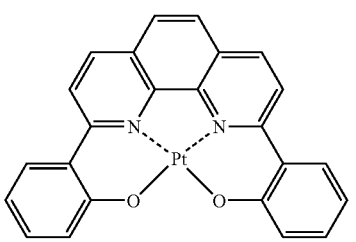
(14)
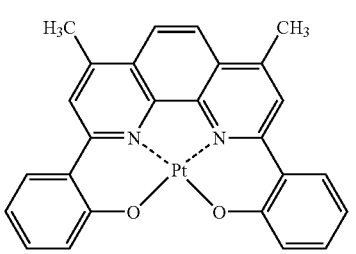

-continued
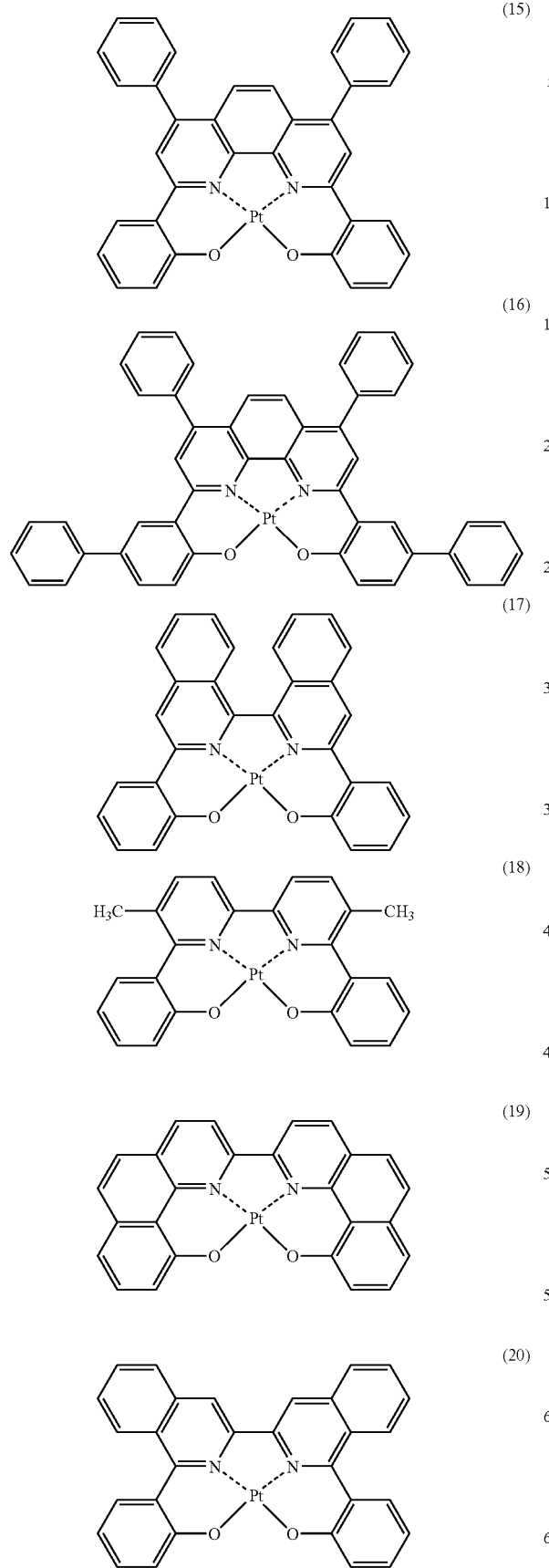
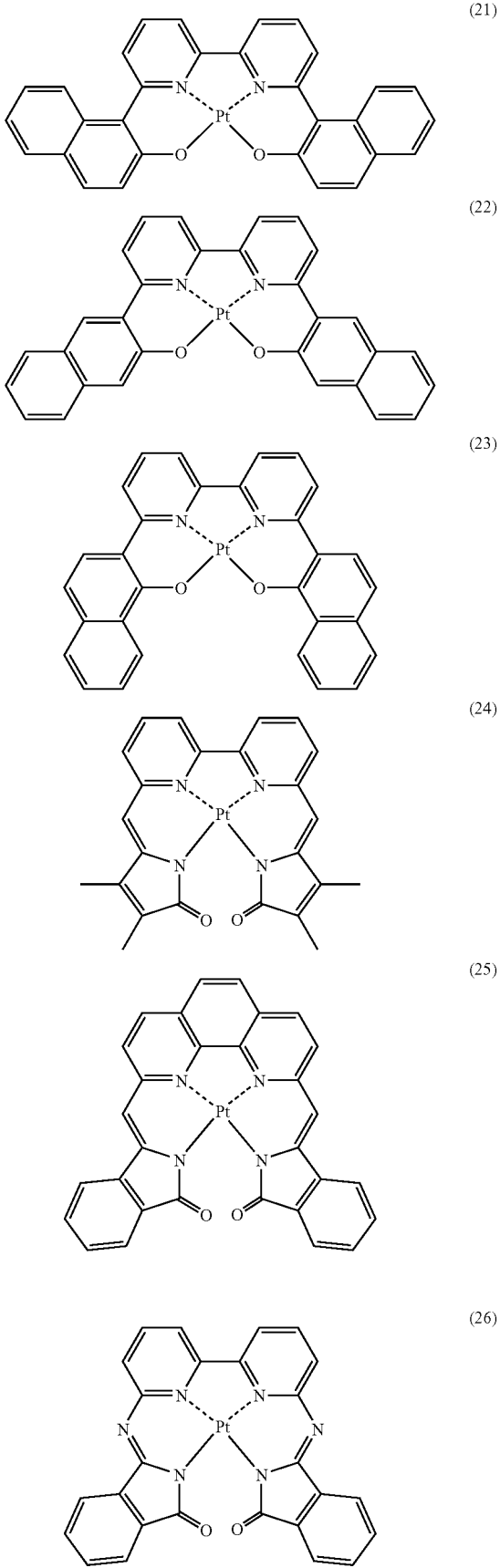

(27) 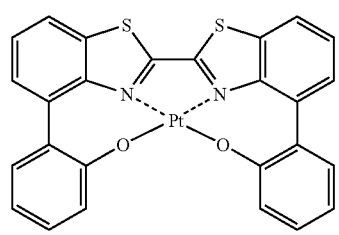
(28) 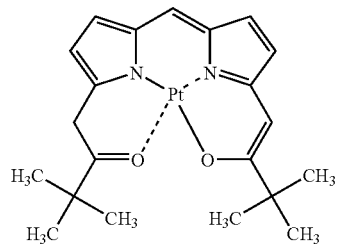
(29) 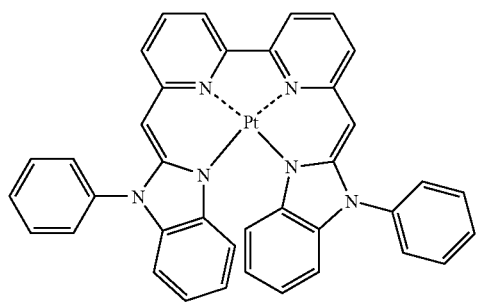
(30) 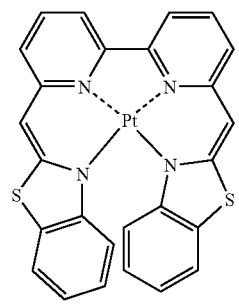
(31) 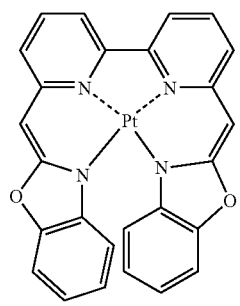
(32) 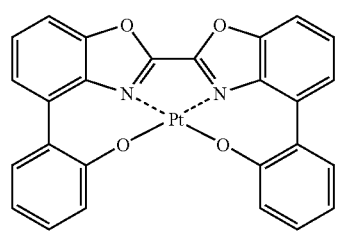
(33) 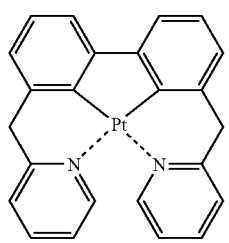
(34) 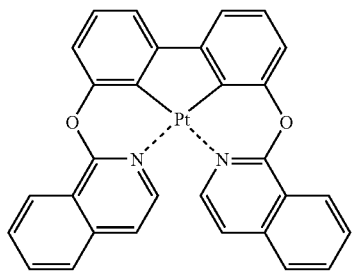
(35) 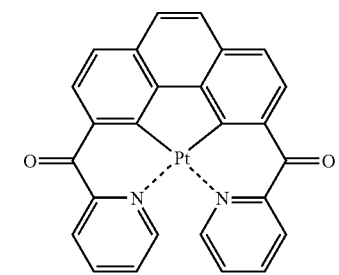
(36) 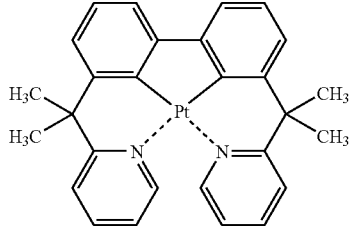
(37) 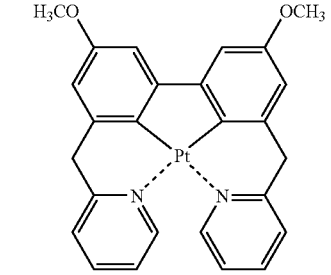
(38) 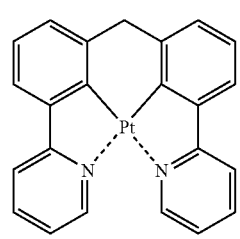

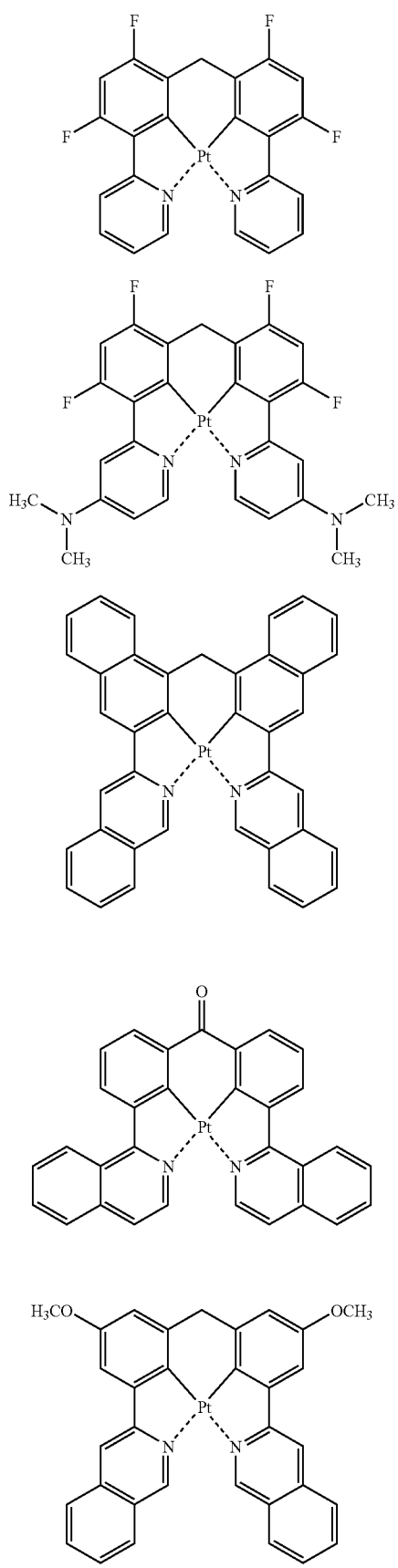
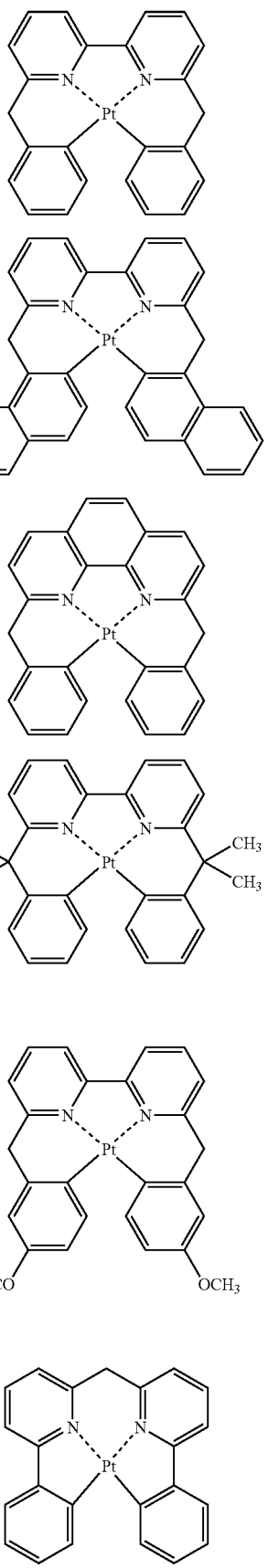

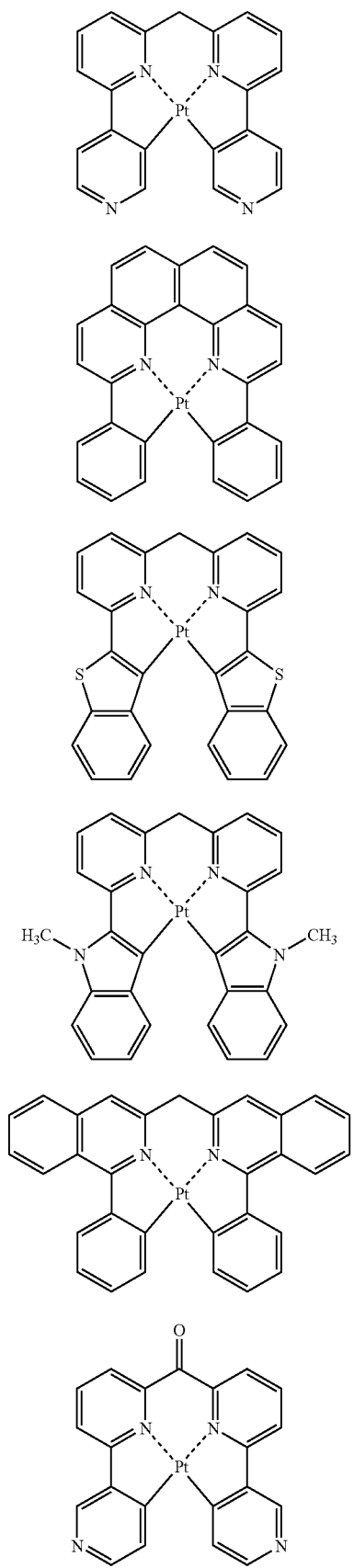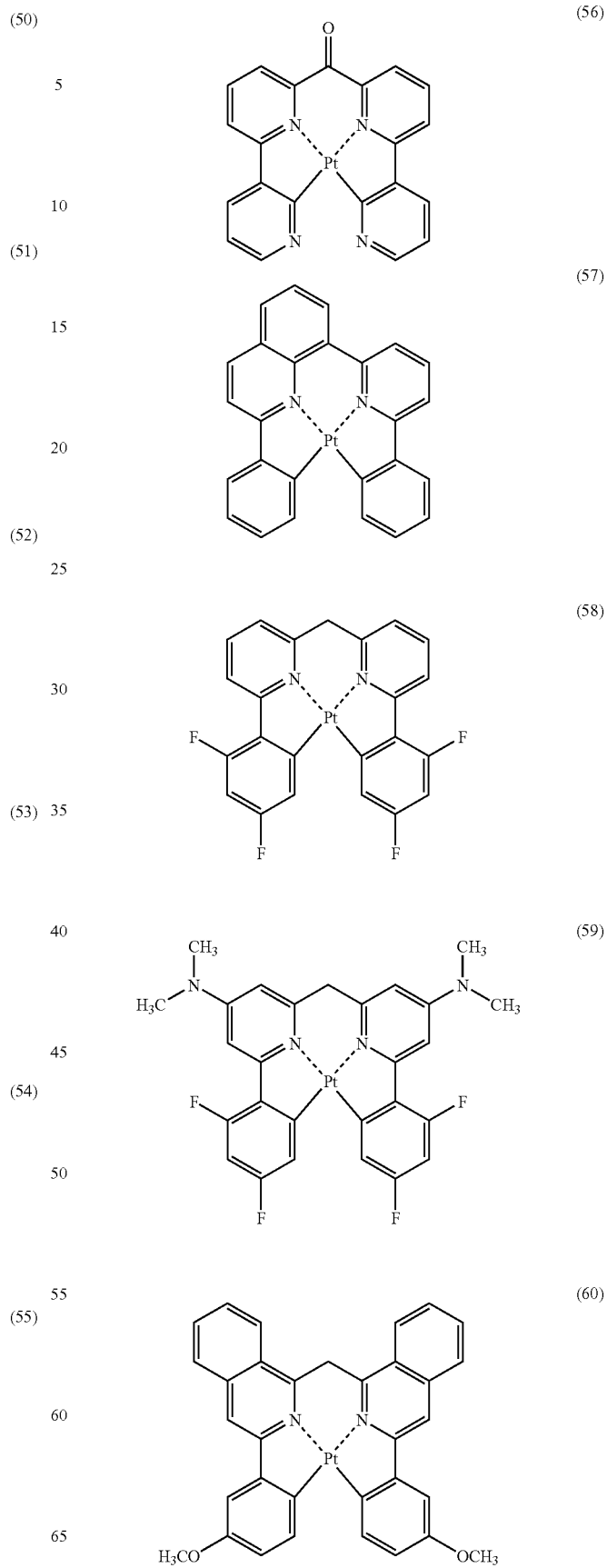

-continued
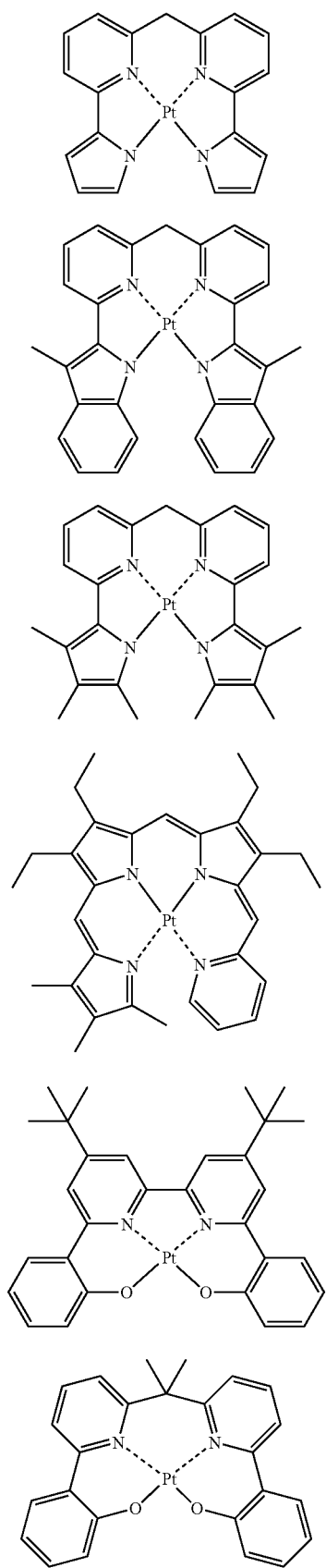
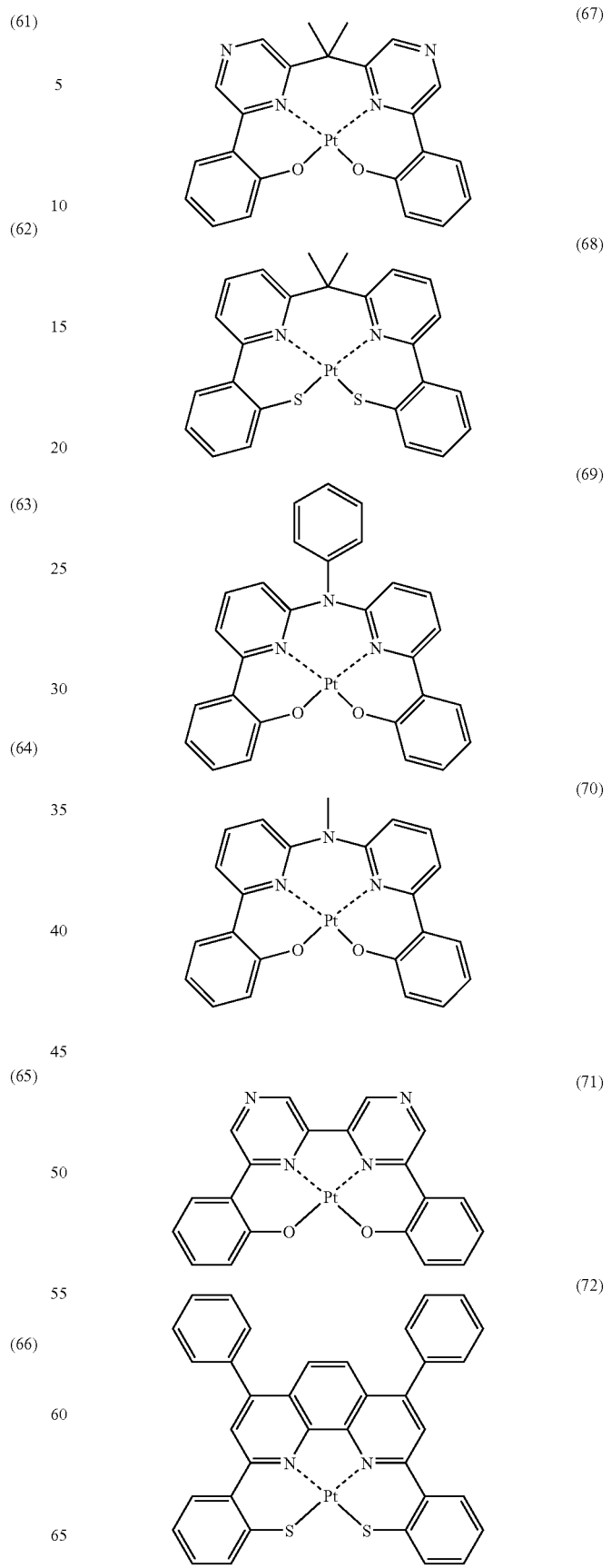

(73)
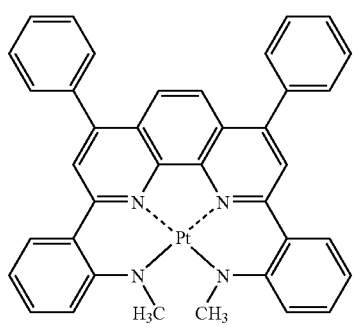
(74)
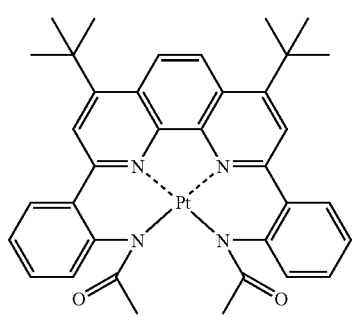
(75)
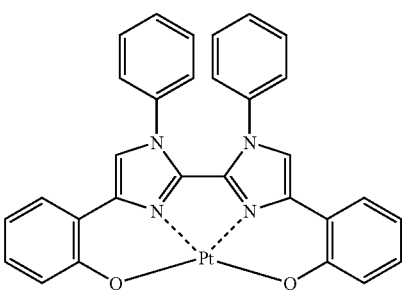
(76)
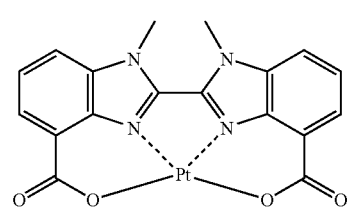
(77)
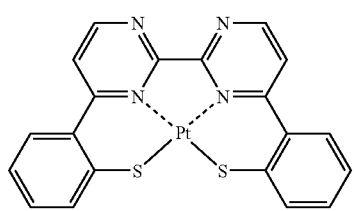
(78)
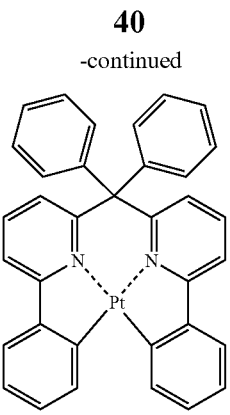
(79)
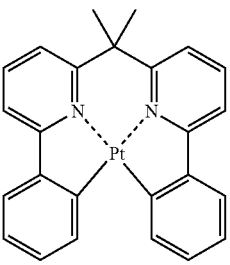
(80)
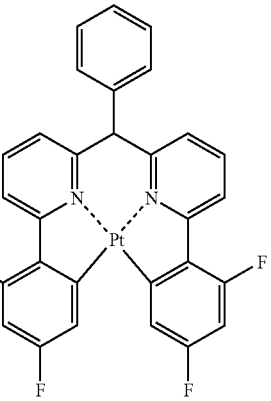
(81)
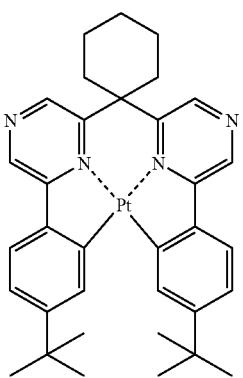

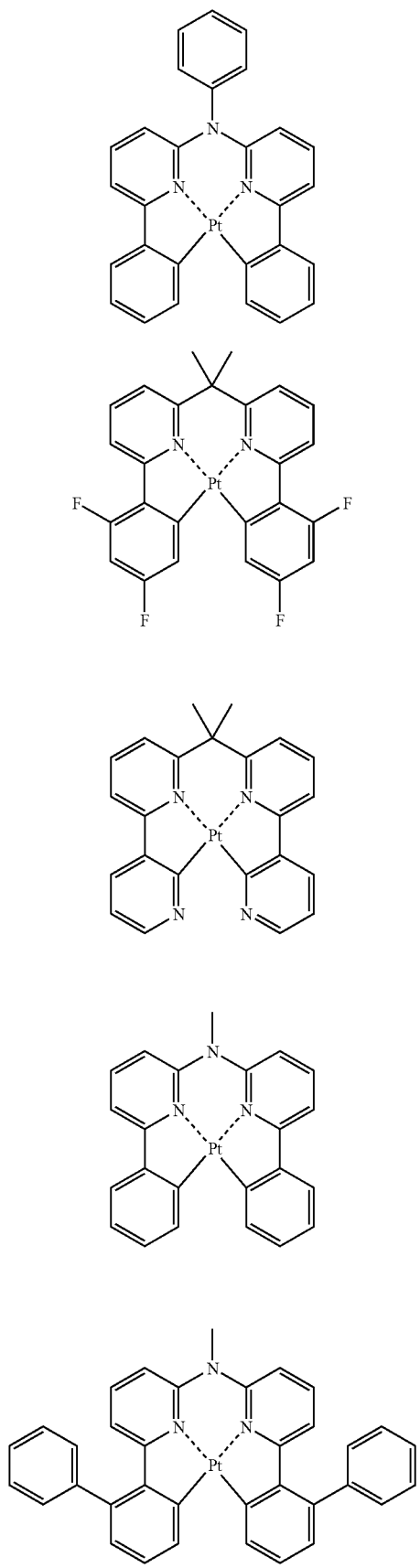
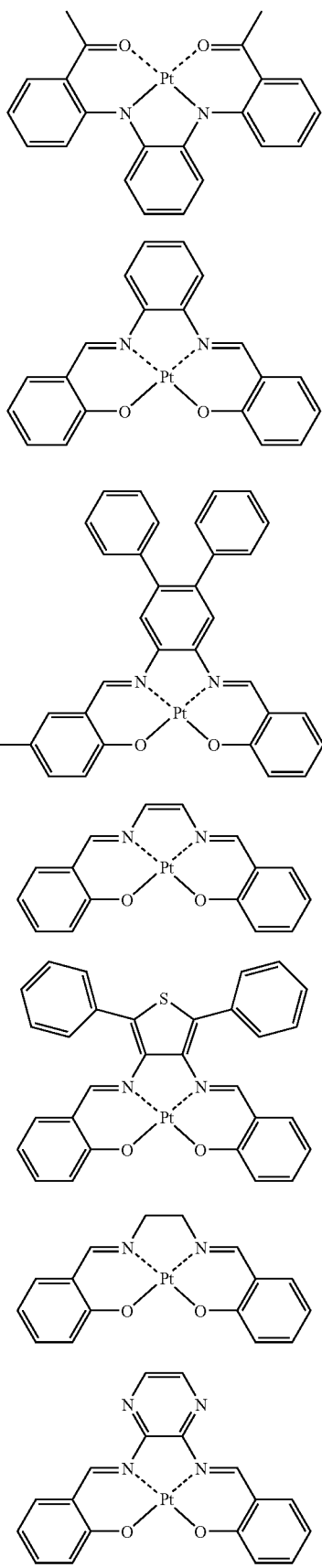

-continued
(94)
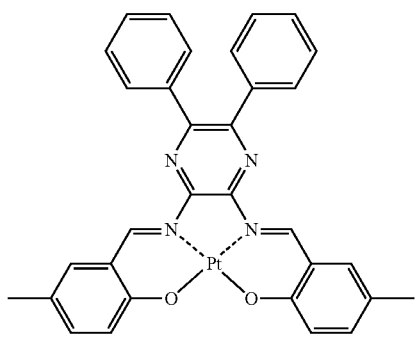
(95)
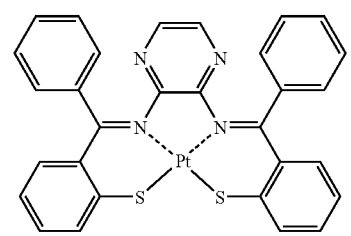
(96)
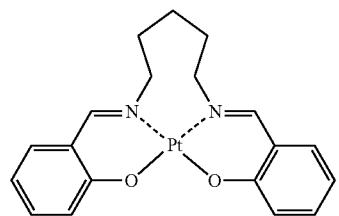
(97)
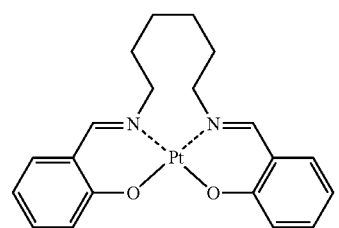
(98)
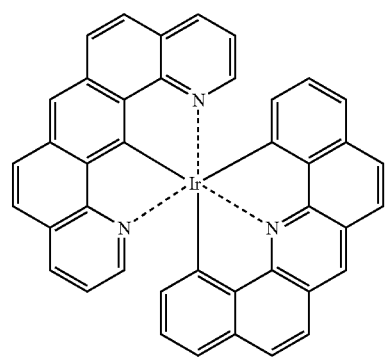
-continued
(99)
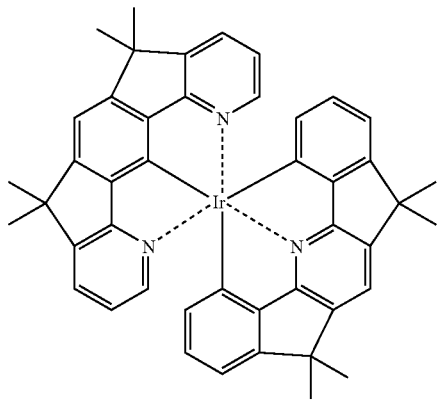
(100)
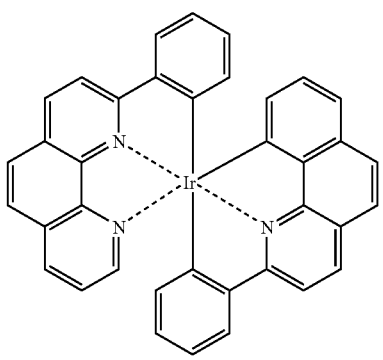
(101)
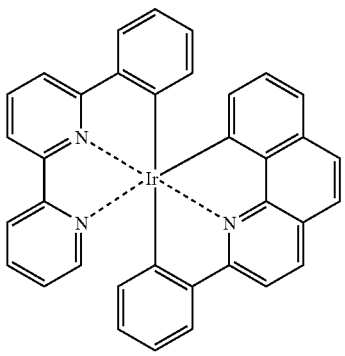
(102)
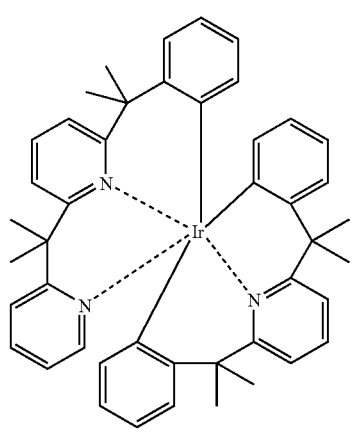

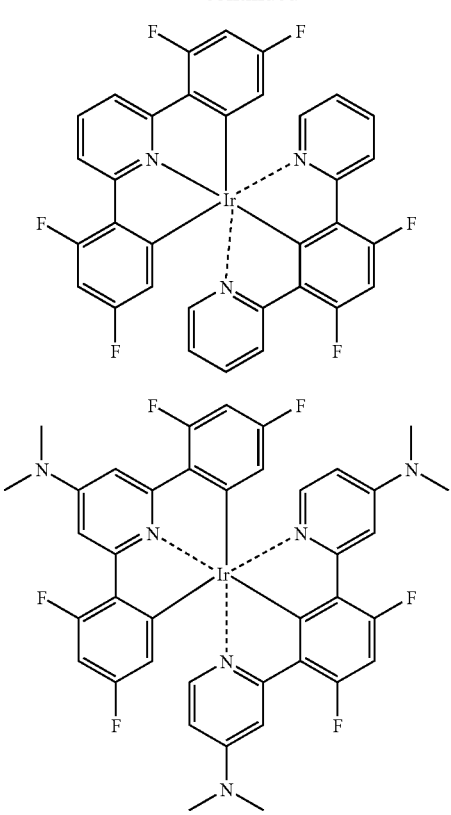
(103)
(104)
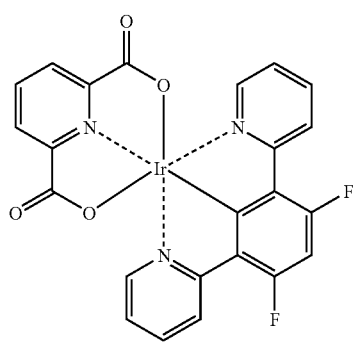
(105)
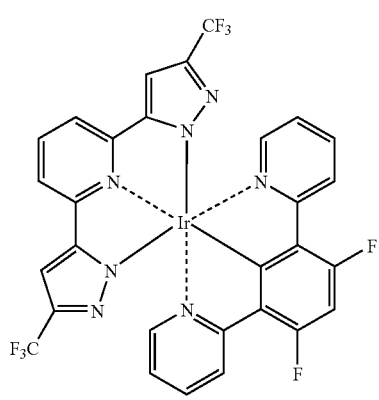
(106)
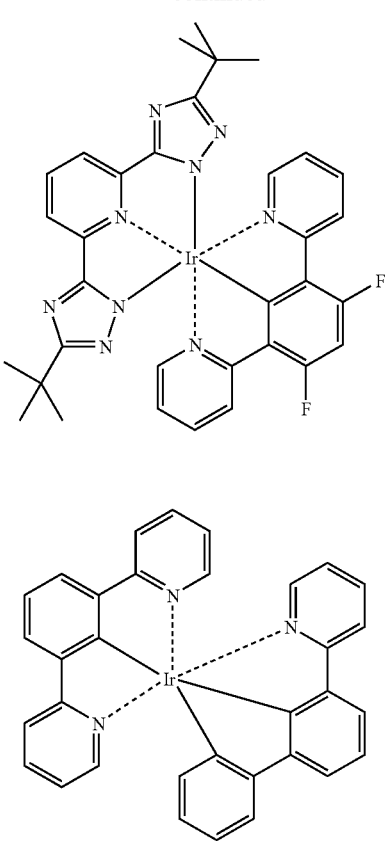
(107)
(108)
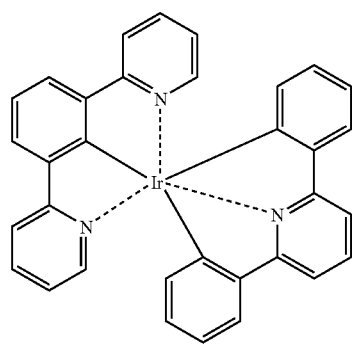
(109)
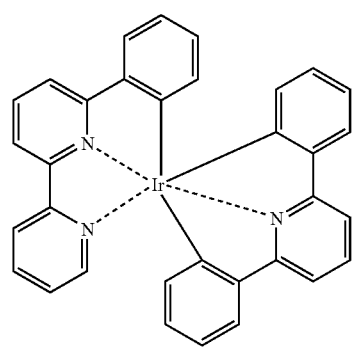
(110)

(111)
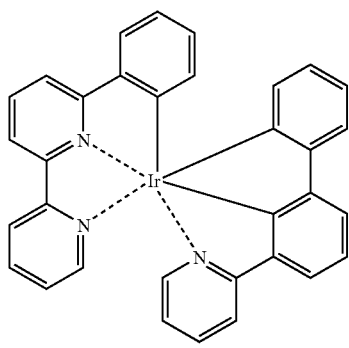
(112)
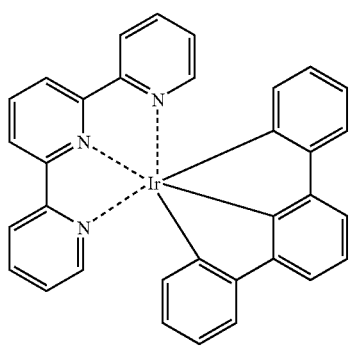
(113)
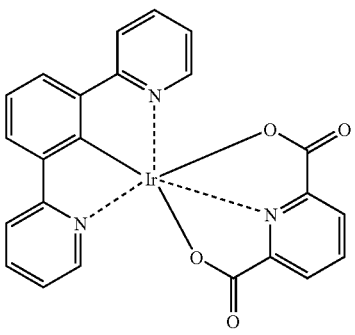
(114)
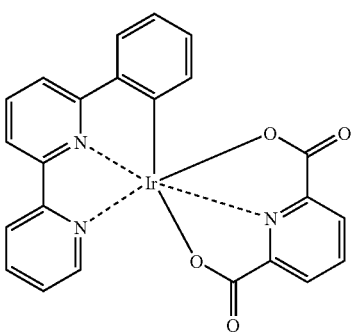
(115)
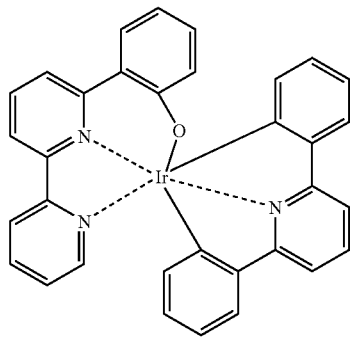
(116)
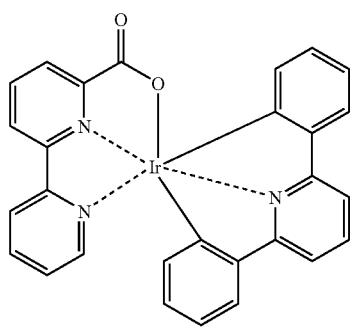
(117)
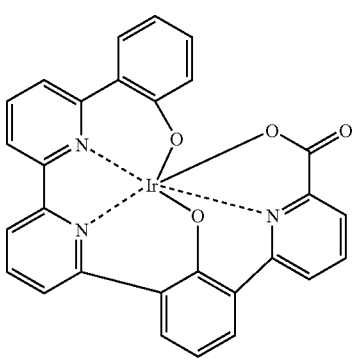
(118)
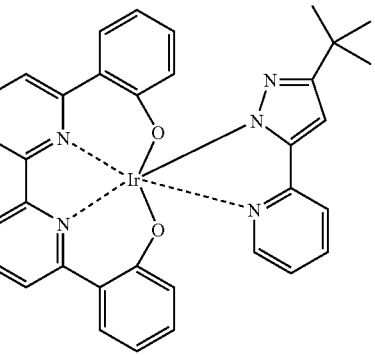

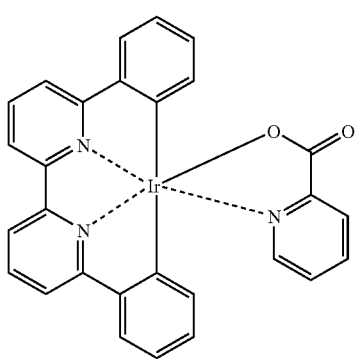
(119)
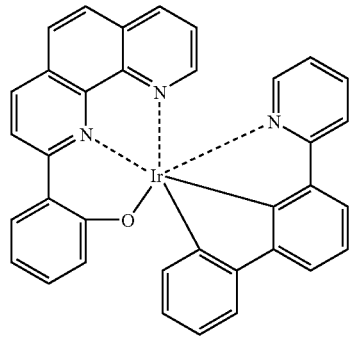
(123)
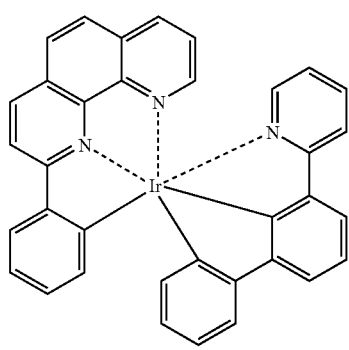
(120)
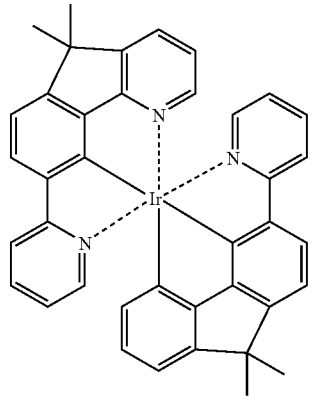
(124)
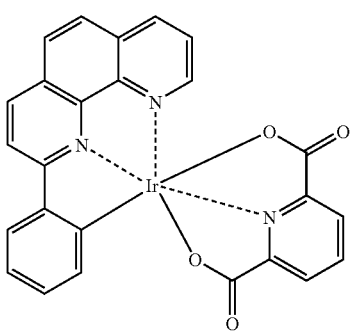
(121)
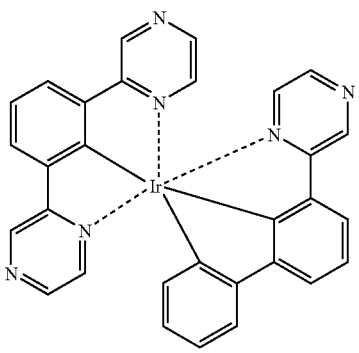
(125)
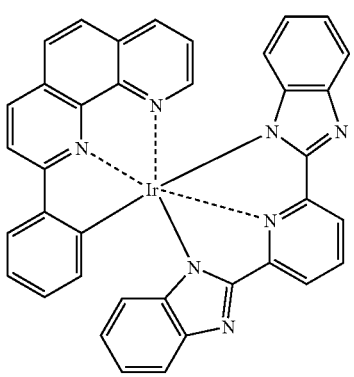
(122)
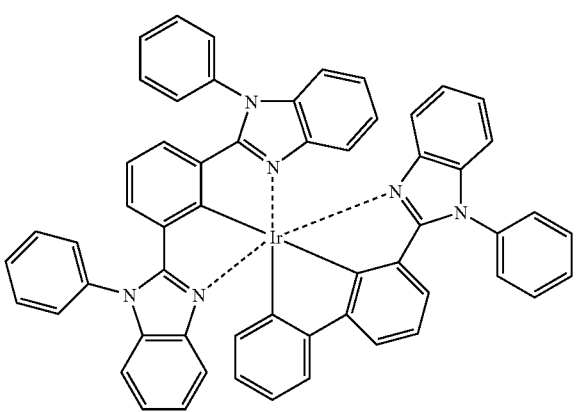
(126)

51
-continued
(127)
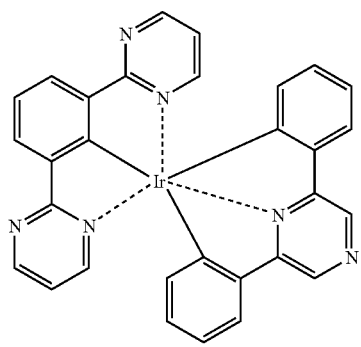
(128)
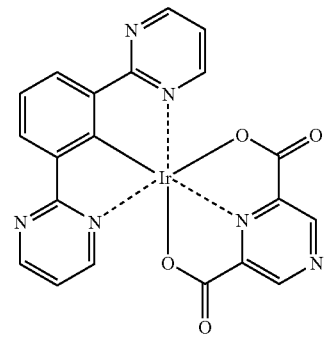
(129)
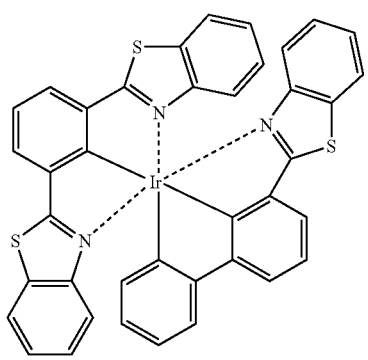
(130)
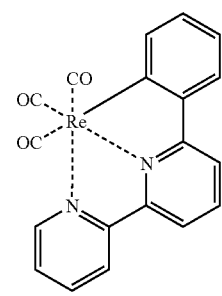
52
-continued
(131)
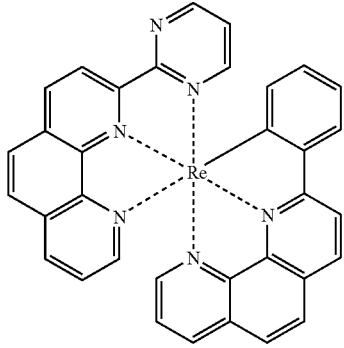
(132)
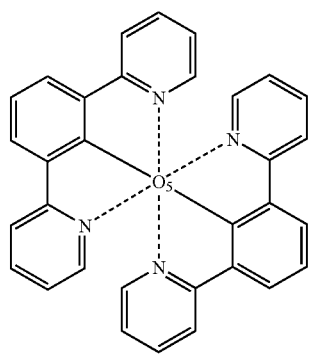
(133)
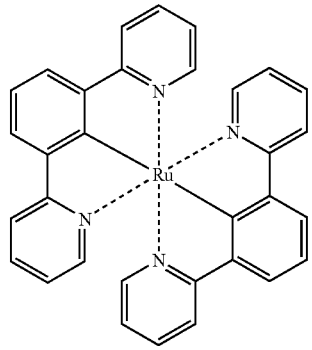
(134)
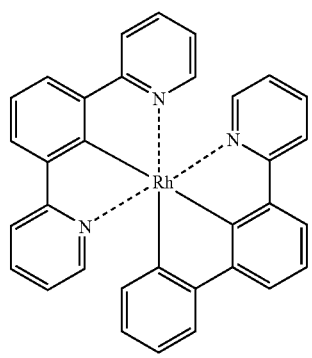

(135) 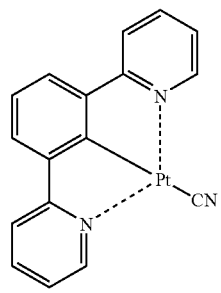
(136) 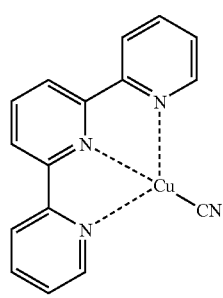
(137) 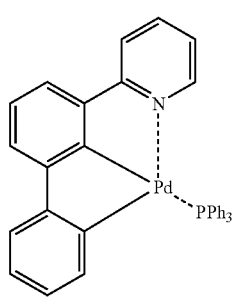
(138) 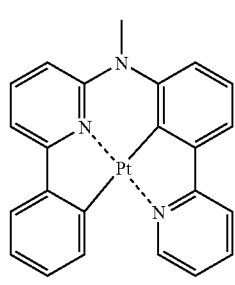
(139) 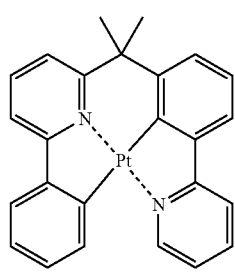
(140) 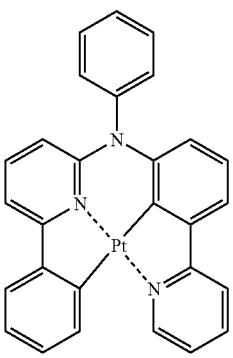
(141) 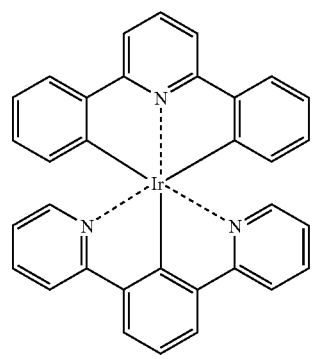
(142) 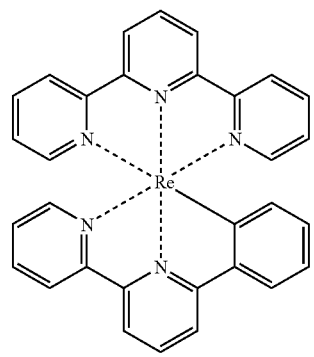
(143) 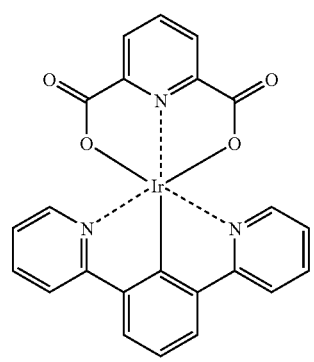

(144) 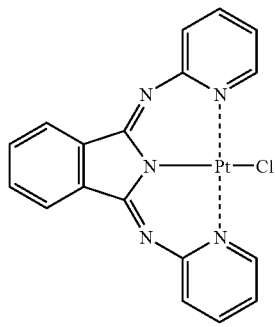
(145) 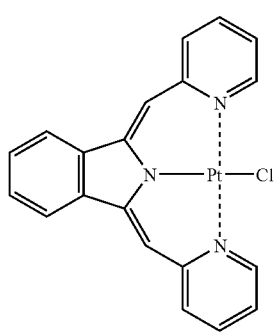
(146) 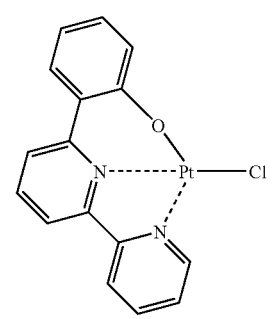
(147) 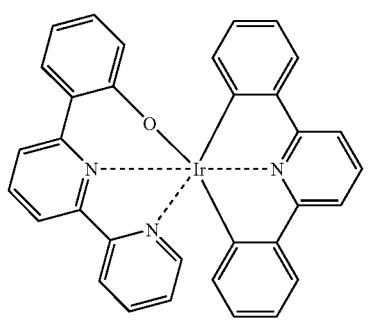
(148) 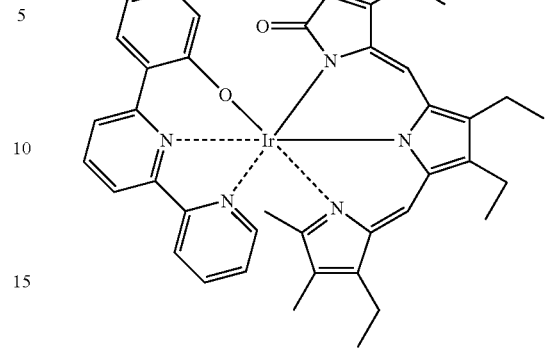
(149) 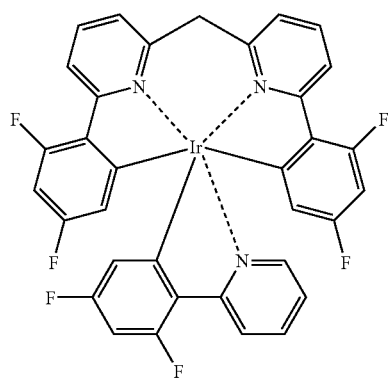
(150) 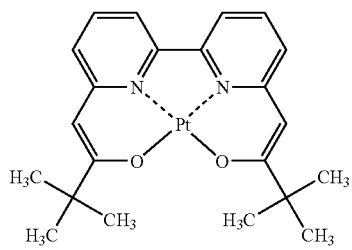
(151) 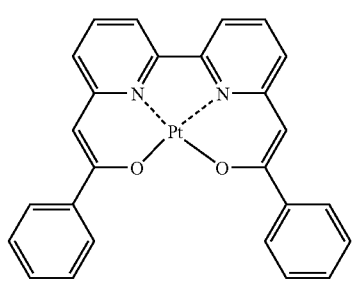
(152) 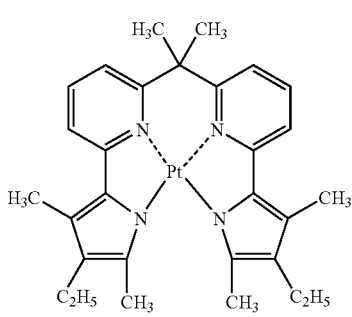

(153)
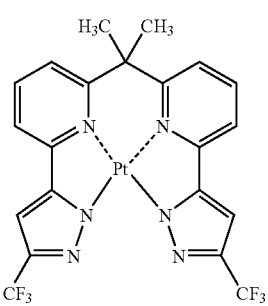
(154)
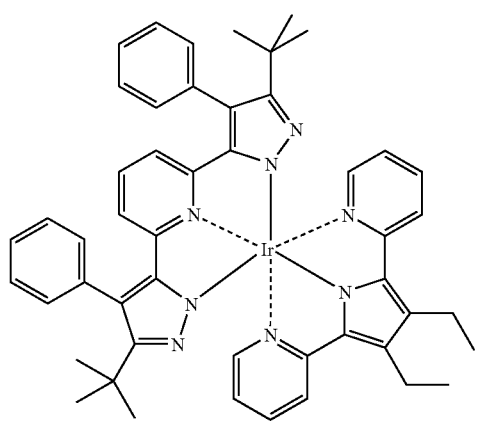
(155)
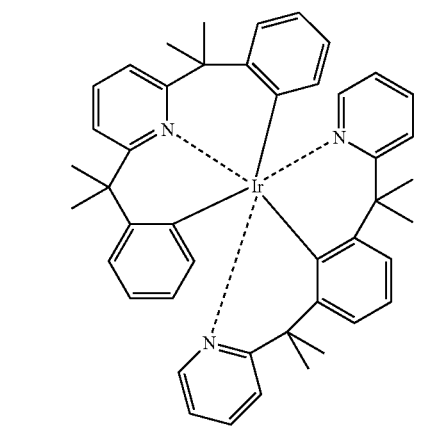
(156)
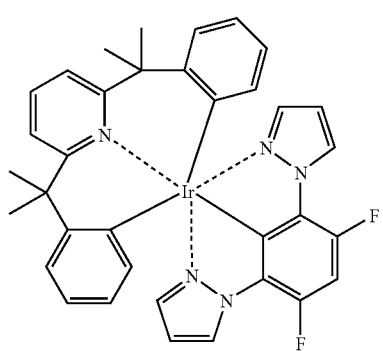
(157)
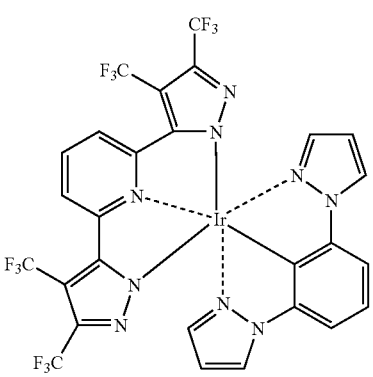
(158)
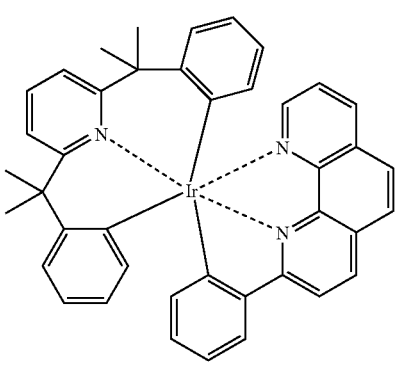
(159)
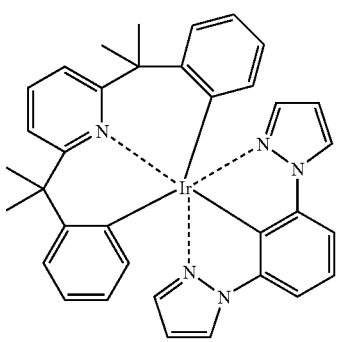
(160)
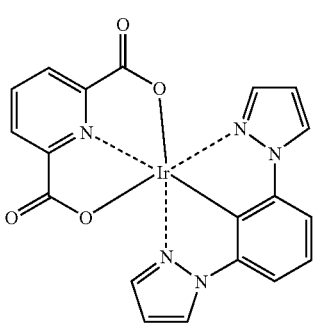

(161)
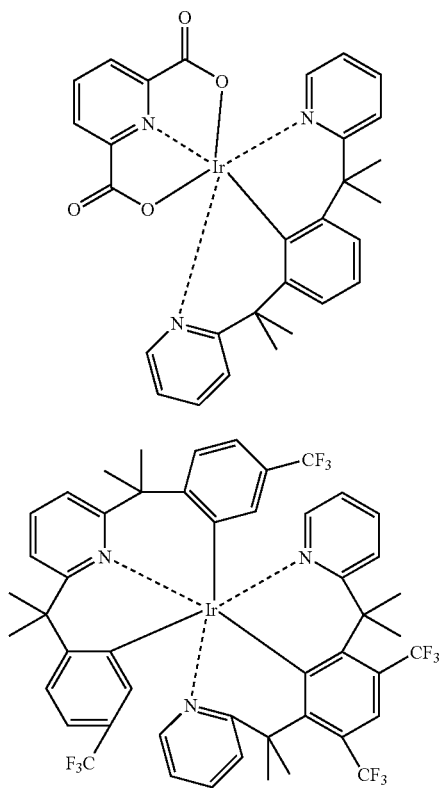
(162)
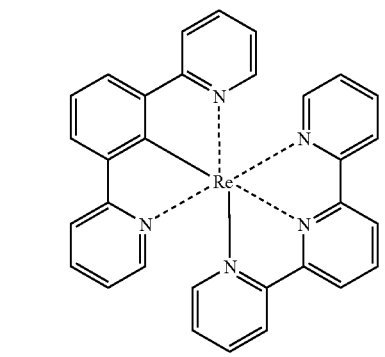
(163)
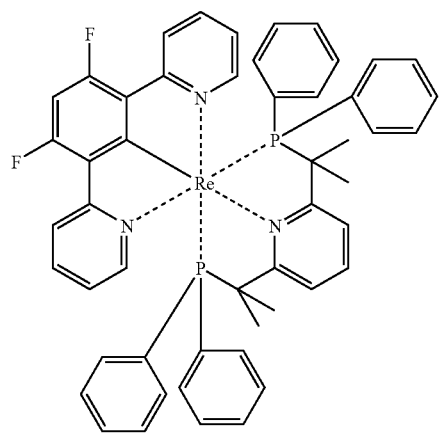
(164)
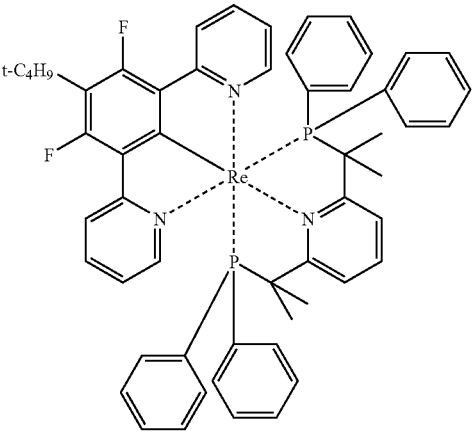
(165)
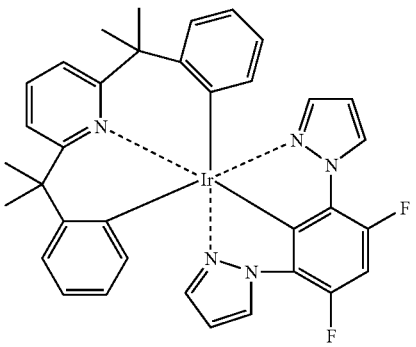
(166)
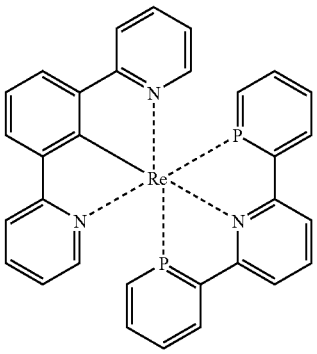
(167)
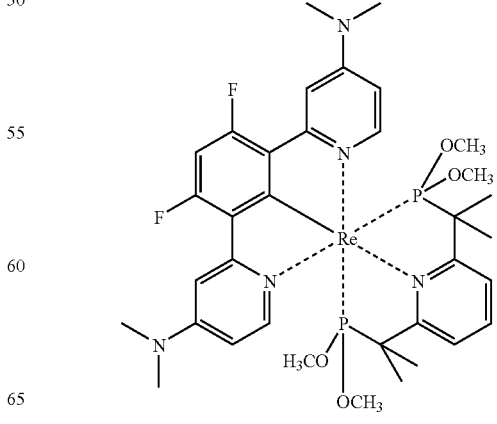
(168)

(169)
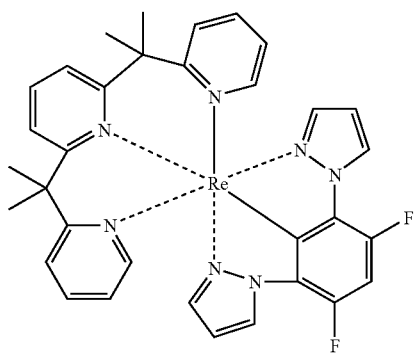
(170)
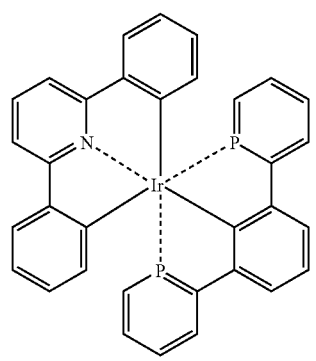
(171)
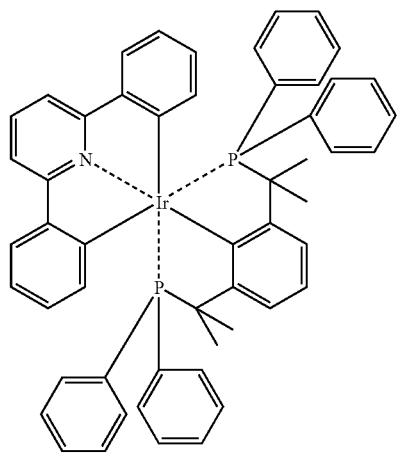
(172)
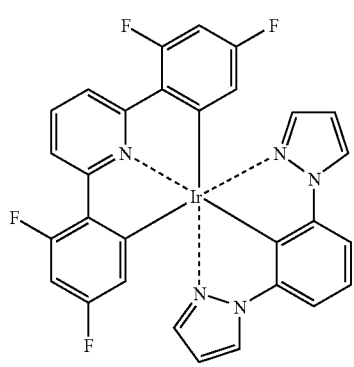
(173)
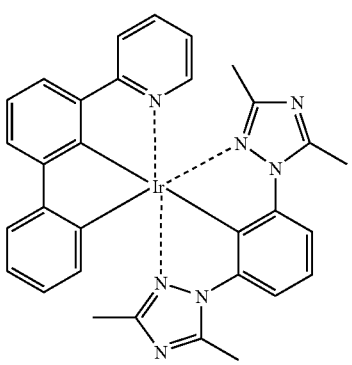
(174)
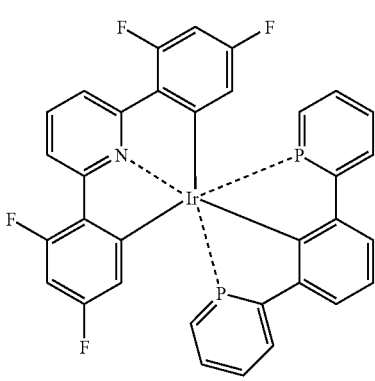
(175)
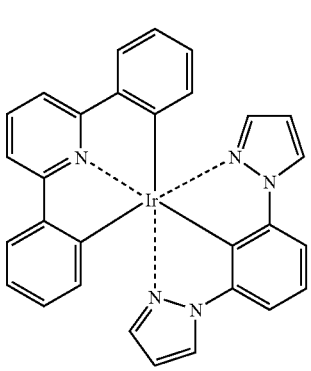
(176)
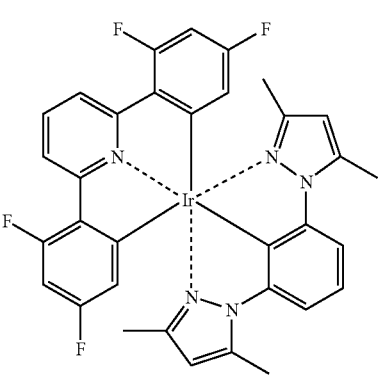

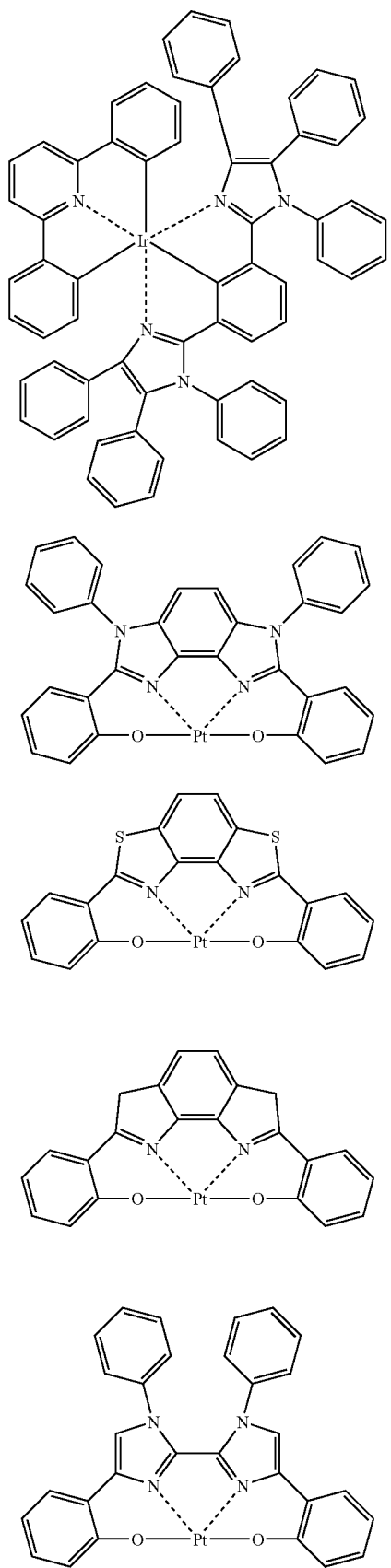
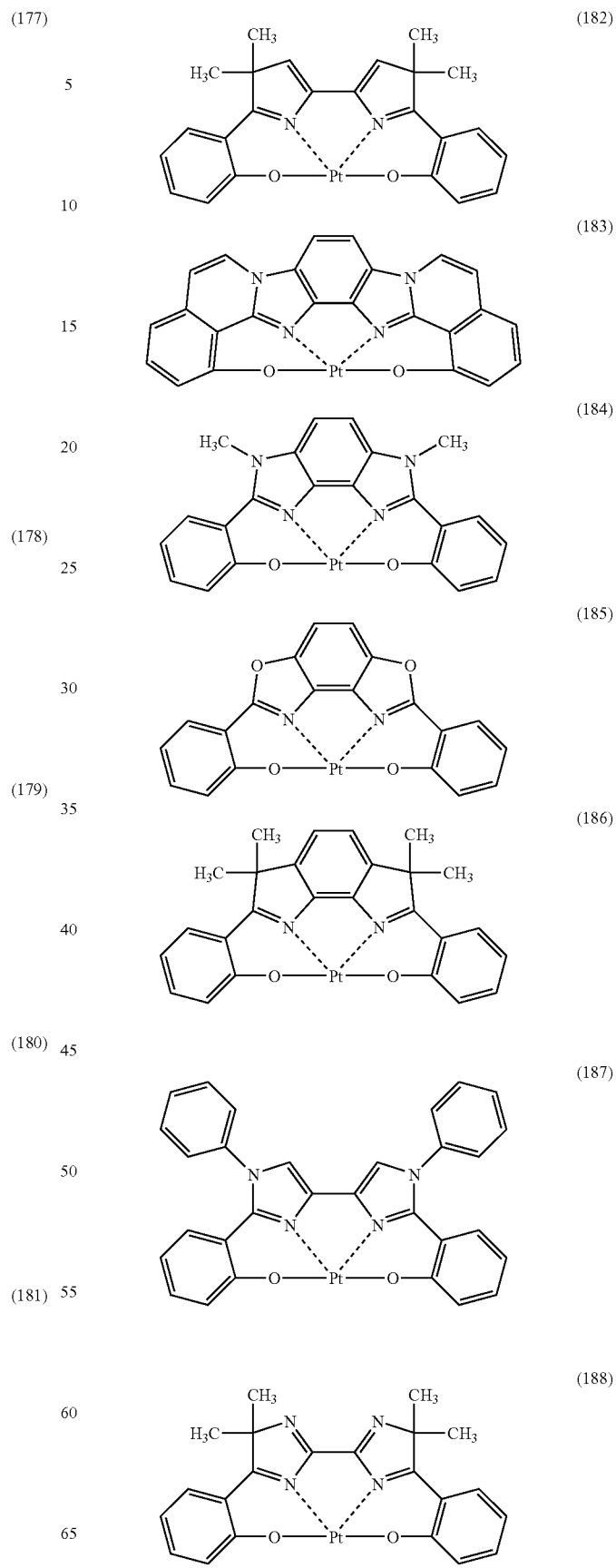

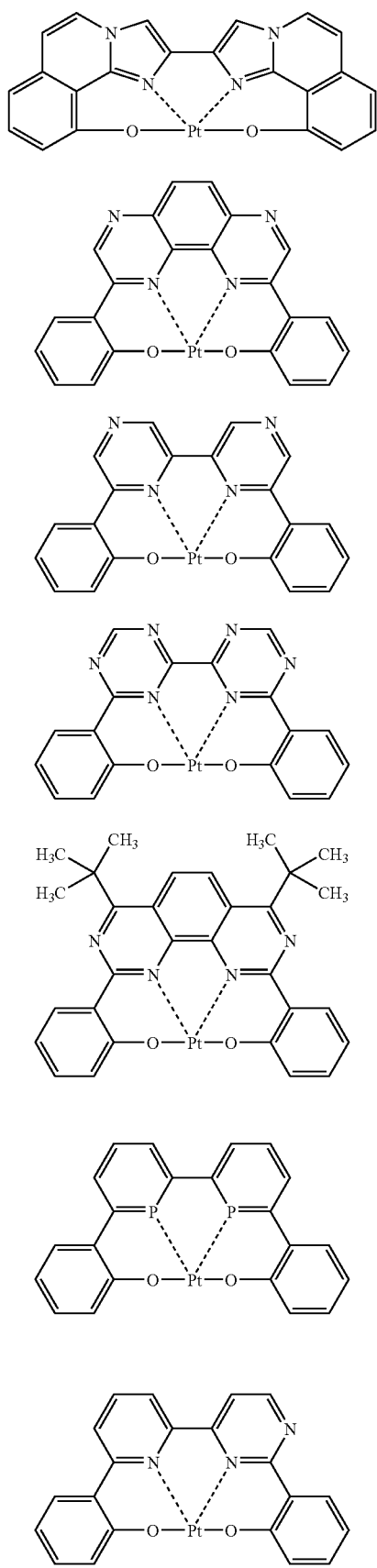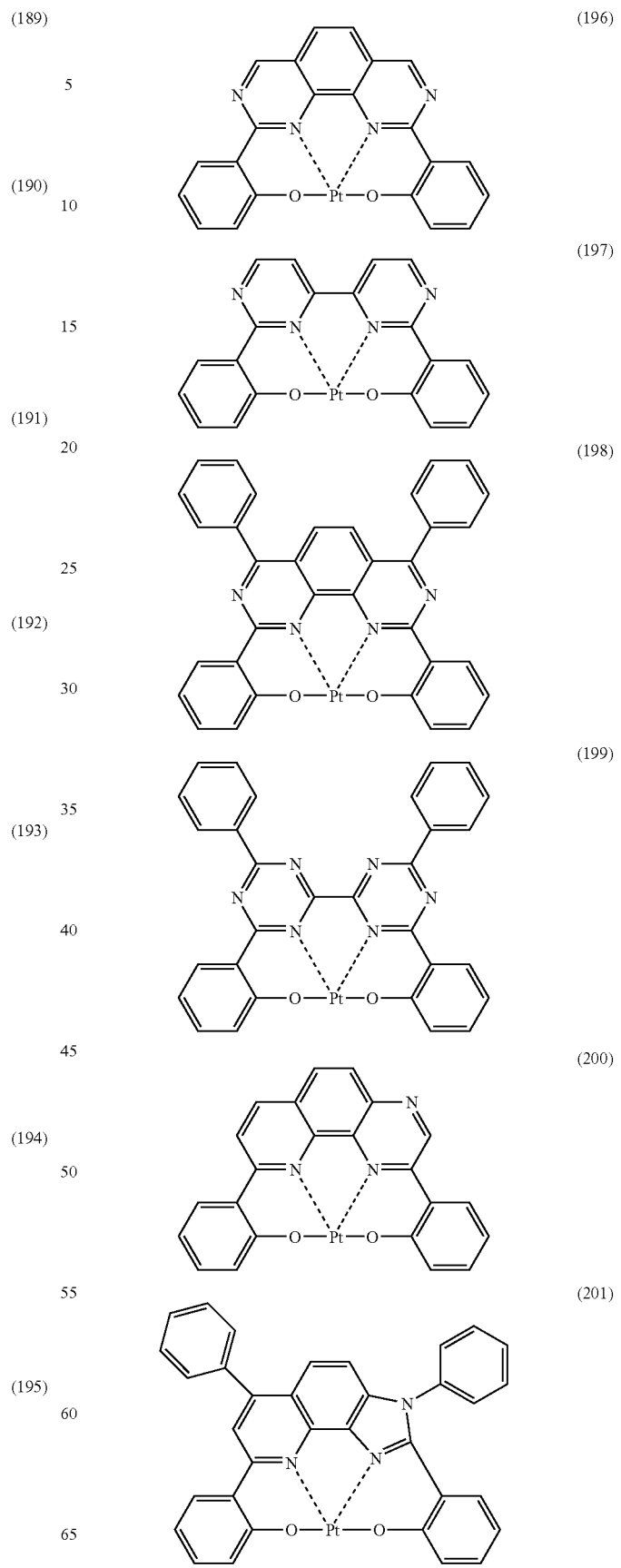

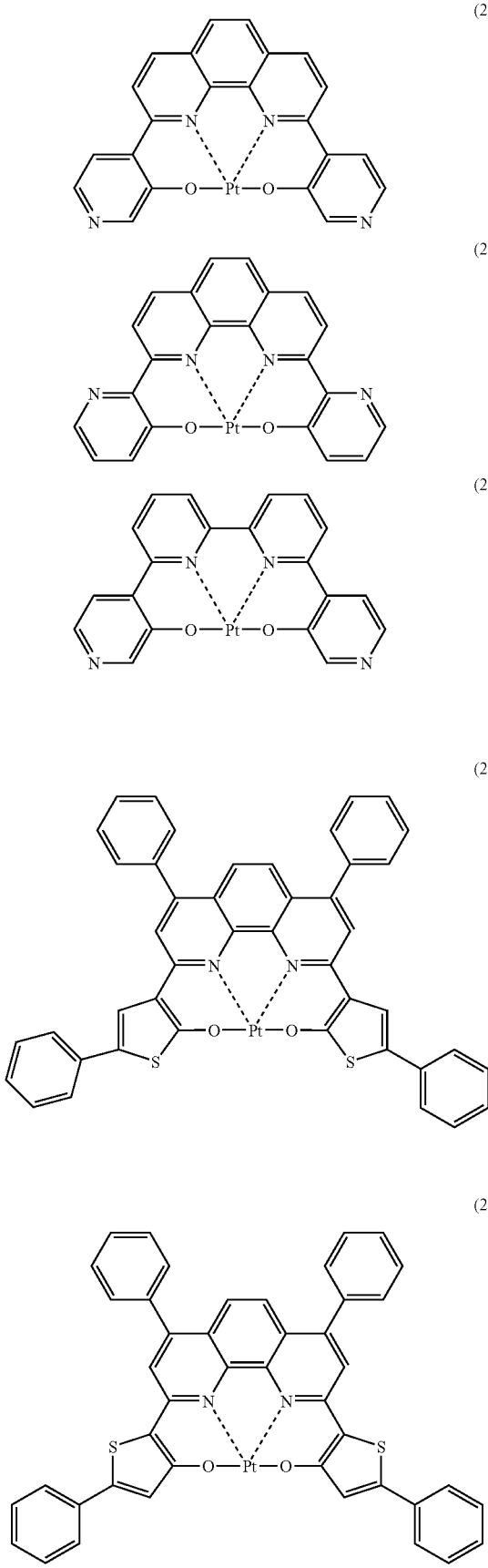
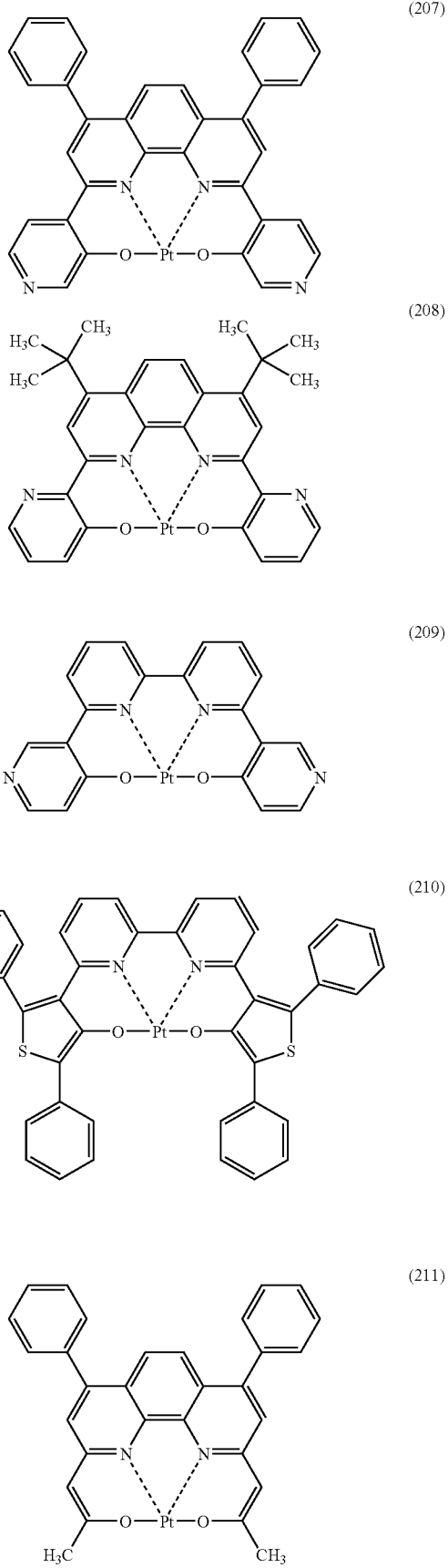

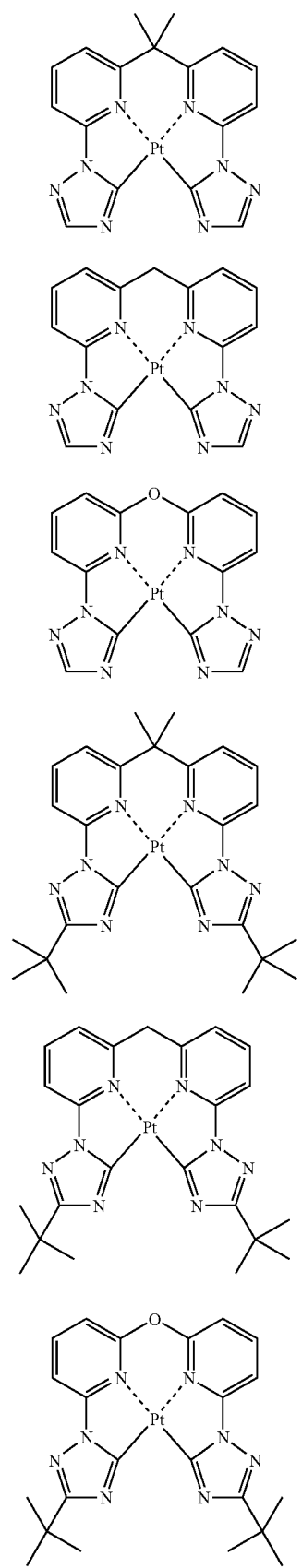
(212)
(213)
(214)
(215)
(216)
(217)
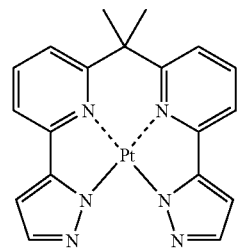
(218)
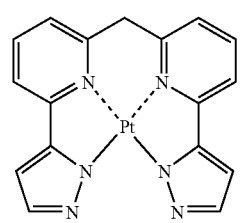
(219)
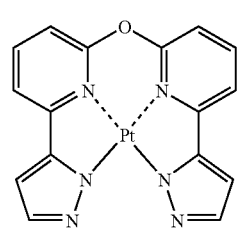
(220)
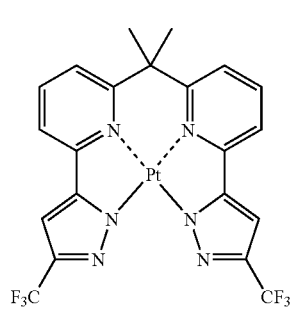
(221)
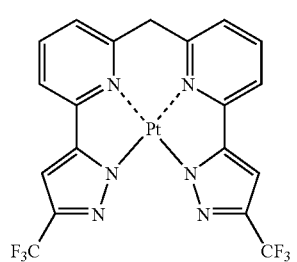
(222)
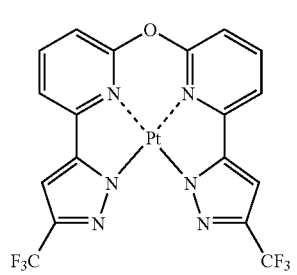
(223)

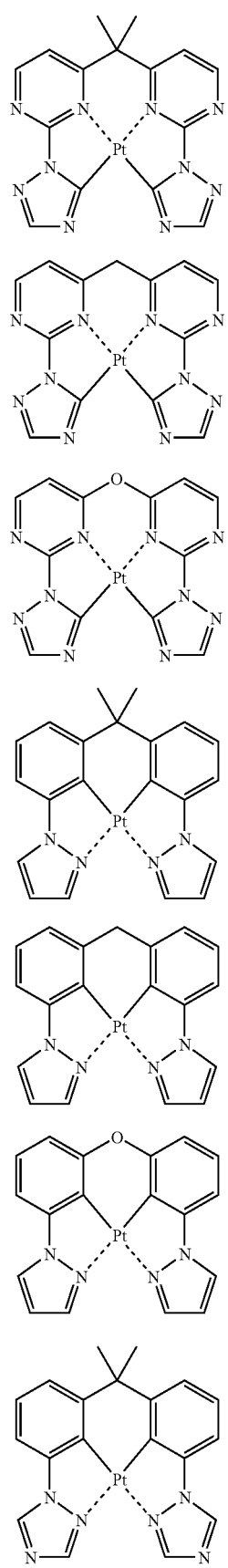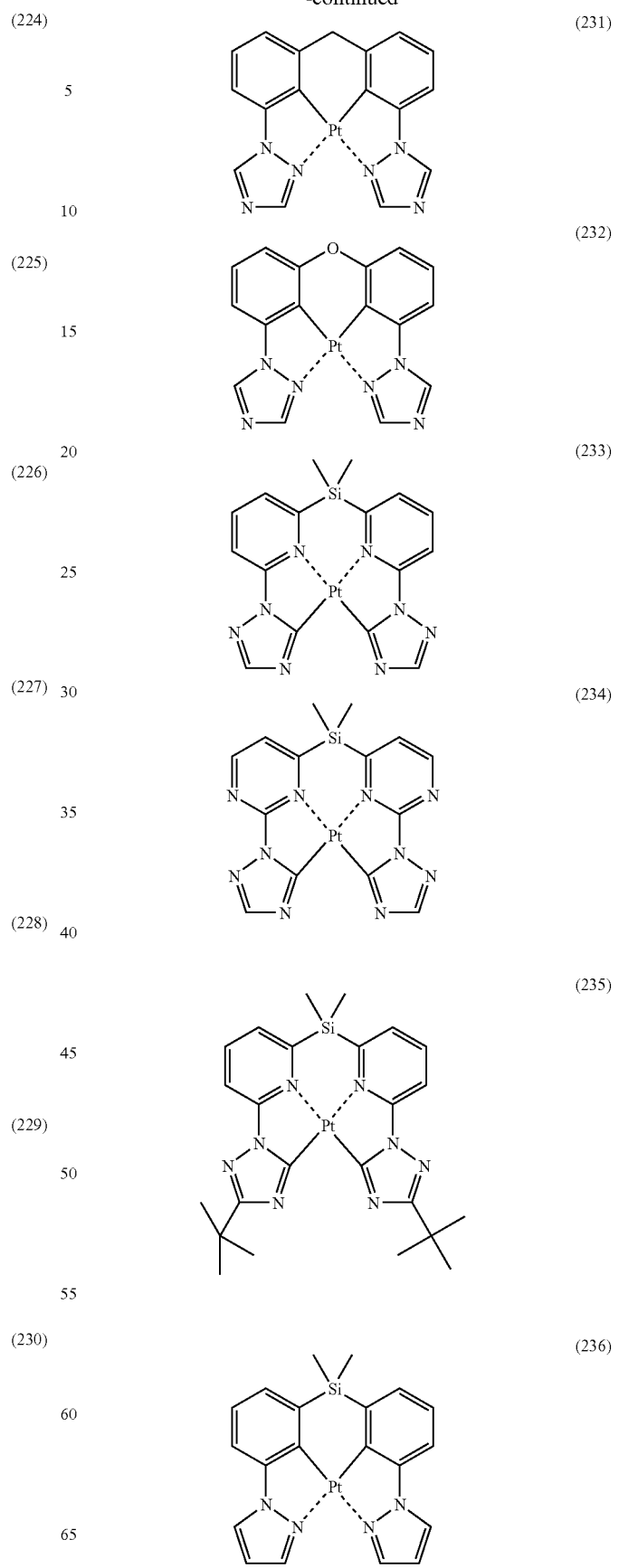

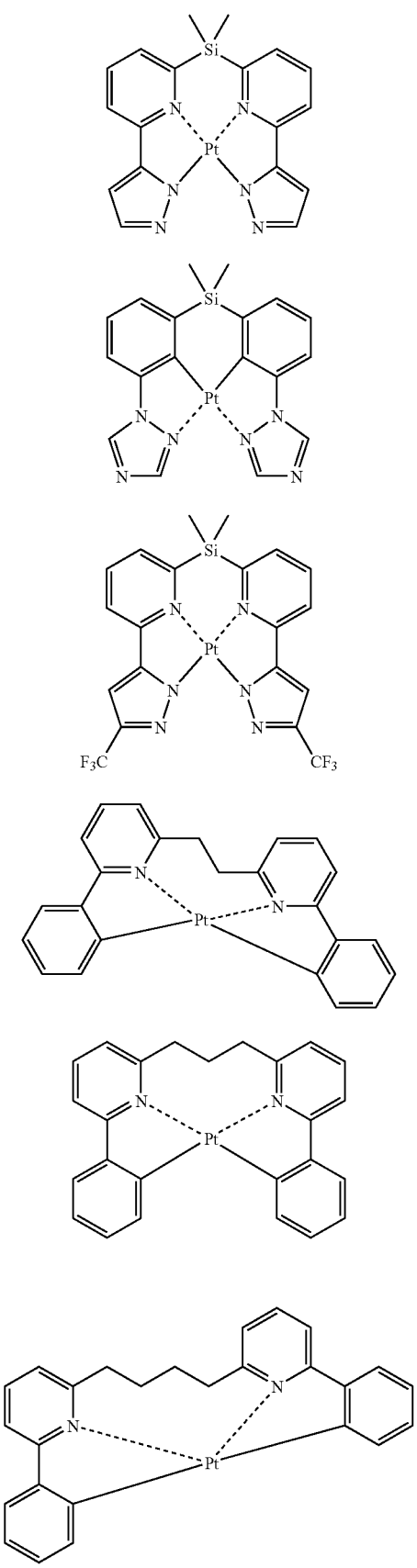

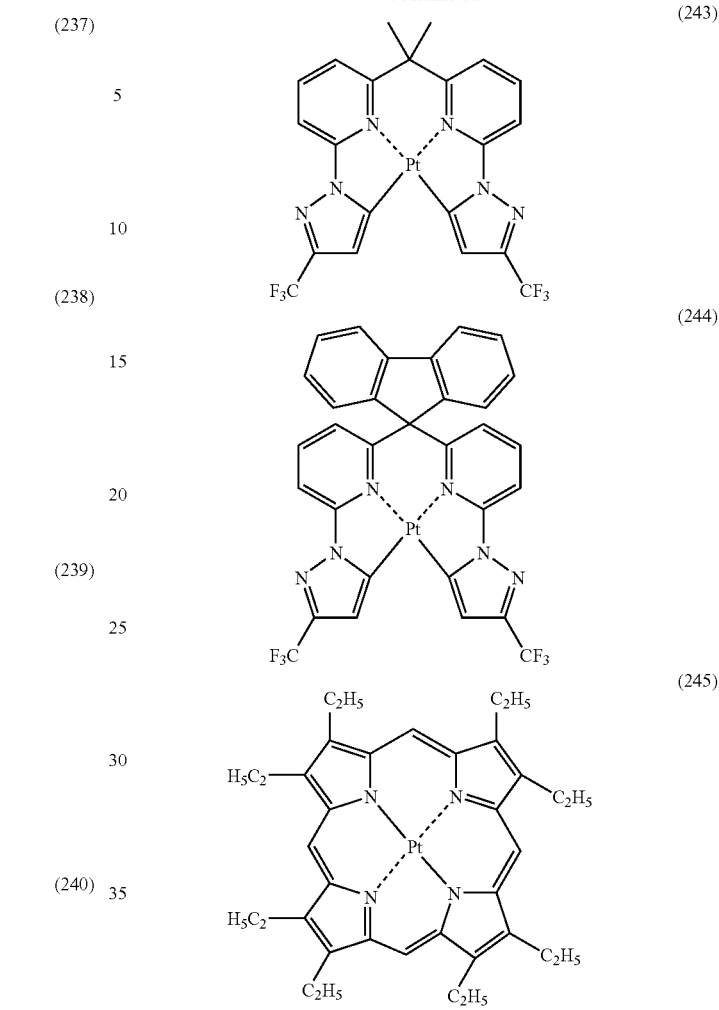

Among compounds represented by the above exemplary compounds, the tetradentate ligands having bipyridyl or phenanthroline as a partial structure thereof, the Schiff base tetradentate ligands, the phenyl bipyridyl tridentate ligands, diphenyl pyridine tridentate ligands, and terpyridine tridentate ligands are preferable.

Method of Preparing Metal Complex in the Invention

The metal complexes used in the invention [compounds represented by Formula (I), (1), (1-A), (2), (3), (3-A), (3-B), (3-C), (4), (4-A), (5), (5-A), (5-B) and Formula (II), (X2), or (X3)] can be prepared by various methods.

For example, a metal complex within the scope of the invention can be prepared by allowing a ligand or a dissociated form of the ligand to react with a metal compound under heating or at a temperature which is not higher than room temperature, 1) in the presence of a solvent (such as a halogenated solvent, an alcohol solvent, an ether solvent, an ester solvent, a ketone solvent, a nitrile solvent, an amide solvent, a sulfone solvent, a sulfoxide solvent, or water), 2) in the absence of a solvent but in the presence of a base (an inorganic or organic base such as sodium methoxide, potassium t-butoxide, triethylamine, or potassium carbonate), or 3) in the absence of a base. The heating may be conducted efficiently by a normal method or by using a microwave.

The reaction period at the preparation of the metal complex used in the invention may be changed according to the activity of the raw materials and is not particularly limited. It is preferably in a range of 1 minute to 5 days, more preferably in a range of 5 minutes to 3 days, and still more preferably in a range of 10 minutes to 1 day.

The reaction temperature for the preparation of the metal complex used in the invention may be changed according to the reaction activity, and is not particularly limited. The reaction temperature is preferably in a range of 0° C. to 300° C., more preferably in a range of 5° C. to 250° C., and still more preferably in a range of 10° C. to 200° C.

Each of the metal complexes used in the invention, i.e., the compounds represented by Formula (I), (1), (1-A), (2), (3), (3-A), (3-B), (3-C), (4), (4-A), (5), (5-A), or (5-B) and the compound represented by Formulae (II), (X2), or (X3), can be prepared by properly selecting a ligand that forms the partial structure of the desirable complex.

For example, a compound represented by Formula (1-A) can be prepared by adding 6,6'-bis(2-hydroxyphenyl)-2,2'-bipyridyl ligand or a modified compound thereof (e.g., 2,9-bis(2-hydroxyphenyl)-1,10-phenanthroline ligand, 2,9-bis(2-hydroxyphenyl)-4,7-diphenyl-1,10-phenanthroline ligand, 6,6'-bis(2-hydroxy-5-tert-butylphenyl)-2,2'-bipyridyl ligand) to a metal compound in an amount of preferably 0.1 to 10 equivalences, more preferably 0.3 to 6 equivalences, and still more preferably 0.5 to 4 equivalences, with respect to the quantity of metal compound. The reaction solvent, reaction time, and reaction temperature at the preparation of the compound represented by Formula (1-A) are the same as in the method for preparing the metal complexes used in the invention described above.

The modified compounds of 6,6'-bis(2-hydroxyphenyl)-2,2'-bipyridyl ligand can be prepared by any one of known preparative methods.

In an embodiment, a modified compound is prepared by allowing a 2,2'-bipyridyl compound (e.g., 1,10-phenanthroline) to react with an anisole compound (e.g., 4-fluoroanisole) according to the method described in Journal of Organic Chemistry, 741, 11, (1946), the disclosure of which is incorporated herein by reference. In another embodiment, a modified compound is prepared by performing Suzuki coupling reaction using a halogenated 2,2'-bipyridyl compound (e.g., 2,9-dibromo-1,10-phenanthroline) and a 2-methoxyphenylboronic acid compound (e.g., 2-methoxy-5-fluorophenylboronic acid) as starting materials and then deprotecting the methyl group (according to the method described in Journal of Organic Chemistry, 741, 11, (1946) or under heating in pyridine hydrochloride salt). In another embodiment, a modified compound can be prepared by performing Suzuki coupling reaction using a 2,2'-bipyridylboronic acid compound [e.g., 6,6'-bis(4,4,5,5-tetramethyl-1,3,2-dioxaboronyl)-2,2'-bipyridyl] and a halogenated anisole compound (e.g., 2-bromoanisole) as starting materials and then deprotecting the methyl group (according to the method described in Journal of Organic Chemistry, 741, 11, (1946) or under heating in pyridine hydrochloride salt).

When the above-mentioned ligand for the metal complex used in the invention is a cyclic ligand, the metal complex is preferably a compound represented by the following Formula (III).

Hereinafter, the compound represented by the following Formula (III) will be described.

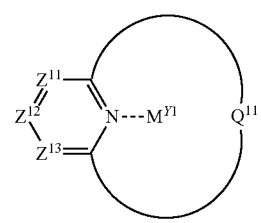

Formula (III)

In Formula (III), $Q^{11}$ represents an atomic group forming a nitrogen-containing heterocycle. $Z^{11}$, $Z^{12}$, and $Z^{13}$ each independently represent a substituted carbon atom, an unsubstituted carbon atom, a substituted nitrogen atom, or an unsubstituted nitrogen atom. $M^{Y1}$ represents a metal ion that may have an additional ligand.

In Formula (III), $Q^{11}$ represents an atomic group forming a nitrogen-containing heterocycle together with the two carbon atoms bonded to $Q^{11}$ and the nitrogen atom directly bonded to these carbon atoms. The number of the atoms constituting the nitrogen-containing heterocycle containing $Q^{11}$ is not particularly limited. It is preferably 12 to 20, more preferably 14 to 16, and still more preferably 16.

$Z^{11}$, $Z^{12}$, and $Z^{13}$ each independently represent a substituted carbon atom, an unsubstituted carbon atom, a substituted nitrogen atom, or an unsubstituted nitrogen atom. At least one of $Z^{11}$, $Z^{12}$, and $Z^{13}$ is preferably a nitrogen atom.

Examples of the substituent on the carbon atom include alkyl groups (preferably having 1 to 30 carbon atoms, more preferably 1 to 20 carbon atoms, and particularly preferably 1 to 10 carbon atoms, and examples thereof include a methyl group, an ethyl group, an iso-propyl group, a tert-butyl group, a n-octyl group, a n-decyl group, a n-hexadecyl group, a cyclopropyl group, a cyclopentyl group, and a cyclohexyl group), alkenyl groups (preferably having 2 to 30 carbon atoms, more preferably 2 to 20 carbon atoms, and particularly preferably 2 to 10 carbon atoms, and examples thereof include a vinyl group, an allyl group, a 2-butenyl group, and a 3-pentenyl group), alkynyl groups (preferably having 2 to 30 carbon atoms, more preferably 2 to 20 carbon atoms, and particularly preferably 2 to 10 carbon atoms, and examples thereof include a propargyl group and a 3-pentynyl group), aryl groups (preferably having 6 to 30 carbon atoms, more preferably 6 to 20 carbon atoms, and particularly preferably 6 to 12 carbon atoms, and examples thereof include a phenyl group, a p-methylphenyl group, a naphthyl group, and a anthranyl group), amino groups (preferably having 0 to 30 carbon atoms, more preferably 0 to 20 carbon atoms, and particularly preferably 0 to 10 carbon atoms, and examples thereof include an amino group, a methylamino group, a dimethylamino group, a diethylamino group, a dibenzylamino group, a diphenylamino group, and a ditolylamino group), alkoxy groups (preferably having 1 to 30 carbon atoms, more preferably 1 to 20 carbon atoms, and particularly preferably 1 to 10 carbon atoms, and examples thereof include a methoxy group, an ethoxy group, a butoxy group, and a 2-ethylhexyloxy group), aryloxy groups (preferably having 6 to 30 carbon atoms, more preferably 6 to 20 carbon atoms, and particularly preferably 6 to 12 carbon atoms, and examples thereof include a phenyloxy group, a 1-naphthyloxy group, and a 2-naphthyloxy group), heterocyclic oxy groups (preferably having 1 to 30 carbon atoms, more preferably 1 to 20 carbon atoms, and particularly preferably 1 to 12 carbon atoms, and examples thereof include a pyridyloxy group, a pyrazyloxy group, a pyrimidyloxy group, and a quinolyloxy group), acyl groups (preferably having 1 to 30 carbon atoms, more preferably 1 to 20 carbon atoms, and particularly preferably 1 to 12 carbon atoms, and examples thereof include an acetyl group, a benzoyl group, a formyl group, and a pivaloyl group), alkoxycarbonyl groups (preferably having 2 to 30 carbon atoms, more preferably 2 to 20 carbon atoms, and particularly preferably 2 to 12 carbon atoms, and examples thereof include a methoxycarbonyl group and a ethoxycarbonyl group), aryloxycarbonyl groups (preferably having 7 to 30 carbon atoms, more preferably 7 to 20 carbon atoms, and particularly preferably 7 to 12 carbon atoms, and examples thereof include a phenyloxycarbonyl group), acyloxy groups (preferably having 2 to 30 carbon atoms, more preferably 2 to 20 carbon atoms, and particularly preferably 2 to 10 carbon atoms, and examples thereof include an acetoxy group and a benzoyloxy group), acylamino groups (preferably having 2 to 30 carbon atoms, more preferably 2 to 20 carbon atoms, and particularly preferably 2 to 10 carbon atoms, and examples thereof include an acetylamino group and a benzoylamino group), alkoxycarbonylamino groups (preferably having 2 to 30 carbon atoms, more preferably 2 to 20 carbon atoms, and particularly preferably 2 to 12 carbon atoms, and examples thereof include a methoxycarbonylamino group), aryloxycarbonylamino groups (preferably having 7 to 30 carbon atoms, more preferably 7 to 20 carbon atoms, and particularly preferably 7 to 12 carbon atoms, and examples thereof include a phenyloxycarbonylamino group), sulfonylamino groups (preferably having 1 to 30 carbon atoms, more preferably 1 to 20 carbon atoms, and particularly preferably 1 to 12 carbon atoms, and examples thereof include a methanesulfonylamino group and a benzene sulfonylamino group), sulfamoyl groups (preferably having 0 to 30 carbon atoms, more preferably 0 to 20 carbon atoms, and particularly preferably 0 to 12 carbon atoms, and examples thereof include a sulfamoyl group, a methylsulfamoyl group, a dimethylsulfamoyl group, and a phenylsulfamoyl group), carbamoyl groups (preferably having 1 to 30 carbon atoms, more preferably 1 to 20 carbon atoms, and particularly preferably 1 to 12 carbon atoms, and examples thereof include a carbamoyl group, a methylcarbamoyl group, a diethylcarbamoyl group, and a phenylcarbamoyl group), alkylthio groups (preferably having 1 to 30 carbon atoms, more preferably 1 to 20 carbon atoms, and particularly preferably 1 to 12 carbon atoms, and examples thereof include a methylthio group and a ethylthio group), arylthio groups (preferably having 6 to 30 carbon atoms, more preferably 6 to 20 carbon atoms, and particularly preferably 6 to 12 carbon atoms, and examples thereof include a phenylthio group), heterocyclic thio groups (preferably having 1 to 30 carbon atoms, more preferably 1 to 20 carbon atoms, and particularly preferably 1 to 12 carbon atoms, and examples thereof include a pyridylthio group, a 2-benzimidazolylthio group, a 2-benzoxazolylthio group, and a 2-benzothiazolylthio group), sulfonyl groups (preferably having 1 to 30 carbon atoms, more preferably 1 to 20 carbon atoms, and particularly preferably 1 to 12 carbon atoms, and examples thereof include a mesyl group and a tosyl group), sulfinyl groups (preferably having 1 to 30 carbon atoms, more preferably 1 to 20 carbon atoms, and particularly preferably 1 to 12 carbon atoms, and examples thereof include a methanesulfinyl group and a benzenesulfinyl group), ureido groups (preferably having 1 to 30 carbon atoms, more preferably 1 to 20 carbon atoms, and particularly preferably 1 to 12 carbon atoms, and examples thereof include a ureido group, a methylureido group, and a phenylureido group), phosphoric amide groups (preferably having 1 to 30 carbon atoms, more preferably 1 to 20 carbon atoms, and particularly preferably 1 to 12 carbon atoms, and examples thereof include a diethylphosphoric amide group and a phenylphosphoric amide group), a hydroxy group, a mercapto group, halogen atoms (e.g., fluorine, chlorine, bromine, and iodine), a cyano group, a sulfo group, a carboxyl group, a nitro group, a hydroxamic acid group, sulfino groups, hydrazino groups, imino groups, heterocyclic groups (preferably having 1 to 30 carbon atoms, and particularly preferably 1 to 12 carbon atoms; the heteroatom(s) may be selected from nitrogen, oxygen and sulfur atoms; examples of the heterocyclic groups include imidazolyl, pyridyl, quinolyl, furyl, thienyl, piperidyl, morpholino, benzoxazolyl, benzimidazolyl, benzothiazolyl, carbazolyl, and azepinyl), silyl groups (preferably having 3 to 40 carbon atoms, more preferably 3 to 30 carbon atoms, and particularly preferably 3 to 24 carbon atoms, and examples thereof include a trimethylsilyl group and a triphenylsilyl group), silyloxy groups (preferably having 3 to 40 carbon atoms, more preferably 3 to 30 carbon atoms, and particularly preferably 3 to 24 carbon atoms, and examples thereof include a trimethylsilyloxy group and a triphenylsilyloxy group), and the like. These substituents may have a substituent(s).

Among these substituents, the substituent on the carbon atom is preferably an alkyl group, an aryl, a heterocyclic group or a halogen atom, more preferably an aryl group or a halogen atom, and still more preferably a phenyl group or a fluorine atom.

The substituent on the nitrogen atom may be selected from the substituents described as examples of the substituent on the carbon atom, and have the same preferable range as in the case of the substituent on the carbon atom.

In Formula (III), $M^{y1}$ represents a metal ion that may have an additional ligand. $M^{y1}$ preferably represents a metal ion having no ligand.

The metal ion represented by $M^{y1}$ is not particularly limited. It is preferably a divalent or trivalent metal ion. The divalent or trivalent metal ion is preferably a cobalt ion, a magnesium ion, a zinc ion, a palladium ion, a nickel ion, a copper ion, a platinum ion, a lead ion, an aluminum ion, an iridium ion, or a europium ion, more preferably a cobalt ion, a magnesium ion, a zinc ion, a palladium ion, a nickel ion, a copper ion, a platinum ion, or a lead ion, still more preferably a copper ion, or a platinum ion, and particularly preferably a platinum ion. $M^{y1}$ may or may not be bound to an atom contained in $Q^{11}$, and is preferably bound to an atom contained in $Q^{11}$.

While the additional ligand that $M^{y1}$ may have is not particularly limited, it is preferably a monodentate or bidentate ligand, and more preferably a bidentate ligand. While the coordinating atom is not particularly limited, it is preferably an oxygen atom, a sulfur atom, a nitrogen atom, a carbon atom, or a phosphorus atom, more preferably an oxygen atom, a nitrogen atom, or a carbon atom, and still more preferably an oxygen atom or a nitrogen atom.

Preferable examples of compounds represented by Formula (III) include compounds represented by the following Formulae (a) to (j) and the tautomers thereof.

Compounds represented by Formula (III) are more preferably selected from compounds represented by Formula (a) or (b) and tautomers thereof, and still more preferably selected from compounds represented by Formula (b).

Compounds represented by Formula (c) or (g) are also preferable as the compounds represented by Formula (III).

A compound represented by Formula (c) is preferably a compound represented by Formula (d), a tautomer of a compound represented by Formula (d), a compound represented by Formula (e), a tautomer of a compound represented by Formula (e), a compound represented by Formula (f) or a tautomer of a compound represented by Formula (f); more preferably a compound represented by Formula (d), a tautomer of a compound represented by Formula (d), a compound represented by Formula (e), or a tautomer of a compound represented by Formula (e); and still more preferably a compound represented by Formula (d) or a tautomer of a compound represented by Formula (d).

A compound represented by Formula (g) is preferably a compound represented by Formula (h), a tautomers of a compound represented by Formula (h), a compound represented by Formula (i), a tautomer of a compound represented by Formula (i), a compounds represented by Formula (j) or a tautomer of a compounds represented by Formula (j); more preferably a compound represented by Formula (h), a tautomers of a compound represented by Formula (h), a compound represented by Formula (i), or a tautomer of a compound represented by Formula (i); and still more preferably a compound represented by Formula (h) or a tautomer of a compound represented by Formula (h).

Hereinafter, the compounds represented by Formulae (a) to (j) will be described in detail.

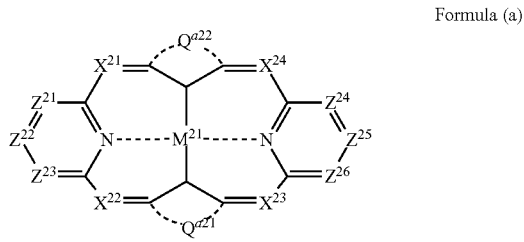

Formula (a)

The compound represented by Formula (a) will be described below.

In Formula (a), the definitions and preferable ranges of $Z^{21}$, $Z^{22}$, $Z^{23}$, $Z^{24}$, $Z^{25}$, $Z^{26}$, and $M^{21}$ are similar to the definitions and preferable ranges of corresponding $Z^{11}$, $Z^{12}$, $Z^{13}$, $Z^{11}$, $Z^{12}$, $Z^{13}$, and $M^{y1}$ in Formula (III), respectively.

$Q^{a21}$ and $Q^{a22}$ each represent a group forming a nitrogen-containing heterocycle. While each of the nitrogen-containing heterocycles formed by $Q^{a21}$ and $Q^{a22}$ is not particularly limited, it is preferably a pyrrole ring, an imidazole ring, a triazole ring, a condensed ring containing one or more of the above rings (e.g., benzopyrrole), or a tautomer of any of the above rings (e.g., in Formula (b) below, the nitrogen-containing five-membered ring substituted by $R^{43}$ and $R^{44}$, or by $R^{45}$ and $R^{46}$ is defined as a tautomer of pyrrole), and more preferably a pyrrole ring or a condensed ring containing a pyrrole ring (e.g., benzopyrrole).

$X^{21}$, $X^{22}$, $X^{23}$, and $X^{24}$ each independently represent a substituted carbon atom, an unsubstituted carbon atom, a substituted nitrogen atom or an unsubstituted nitrogen atom, preferably an unsubstituted carbon atom or an unsubstituted nitrogen atom, and more preferably a nitrogen atom.

The compound represented by Formula (b) will be described below.

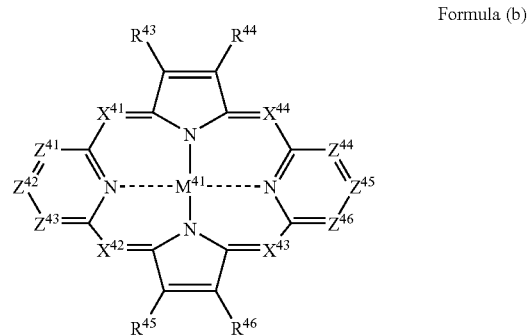

Formula (b)

In Formula (b), the definitions and preferable ranges of $Z^{41}$, $Z^{42}$, $Z^{43}$, $Z^{44}$, $Z^{45}$, $Z^{46}$, $X^{41}$, $X^{42}$, $X^{43}$, $X^{44}$, and $M^{41}$ are similar to the definitions and preferable ranges of $Z^{21}$, $Z^{22}$, $Z^{23}$, $Z^{24}$, $Z^{25}$, $Z^{26}$, $X^{21}$, $X^{22}$, $X^{23}$, $X^{24}$, and $M^{21}$ in Formula (a), respectively.

$R^{43}$, $R^{44}$, $R^{45}$, and $R^{46}$ are each preferably selected from a hydrogen atom and a substituent described as examples of the substituent on $Z^{11}$ or $Z^{12}$ in Formula (III), and preferable examples thereof include an alkyl group, an aryl group, a group in which $R^{43}$ and $R^{44}$ are bonded to each other to form a ring structure (e.g., a benzo-condensed ring or a pyridine-condensed ring) and a group in which $R^{45}$ and $R^{46}$ are bonded to each other to form a ring structure (e.g., a benzo-condensed ring or a pyridine-condensed ring). $R^{43}$, $R^{44}$, $R^{45}$, and $R^{46}$ are each more preferably selected from an alkyl group, an aryl group, a group in which $R^{43}$ and $R^{44}$ are bonded to each other to form a ring structure (e.g., a benzo-condensed ring or a pyridine-condensed ring) and a group in which $R^{45}$ and $R^{46}$ are bonded to each other to form a ring structure (e.g., a benzo-condensed ring or a pyridine-condensed ring). It is still more preferable that $R^{43}$ and $R^{44}$ are bonded to each other to form a ring structure (e.g., a benzo-condensed ring or a pyridine-condensed ring) and/or $R^{45}$ and $R^{46}$ are bonded to each other to form a ring structure (e.g., a benzo-condensed ring or a pyridine-condensed ring).

$R^{43}$, $R^{44}$, $R^{45}$, and $R^{46}$ each independently represent a hydrogen atom or a substituent. Examples of the substituent include the groups described as examples of the substituent on the carbon atom represented by $Z^{11}$ or $Z^{12}$ in Formula (III).

The compound represented by Formula (c) will be described below.

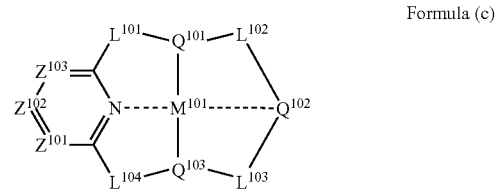

Formula (c)

In Formula (c), $Z^{101}$, $Z^{102}$, and $Z^{103}$ each independently represent a substituted or unsubstituted carbon or nitrogen atom. At least one of $Z^{101}$, $Z^{102}$, and $Z^{103}$ is preferably a nitrogen atom.

$L^{101}$, $L^{102}$, $L^{103}$, and $L^{104}$ each independently represent a single bond or a connecting group. The connecting group is not particularly limited, and examples thereof include a carbonyl connecting group, an alkylene group, an alkenylene group, an arylene group, a heteroarylene group, a nitrogen-containing heterocycle connecting group, a connecting group which connects moieties via an oxygen atom, a sulfur atom or a silicon atom, an amino connecting group, an imino connecting group, a carbonyl connecting group, and connecting groups comprising combinations thereof.

$L^{101}$, $L^{102}$, $L^{103}$, and $L^{104}$ are each preferably a single bond, an alkylene group, an alkenylene group, an amino connecting group, or an imino connecting group, more preferably a single bond, an alkylene connecting group, an alkenylene connecting group, or an imino connecting group, and still more preferably a single bond or an alkylene connecting group.

$Q^{101}$ and $Q^{103}$ each independently represent a group containing a carbon atom coordinating to $M^{101}$, a group containing a nitrogen atom coordinating to $M^{101}$, a group containing a phosphorus atom coordinating to $M^{101}$, a group containing an oxygen atom coordinating to $M^{101}$, or a group containing a sulfur atom coordinating to $M^{101}$.

The group containing a carbon atom coordinating to $M^{101}$ is preferably an aryl group containing a coordinating carbon atom, a five-membered ring heteroaryl group containing a coordinating carbon atom, or a six-membered ring heteroaryl group containing a coordinating carbon atom; more preferably, an aryl group containing a coordinating carbon atom, a nitrogen-containing five-membered ring heteroaryl group containing a coordinating carbon atom, or a nitrogen-containing six-membered ring heteroaryl group containing a coordinating carbon atom; and still more preferably, an aryl group containing a coordinating carbon atom.

The group containing a nitrogen atom coordinating to $M^{101}$ is preferably a nitrogen-containing five-membered ring heteroaryl group containing a coordinating nitrogen atom or a nitrogen-containing six-membered ring heteroaryl group containing a coordinating nitrogen atom, and more preferably a nitrogen-containing six-membered ring heteroaryl group containing a coordinating nitrogen atom.

The group containing a phosphorus atom coordinating to $M^{101}$ is preferably an alkyl phosphine group containing a coordinating phosphorus atom, an aryl phosphine group containing a coordinating phosphorus atom, an alkoxyphosphine group containing a coordinating phosphorus atom, an aryloxyphosphine group containing a coordinating phosphorus atom, a heteroaryloxyphosphine group containing a coordinating phosphorus atom, a phosphinine group containing a coordinating phosphorus atom, or a phosphor group containing a coordinating phosphorus atom; more preferably, an alkyl phosphine group containing a coordinating phosphorus atom or an aryl phosphine group containing a coordinating phosphorus atom.

The group containing an oxygen atom coordinating to $M^{101}$ is preferably an oxy group or a carbonyl group containing a coordinating oxygen atom, and more preferably an oxy group.

The group containing a sulfur atom coordinating to $M^{101}$ is preferably a sulfide group, a thiophene group, or a thiazole group, and more preferably a thiophene group.

Each of $Q^{101}$ and $Q^{103}$ is preferably a group containing a carbon atom coordinating to $M^{101}$, a group containing a nitrogen atom coordinating to $M^{101}$, or a group containing a an oxygen atom coordinating to $M^{101}$; more preferably a group containing a carbon atom or a group containing a nitrogen atom coordinating to $M^{101}$; and still more preferably a group containing a carbon atom coordinating to $M^{101}$.

$Q^{102}$ represents a group containing a nitrogen atom coordinating to $M^{101}$, a group containing a phosphorus atom coordinating to $M^{101}$, a group containing an oxygen atom coordinating to $M^{101}$ or a group containing a sulfur atom coordinating to $M^{101}$, and preferably a group containing a nitrogen atom coordinating to $M^{101}$.

The definition of $M^{101}$ is similar to that of $M^{11}$ in Formula (I), and their preferable ranges are also similar.

The compound represented by Formula (d) will be described below.

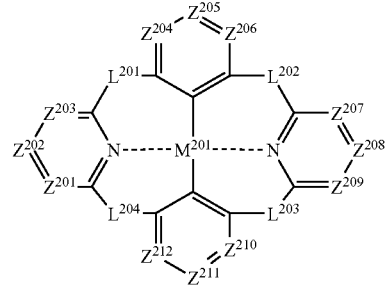

Formula (d)

In Formula (d), the definitions and preferable ranges of $Z^{201}$, $Z^{202}$, $Z^{203}$, $Z^{207}$, $Z^{208}$, $Z^{209}$, $L^{201}$, $L^{202}$, $L^{203}$, $L^{204}$, and $M^{201}$ are similar to the definitions and preferable ranges $Z^{101}$, $Z^{102}$, $Z^{103}$, $Z^{101}$, $Z^{102}$, $Z^{103}$, $L^{101}$, $L^{102}$, $L^{103}$, $L^{104}$, and $M^{101}$ in Formula (c), respectively. $Z^{204}$, $Z^{205}$, $Z^{206}$, $Z^{210}$, $Z^{211}$, and $Z^{212}$ each represent a substituted or unsubstituted carbon or a substituted or unsubstituted nitrogen atom, and preferably a substituted or unsubstituted carbon atom.

The compound represented by Formula (e) will be described below.

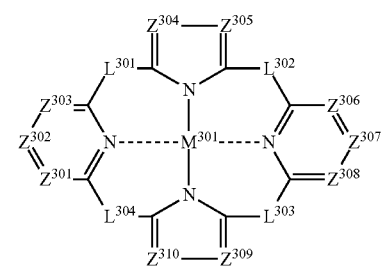

Formula (e)

In Formula (e), the definitions and preferable ranges of $Z^{301}$, $Z^{302}$, $Z^{303}$, $Z^{304}$, $Z^{305}$, $Z^{306}$, $Z^{307}$, $Z^{308}$, $Z^{309}$, $Z^{310}$, $L^{301}$, $L^{302}$, $L^{303}$, $L^{304}$ and $M^{301}$ are similar to the definitions and preferable ranges of corresponding $Z^{201}$, $Z^{202}$, $Z^{203}$, $Z^{204}$, $Z^{206}$, $Z^{207}$, $Z^{208}$, $Z^{209}$, $Z^{210}$, $Z^{212}$, $L^{101}$, $L^{102}$, $L^{103}$, $L^{104}$, and $M^{101}$ in formulae (d) and (c), respectively.

The compound represented by Formula (f) will be described below.

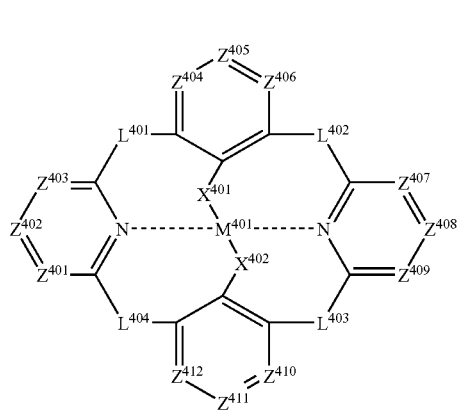

Formula (f)

In Formula (f), the definitions and preferable ranges of $Z^{401}, Z^{402}, Z^{403}, Z^{404}, Z^{405}, Z^{406}, Z^{407}, Z^{408}, Z^{409}, Z^{410}, Z^{411}, Z^{412}, L^{401}, L^{402}, L^{403}, L^{404}$, and $M^{401}$ are similar to the definitions and preferable ranges of corresponding $Z^{201}, Z^{202}, Z^{203}, Z^{204}, Z^{205}, Z^{206}, Z^{207}, Z^{208}, Z^{209}, Z^{210}, Z^{211}, Z^{212}, L^{101}, L^{102}, L^{103}, L^{104}$, and $M^{101}$ in formulae (d) and (c), respectively. $X^{401}$ and $X^{402}$ each represent an oxygen atom or a substituted or unsubstituted nitrogen or a sulfur atom, preferably an oxygen atom or a substituted nitrogen atom, and more preferably an oxygen atom.

The compound represented by Formula (g) will be described below.

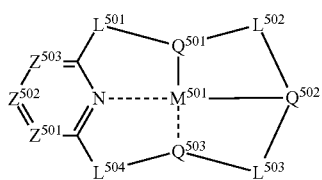

Formula (g)

In Formula (g), the definitions and preferable ranges of $Z^{501}, Z^{502}, Z^{503}, L^{501}, L^{502}, L^{503}, L^{504}, Q^{501}, Q^{502}, Q^{503}$, and $M^{501}$ are similar to the definitions and preferable ranges of corresponding $Z^{101}, Z^{102}, Z^{103}, L^{101}, L^{102}, L^{103}, L^{104}, Q^{101}, Q^{103}, Q^{102}$, and $M^{101}$ in Formula (c), respectively.

The compound represented by Formula (h) will be described below.

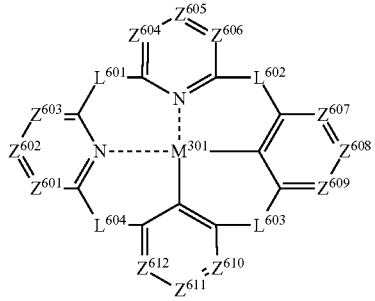

Formula (h)

In Formula (h), the definitions and preferable ranges of $Z^{601}, Z^{602}, Z^{603}, Z^{604}, Z^{605}, Z^{606}, Z^{607}, Z^{608}, Z^{609}, Z^{610}, Z^{611}, Z^{612}, L^{601}, L^{602}, L^{603}, L^{604}$, and $M^{601}$ are similar to the definitions and preferable ranges of corresponding $Z^{201}, Z^{202}, Z^{203}, Z^{207}, Z^{208}, Z^{209}, Z^{204}, Z^{205}, Z^{206}, Z^{210}, Z^{211}, Z^{212}, L^{101}, L^{102}, L^{103}, L^{104}$, and $M^{101}$ in Formulae (d) and (c), respectively.

The compound represented by Formula (i) will be described below.

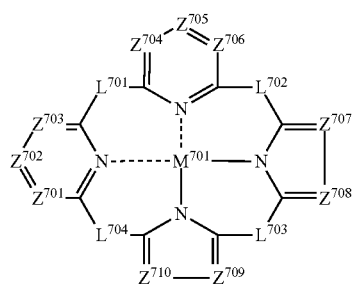

Formula (i)

In Formula (i), the definitions and preferable ranges of $Z^{701}, Z^{702}, Z^{703}, Z^{704}, Z^{705}, Z^{706}, Z^{707}, Z^{708}, Z^{709}, Z^{710}, L^{701}, L^{702}, L^{703}, L^{704}$, and $M^{701}$ are similar to the definitions and preferable ranges of corresponding $Z^{201}, Z^{202}, Z^{203}, Z^{207}, Z^{208}, Z^{209}, Z^{204}, Z^{206}, Z^{210}, Z^{212}, L^{101}, L^{102}, L^{103}, L^{104}$, and $M^{101}$ in Formulae (d) and (c), respectively.

The compound represented by Formula (j) will be described below.

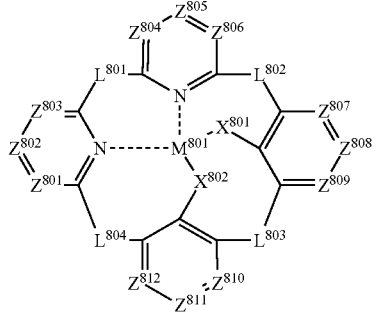

Formula (j)

In Formula (j), the definitions and preferable ranges of $Z^{801}, Z^{802}, Z^{803}, Z^{804}, Z^{805}, Z^{806}, Z^{807}, Z^{808}, Z^{809}, Z^{810}, Z^{811}, Z^{812}, L^{801}, L^{802}, L^{803}, L^{804}, M^{801}, X^{801}$, and $X^{802}$ are similar to the definitions and preferable ranges of corresponding $Z^{201}, Z^{202}, Z^{203}, Z^{207}, Z^{208}, Z^{209}, Z^{204}, Z^{205}, Z^{206}, Z^{210}, Z^{211}, Z^{212}, L^{101}, L^{102}, L^{103}, L^{104}, M^{101}, X^{401}$, and $X^{402}$ in Formulae (d), (c), and (f), respectively.

Specific examples of compounds represented by Formula (III) include compounds (2) to (8), compounds (15) to (20), compound (27) to (32), compounds (36) to (38), compounds (42) to (44), compounds (50) to (52), and compounds (57) to (154) described in Japanese Patent Application No. 2004-88575, the disclosure of which is incorporated herein by reference. The structures of the above compounds are shown below, however, the scope of the invention is not limited thereto.

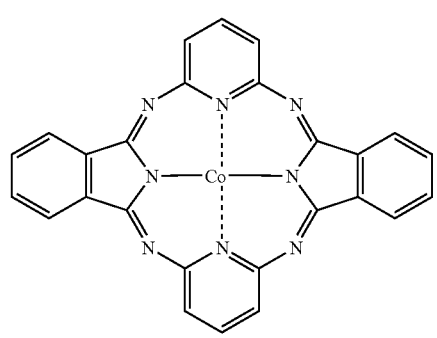

(2)

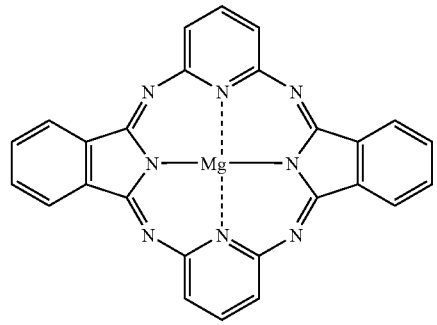

(3)

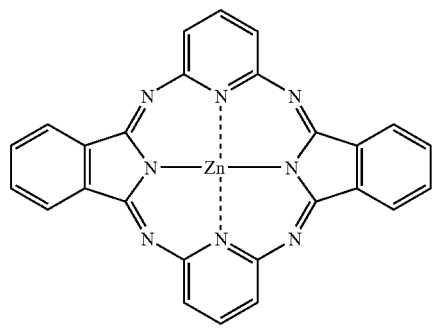
(4)
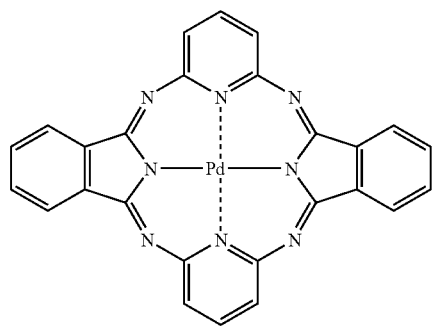
(5)
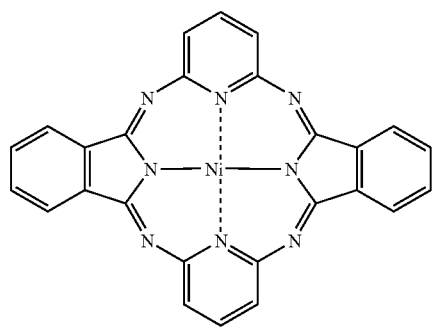
(6)
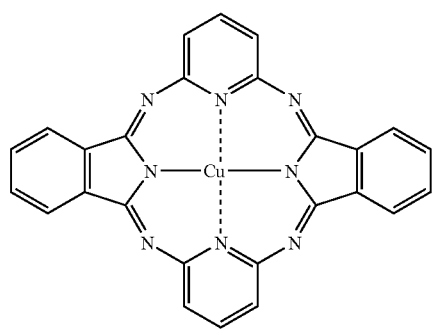
(7)
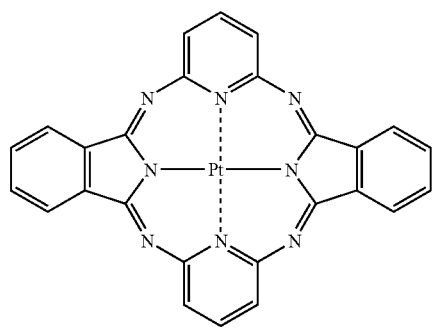
(8)
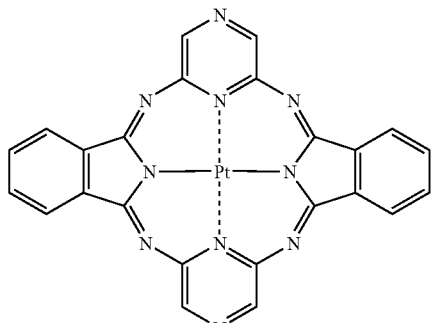
(15)
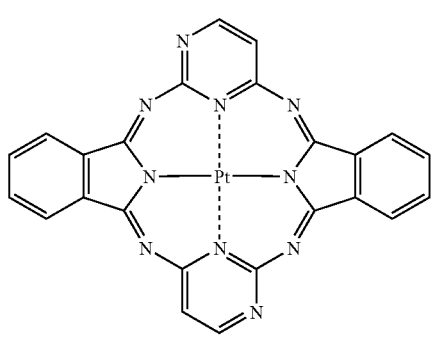
(16)
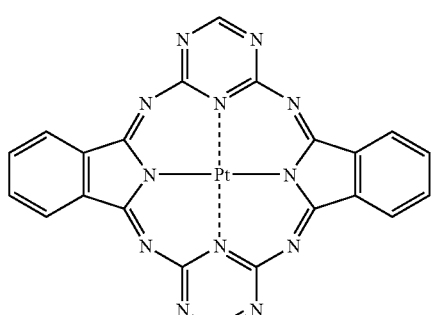
(17)
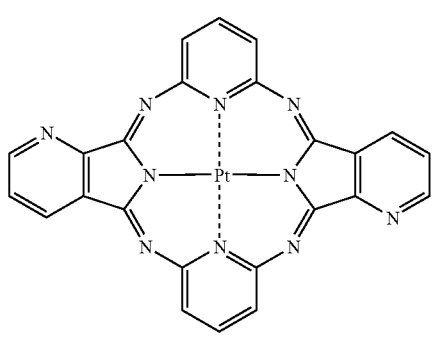
(18)
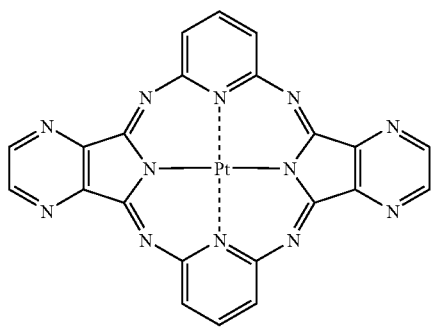
(19)

-continued
(20)
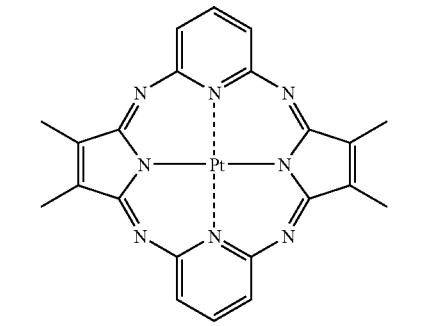
(27)
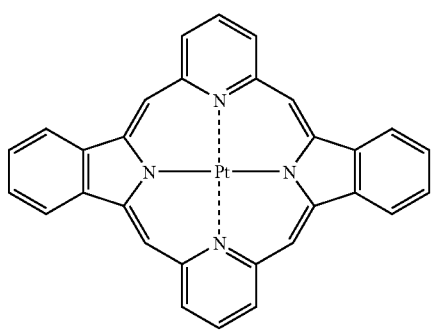
(28)
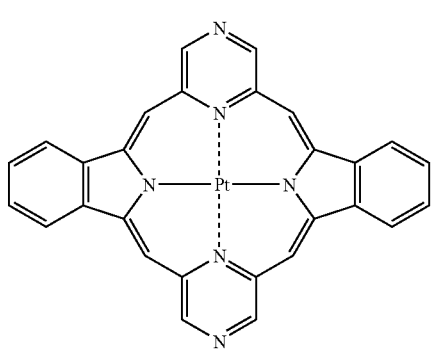
(29)
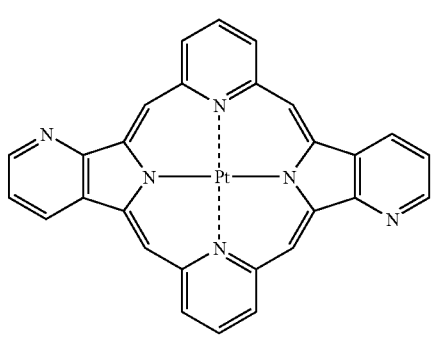
(30)
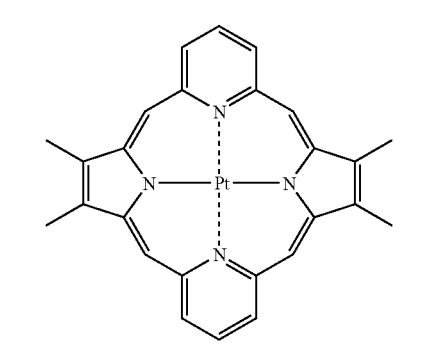
-continued
(31)
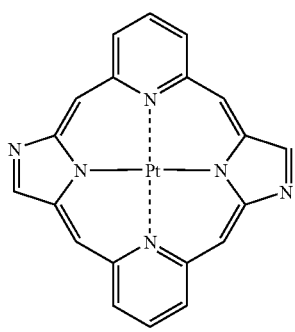
(32)
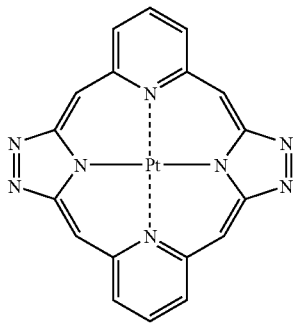
(36)
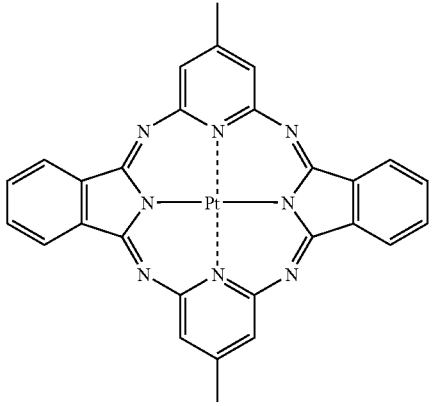
(37)
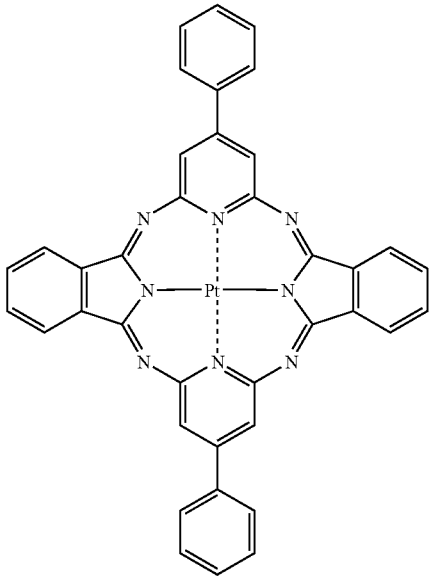

(38)
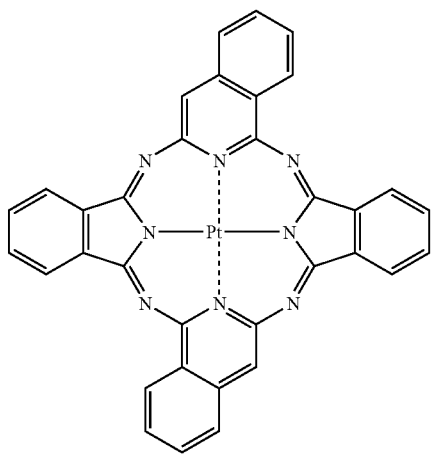
(42)
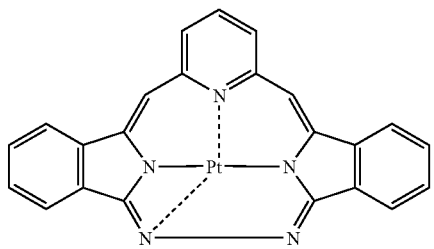
(43)
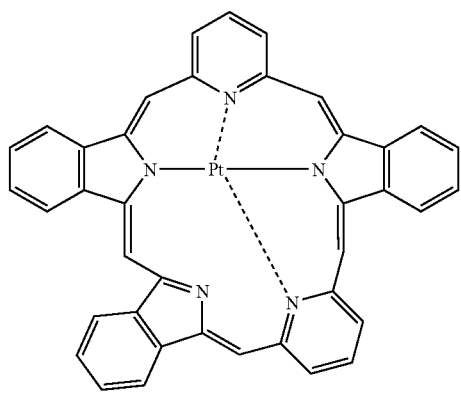
(44)
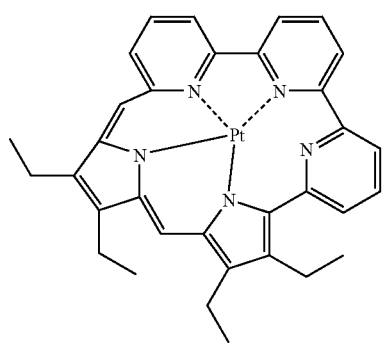
(50)
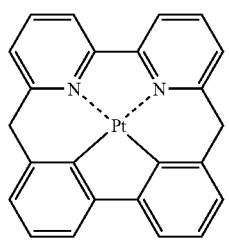
(51)
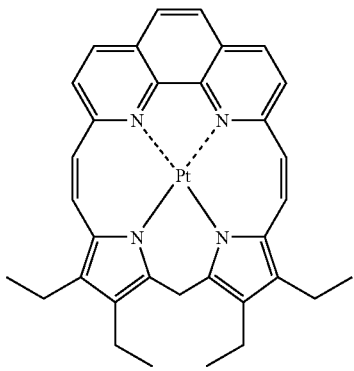
(52)
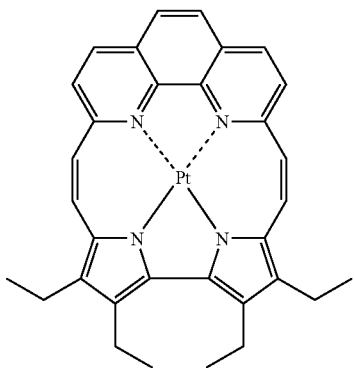
(57)
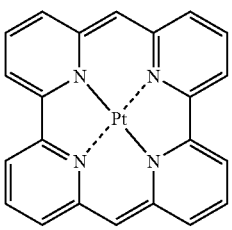
(58)
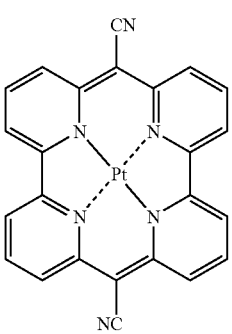

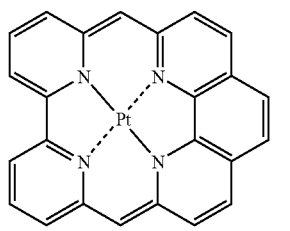
(59)
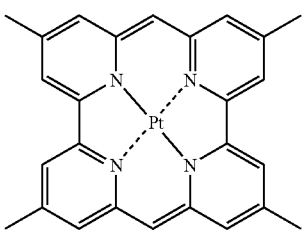
(60)
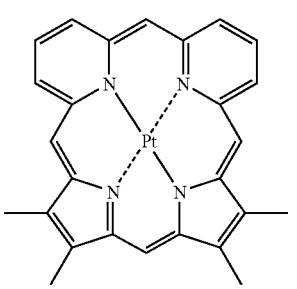
(61)
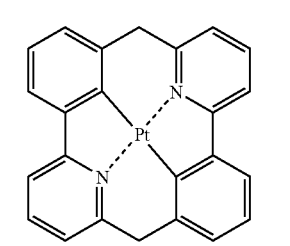
(62)
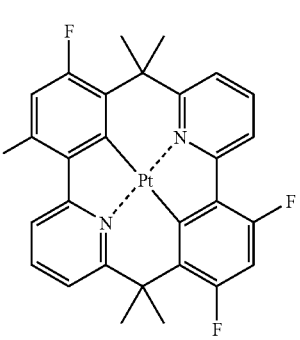
(63)
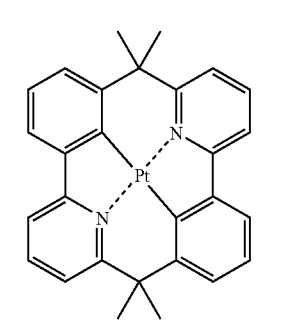
(64)
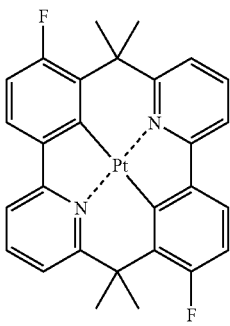
(65)
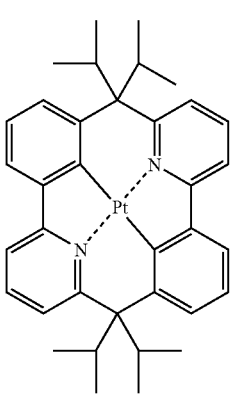
(66)
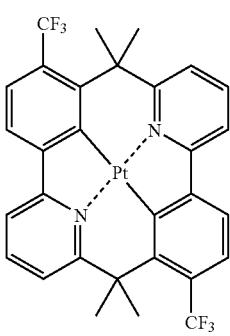
(67)
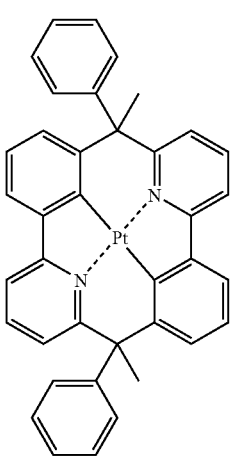
(68)

-continued
(69) 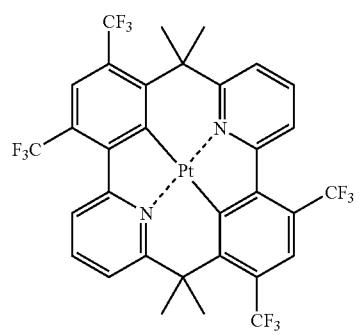
(70) 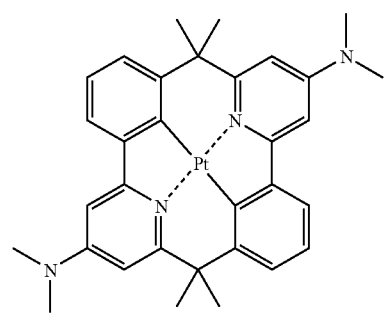
(71) 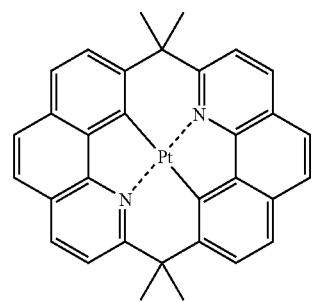
(72) 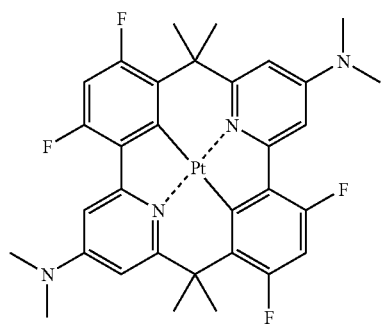
(73) 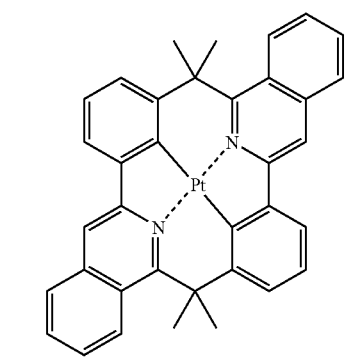
-continued
(74) 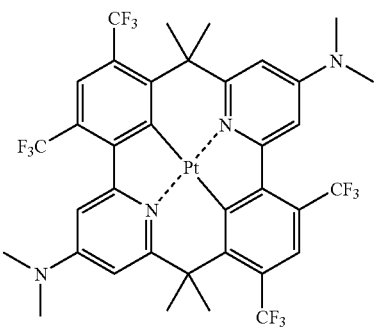
(75) 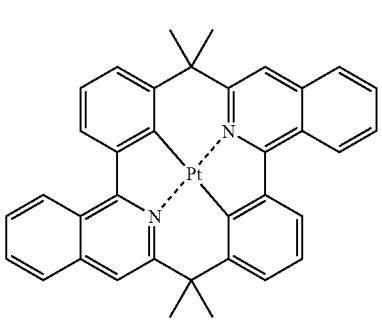
(76) 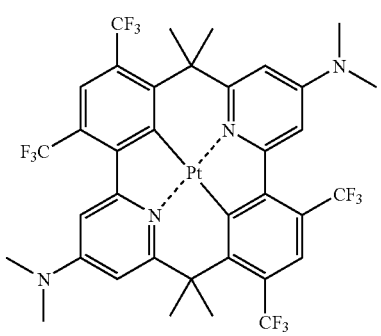
(77) 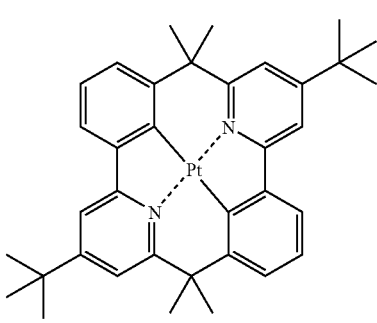
(78) 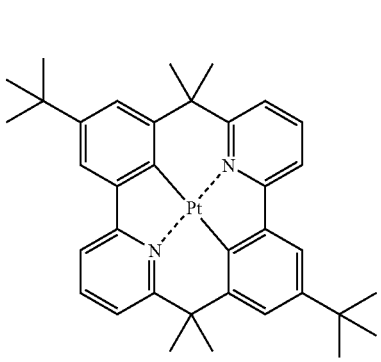

-continued
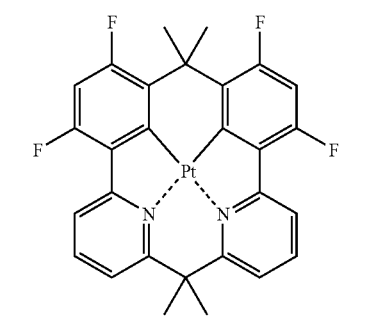
(79)
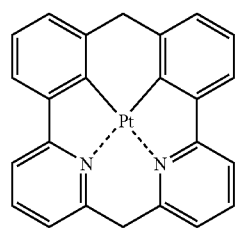
(80)
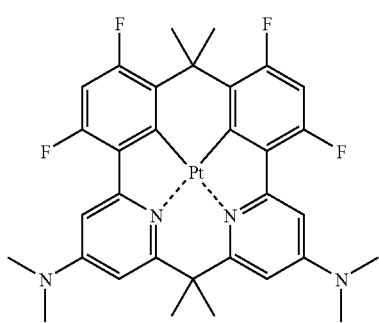
(81)
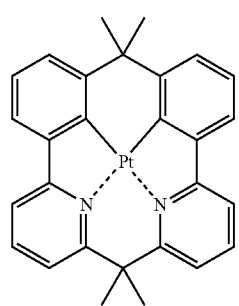
(82)
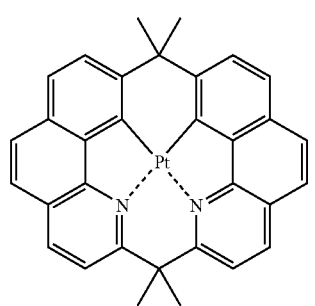
(83)
-continued
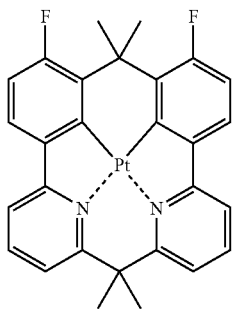
(84)
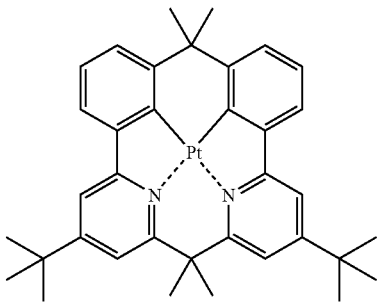
(85)
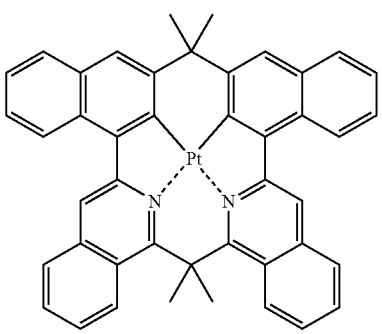
(86)
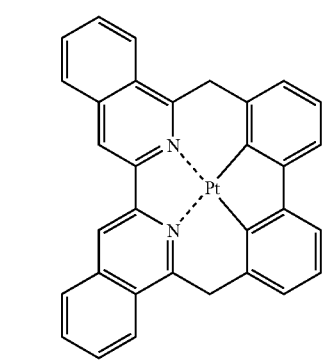
(87)
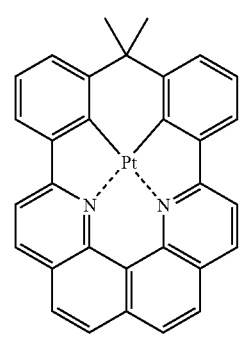
(88)

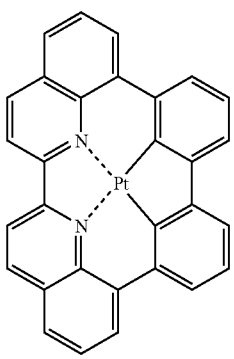 (89)
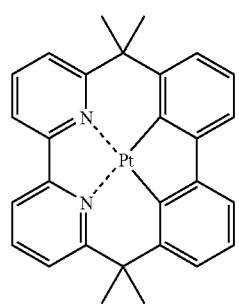 (90)
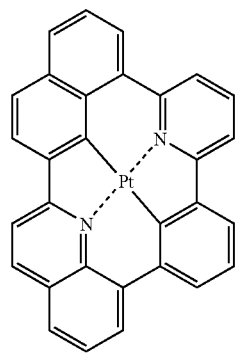 (91)
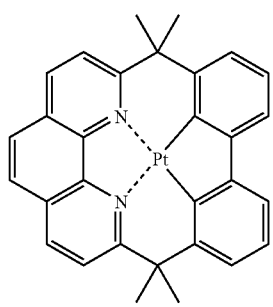 (92)
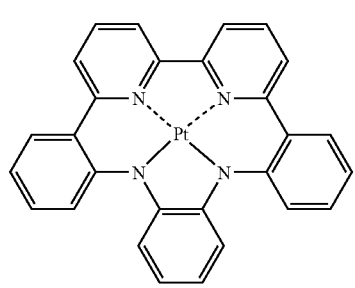 (93)
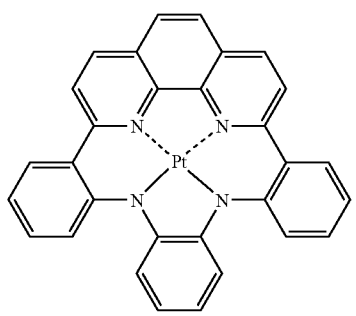 (94)
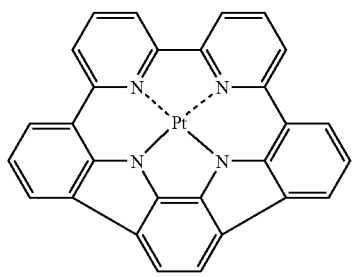 (95)
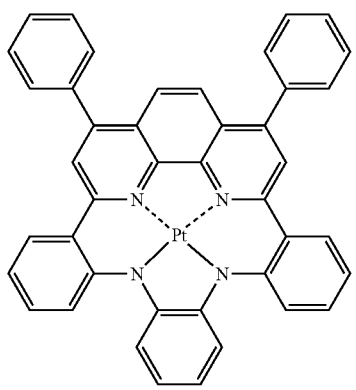 (96)
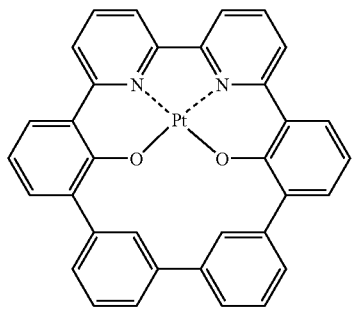 (97)
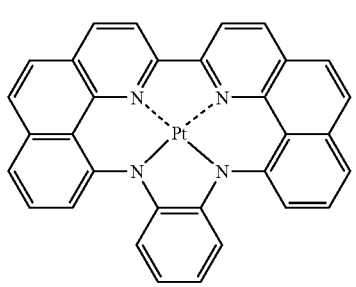 (98)

(99) 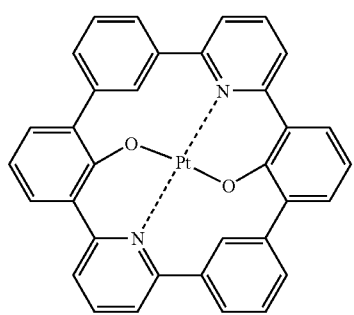
(100) 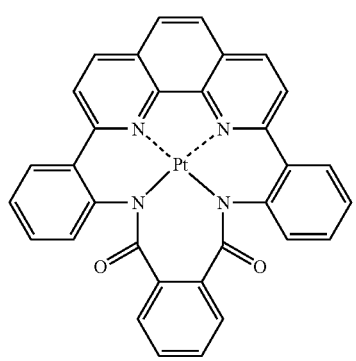
(101) 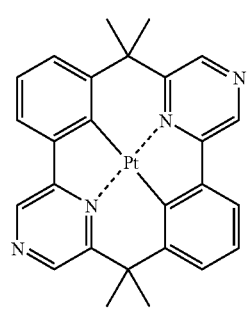
(102) 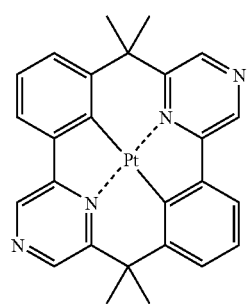
(103) 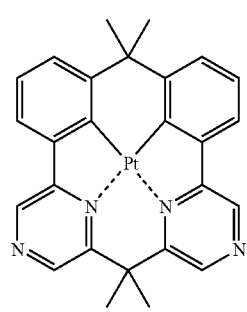
(104) 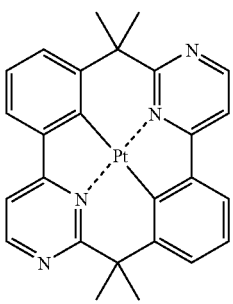
(105) 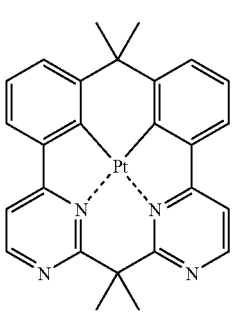
(106) 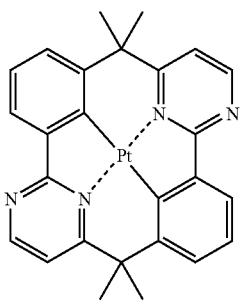
(107) 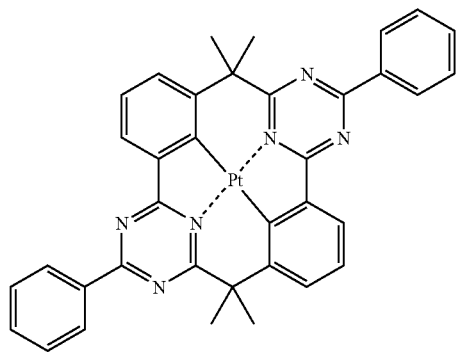
(108) 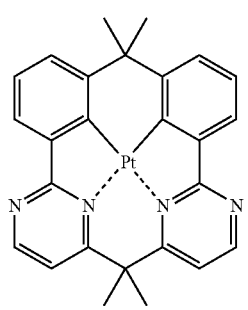

-continued
(109)
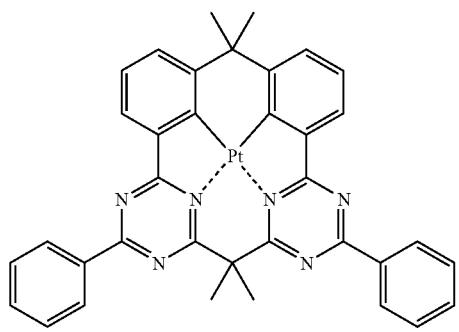
(110)
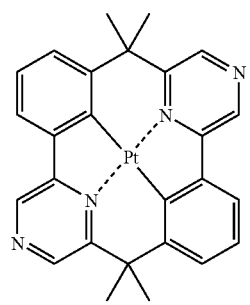
(111)
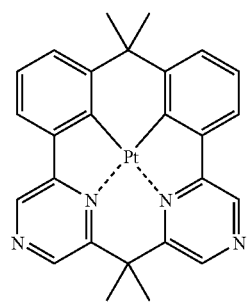
(112)
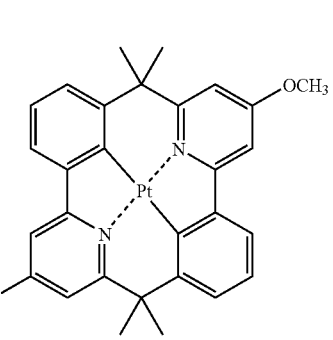
(113)
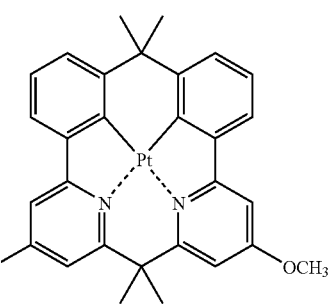
-continued
(114)
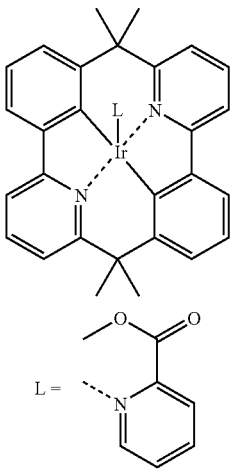
(115)
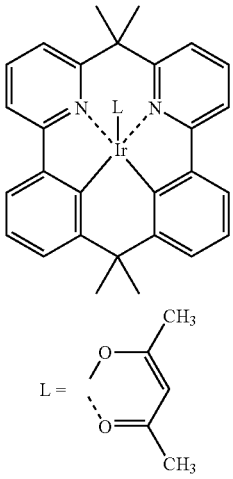
(116)
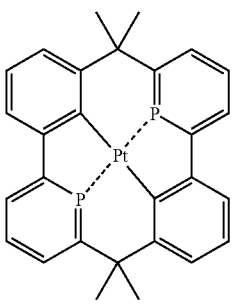
(117)
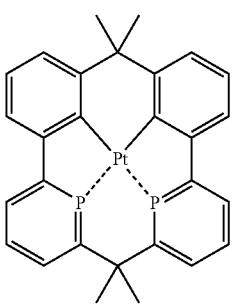

(118) 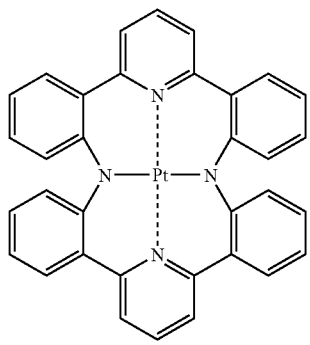
(119) 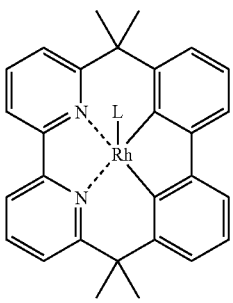
(120) 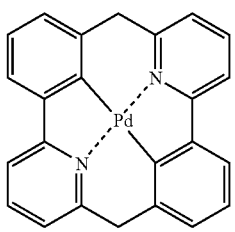
(121) 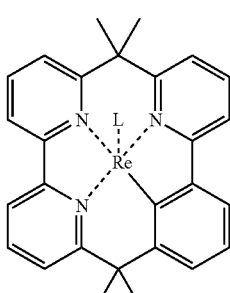
L = 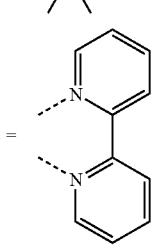
(122) 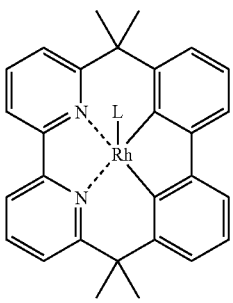
L = 
(123) 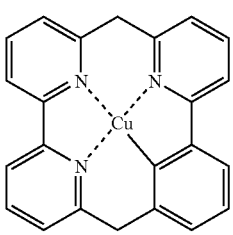
(124) 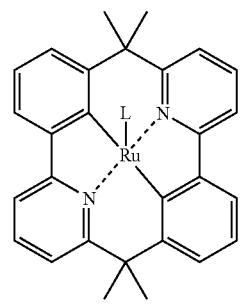
L =
(125) 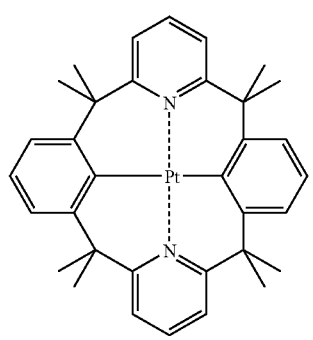

(126) 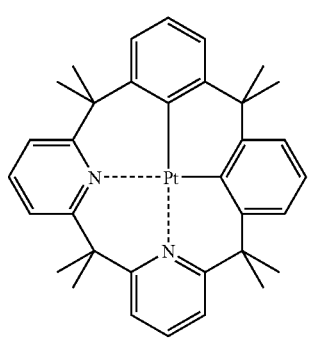
(127) 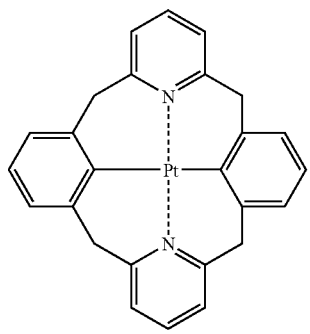
(128) 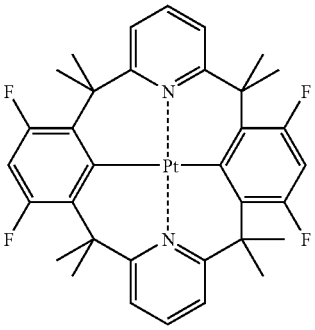
(129) 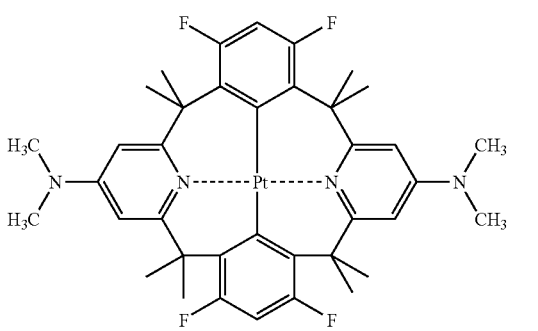
(130) 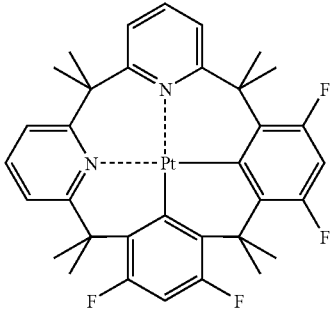
(131) 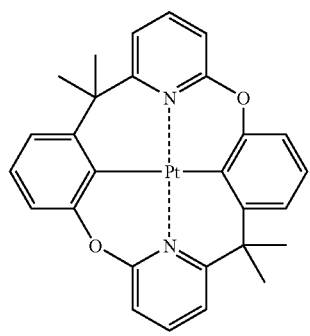
(132) 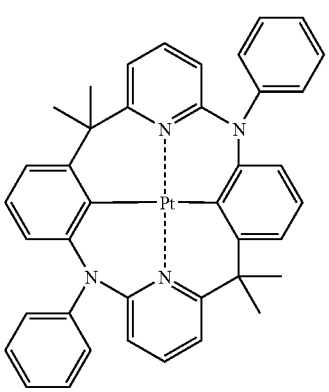
(133) 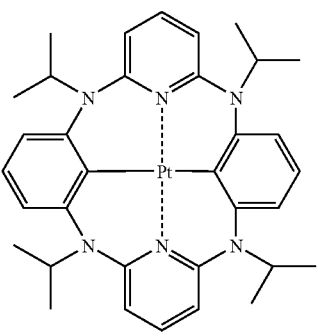
(134) 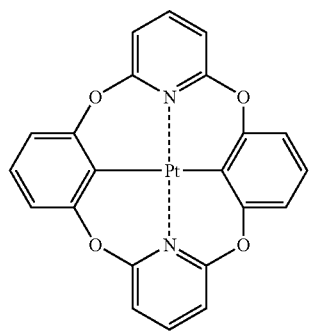

(135) 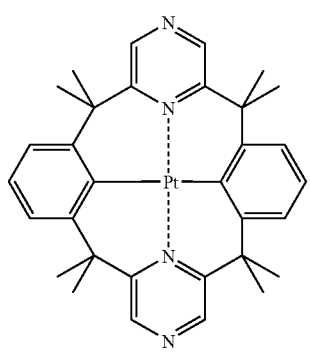
(136) 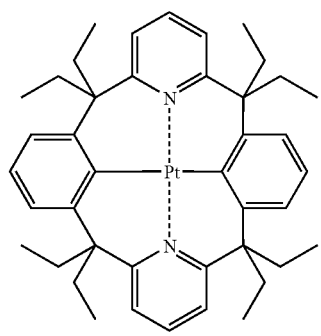
(137) 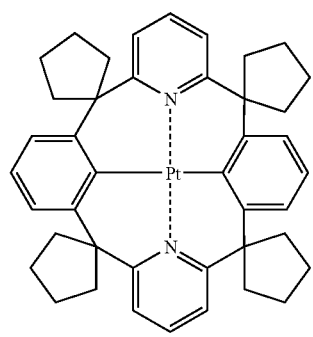
(138) 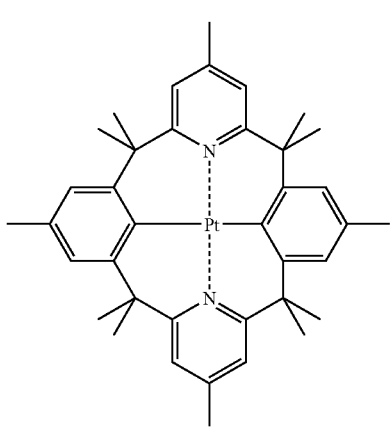
(139) 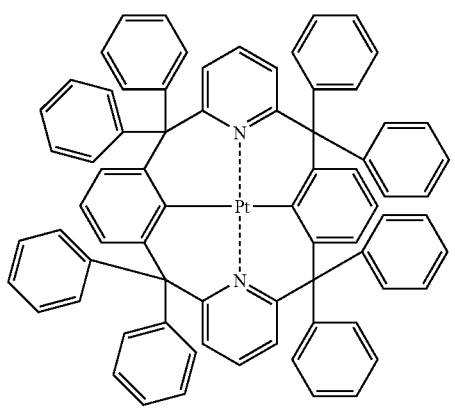
(140) 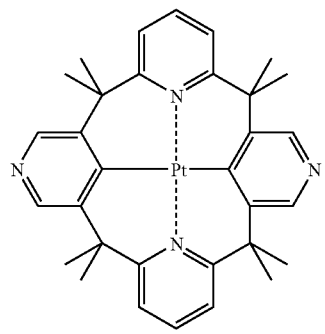
(141) 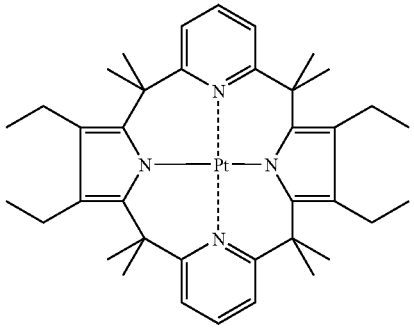
(142) 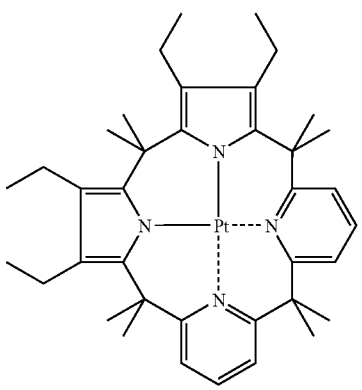

-continued
(143)
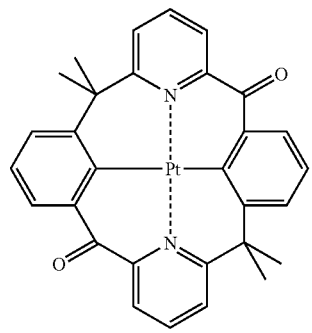
(144)
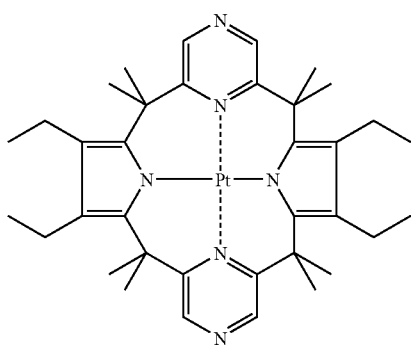
(145)
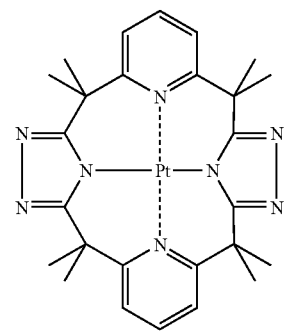
(146)
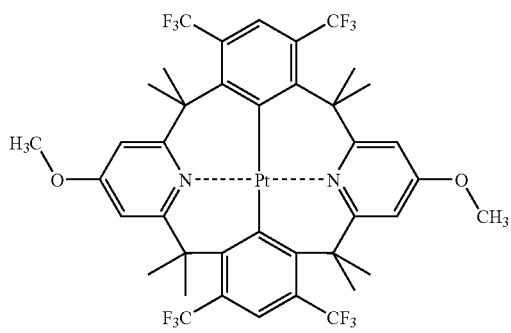
-continued
(147)
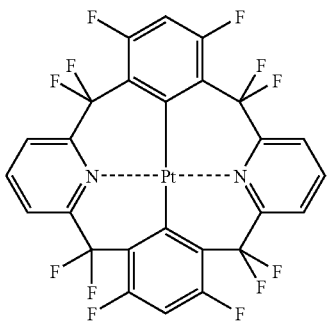
(148)
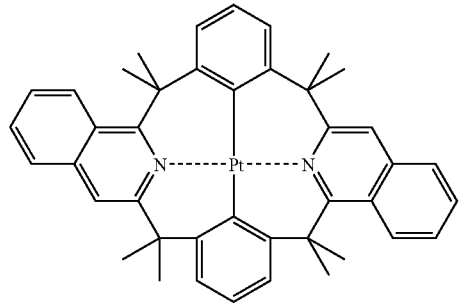
(149)
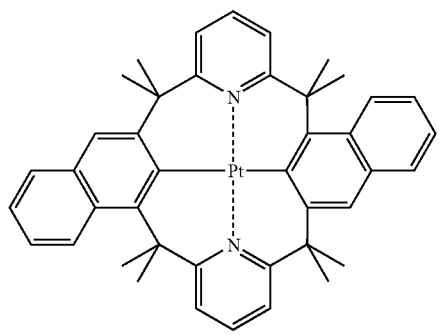
(150)
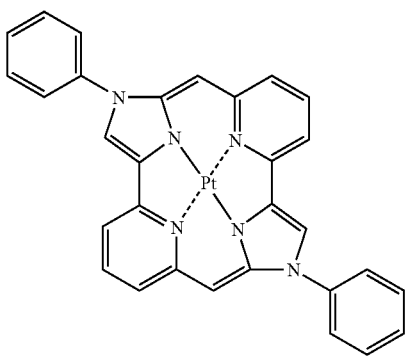
(151)
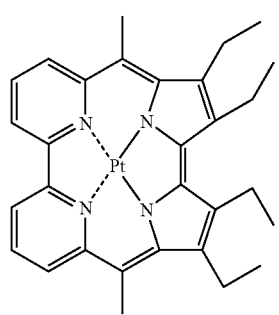

(152)

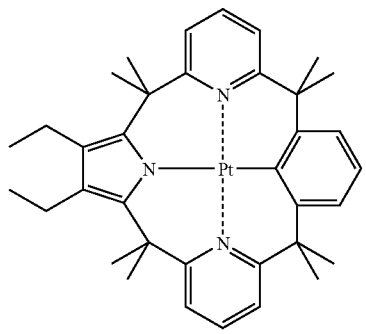

(153)

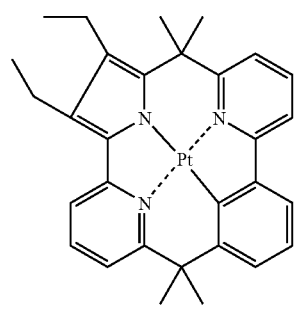

(154)

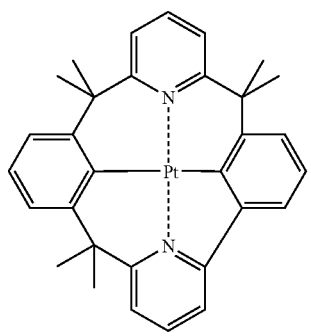

Preferable examples of the metal complex usable in the invention further include compounds represented by Formulae (A-1), (B-1), (C-1), (D-1), (E-1), or (F-1) described below.

Formula (A-1) is described below.

Formula (A-1)

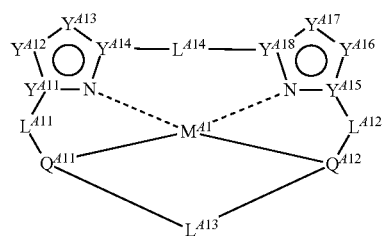

In Formula (A-1), $M^{41}$ represents a metal ion. $Y^{411}$, $Y^{414}$, $Y^{415}$ and $Y^{418}$ each independently represent a carbon atom or a nitrogen atom. $Y^{412}$, $Y^{413}$, $Y^{416}$ and $Y^{417}$ each independently represent a substituted or unsubstituted carbon atom, a substituted or unsubstituted nitrogen atom, an oxygen atom or a sulfur atom. $L^{411}$, $L^{412}$, $L^{413}$ and $L^{414}$ each represent a connecting group, and may be the same as each other or different from each other. $Q^{411}$ and $Q^{412}$ each independently represent a partial structure containing an atom bonded to $M^{41}$ via any one of a coordinate bond, an ionic bond and a covalent bond.

The compound represented by Formula (A-1) will be described in detail.

$M^{41}$ represents a metal ion. The metal ion is not particularly limited. It is preferably a divalent metal ion, more preferably $Pt^{2+}$, $Pd^{2+}$, $Cu^{2+}$, $Ni^{2+}$, $Co^{2+}$, $Zn^{2+}$, $Mg^{2+}$ or $Pb^{2+}$, still more preferably $Pt^{2+}$ or $Cu^{2+}$, and further more preferably $Pt^{2+}$.

$Y^{411}$, $Y^{414}$, $Y^{415}$ and $Y^{418}$ each independently represent a carbon atom or a nitrogen atom. Each of $Y^{411}$, $Y^{414}$, $Y^{415}$ and $Y^{418}$ is preferably a carbon atom.

$Y^{412}$, $Y^{413}$, $Y^{416}$ and $Y^{417}$ each independently represent a substituted or unsubstituted carbon atom, a substituted or unsubstituted nitrogen atom, an oxygen atom or a sulfur atom. Each of $Y^{412}$, $Y^{413}$, $Y^{416}$ and $Y^{417}$ is preferably a substituted or unsubstituted carbon atom or a substituted or unsubstituted nitrogen atom.

$L^{411}$, $L^{412}$, $L^{413}$ and $L^{414}$ each independently represent a divalent connecting group. The divalent connecting group represented by $L^{411}$, $L^{412}$, $L^{413}$ or $L^{414}$ may be, for example, a single bond or a connecting group formed of atoms selected from carbon, nitrogen, silicon, sulfur, oxygen, germanium, phosphorus and the like, more preferably a single bond, a substituted or unsubstituted carbon atom, a substituted or unsubstituted nitrogen atom, a substituted silicon atom, an oxygen atom, a sulfur atom, a divalent aromatic hydrocarbon cyclic group or a divalent aromatic heterocyclic group, still more preferably a single bond, a substituted or unsubstituted carbon atom, a substituted or unsubstituted nitrogen atom, a substituted silicon atom, a divalent aromatic hydrocarbon cyclic group or a divalent aromatic heterocyclic group, and further more preferably a single bond or a substituted or unsubstituted methylene group. Examples of the divalent connecting group represented by $L^{411}$, $L^{412}$, $L^{413}$ or $L^{414}$ include the following groups:

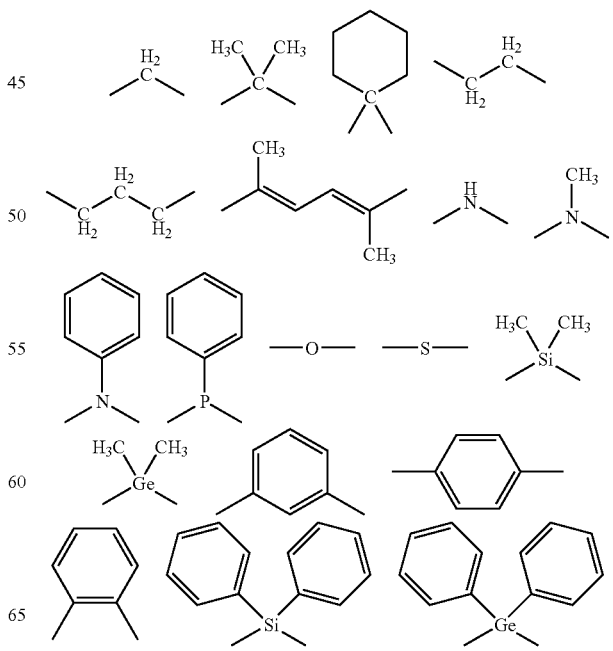

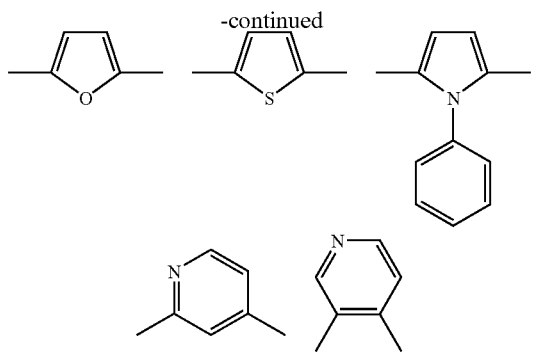

The divalent connecting group represented by $L^{A11}$, $L^{A12}$, $L^{A13}$ or $L^{A14}$ may further have a substituent. The substituent which can be introduced into the divalent connecting group may be, and examples thereof include, an alkyl group (preferably those having 1 to 30 carbon atoms, more preferably those having 1 to 20 carbon atoms, particularly preferably those having 1 to 10 carbon atoms, and examples thereof include a methyl group, an ethyl group, an iso-propyl group, a tert-butyl group, a n-octyl group, a n-decyl group, a n-hexadecyl group, a cyclopropyl group, a cyclopentyl group, a cyclohexyl group, and the like), an alkenyl group (preferably those having 2 to 30 carbon atoms, more preferably those having 2 to 20 carbon atoms, particularly preferably those having 2 to 10 carbon atoms, and examples thereof include a vinyl group, an allyl group, a 2-butenyl group, a 3-pentenyl group, and the like), an alkynyl group (preferably those having 2 to 30 carbon atoms, more preferably those having 2 to 20 carbon atoms, particularly preferably those having 2 to 10 carbon atoms, and examples thereof include a propargyl group, a 3-pentynyl group, and the like), an aryl group (preferably those having 6 to 30 carbon atoms, more preferably those having 6 to 20 carbon atoms, particularly preferably those having 6 to 12 carbon atoms, and examples thereof include a phenyl group, a p-methylphenyl group, a naphthyl group, an anthranyl group, and the like), an amino group preferably those having 0 to 30 carbon atoms, more preferably those having 0 to 20 carbon atoms, particularly preferably those having 0 to 10 carbon atoms, and examples thereof include an amino group, a methylamino group, a dimethylamino group, a diethylamino group, a dibenzylamino group, a diphenylamino group, a ditolylamino group, a methylphenylamino group, and the like), an alkoxy group (preferably those having 1 to 30 carbon atoms, more preferably those having 1 to 20 carbon atoms, particularly preferably those having 1 to 10 carbon atoms, and examples thereof include a methoxy group, an ethoxy group, a butoxy group, a 2-ethylhexyloxy group, and the like), an aryloxy group (preferably those having 6 to 30 carbon atoms, more preferably those having 6 to 20 carbon atoms, particularly preferably those having 6 to 12 carbon atoms, and examples thereof include a phenyloxy group, a 1-naphthyloxy group, a 2-naphthyloxy group, 4-phenylphenyloxy group, 4-cyanophenyloxy group, and the like), a heterocyclic oxy group (preferably those having 1 to 30 carbon atoms, more preferably those having 1 to 20 carbon atoms, particularly preferably those having 1 to 12 carbon atoms, and examples thereof include a pyridyloxy group, a pyrazyloxy group, a pyrimidyloxy group, a quinolyloxy group, and the like), an acyl group (preferably those having 1 to 30 carbon atoms, more preferably those having 1 to 20 carbon atoms, particularly preferably those having 1 to 12 carbon atoms, and examples thereof include an acetyl group, a benzoyl group, a formyl group, a pivaloyl group, and the like), an alkoxycarbonyl group (preferably those having 2 to 30 carbon atoms, more preferably those having 2 to 20 carbon atoms, particularly preferably those having 2 to 12 carbon atoms, and examples thereof include a methoxycarbonyl group, an ethoxycarbonyl group, and the like), an aryloxycarbonyl group (preferably those having 7 to 30 carbon atoms, more preferably those having 7 to 20 carbon atoms, particularly preferably those having 7 to 12 carbon atoms, and examples thereof include a phenyloxycarbonyl group and the like), an acyloxy group (preferably those having 2 to 30 carbon atoms, more preferably those having 2 to 20 carbon atoms, particularly preferably those having 2 to 10 carbon atoms, and examples thereof include an acetoxy group, a benzoyloxy group, and the like), an acylamino group (preferably those having 2 to 30 carbon atoms, more preferably those having 2 to 20 carbon atoms, particularly preferably those having 2 to 10 carbon atoms, and examples thereof include an acetylamino group, a benzoylamino group and the like), an alkoxycarbonylamino group (preferably those having 2 to 30 carbon atoms, more preferably those having 2 to 20 carbon atoms, particularly preferably those having 2 to 12 carbon atoms, and examples thereof include a methoxycarbonylamino group and the like), an aryloxycarbonylamino group (preferably those having 7 to 30 carbon atoms, more preferably those having 7 to 20 carbon atoms, particularly preferably those having 7 to 12 carbon atoms, and examples thereof include a phenyloxycarbonylamino group and the like), a sulfonylamino group (preferably those having 1 to 30 carbon atoms, more preferably those having 1 to 20 carbon atoms, particularly preferably those having 1 to 12 carbon atoms, and examples thereof include a methanesulfonylamino group, a benzenesulfonylamino group and the like), a sulfamoyl group (preferably those having 0 to 30 carbon atoms, more preferably those having 0 to 20 carbon atoms, particularly preferably those having 0 to 12 carbon atoms, and examples thereof include a sulfamoyl group, a methylsulfamoyl group, a dimethylsulfamoyl group, a phenylsulfamoyl group and the like), a carbamoyl group (preferably those having 1 to 30 carbon atoms, more preferably those having 1 to 20 carbon atoms, particularly preferably those having 1 to 12 carbon atoms, and examples thereof include a carbamoyl group, a methylcarbamoyl group, a diethylcarbamoyl group, a phenylcarbamoyl group and the like), an alkylthio group (preferably those having 1 to 30 carbon atoms, more preferably those having 1 to 20 carbon atoms, particularly preferably those having 1 to 12 carbon atoms, and examples thereof include a methylthio group, an ethylthio group, and the like), an arylthio group (preferably those having 6 to 30 carbon atoms, more preferably those having 6 to 20 carbon atoms, particularly preferably those having 6 to 12 carbon atoms, and examples thereof include a phenylthio group and the like), a heterocyclic thio group (preferably those having 1 to 30 carbon atoms, more preferably those having 1 to 20 carbon atoms, particularly preferably those having 1 to 12 carbon atoms, and examples thereof include a pyridylthio group, a 2-benzimidazolylthio group, a 2-benzoxazolylthio group, a 2-benzthiazolylthio group and the like), a sulfonyl group (preferably those having 1 to 30 carbon atoms, more preferably those having 1 to 20 carbon atoms, particularly preferably those having 1 to 12 carbon atoms, and examples thereof include a mesyl group, a tosyl group and the like), a sulfinyl group (preferably those having 1 to 30 carbon atoms, more preferably those having 1 to 20 carbon atoms, particularly preferably those having 1 to 12 carbon atoms, and examples thereof include a methanesulfinyl group, a benzenesulfinyl group and the like), a ureido group (preferably those having 1 to 30 carbon atoms, more preferably those having 1 to 20 carbon atoms, particularly preferably those having 1 to 12 carbon atoms, and examples thereof include a ureido group, a methylureido group, a phenylureido group and the like), a phosphoric amide group (preferably those having 1 to 30 carbon atoms, more preferably those having 1 to 20 carbon atoms, particularly preferably those having 1 to 12 carbon atoms, and examples thereof include a diethylphosphoric amide group, a phenylphosphoric amide group, and the like), a hydroxy group, a mercapto group, a halogen atom (and examples thereof include a fluorine atom, chlorine atom, bromine atom, iodine atom), a cyano group, a sulfo group, a carboxyl group, a nitro group, a hydroxamic acid group, a sulfino group, a hydrazino group, an imino group, a heterocyclic group (preferably those having 1 to 30 carbon atoms, more preferably those having 1 to 12 carbon atoms containing a heteroatom such as a nitrogen atom, an oxygen atom or a sulfur atom, specific examples thereof include an imidazolyl group, a pyridyl group, a quinolyl group, a furyl group, a thienyl group, a piperidyl group, a morpholino group, a benzoxazolyl group, a benzimidazolyl group, a benzthiazolyl group, a carbazolyl group, an azepinyl group, and the like), a silyl group (preferably those having 3 to 40 carbon atoms, more preferably those having 3 to 30 carbon atoms, particularly preferably those having 3 to 24 carbon atoms, and examples thereof include a trimethylsilyl group, a triphenylsilyl group and the like) or a silyloxy group (preferably those having 3 to 40 carbon atoms, more preferably those having 3 to 30 carbon atoms, particularly preferably those having 3 to 24 carbon atoms, and examples thereof include a trimethylsilyloxy group, a triphenylsilyloxy group and the like).

These substituents may further have a substituent(s). Substituents which can be introduced to these substituents are each preferably selected from an alkyl group, an aryl group, a heterocyclic group, a halogen atom and a silyl group, more preferably selected from an alkyl group, an aryl group, a heterocyclic group and a halogen atom, and still more preferably selected from an alkyl group, an aryl group, an aromatic heterocyclic group and a fluorine atom.

$Q^{411}$ and $Q^{412}$ each independently represent a partial structure containing an atom covalently bonded to $M^{41}$. $Q^{411}$ and $Q^{412}$ each independently preferably represent a group having a carbon atom bonded to $M^{41}$, a group having a nitrogen atom bonded to $M^{41}$, a group having a silicon atom bonded to $M^{41}$, a group having a phosphorus atom bonded to $M^{41}$, a group having an oxygen atom bonded to $M^{41}$ or a group having a sulfur atom bonded to $M^{41}$, more preferably a group having a carbon atom, a nitrogen atom, an oxygen atom, or a sulfur atom bonded to $M^{41}$, still more preferably a group having a carbon group or nitrogen atom bonded to $M^{41}$, and further more preferably a group having a carbon atom bonded to $M^{41}$.

The group bonded to $M^{41}$ via a carbon atom is preferably an aryl group having a carbon atom bonded to $M^{41}$, a 5-membered cyclic heteroaryl group having a carbon atom bonded to $M^{41}$, or a 6-membered cyclic heteroaryl group having a carbon atom bonded to $M^{41}$, more preferably an aryl group having a carbon atom bonded to $M^{41}$, a nitrogen-containing 5-membered cyclic heteroaryl group having a carbon atom bonded to $M^{41}$ or a nitrogen-containing 6-membered cyclic heteroaryl group having a carbon atom bonded to $M^{41}$, and still more preferably an aryl group having a carbon atom bonded to $M^{41}$.

The group bonded to $M^{41}$ via a nitrogen atom is preferably a substituted amino group or a nitrogen-containing 5-membered cyclic heteroaryl group having a nitrogen atom bonded to $M^{41}$, more preferably a nitrogen-containing 5-membered cyclic heteroaryl group having a nitrogen atom bonded to $M^{41}$.

The group bonded to $M^{41}$ via a phosphorus atom is preferably a substituted phosphino group. The group having a silicon atom bonded to $M^{41}$ is preferably a substituted silyl group. The group having an oxygen atom bonded to $M^{41}$ is preferably an oxy group, and the group having a sulfur atom bonded to $M^{41}$ is preferably a sulfide group.

The compound represented by Formula (A-1) is more preferably a compound represented by the following Formula (A-2), (A-3) or (A-4).

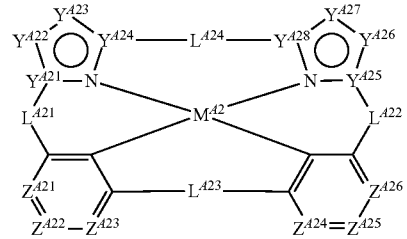

Formula (A-2)

In Formula (A-2), $M^{42}$ represents a metal ion $Y^{421}$, $Y^{424}$, $Y^{425}$ and $Y^{428}$ each independently represent a carbon atom or a nitrogen atom. $Y^{422}$, $Y^{423}$, $Y^{426}$ and $Y^{427}$ each independently represent a substituted or unsubstituted carbon atom, a substituted or unsubstituted nitrogen atom, an oxygen atom or a sulfur atom. $L^{421}$, $L^{422}$, $L^{423}$ and $L^{424}$ each independently represent a connecting group. $Z^{421}$, $Z^{422}$, $Z^{423}$, $Z^{424}$, $Z^{425}$ and $Z^{426}$ each independently represent a nitrogen atom or a substituted or unsubstituted carbon atom.

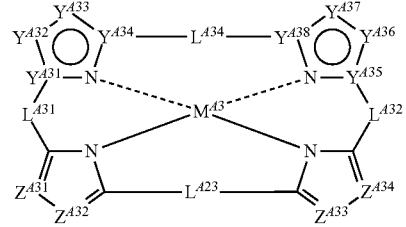

Formula (A-3)

In Formula (A-3), $M^{43}$ represents a metal ion. $Y^{431}$, $Y^{434}$, $Y^{435}$ and $Y^{438}$ each independently represent a carbon atom or a nitrogen atom. $Y^{432}$, $Y^{433}$, $Y^{436}$ and $Y^{437}$ each independently represent a substituted or unsubstituted carbon atom, a substituted or unsubstituted nitrogen atom, an oxygen atom or a sulfur atom. $L^{431}$, $L^{432}$, $L^{433}$ and $L^{434}$ each independently represent a connecting group. $Z^{431}$, $Z^{432}$, $Z^{433}$ and $Z^{434}$ each independently represent a nitrogen atom or a substituted or unsubstituted carbon atom.

Formula (A-4)

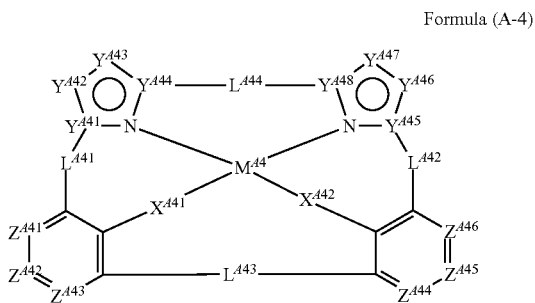

In Formula (A-4), $M^{A4}$ represents a metal ion. $Y^{A41}$, $Y^{A44}$, $Y^{A45}$ and $Y^{A48}$ each independently represent a carbon atom or a nitrogen atom. $Y^{A42}$, $Y^{A43}$, $Y^{A46}$ and $Y^{A47}$ each independently represent a substituted or unsubstituted carbon atom, a substituted or unsubstituted nitrogen atom, an oxygen atom or a sulfur atom. $L^{A41}$, $L^{A42}$, $L^{A43}$ and $L^{A44}$ each independently represent a connecting group. $Z^{A41}$, $Z^{A42}$, $Z^{A43}$, $Y^{A44}$, $Z^{A45}$ and $Z^{A46}$ each independently represent a nitrogen atom or a substituted or unsubstituted carbon atom. $X^{A41}$ and $X^{A42}$ each independently represent an oxygen atom, a sulfur atom or a substituted or unsubstituted nitrogen atom.

The compound represented by Formula (A-2) will be described in detail.

$M^{A2}$, $Y^{A21}$, $Y^{A24}$, $Y^{A25}$, $Y^{A28}$, $Y^{A22}$, $Y^{A23}$, $Y^{A26}$, $Y^{A27}$, $L^{A21}$, $L^{A22}$, $L^{A23}$ and $L^{A24}$ have the same definitions as corresponding $M^{A1}$, $Y^{A11}$, $Y^{A14}$, $Y^{A15}$, $Y^{A18}$, $Y^{A12}$, $Y^{A13}$, $Y^{A16}$, $Y^{A17}$, $L^{A11}$, $L^{A12}$, $L^{A13}$ and $L^{A14}$ in Formula (A-1) respectively, and their preferable examples are also the same.

$Z^{A21}$, $Z^{A22}$, $Z^{A23}$, $Z^{A24}$, $Z^{A25}$ and $Z^{A26}$ each independently represent a nitrogen atom or a substituted or unsubstituted carbon atom. $Z^{A21}$, $Z^{A22}$, $Z^{A23}$, $Z^{A24}$, $Z^{A25}$ and $Z^{A26}$ each independently represent preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

The compound represented by Formula (A-3) will be described in detail.

$M^{A3}$, $Y^{A31}$, $Y^{A34}$, $Y^{A35}$, $Y^{A38}$, $Y^{A32}$, $Y^{A33}$, $Y^{A36}$, $Y^{A37}$, $L^{A31}$, $L^{A32}$, $L^{A33}$ and $L^{A34}$ have the same definitions as corresponding $M^{A1}$, $Y^{A11}$, $Y^{A14}$, $Y^{A15}$, $Y^{A18}$, $Y^{A12}$, $Y^{A13}$, $Y^{A16}$, $Y^{A17}$, $L^{A11}$, $L^{A12}$, $L^{A13}$ and $L^{A14}$ in Formula (A-1) respectively, and their preferable examples are also the same.

$Z^{A31}$, $Z^{A32}$, $Z^{A33}$ and $Z^{A34}$ each independently represent a nitrogen atom or a substituted or unsubstituted carbon atom. Each of $Z^{A31}$, $Z^{A32}$, $Z^{A33}$ and $Z^{A34}$ is preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

The compound represented by Formula (A-4) will be described in detail.

$M^{A4}$, $Y^{A41}$, $Y^{A44}$, $Y^{A45}$, $Y^{A48}$, $Y^{A42}$, $Y^{A43}$, $Y^{A46}$, $Y^{A47}$, $L^{A41}$, $L^{A42}$, $L^{A43}$ and $L^{A44}$ have the same definitions as corresponding $M^{A1}$, $Y^{A11}$, $Y^{A14}$, $Y^{A15}$, $Y^{A18}$, $Y^{A12}$, $Y^{A13}$, $Y^{A16}$, $Y^{A17}$, $L^{A11}$, $L^{A12}$, $L^{A13}$ and $L^{A14}$ in Formula (A-1) respectively, and their preferable examples are also the same.

$Z^{A41}$, $Z^{A42}$, $Z^{A43}$, $Z^{A44}$, $Z^{A45}$ and $Z^{A46}$ each independently represent a nitrogen atom or a substituted or unsubstituted carbon atom. Each of $Z^{A41}$, $Z^{A42}$, $Z^{A43}$, $Z^{A44}$, $Z^{A45}$ and $Z^{A46}$ is preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

$X^{A41}$ and $X^{A42}$ each independently represent an oxygen atom, a sulfur atom or a substituted or unsubstituted nitrogen atom. Each of $X^{A41}$ and $X^{A42}$ is preferably an oxygen atom or a sulfur atom, and more preferably an oxygen atom.

Specific examples of the compound represented by Formula (A-1) are shown below. However, the specific examples should not be construed as limiting the invention.

(A1)

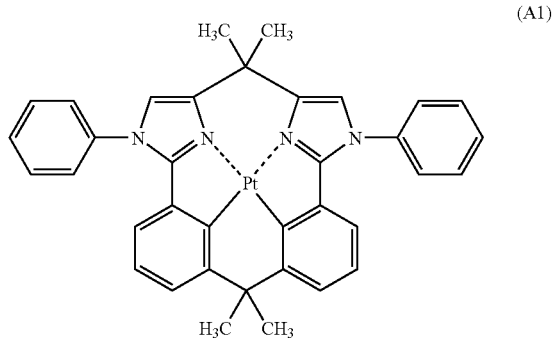

(A2)

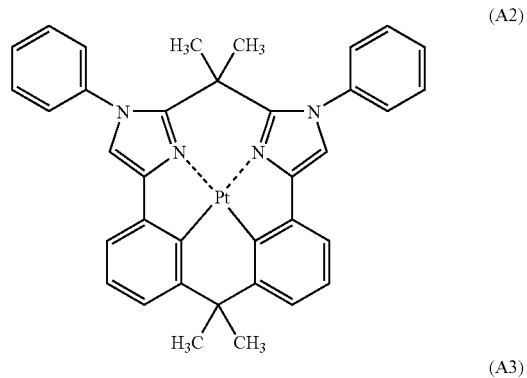

(A3)

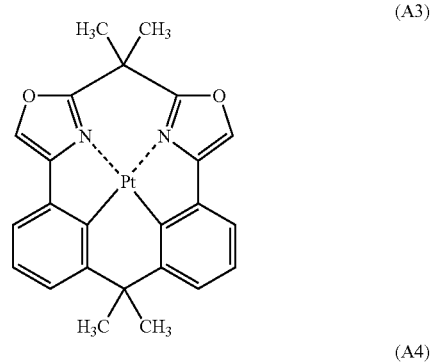

(A4)

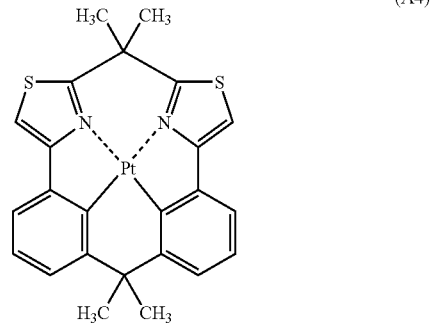

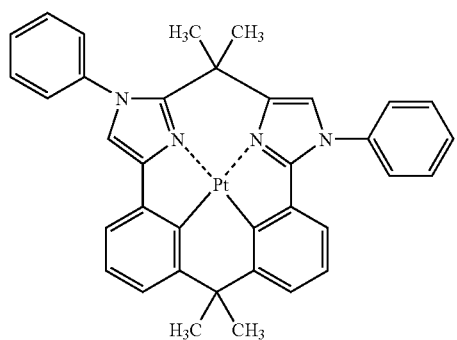 (A5)
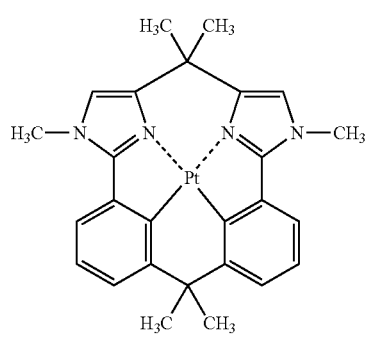 (A6)
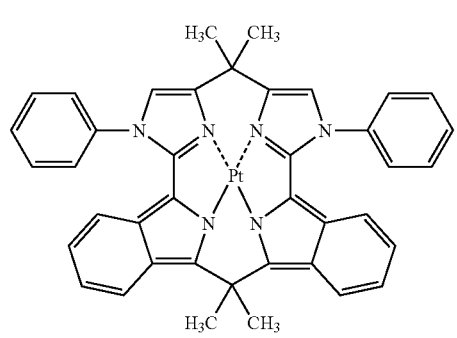 (A7)
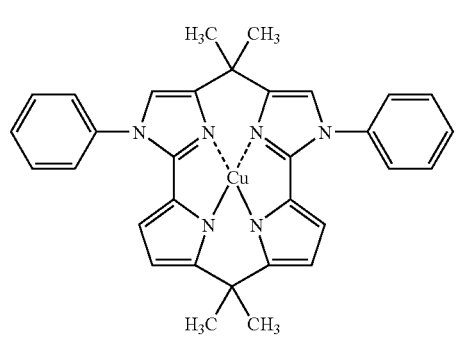 (A8)
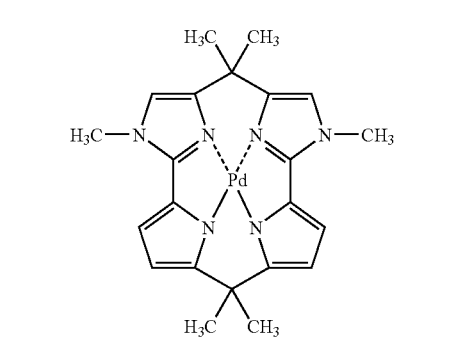 (A9)
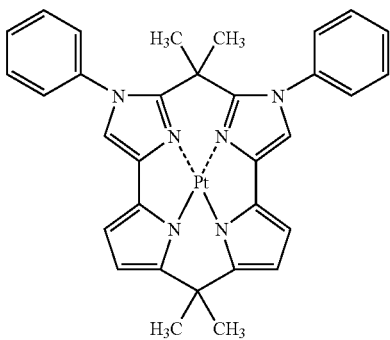 (A10)
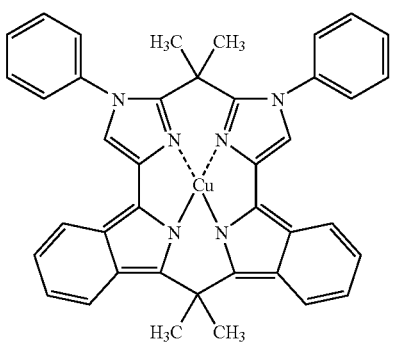 (A11)
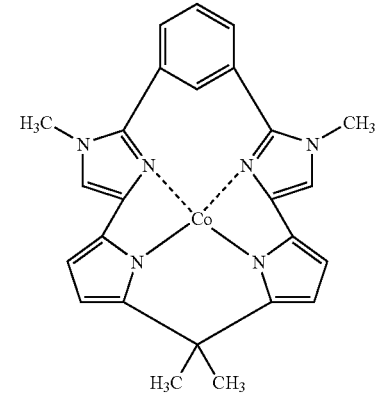 (A12)
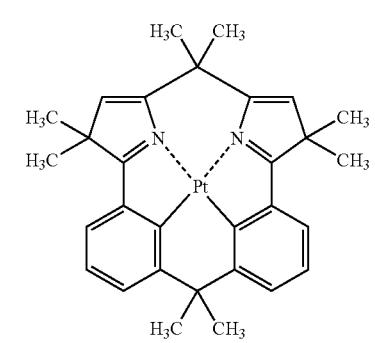 (A13)

-continued
(A14)
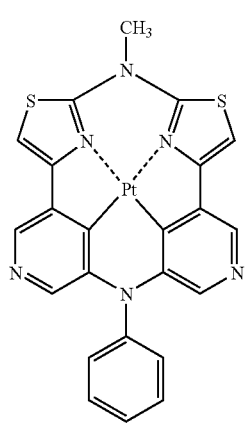
(A15)
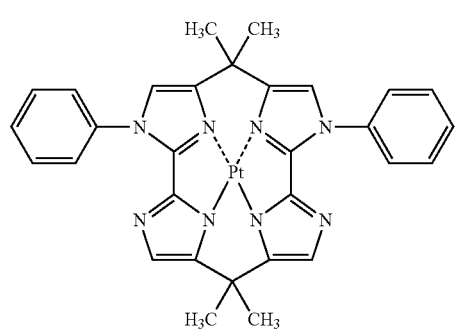
(A16)
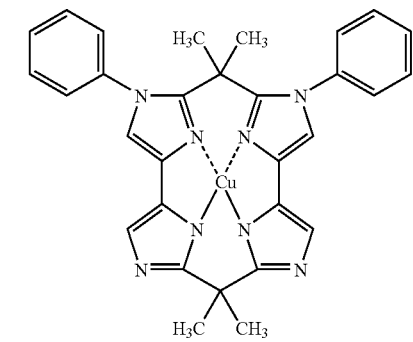
(A17)
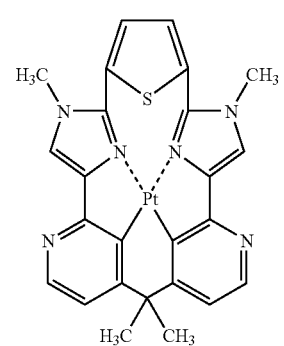
-continued
(A18)
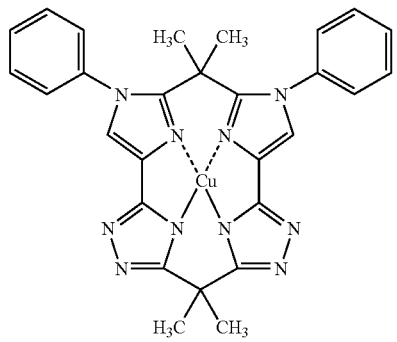
(A19)
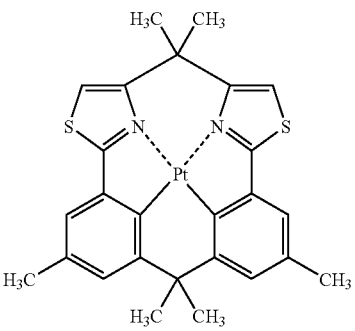
(A20)
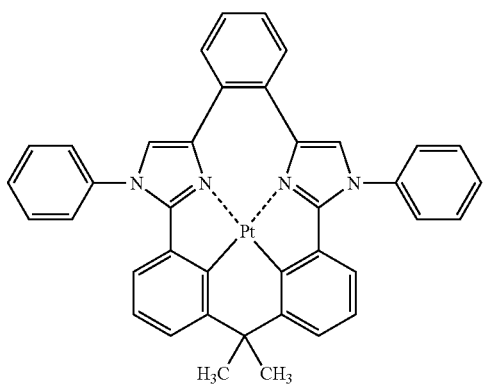
(A21)
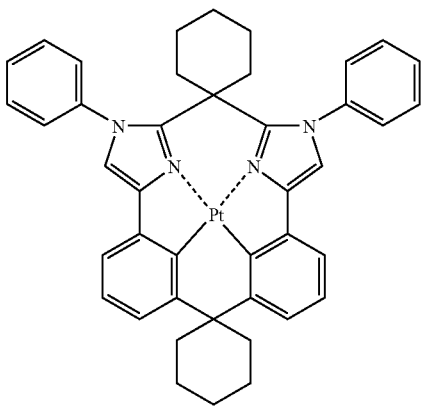

(A22)
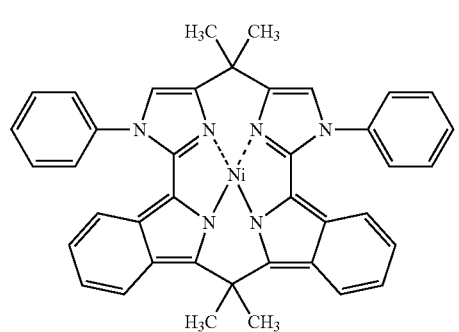
(A23)
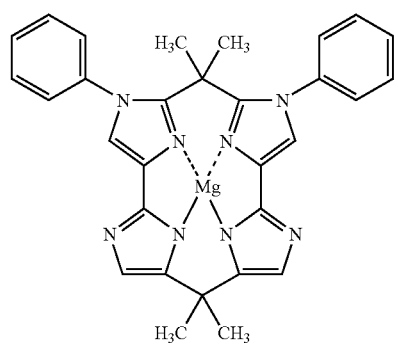
(A24)
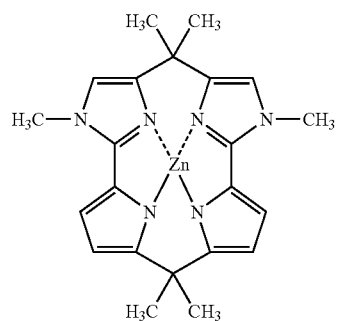
(A25)
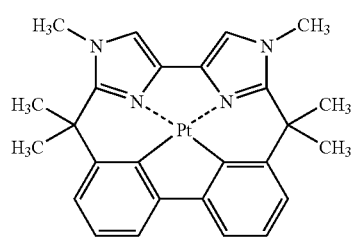
(A26)
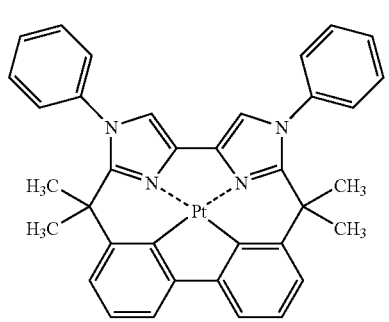
(A27)
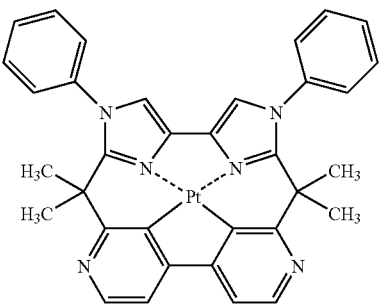
(A28)
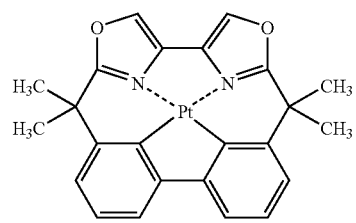
(A29)
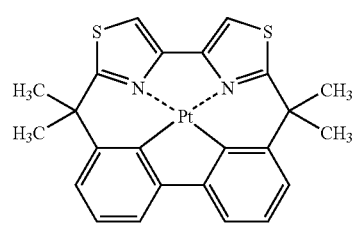
(A30)
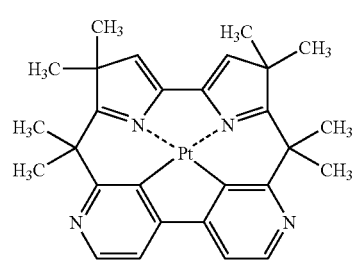
(A31)
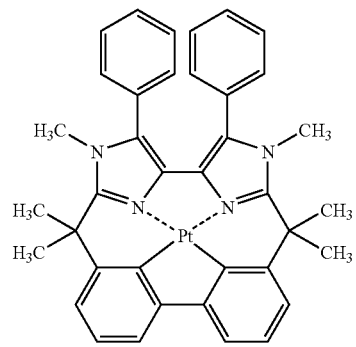

-continued
(A32) 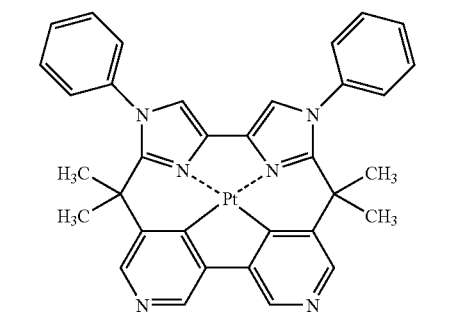
(A33) 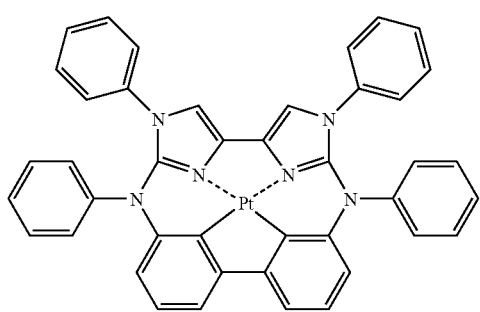
(A34) 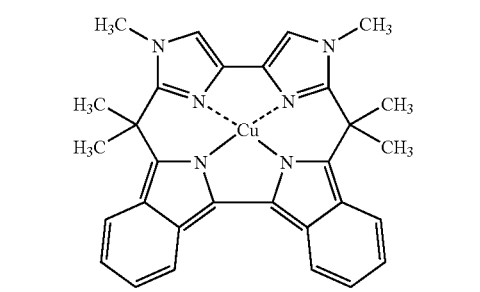
(A35) 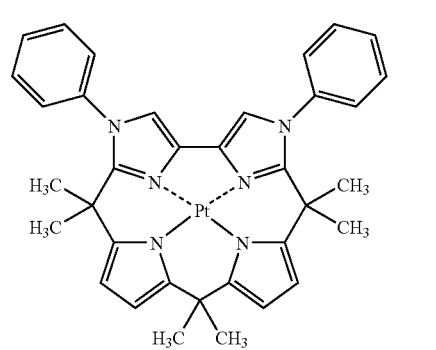
(A36) 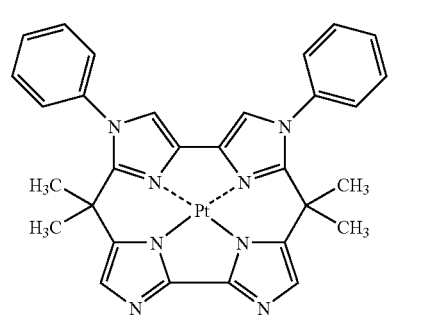
-continued
(A37) 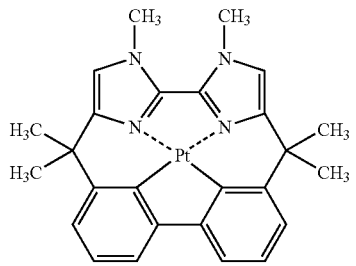
(A38) 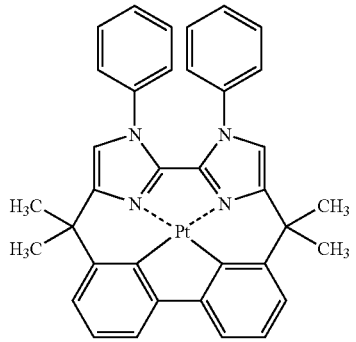
(A39) 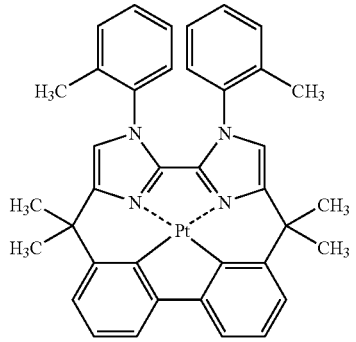
(40) 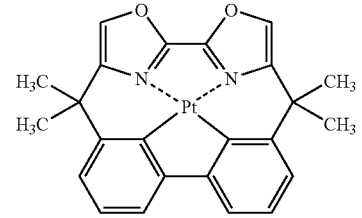
(A41) 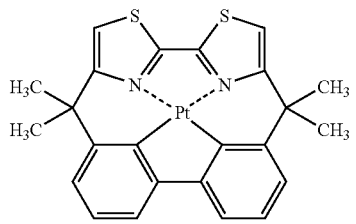

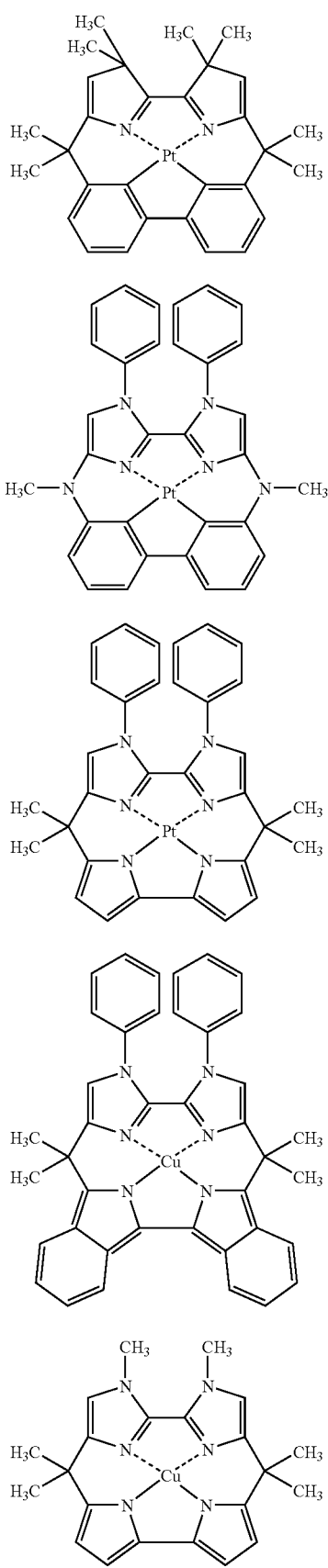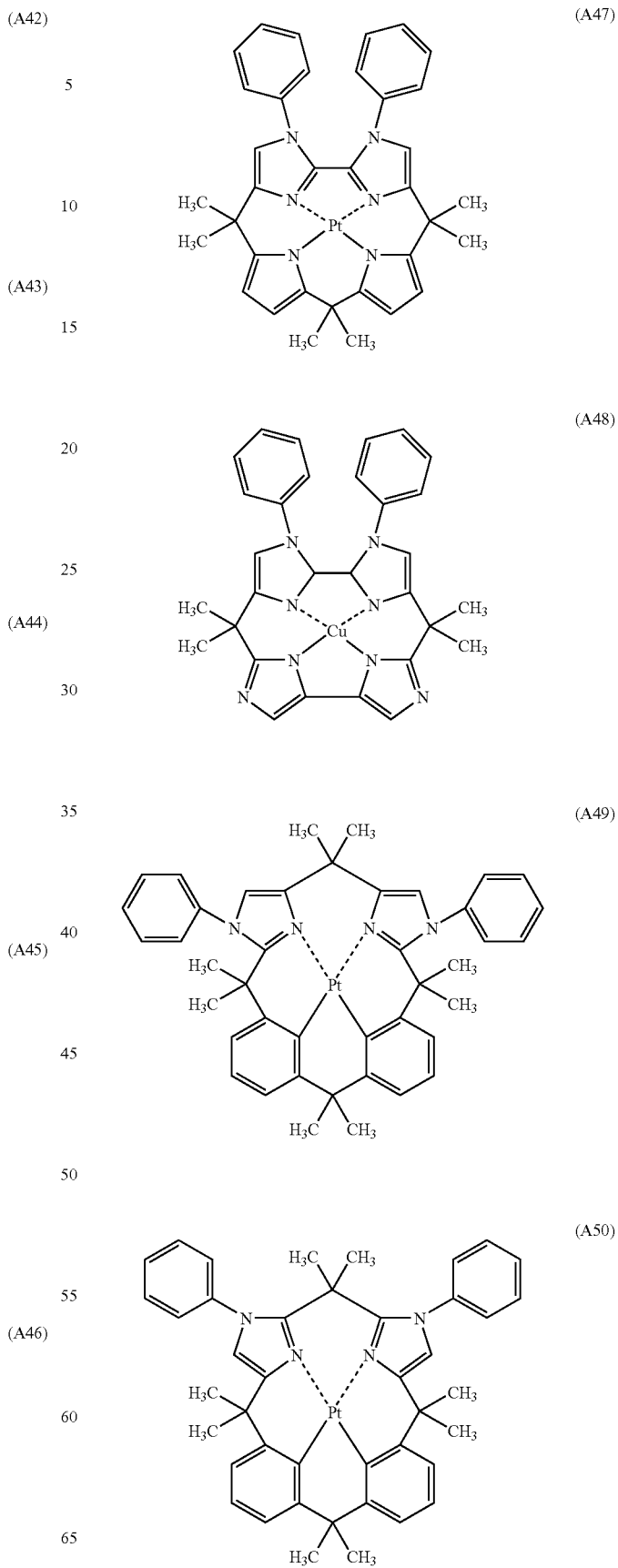

-continued
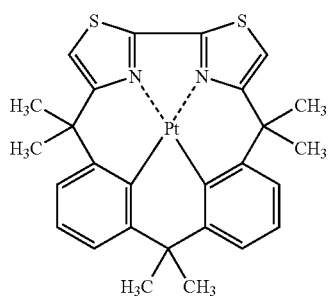
(A51)
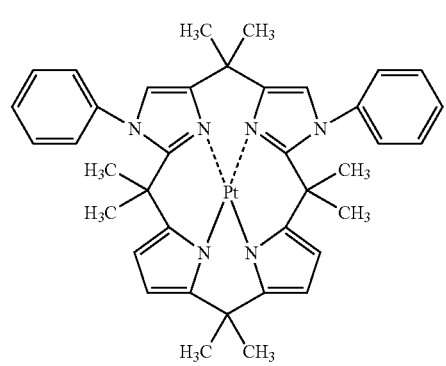
(A52)
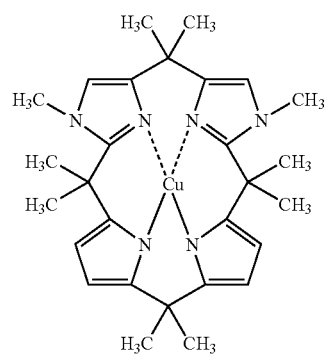
(A53)
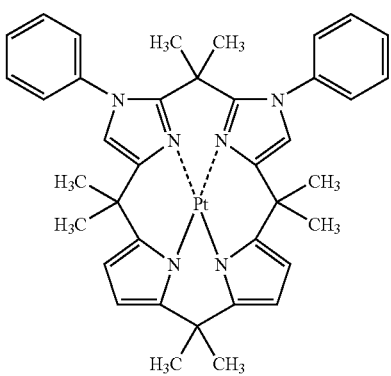
(A54)
-continued
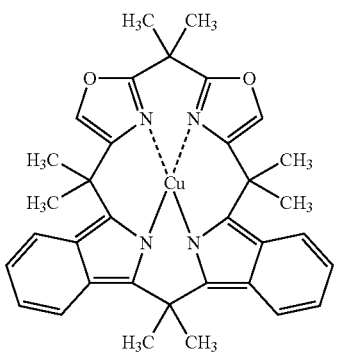
(A55)
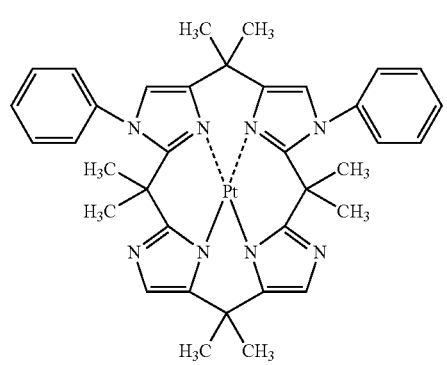
(A56)
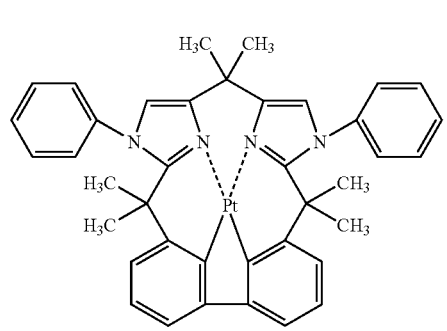
(A57)
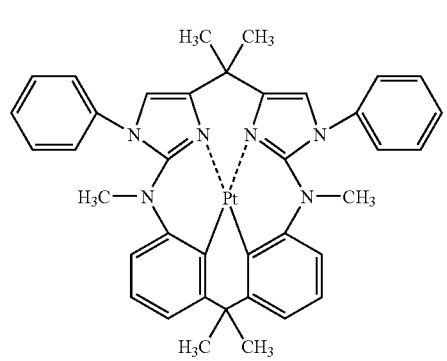
(A58)

-continued
(A59) 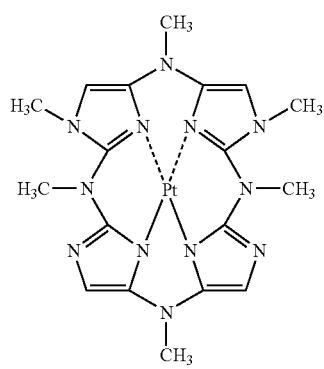
(A60) 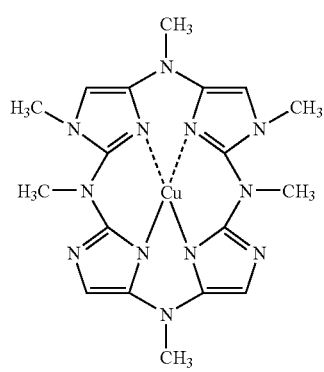
(A61) 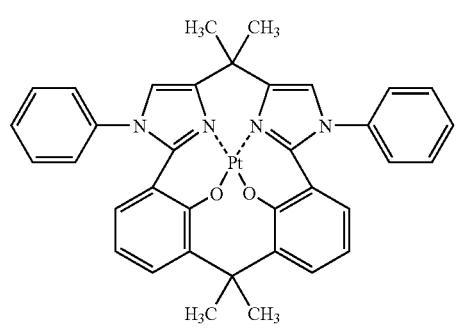
(A62) 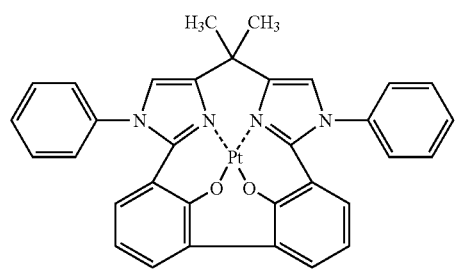
-continued
(A63) 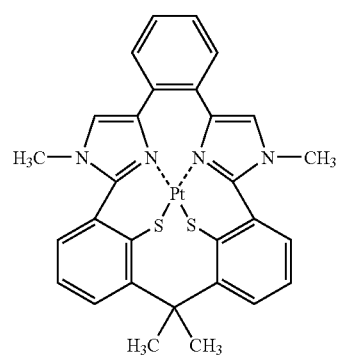
(A64) 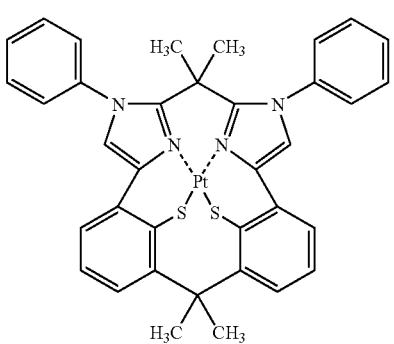
(A65) 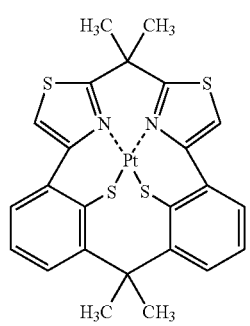
(A66) 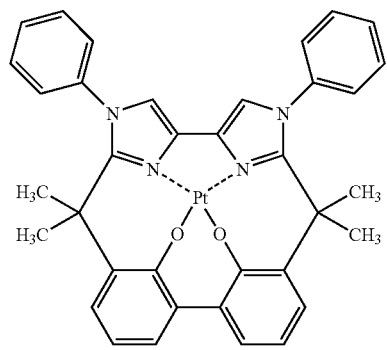

133
-continued
(A67)
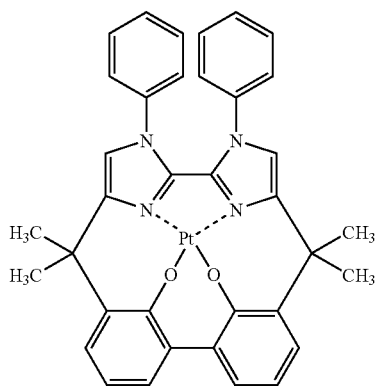
(A68)
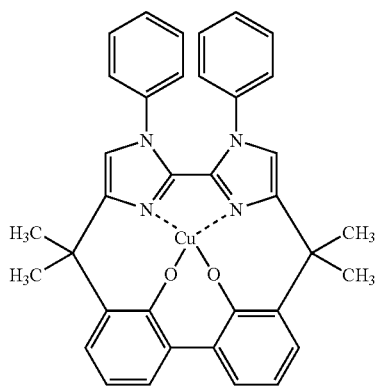
(A69)
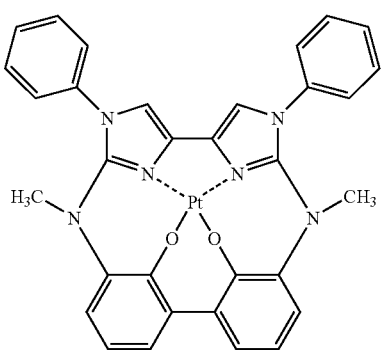
(A70)
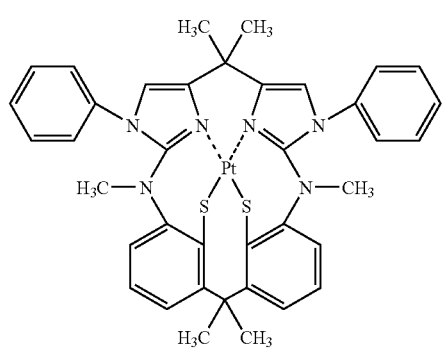
134
-continued
(A71)
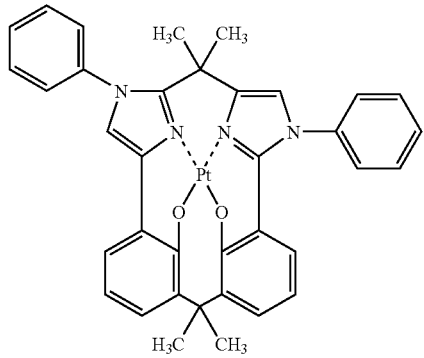
(A72)
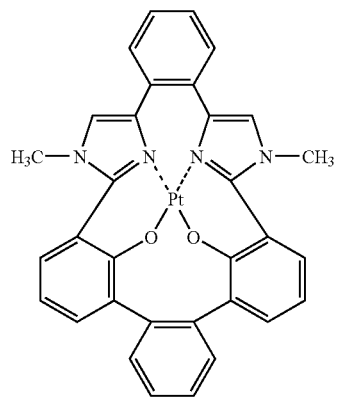
(A73)
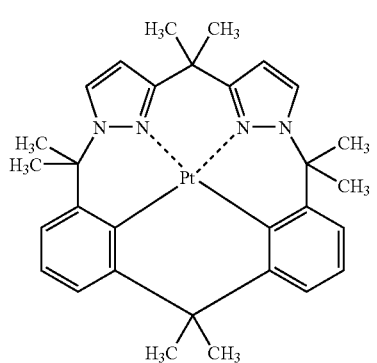
(A74)
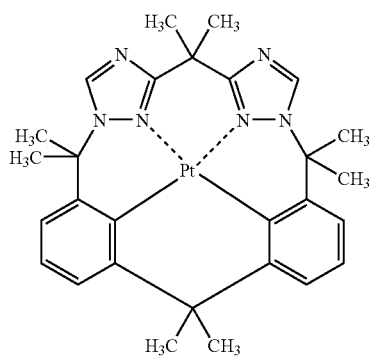

(A75)
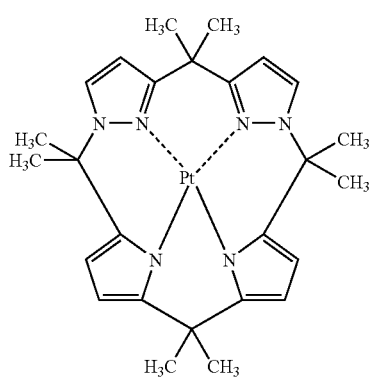

(A76)
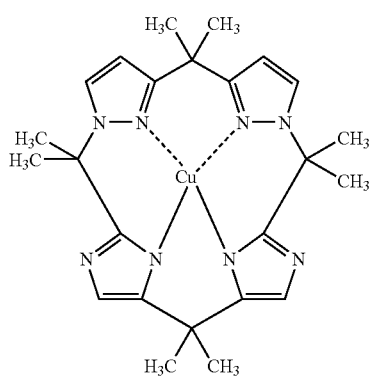

(A77)
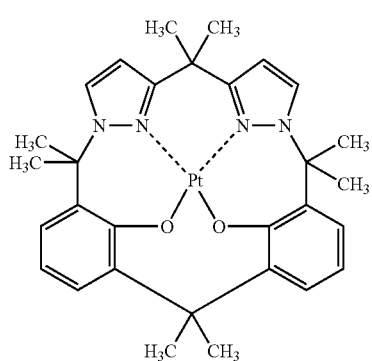

(A78)
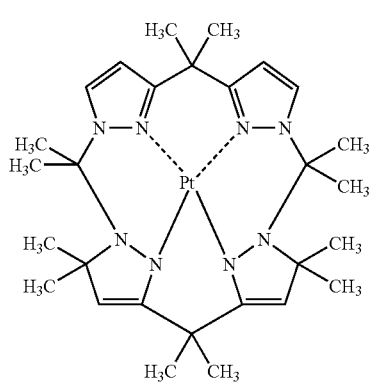

(A79)
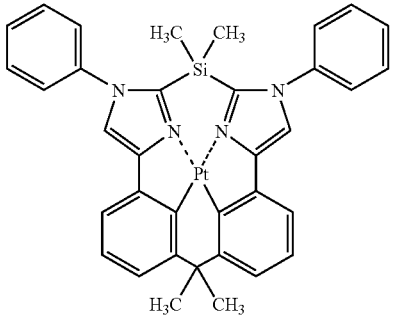

(A80)
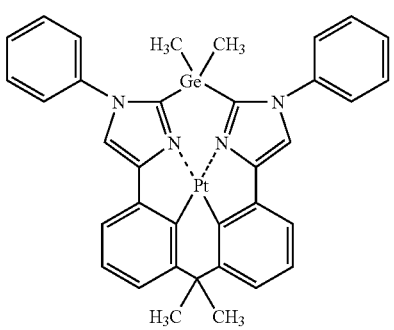

Compounds represented by Formula (B-1) shown below are also preferable as metal complexes usable in the invention.

Formula (B-1)
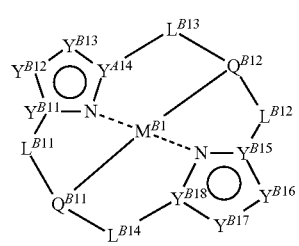

In Formula (B-1), $M^{B1}$ represents a metal ion. $Y^{B11}$, $Y^{B14}$, $Y^{B15}$ and $Y^{B18}$ each independently represent a carbon atom or a nitrogen atom. $Y^{B12}$, $Y^{B13}$, $Y^{B16}$ and $Y^{B17}$ each independently represent a substituted or unsubstituted carbon atom, a substituted or unsubstituted nitrogen atom, an oxygen atom or a sulfur atom. $L^{B11}$, $L^{B12}$, $L^{B13}$ and $L^{B14}$ each independently represent a connecting group. $Q^{B11}$ and $Q^{B12}$ each independently represent a partial structure containing an atom bonded to $M^{B1}$ via any one of a coordinate bond, an ionic bond, and a covalent bond.

The compound represented by Formula (B-1) will be described in detail.

In Formula (B-1), $M^{B1}$, $Y^{B11}$, $Y^{B14}$, $Y^{B15}$, $Y^{B18}$, $Y^{B12}$, $Y^{B13}$, $Y^{B16}$, $Y^{B17}$, $L^{B11}$, $L^{B12}$, $L^{B13}$, $L^{B14}$, $Q^{B11}$ and $Q^{B12}$ have the same definitions as corresponding $M^{A1}$, $Y^{A11}$, $Y^{A14}$, $Y^{A15}$, $Y^{A18}$, $Y^{A12}$, $Y^{A13}$, $Y^{A16}$, $Y^{A17}$, $L^{A11}$, $L^{A12}$, $L^{A13}$, $L^{A14}$, $Q^{A11}$ and $Q^{A12}$ in Formula (A-1) respectively, and their preferable examples are also the same.

More preferable examples of the compound represented by Formula (B-1) include compounds represented by the following Formula (B-2), (B-3) or (B-4).

Formula (B-2)

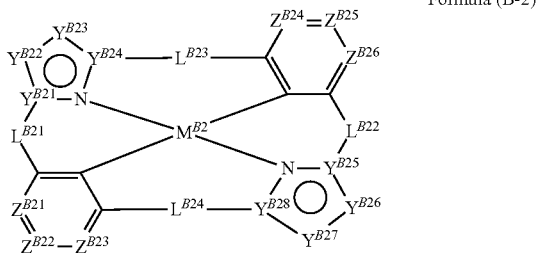

In Formula (B-2), $M^{B2}$ represents a metal ion. $Y^{B21}$, $Y^{B24}$, $Y^{B25}$ and $Y^{B28}$ each independently represent a carbon atom or a nitrogen atom. $Y^{B22}$, $Y^{B23}$, $Y^{B26}$ and $Y^{B27}$ each independently represent a substituted or unsubstituted carbon atom, a substituted or unsubstituted nitrogen atom, an oxygen atom or a sulfur atom. $L^{B21}$, $L^{B22}$, $L^{B23}$ and $L^{B24}$ each independently represent a connecting group. $Z^{B21}$, $Z^{B22}$, $Z^{B23}$, $Z^{B24}$, $Z^{B25}$ and $Z^{B26}$ each independently represent a nitrogen atom or a substituted or unsubstituted carbon atom.

Formula (B-3)

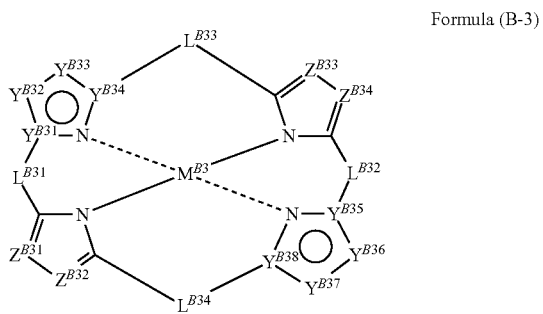

In Formula (B-3), $M^{B3}$ represents a metal ion. $Y^{B31}$, $Y^{B34}$, $Y^{B35}$ and $Y^{B38}$ each independently represent a carbon atom or a nitrogen atom. $Y^{B32}$, $Y^{B33}$, $Y^{B36}$ and $Y^{B37}$ each independently represent a substituted or unsubstituted carbon atom, a substituted or unsubstituted nitrogen atom, an oxygen atom or a sulfur atom. $L^{B31}$, $L^{B32}$, $L^{B33}$ and $L^{B34}$ each independently represent a connecting group. $Z^{B31}$, $Z^{B32}$, $Z^{B33}$ and $Z^{B34}$ each independently represent a nitrogen atom or a substituted or unsubstituted carbon atom.

Formula (B-4)

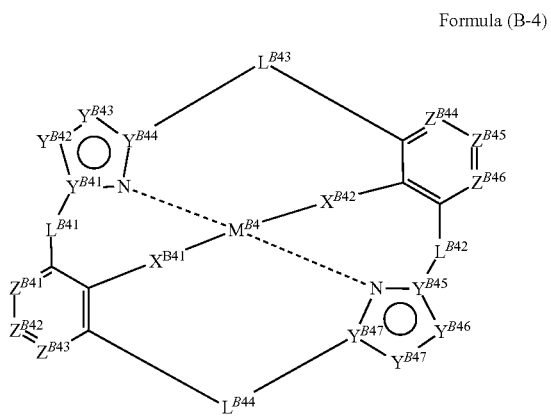

In Formula (B-4), $M^{B4}$ represents a metal ion. $Y^{B41}$, $Y^{B44}$, $Y^{B45}$ and $Y^{B48}$ each independently represent a carbon atom or a nitrogen atom. $Y^{B42}$, $Y^{B43}$, $Y^{B46}$ and $Y^{B47}$ each independently represent a substituted or unsubstituted carbon atom, a substituted or unsubstituted nitrogen atom, an oxygen atom or a sulfur atom. $L^{B41}$, $L^{B42}$, $L^{B43}$ and $L^{B44}$ each independently represent a connecting group. $Z^{B41}$, $Z^{B42}$, $Z^{B43}$, $Z^{B44}$, $Z^{B45}$ and $Z^{B46}$ each independently represent a nitrogen atom or a substituted or unsubstituted carbon atom. $X^{B41}$ and $X^{B42}$ each independently represent an oxygen atom, a sulfur atom or a substituted or unsubstituted nitrogen atom.

The compound represented by Formula (B-2) will be described in detail.

In Formula (B-2), $M^{B2}$, $Y^{B21}$, $Y^{B24}$, $Y^{B25}$, $Y^{B28}$, $Y^{B22}$, $Y^{B23}$, $Y^{B26}$, $Y^{B27}$, $L^{B21}$, $L^{B22}$, $L^{B23}$ and $L^{B24}$ have the same definitions as corresponding $M^{B1}$, $Y^{B11}$, $Y^{B14}$, $Y^{B15}$, $Y^{B18}$, $Y^{B12}$, $Y^{B13}$, $Y^{B16}$, $Y^{B17}$, $L^{B11}$, $L^{B12}$, $L^{B13}$ and $L^{B14}$ in Formula (B-1) respectively, and their preferable examples are also the same.

$Z^{B21}$, $Z^{B22}$, $Z^{B23}$, $Z^{B24}$, $Z^{B25}$ and $Z^{B26}$ each independently represent a nitrogen atom or a substituted or unsubstituted carbon atom. Each of $Z^{B21}$, $Z^{B22}$, $Z^{B23}$, $Z^{B24}$, $Z^{B25}$ and $Z^{B26}$ is preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

The compound represented by Formula (B-3) will be described in detail.

In Formula (B-3), $M^{B3}$, $Y^{B31}$, $Y^{B34}$, $Y^{B35}$, $Y^{B38}$, $Y^{B32}$, $Y^{B33}$, $Y^{B36}$, $Y^{B37}$, $L^{B31}$, $L^{B32}$, $L^{B33}$ and $L^{B34}$ have the same definitions as corresponding $M^{B1}$, $Y^{B11}$, $Y^{B14}$, $Y^{B15}$, $Y^{B18}$, $Y^{B12}$, $Y^{B13}$, $Y^{B16}$, $Y^{B17}$, $L^{B11}$, $L^{B12}$, $L^{B13}$ and $L^{B14}$ in Formula (B-1) respectively, and their preferable examples are also the same.

$Z^{B31}$, $Z^{B32}$, $Z^{B33}$ and $Z^{B34}$ each independently represent a nitrogen atom or a substituted or unsubstituted carbon atom. Each of $Z^{B31}$, $Z^{B32}$, $Z^{B33}$ and $Z^{B34}$ is preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

The compound represented by Formula (B-4) will be described in detail.

In Formula (B-4), $M^{B4}$, $Y^{B41}$, $Y^{B44}$, $Y^{B45}$, $Y^{B48}$, $Y^{B42}$, $Y^{B43}$, $Y^{B46}$, $Y^{B47}$, $L^{B41}$, $L^{B42}$, $L^{B43}$ and $L^{B44}$ have the same definitions as corresponding $M^{B1}$, $Y^{B11}$, $Y^{B14}$, $Y^{B15}$, $Y^{B18}$, $Y^{B12}$, $Y^{B13}$, $Y^{B16}$, $Y^{B17}$, $L^{B11}$, $L^{B12}$, $L^{B13}$ and $L^{B14}$ in Formula (B-1) respectively, and their preferable examples are also the same.

$Z^{B41}$, $Z^{B42}$, $Z^{B43}$, $Z^{B44}$, $Z^{B45}$ and $Z^{B46}$ each independently represent a nitrogen atom or a substituted or unsubstituted carbon atom. Each of $Z^{B41}$, $Z^{B42}$, $Z^{B43}$, $Z^{B44}$, $Z^{B45}$ and $Z^{B46}$ is preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

$X^{B41}$ and $X^{B42}$ each independently represent an oxygen atom, a sulfur atom or a substituted or unsubstituted nitrogen atom. Each of $X^{B41}$ and $X^{B42}$ is preferably an oxygen atom or a sulfur atom, and more preferably an oxygen atom.

Specific examples of the compounds represented by Formula (B-1) are illustrated below, but the invention is not limited thereto.

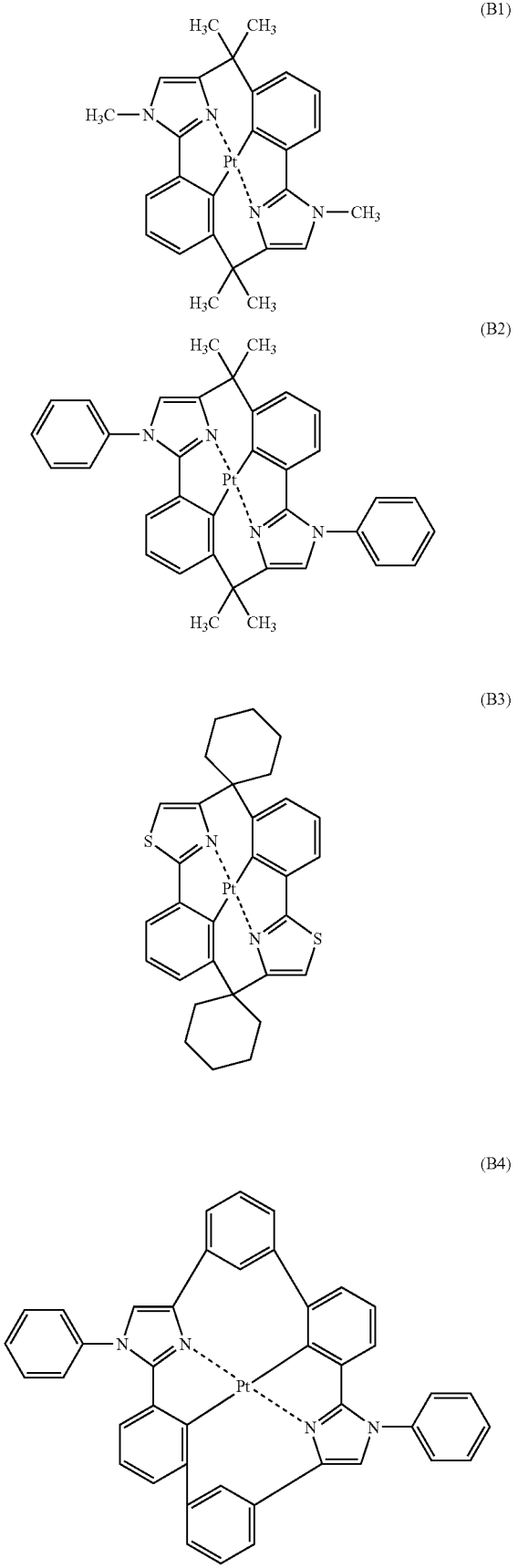
(B1)
(B2)
(B3)
(B4)
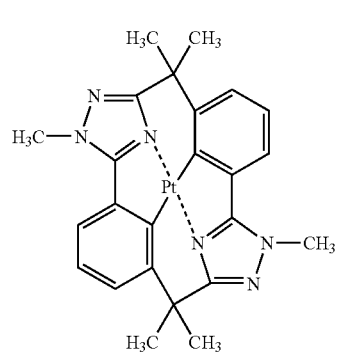
(B5)
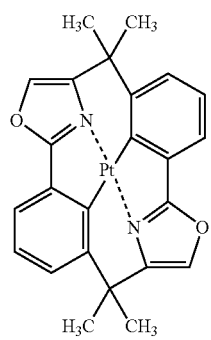
(B6)
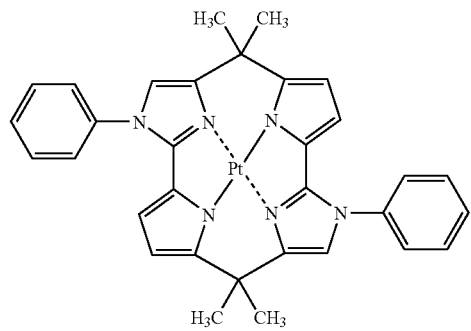
(B7)
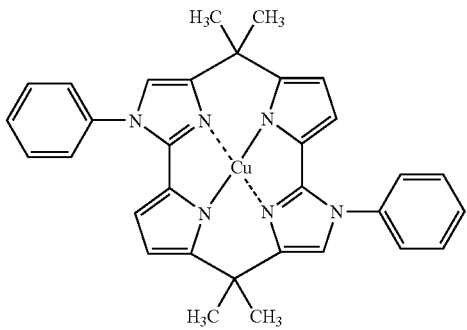
(B8)

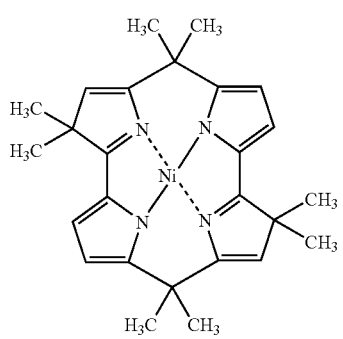
(B9)
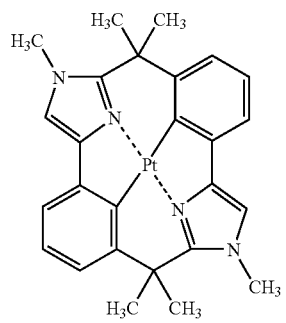
(B13)
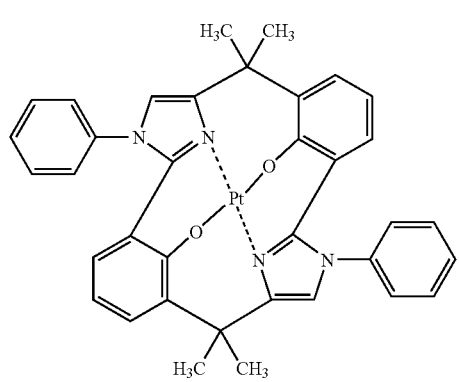
(B10)
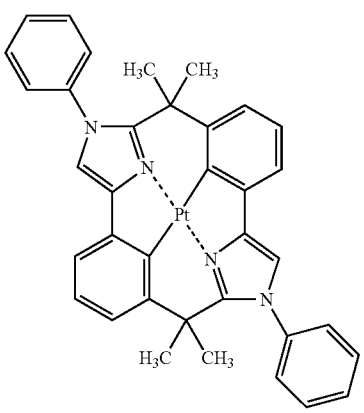
(B14)
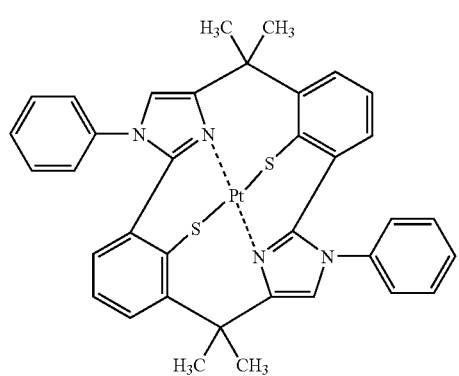
(B11)
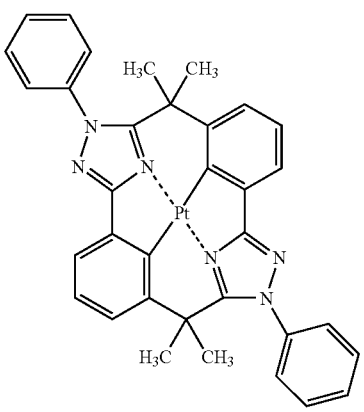
(B15)
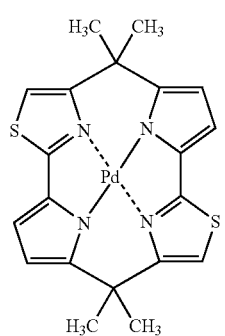
(B12)
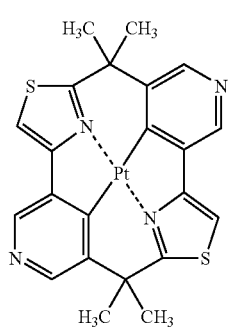
(B16)

(B17)
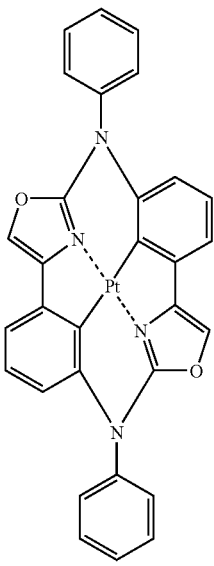
(B18)
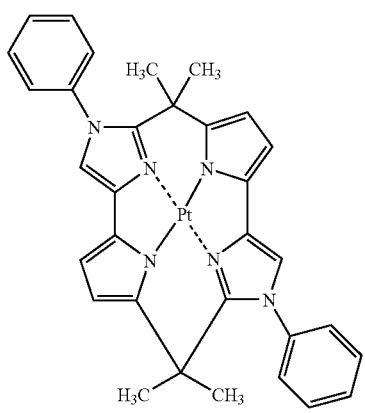
(B19)
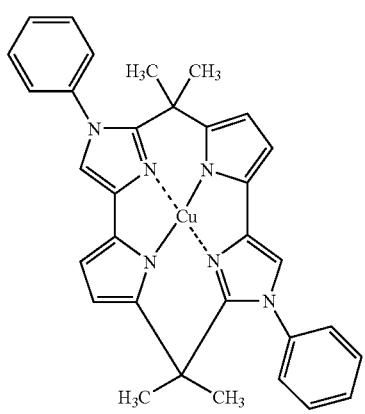
(B20)
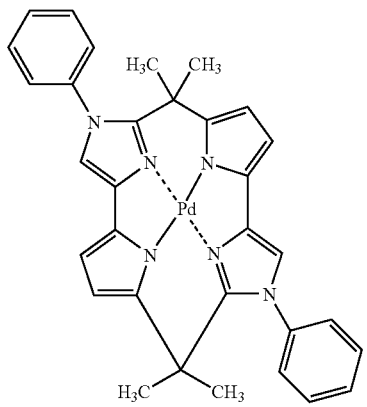
(B21)
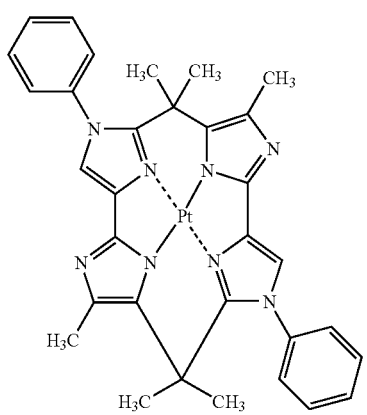
(B22)
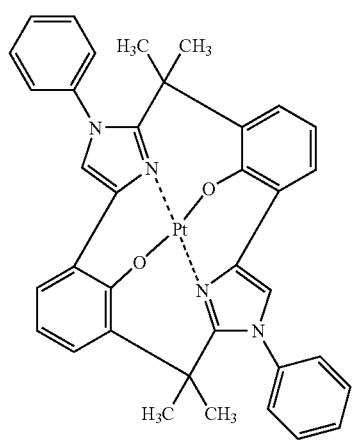

(B23)
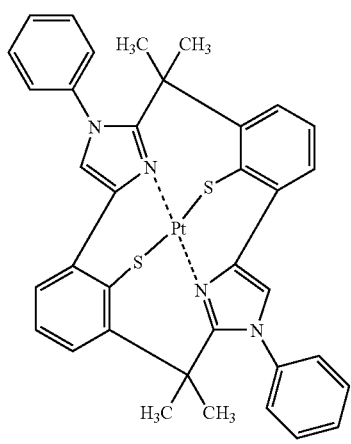
(B24)
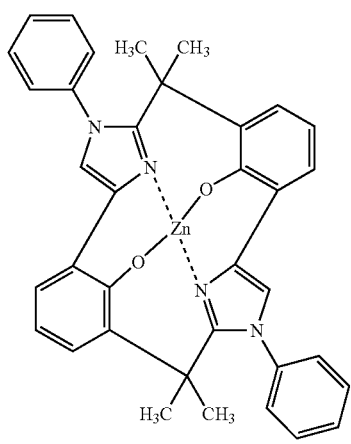
(B25)
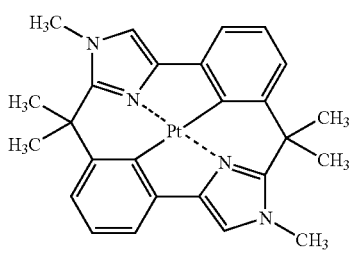
(B26)
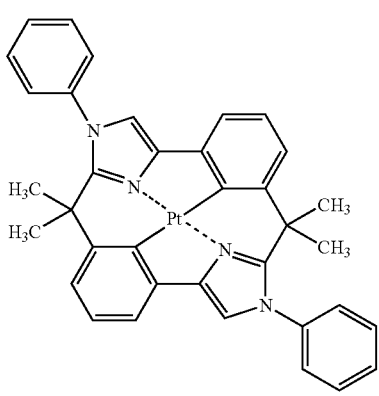
(B27)
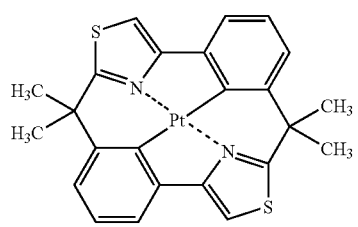
(B28)
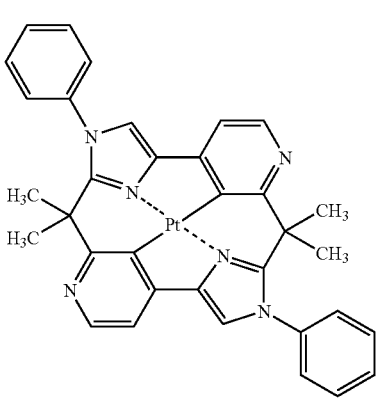
(B29)
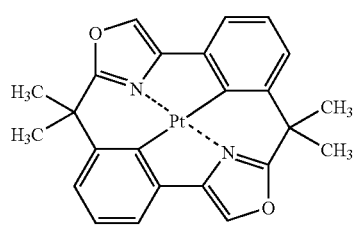
(B30)
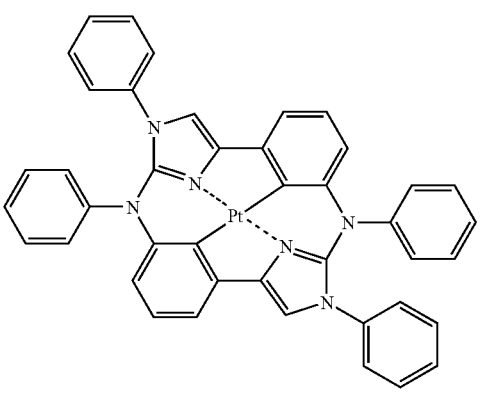

(B31) 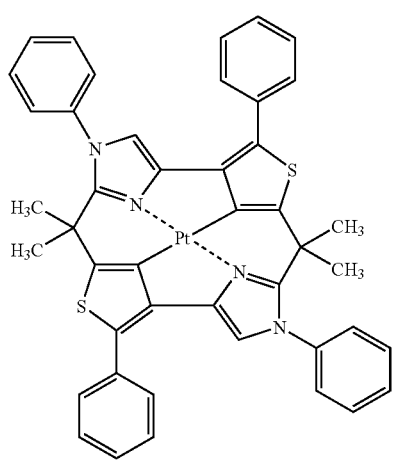
(B32) 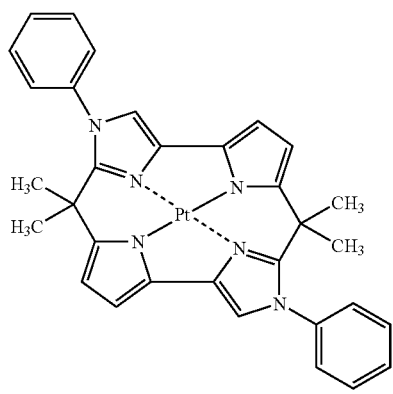
(B33) 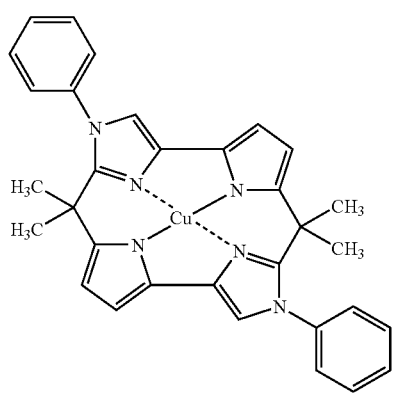
(B34) 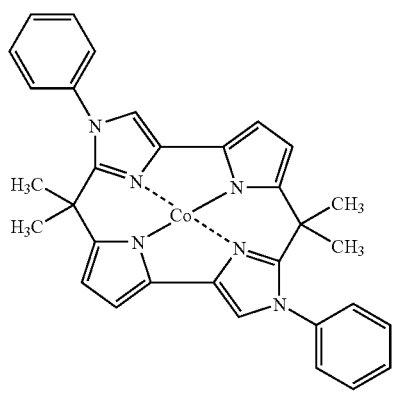
(B35) 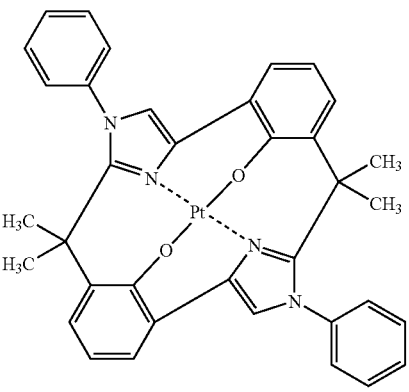
(B36) 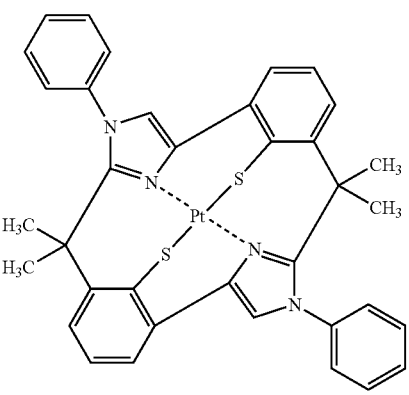
(B37) 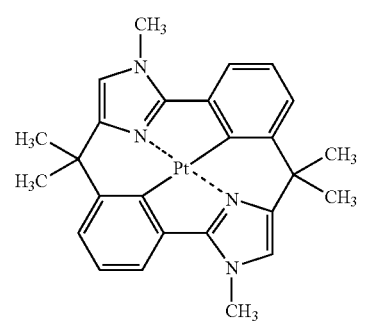
(B38) 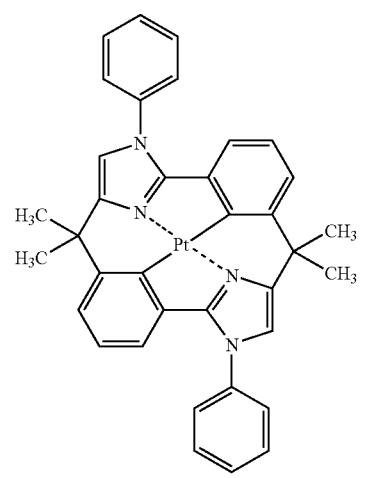

(B39)
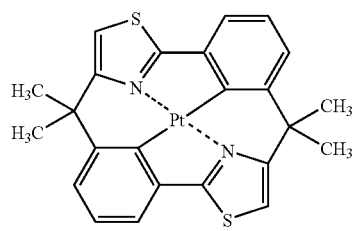
(B40)
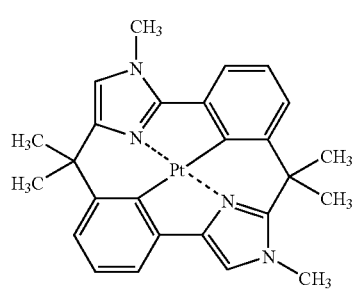
(B41)
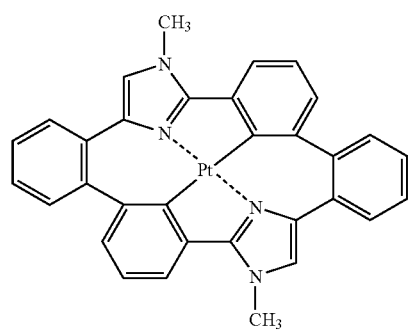
(B42)
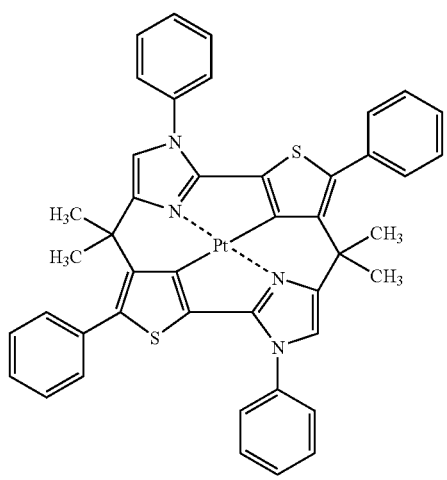
(B43)
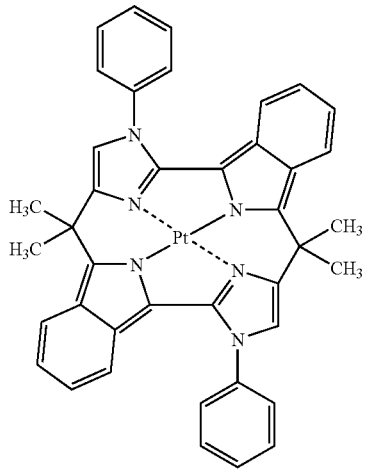
(B44)
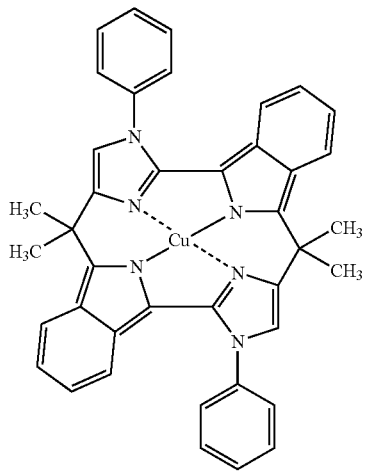
(B45)
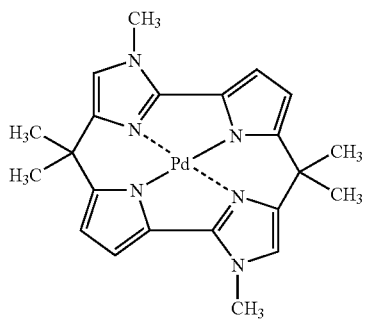

(B46) 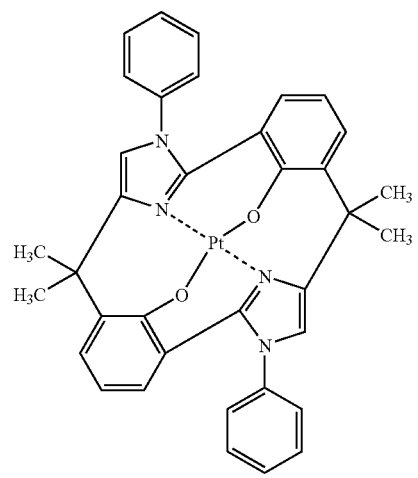
(B47) 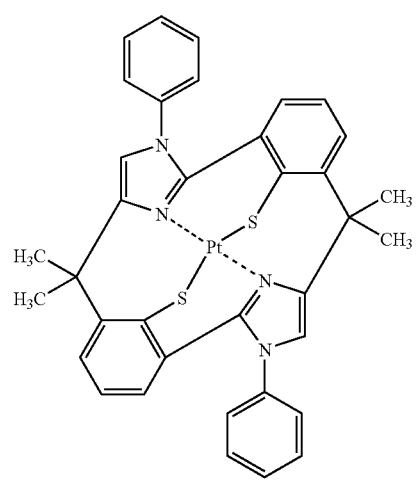
(B48) 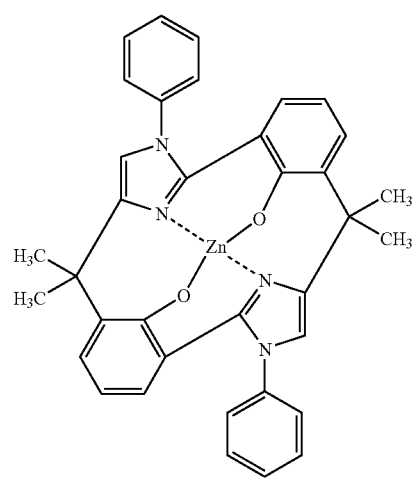
(B49) 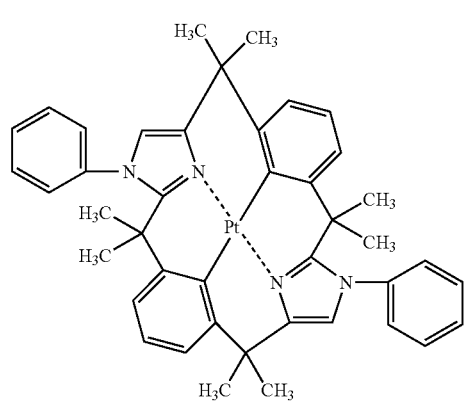
(B50) 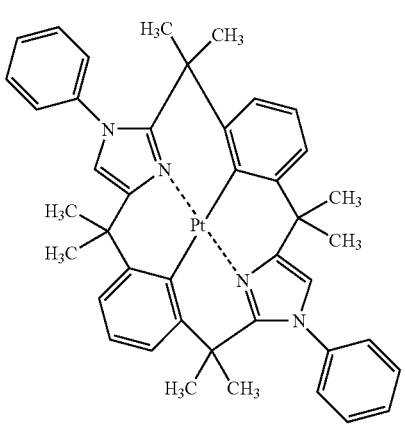
(B51) 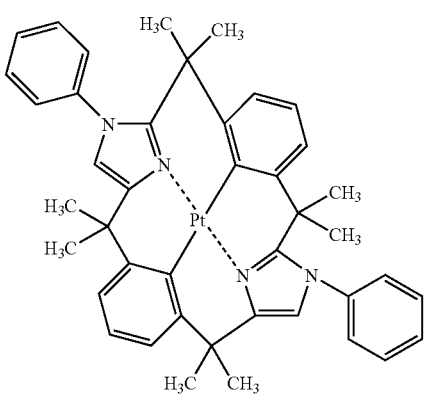
(B52) 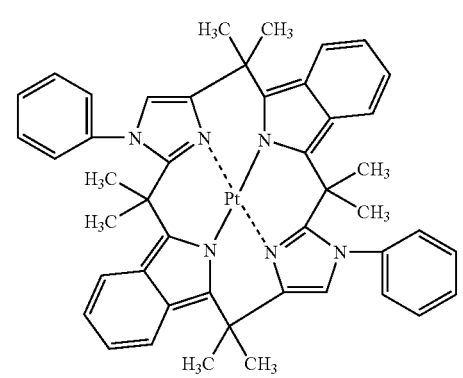

-continued

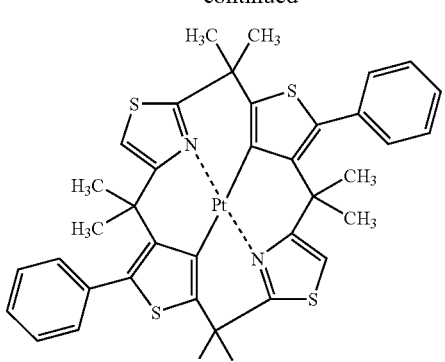
(B53)

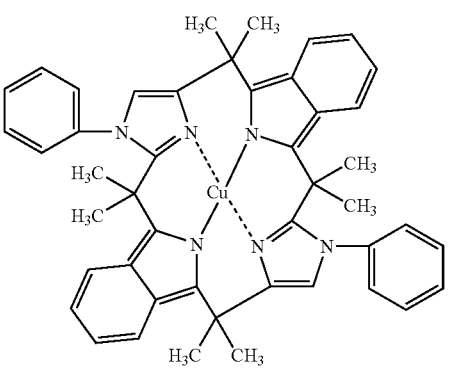
(B54)

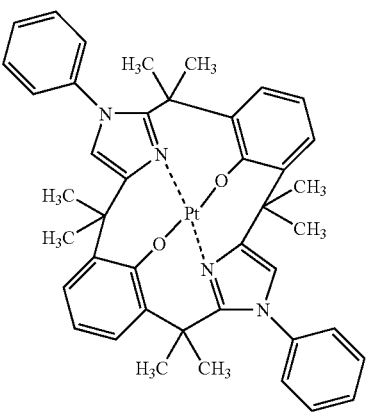
(B55)

An example of preferable metal complexes usable in the invention is a compound represented by the following Formula (C-1).

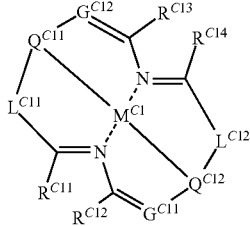
Formula (C-1)

In Formula (C-1), $M^{C1}$ represents a metal ion. $R^{C11}$ and $R^{C12}$ each independently represent a hydrogen atom or a substituent. When $R^{C11}$ and $R^{C12}$ represent substituents, the substituents may be bonded to each other to form a 5-membered ring. $R^{C13}$ and $R^{C14}$ each independently represent a hydrogen atom or a substituent. When $R^{C13}$ and $R^{C14}$ represent substituents, the substituents may be bonded to each other to form a 5-membered ring. $G^{C11}$ and $G^{C12}$ each independently represent a nitrogen atom or a substituted or unsubstituted carbon atom. $L^{C11}$ and $L^{C12}$ each independently represent a connecting group. $Q^{C11}$ and $Q^{C12}$ each independently represent a partial structure containing an atom bonded to $M^{C1}$ via any one of a coordinate bond, an ionic bond, and a covalent bond.

Formula (C-1) will be described in detail.

In Formula (C-1), $M^{C1}$, $L^{C11}$, $L^{C12}$, $Q^{C11}$ and $Q^{C12}$ have the same definitions as corresponding $M^{A1}$, $L^{A11}$, $L^{A12}$, $Q^{A11}$ and $Q^{A12}$ in Formula (A-1) respectively, and their preferable examples are also the same.

$G^{C11}$ and $G^{C12}$ each independently represent a nitrogen atom or a substituted or unsubstituted carbon atom, preferably a nitrogen atom or an unsubstituted carbon atom, and more preferably a nitrogen atom.

$R^{C11}$ and $R^{C12}$ each independently represent a hydrogen atom or a substituent. $R^{C11}$ and $R^{C12}$ may be bonded to each other to form a 5-membered ring. $R^{C13}$ and $R^{C14}$ each independently represent a hydrogen atom or a substituent. $R^{C13}$ and $R^{C14}$ may be bonded to each other to form a 5-membered ring.

The substituent represented by $R^{C11}$, $R^{C12}$, $R^{C13}$ or $R^{C14}$ may be, for example, an alkyl group (preferably having 1 to 30 carbon atoms, more preferably having 1 to 20 carbon atoms, particularly preferably having 1 to 10 carbon atoms; and examples thereof include a methyl group, an ethyl group, an iso-propyl group, a group, a tert-butyl group, a n-octyl group, a n-decyl group, a n-hexadecyl group, a cyclopropyl group, a cyclopentyl group, a cyclohexyl group, etc.), an alkenyl group (preferably having 2 to 30 carbon atoms, more preferably having 2 to 20 carbon atoms, particularly preferably having 2 to 10 carbon atoms; and examples thereof include a vinyl group, an allyl group, a 2-butenyl group, a 3-pentenyl group and the like), an alkynyl group (preferably having 2 to 30 carbon atoms, more preferably having 2 to 20 carbon atoms, particularly preferably having 2 to 10 carbon atoms; and examples thereof include a propargyl group, a 3-pentynyl group and the like), an aryl group (preferably having 6 to 30 carbon atoms, more preferably having 6 to 20 carbon atoms, particularly preferably having 6 to 12 carbon atoms; and examples thereof include phenyl, p-methylphenyl, naphthyl, anthranyl, etc.), an amino group (preferably having 0 to 30 carbon atoms, more preferably having 0 to 20 carbon atoms, particularly preferably having 0 to 10 carbon atoms; and examples thereof include an amino group, a methylamino group, a dimethylamino group, a diethylamino group, a dibenzylamino group, a diphenylamino group, a ditolylamino group and the like), an alkoxy group (preferably having 1 to 30 carbon atoms, more preferably having 1 to 20 carbon atoms, particularly preferably having 1 to 10 carbon atoms; and examples thereof include a methoxy group, an ethoxy group, a butoxy group, a 2-ethylhexyloxy group and the like), an aryloxy group (preferably a having 6 to 30 carbon atoms, more preferably having 6 to 20 carbon atoms, particularly preferably having 6 to 12 carbon atoms; and examples thereof include a phenyloxy group, a 1-naphthyloxy group, a 2-naphthyloxy group and the like), a heterocyclic oxy group (preferably having 1 to 30 carbon atoms, more preferably having 1 to 20 carbon atoms, particularly preferably having 1 to 12 carbon atoms; and examples thereof include a pyridyloxy group, a pyrazyloxy group, a pyrimidyloxy group, a quinolyloxy group and the like), an acyl group (preferably having 1 to 30 carbon atoms, more preferably having 1 to 20 carbon atoms, particularly preferably having 1 to 12 carbon atoms; and examples thereof include an acetyl group, a benzoyl group, a formyl group, a pivaloyl group and the like), an alkoxycarbonyl group (preferably having 2 to 30 carbon atoms, more preferably having 2 to 20 carbon atoms, particularly preferably having 2 to 12 carbon atoms; and examples thereof include a methoxycarbonyl group, an ethoxycarbonyl group and the like), an aryloxycarbonyl group (preferably having 7 to 30 carbon atoms, more preferably having 7 to 20 carbon atoms, particularly preferably having 7 to 12 carbon atoms; and examples thereof include a phenyloxycarbonyl group and the like), an acyloxy group (preferably having 2 to 30 carbon atoms, more preferably having 2 to 20 carbon atoms, particularly preferably having 2 to 10 carbon atoms; and examples thereof include an acetoxy group, a benzoyloxy group and the like), an acylamino group (preferably having 2 to 30 carbon atoms, more preferably having 2 to 20 carbon atoms, particularly preferably having 2 to 10 carbon atoms; and examples thereof include an acetylamino group, a benzoylamino group and the like), an alkoxycarbonylamino group (preferably having 2 to 30 carbon atoms, more preferably having 2 to 20 carbon atoms, particularly preferably having 2 to 12 carbon atoms; and examples thereof include a methoxycarbonylamino group and the like), an aryloxycarbonylamino group (preferably having 7 to 30 carbon atoms, more preferably having 7 to 20 carbon atoms, particularly preferably having 7 to 12 carbon atoms; and examples thereof include a phenyloxycarbonylamino group and the like), an alkylthio group (preferably having 1 to 30 carbon atoms, more preferably having 1 to 20 carbon atoms, particularly preferably having 1 to 12 carbon atoms; and examples thereof include a methylthio group, an ethylthio group and the like), an arylthio group (preferably having 6 to 30 carbon atoms, more preferably having 6 to 20 carbon atoms, particularly preferably having 6 to 12 carbon atoms; and examples thereof include a phenylthio group and the like), a heterocyclic thio group (preferably having 1 to 30 carbon atoms, more preferably having 1 to 20 carbon atoms, particularly preferably having 1 to 12 carbon atoms; and examples thereof include a pyridylthio group, a 2-benzimidazolylthio group, a 2-benzoxazolylthio group, a 2-benzthiazolylthio group and the like), a halogen atom (such as a fluorine atom, chlorine atom, bromine atom, iodine atom), a cyano group, a heterocyclic group (preferably having 1 to 30 carbon atoms, more preferably having 1 to 12 carbon atoms, and containing a heteroatom such as a nitrogen atom, oxygen atom or a sulfur atom, specifically an imidazolyl group, a pyridyl group, a quinolyl group, a furyl group, a thienyl group, a, piperidyl group, a morpholino group, a benzoxazolyl group, a benzimidazolyl group, a benzthiazolyl group, a carbazolyl group, azepinyl group and the like), a silyl group (preferably having 3 to 40 carbon atoms, more preferably having 3 to 30 carbon atoms, particularly preferably having 3 to 24 carbon atoms; and examples thereof include a trimethylsilyl group, a triphenylsilyl group and the like) or a silyloxy group (preferably having 3 to 40 carbon atoms, more preferably having 3 to 30 carbon atoms, particularly preferably having 3 to 24 carbon atoms; and examples thereof include a trimethylsilyloxy group, a triphenylsilyloxy group and the like).

The substituent represented by $R^{C11}$, $R^{C12}$, $R^{C13}$ or $R^{C14}$ is preferably an alkyl group, an aryl group, or such a group that $R^{C11}$ and $R^{C12}$, or $R^{C13}$ and $R^{C14}$, are bonded to each other to form a 5-membered ring. In a particularly preferable embodiment, $R^{C11}$ and $R^{C12}$, or $R^{C13}$ and $R^{C14}$, are bonded to each other to form a 5-membered ring.

The compound represented by Formula (C-1) is more preferably a compound represented by Formula (C-2).

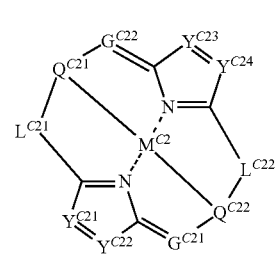

Formula (C-2)

In Formula (C-2), $M^{C2}$ represents a metal ion. $Y^{C21}$, $Y^{C22}$, $Y^{C23}$ and $Y^{C24}$ each independently represent a nitrogen atom or a substituted or unsubstituted carbon atom. $G^{C21}$ and $G^{C22}$ each independently represent a nitrogen atom or a substituted or unsubstituted carbon atom. $L^{C21}$ and $L^{C22}$ each independently represent a connecting group. $Q^{C21}$ and $Q^{C22}$ each independently represent a partial structure containing an atom bonded to $M^{C2}$ via any one of a coordinate bond, an ionic bond, and a covalent bond.

Formula (C-2) will be described in detail.

In Formula (C-2), $M^{C2}$, $L^{C21}$, $L^{C22}$, $Q^{C21}$, $Q^{C22}$, $G^{C21}$ and $G^{C22}$ have the same definitions as corresponding $M^{C1}$, $L^{C11}$, $L^{C12}$, $Q^{C11}$, $Q^{C12}$, $G^{C11}$ and $G^{C12}$ in Formula (C-1) respectively, and their preferable examples are also the same.

$Y^{C21}$, $Y^{C22}$, $Y^{C23}$ and $Y^{C24}$ each independently represent a nitrogen atom or a substituted or unsubstituted carbon atom, preferably a substituted or unsubstituted carbon atom, and more preferably an unsubstituted carbon atom.

The compound represented by Formula (C-2) is more preferably a compound represented by the following Formula (C-3), (C-4) or (C-5).

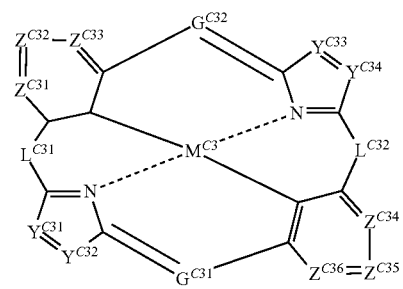

Formula (C-3)

In Formula (C-3), $M^{C3}$ represents a metal ion.

$Y^{C31}$, $Y^{C32}$, $Y^{C33}$ and $Y^{C34}$ each independently represent a nitrogen atom or a substituted or unsubstituted carbon atom. $G^{C31}$ and $G^{C32}$ each independently represent a nitrogen atom or a substituted or unsubstituted carbon atom. $L^{C31}$ and $L^{C32}$ each independently represent a connecting group. $Z^{C31}$, $Z^{C32}$, $Z^{C33}$, $Z^{C34}$, $Z^{C35}$ and $Z^{C36}$ each independently represent a nitrogen atom or a substituted or unsubstituted carbon atom.

Formula (C-4)

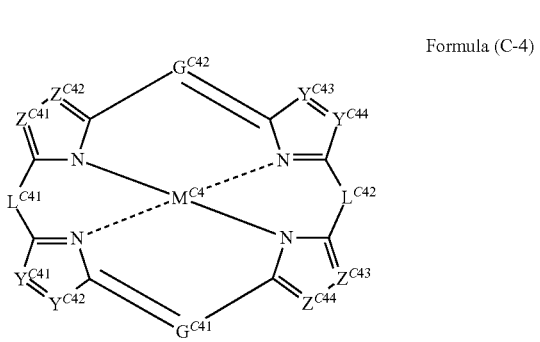

In Formula (C-4), $M^{C4}$ represents a metal ion.
$Y^{C41}$, $Y^{C42}$, $Y^{C43}$ and $Y^{C44}$ each independently represent a nitrogen atom or a substituted or unsubstituted carbon atom. $G^{C41}$ and $G^{C42}$ each independently represent a nitrogen atom or a substituted or unsubstituted carbon atom. $L^{C41}$ and $L^{C42}$ each independently represent a connecting group. $Z^{C41}$, $Z^{C42}$, $Z^{C43}$ and $Z^{C44}$ each independently represent a nitrogen atom or a substituted or unsubstituted carbon atom.

Formula (C-5)

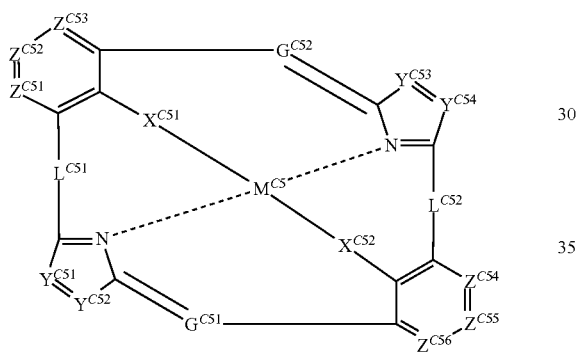

In Formula (C-5), $M^{C5}$ represents a metal ion.
$Y^{C51}$, $Y^{C52}$, $Y^{C53}$ and $Y^{C54}$ each independently represent a nitrogen atom or a substituted or unsubstituted carbon atom. $G^{C51}$ and $G^{C52}$ each independently represent a nitrogen atom or a substituted or unsubstituted carbon atom. $L^{C51}$ and $L^{C52}$ each independently represent a connecting group. $Z^{C51}$, $Z^{C52}$, $Z^{C53}$, $Z^{C54}$, $Z^{C55}$ and $Z^{C56}$ each independently represent a nitrogen atom or a substituted or unsubstituted carbon atom. $X^{C51}$ and $X^{C52}$ each independently represent an oxygen atom, a sulfur atom or a substituted or unsubstituted nitrogen atom.

The compound represented by Formula (C-3) will be described in detail.

In Formula (C-3), $M^{C3}$, $L^{C31}$, $L^{C32}$, $G^{C31}$ and $G^{C32}$ have the same definitions as corresponding $M^{C1}$, $L^{C11}$, $L^{C12}$, $G^{C11}$ and $G^{C12}$ in Formula (C-1) respectively, and their preferable examples are also the same.

$Z^{C31}$, $Z^{C32}$, $Z^{C33}$, $Z^{C34}$, $Z^{C35}$ and $Z^{C36}$ each independently represent a nitrogen atom or a substituted or unsubstituted carbon atom. Each of $Z^{C31}$, $Z^{C32}$, $Z^{C33}$, $Z^{C34}$, $Z^{C35}$ and $Z^{C36}$ is preferably a substituted or unsubstituted carbon atom, and more preferably an unsubstituted carbon atom.

The compound represented by Formula (C-4) is described in more detail.

In Formula (C-4), $M^{C4}$, $L^{C41}$, $L^{C42}$, $G^{C41}$ and $G^{C42}$ have the same definitions as corresponding $M^{C1}$, $L^{C11}$, $L^{C12}$, $G^{C11}$ and $G^{C12}$ in Formula (C-1) respectively, and their preferable examples are also the same.

$Z^{C41}$, $Z^{C42}$, $Z^{C43}$, and $Z^{C44}$ each independently represent a nitrogen atom or a substituted or unsubstituted carbon atom. Each of $Z^{C41}$, $Z^{C42}$, $Z^{C43}$ and $Z^{C44}$ is preferably a substituted or unsubstituted carbon atom, and more preferably an unsubstituted carbon atom.

The compound represented by Formula (C-5) is described in more detail.

$M^{C5}$, $L^{C51}$, $L^{C52}$, $G^{C51}$ and $G^{C52}$ have the same definitions as corresponding $M^{C1}$, $L^{C11}$, $L^{C12}$ $G^{C11}$ and $G^{C12}$ in Formula (C-1) respectively, and their preferable examples are also the same.

$Z^{C51}$, $Z^{C52}$, $Z^{C53}$, $Z^{C54}$, $Z^{C55}$ and $Z^{C56}$ each independently represent a nitrogen atom or a substituted or unsubstituted carbon atom. Each of $Z^{C51}$, $Z^{C52}$, $Z^{C53}$, $Z^{C54}$, $Z^{C55}$ and $Z^{C56}$ is preferably a substituted or unsubstituted carbon atom, and more preferably an unsubstituted carbon atom.

$X^{C51}$ and $X^{C52}$ each independently represent an oxygen atom, a sulfur atom or a substituted or unsubstituted nitrogen atom. Each of $X^{C51}$ and $X^{C52}$ is preferably an oxygen atom or a sulfur atom, and more preferably an oxygen atom.

Specific examples of the compounds represented by Formula (C-1) are illustrated below, however, the invention is not limited thereto.

(C1)

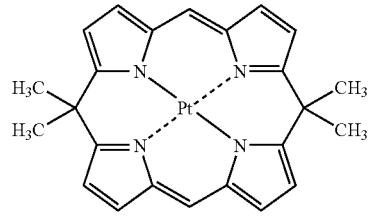

(C2)

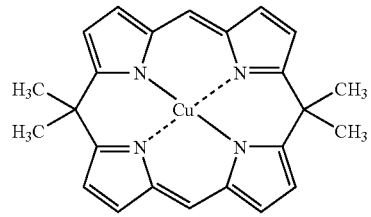

(C3)

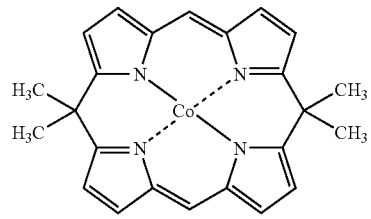

(C4)

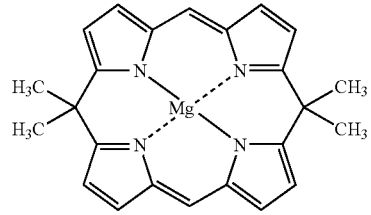

-continued
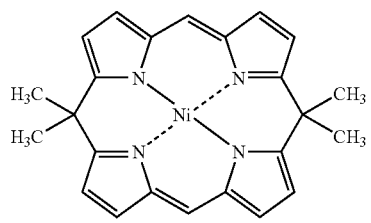 (C5)
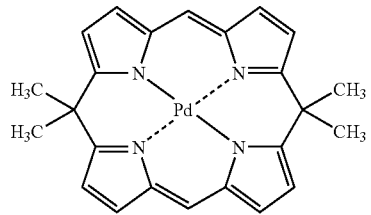 (C6)
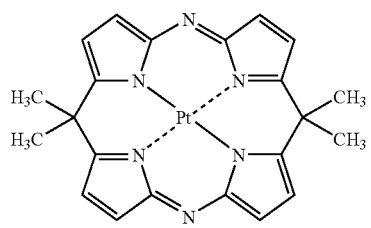 (C7)
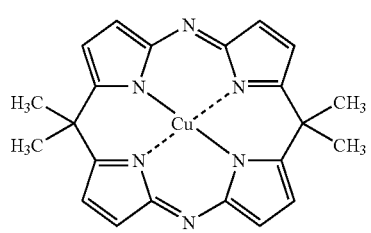 (C8)
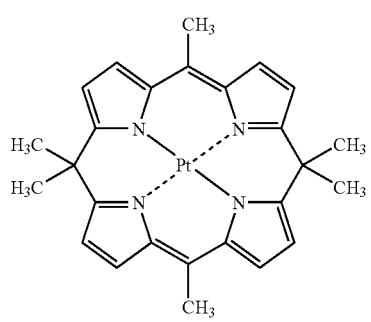 (C9)
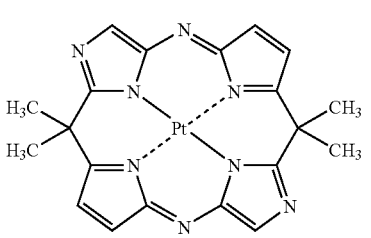 (C10)
-continued
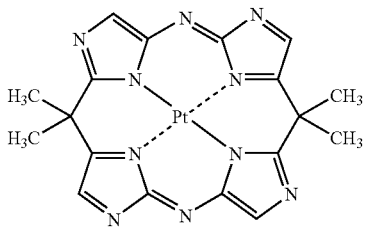 (C11)
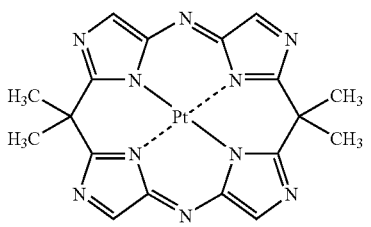 (C12)
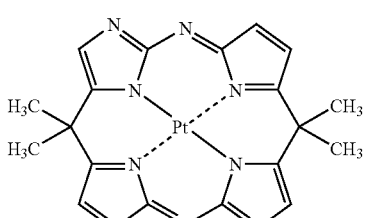 (C13)
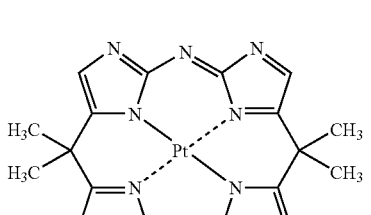 (C14)
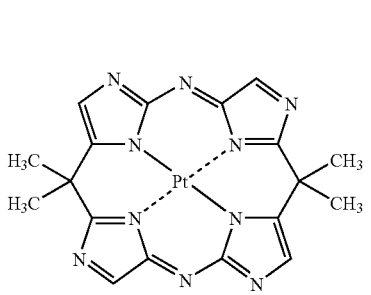 (C15)
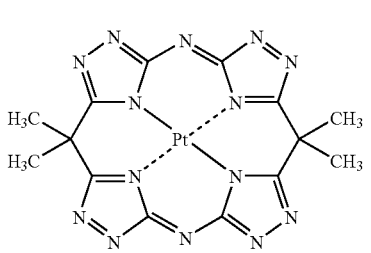 (C16)

(C17)
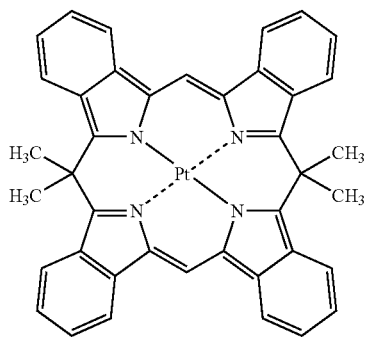
(C18)
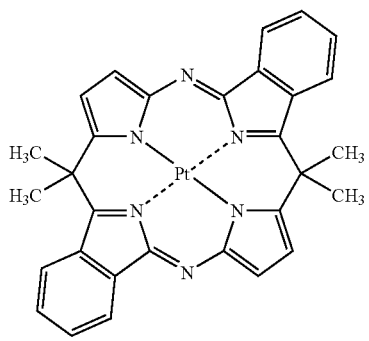
(C19)
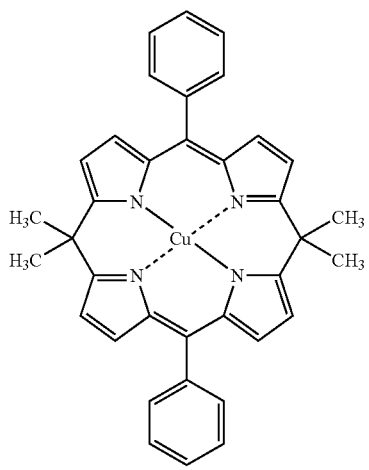
(C20)
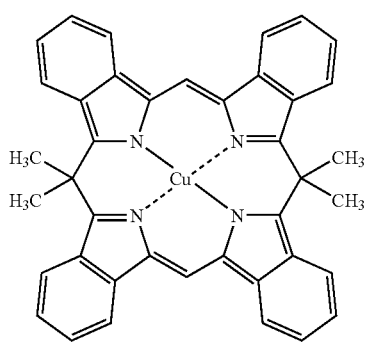
(C21)
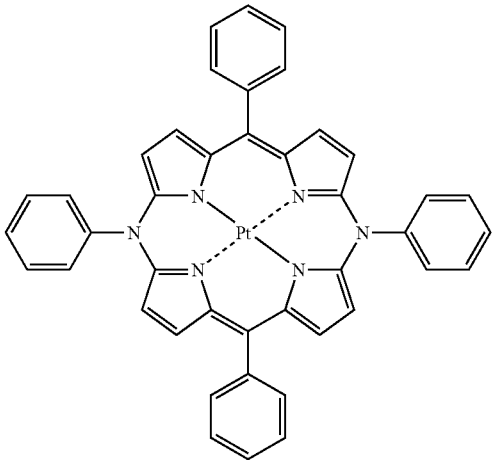
(C22)
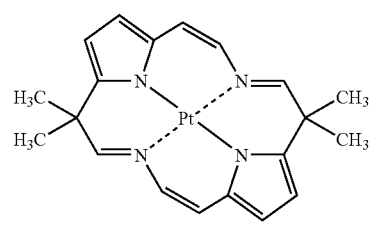
(C23)
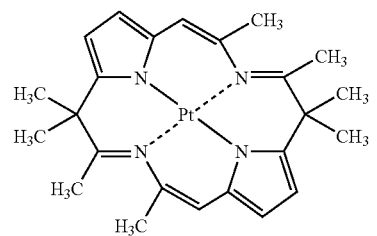
(C24)
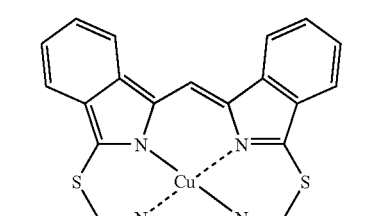
(C25)
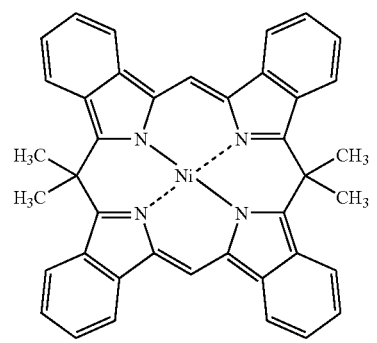

(C26)
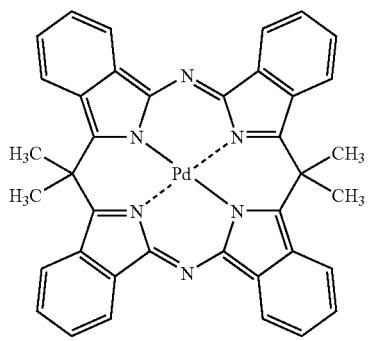
(C27)
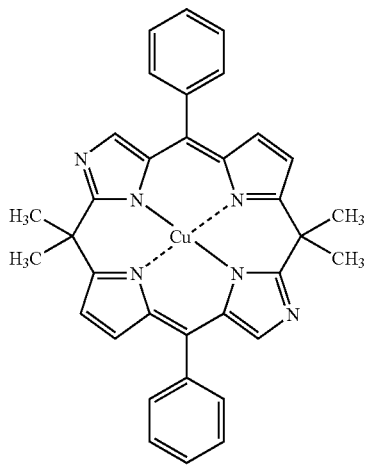
(C28)
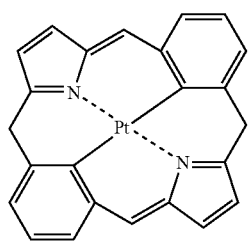
(C29)
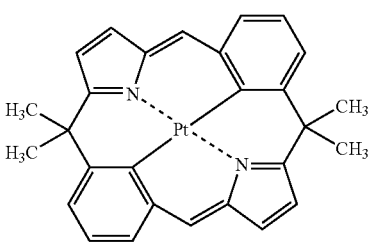
(C30)
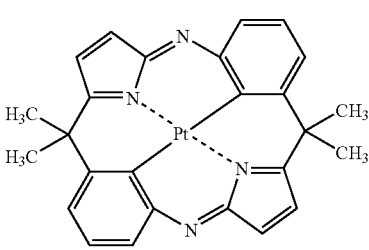
(C31)
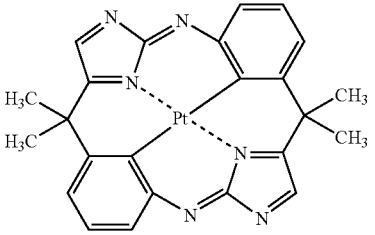
(C32)
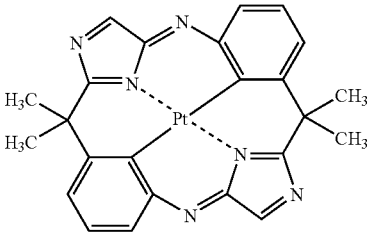
(C33)
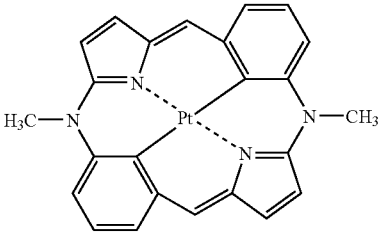
(C34)
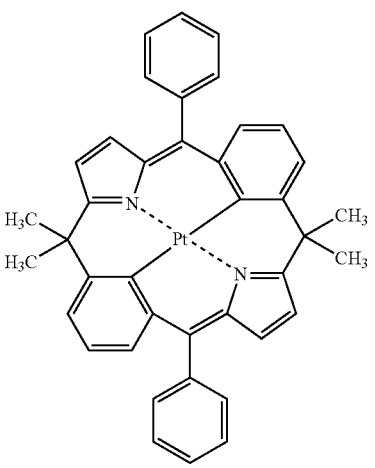
(C35)
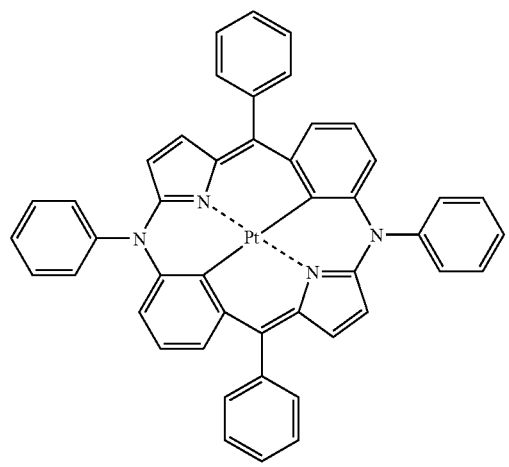

-continued
(C36) 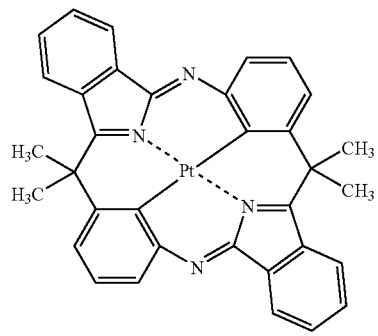
(C37) 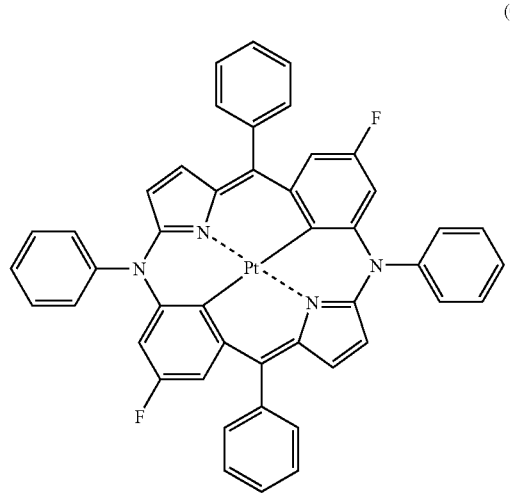
(C38) 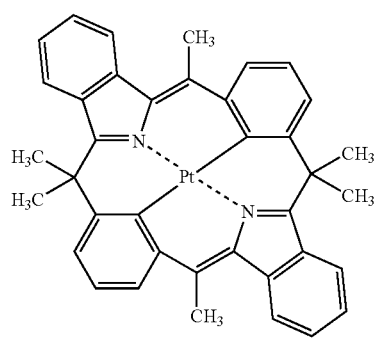
(C39) 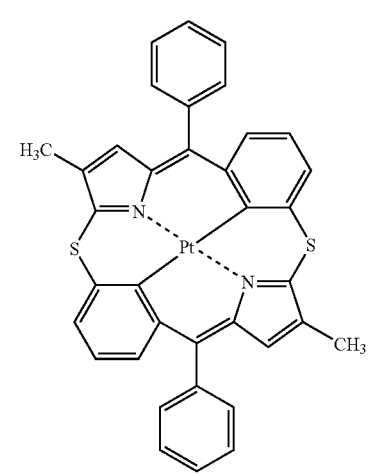
-continued
(C40) 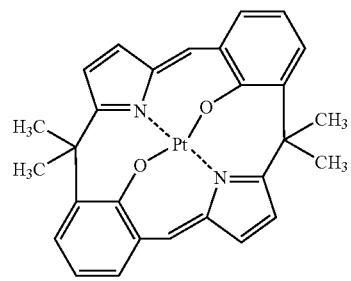
(C41) 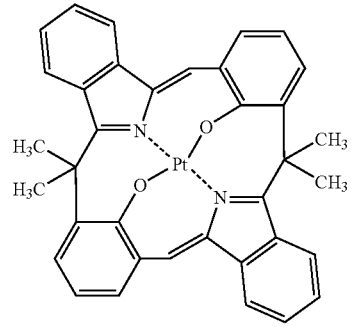
(C42) 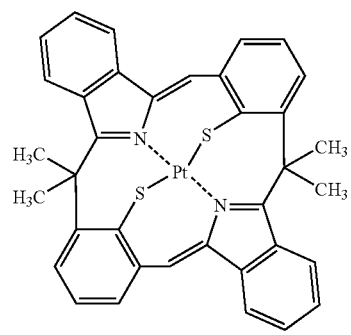
(C43) 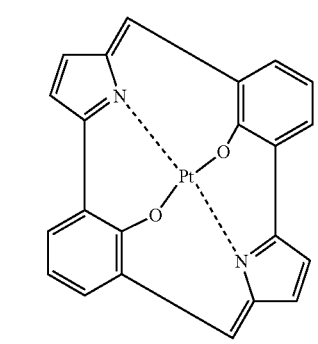
(C44) 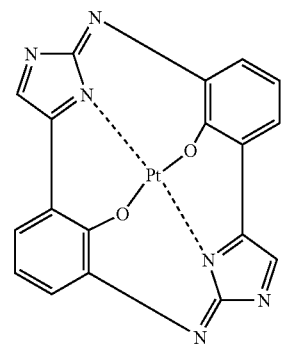

167
-continued
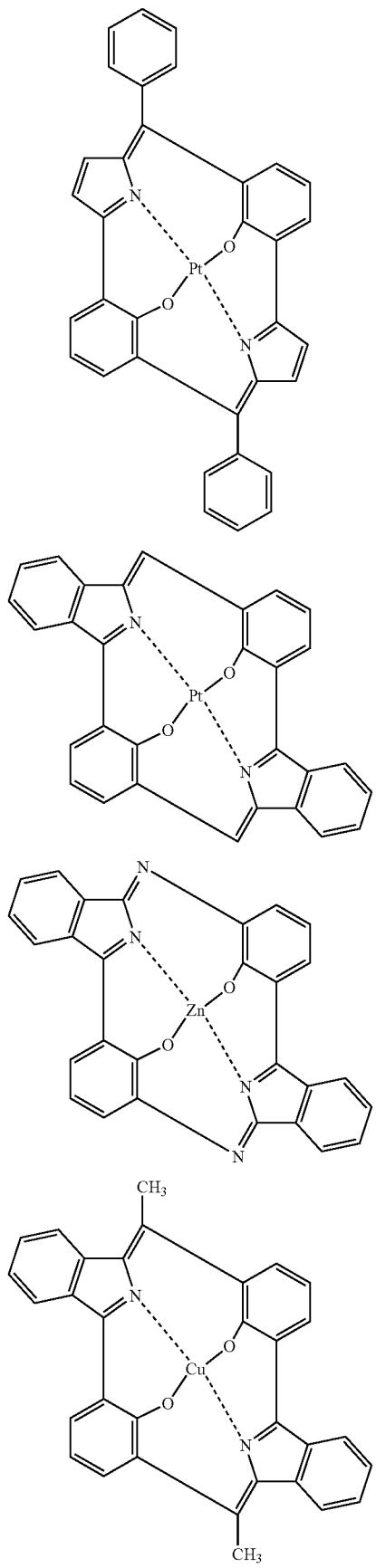
(C45)
(C46)
(C47)
(C48)
168
-continued
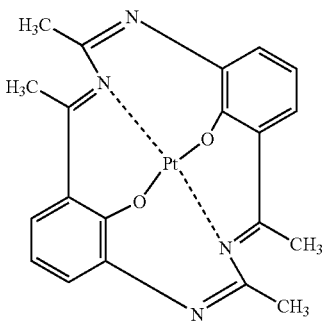
(C49)
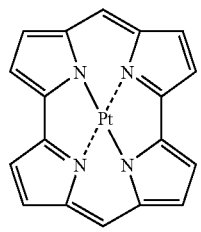
(C50)
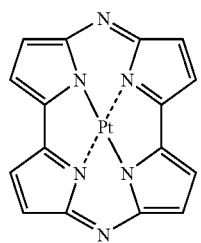
(C51)
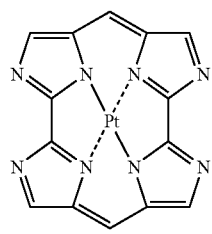
(C52)
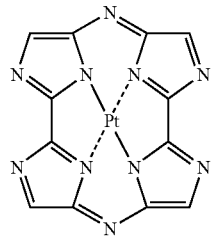
(C53)

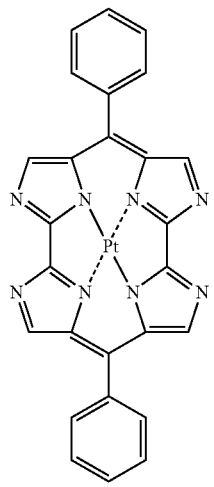
(C54)
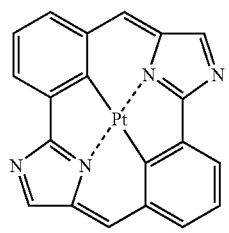
(C55)
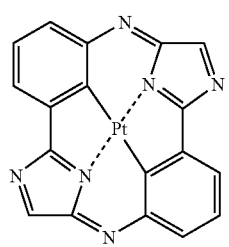
(C56)
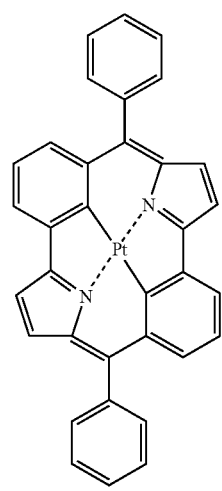
(C57)
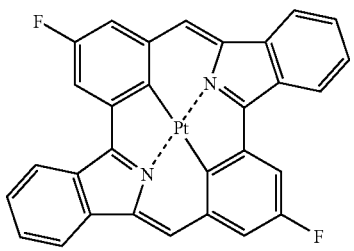
(C58)
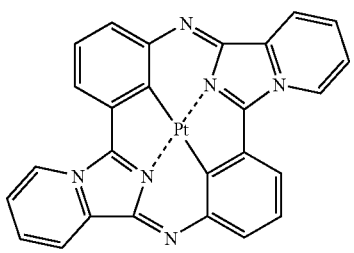
(C59)
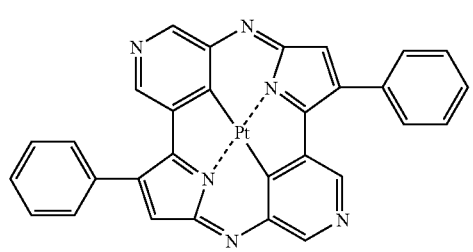
(C60)
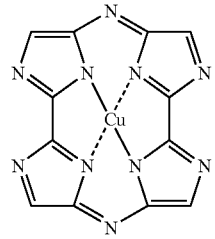
(C61)
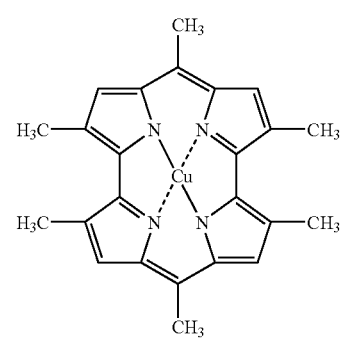
(C62)

The compound represented by Formula (D-1) is more preferably a compound represented by the following Formula (D-2), (D-3) or (D-4).

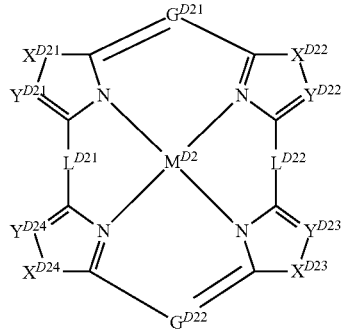

Formula (D-2)

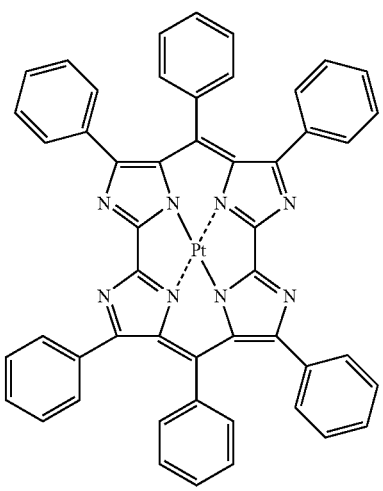

(C63)

An example of preferable metal complexes usable in the invention is a compound represented by the following Formula (D-1).

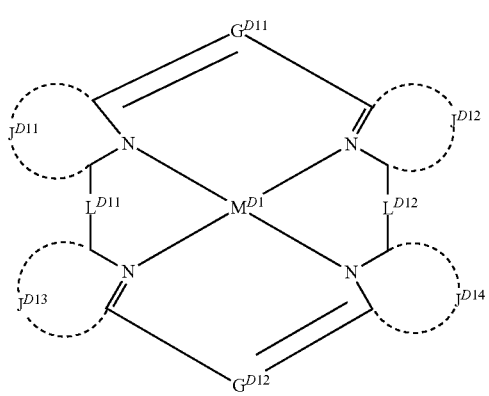

Formula (D-1)

In Formula (D-1), $M^{D1}$ represents a metal ion.

$G^{D11}$ and $G^{D12}$ each independently represent a nitrogen atom or a substituted or unsubstituted carbon atom. $J^{D11}$, $J^{D12}$, $J^{D13}$ and $J^{D14}$ each independently represent an atomic group necessary for forming a 5-membered ring. $L^{D11}$ and $L^{D12}$ each independently represent a connecting group.

Formula (D-1) will be described in detail.

In Formula (D-1), $M^{D1}$, $L^{D11}$ and $L^{D12}$ have the same definitions as corresponding $M^{A1}$, $L^{A11}$ and $L^{A12}$ in Formula (A-1) respectively, and their preferable examples are also the same.

$G^{D11}$ and $G^{D12}$ have the same definitions as corresponding $G^{C11}$ and $G^{C12}$ in Formula (C-1) respectively, and their preferable examples are also the same.

$J^{D11}$, $J^{D12}$, $J^{D13}$ and $J^{D14}$ each independently represent such an atomic group that a nitrogen-containing 5-membered heterocycle containing the atomic group is formed.

In Formula (D-2), $M^{D2}$ represents a metal ion.

$G^{D21}$ and $G^{D22}$ each independently represent a nitrogen atom or a substituted or unsubstituted carbon atom.

$Y^{D21}$, $Y^{D22}$, $Y^{D23}$ and $Y^{D24}$ each independently represent a nitrogen atom or a substituted or unsubstituted carbon atom.

$X^{D21}$, $X^{D22}$, $X^{D23}$ and $X^{D24}$ each independently represent an oxygen atom, a sulfur atom, $-NR^{D21}-$ or $-C(R^{D22})R^{D23}-$.

$R^{D21}$, $R^{D22}$ and $R^{D23}$ each independently represent a hydrogen atom or a substituent. $L^{D21}$ and $L^{D22}$ each independently represent a connecting group.

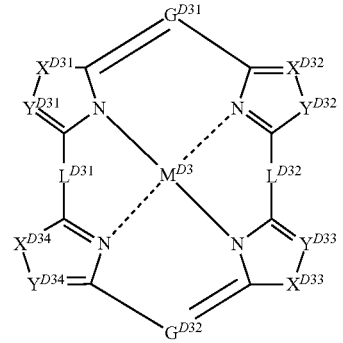

Formula (D-3)

In Formula (D-3), $M^{D3}$ represents a metal ion.

$G^{D31}$ and $G^{D32}$ each independently represent a nitrogen atom or a substituted or unsubstituted carbon atom.

$Y^{D31}$, $Y^{D32}$, $Y^{D33}$ and $Y^{D34}$ each independently represent a nitrogen atom or a substituted or unsubstituted carbon atom.

$X^{D31}$, $X^{D32}$, $X^{D33}$ and $X^{D34}$ each independently represent an oxygen atom, a sulfur atom, $-NR^{D31}-$ or $-C(R^{D32})R^{D33}-$.

$R^{D31}$, $R^{D32}$ and $R^{D33}$ each independently represent a hydrogen atom or a substituent. $L^{D31}$ and $L^{D32}$ each independently represent a connecting group.

Formula (D-4)

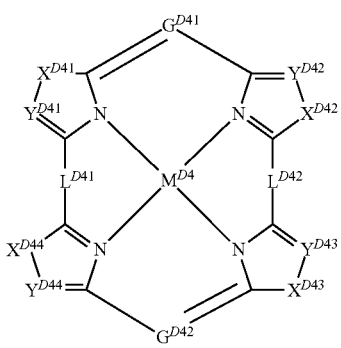

In Formula (D-4), $M^{D4}$ represents a metal ion.

$G^{D41}$ and $G^{D42}$ each independently represent a nitrogen atom or a substituted or unsubstituted carbon atom.

$Y^{D41}$, $Y^{D42}$, $Y^{D43}$ and $Y^{D44}$ each independently represent a nitrogen atom or a substituted or unsubstituted carbon atom.

$X^{D41}$, $X^{D42}$, $X^{D43}$ and $X^{D44}$ each independently represent an oxygen atom, a sulfur atom, $-NR^{D41}-$ or $-C(R^{D42})R^{D43}-$. $R^{D41}$, $R^{D42}$ and $R^{D43}$ each independently represent a hydrogen atom or a substituent. $L^{D41}$ and $L^{D42}$ each independently represent a connecting group.

Formula (D-2) will be described in detail.

In Formula (D-2), $M^{D2}$, $L^{D21}$, $L^{D22}$, $G^{D21}$ and $G^{D22}$ have the same definitions as corresponding $M^{D1}$, $L^{D11}$, $L^{D12}$, $G^{D11}$ and $G^{D12}$ in Formula (D-1) respectively, and their preferable examples are also the same.

$Y^{D21}$, $Y^{D22}$, $Y^{D23}$ and $Y^{D24}$ each independently represent a nitrogen atom or a substituted or unsubstituted carbon atom, preferably a substituted or unsubstituted carbon atom, and more preferably an unsubstituted carbon atom.

$X^{D21}$, $X^{D22}$, $X^{D23}$ and $X^{D24}$ each independently represent an oxygen atom, a sulfur atom, $-NR^{D21}-$ or $-C(R^{D22})R^{D23}-$, preferably a sulfur atom, $-NR^{D21}-$ or $-C(R^{D22})R^{D23}-$, more preferably $-NR^{D21}-$ or $-C(R^{D22})R^{D23}-$, and further more preferably $-NR^{D21}-$.

$R^{D21}$, $R^{D22}$ and $R^{D23}$ each independently represent a hydrogen atom or a substituent. The substituent represented by $R^{D21}$, $R^{D22}$ or $R^{D23}$ may be, for example, an alkyl group (preferably those having 1 to 20 carbon atoms, more preferably those having 1 to 12 carbon atoms, particularly preferably those having 1 to 8 carbon atoms, and examples thereof include a methyl group, an ethyl group, an iso-propyl group, a tert-butyl group, a n-octyl group, a n-decyl group, a n-hexadecyl group, a cyclopropyl group, a cyclopentyl group, a cyclohexyl group and the like), an alkenyl group (preferably those having 2 to 20 carbon atoms, more preferably those having 2 to 12 carbon atoms, particularly preferably those having 2 to 8 carbon atoms, and examples thereof include a vinyl group, an allyl group, a 2-butenyl group, a 3-pentenyl group and the like), an alkynyl group (preferably those having 2 to 20 carbon atoms, more preferably those having 2 to 12 carbon atoms, particularly preferably those having 2 to 8 carbon atoms, and examples thereof include a propargyl group, a 3-pentynyl group and the like), an aryl group (preferably those having 6 to 30 carbon atoms, more preferably those having 6 to 20 carbon atoms, particularly preferably those having 6 to 12 carbon atoms group, and examples thereof include a phenyl group, a p-methylphenyl group, a naphthyl group, and the like), a substituted carbonyl group (preferably those having 1 to 20 carbon atoms, more preferably those having 1 to 16 carbon atoms, particularly preferably those having 1 to 12 carbon atoms group, and examples thereof include a acetyl group, a benzoyl group, a methoxycarbonyl group, a phenyloxycarbonyl group, a dimethylaminocarbonyl group, a phenylaminocarbonyl group, and the like), a substituted sulfonyl group (preferably those having 1 to 20 carbon atoms, more preferably those having 1 to 16 carbon atoms, particularly preferably those having 1 to 12 carbon atoms group, and examples thereof include a mesyl group, a tosyl group and the like), or a heterocyclic group (including an aliphatic heterocyclic group and aromatic heterocyclic group, preferably those having 1 to 50 carbon atoms, more preferably those having 1 to 30 carbon atoms, more preferably those having 2 to 12 carbon atoms, preferably containing an oxygen atom, a sulfur atom or a nitrogen atom, and examples thereof include an imidazolyl group, a pyridyl group, a furyl group, a piperidyl group, a morpholino group, a benzoxazolyl group, a triazolyl group, a quinolyl group, a carbazoyl group, a thienyl group and the like). Each of $R^{D21}$, $R^{D22}$ and $R^{D23}$ is preferably an alkyl group, aryl group or aromatic heterocyclic group, more preferably an alkyl or aryl group, and still more preferably an aryl group.

Formula (D-3) will be described in detail.

In Formula (D-3), $M^{D3}$, $L^{D31}$, $L^{D32}$, $G^{D31}$ and $G^{D32}$ have the same definitions as corresponding $M^{D1}$, $L^{D11}$, $L^{D12}$, $G^{D11}$ and $G^{D12}$ in Formula (D-1) respectively, and their preferable examples are also the same.

$X^{D31}$, $X^{D32}$, $X^{D33}$ and $X^{D34}$ have the same definitions as corresponding $X^{D21}$, $X^{D22}$, $X^{D23}$ and $X^{D24}$ in Formula (D-2) respectively, and their preferable examples are also the same.

$Y^{D31}$, $Y^{D32}$, $Y^{D33}$ and $Y^{D34}$ have the same definitions as corresponding $Y^{D21}$, $Y^{D22}$, $Y^{D23}$ and $Y^{D24}$ in Formula (D-2) respectively, and their preferable examples are also the same.

Formula (D-4) will be described in detail.

In Formula (D-4), $M^{D4}$, $L^{D41}$, $L^{D42}$, $G^{D41}$ and $G^{D42}$ have the same definitions as corresponding $M^{D1}$, $L^{D11}$, $L^{D12}$ and $G^{D12}$ in Formula (D-1) respectively, and their preferable examples are also the same.

$X^{D41}$, $X^{D42}$, $X^{D43}$ and $X^{D44}$ have the same definitions as corresponding $X^{D21}$, $X^{D22}$, $X^{D23}$ and $X^{D24}$ in Formula (D-2) respectively, and their preferable examples are also the same. $Y^{D41}$, $Y^{D42}$, $Y^{D43}$ and $Y^{D44}$ have the same definitions as corresponding $Y^{D21}$, $Y^{D22}$, $Y^{D23}$ and $Y^{D24}$ in Formula (D-2) respectively, and their preferable examples are also the same.

Specific examples of the compounds represented by Formula (D-1) are illustrated below, but the invention is not limited thereto.

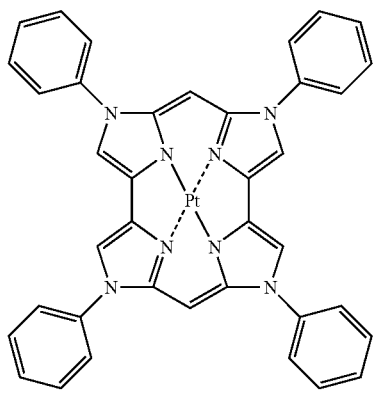

(D1)

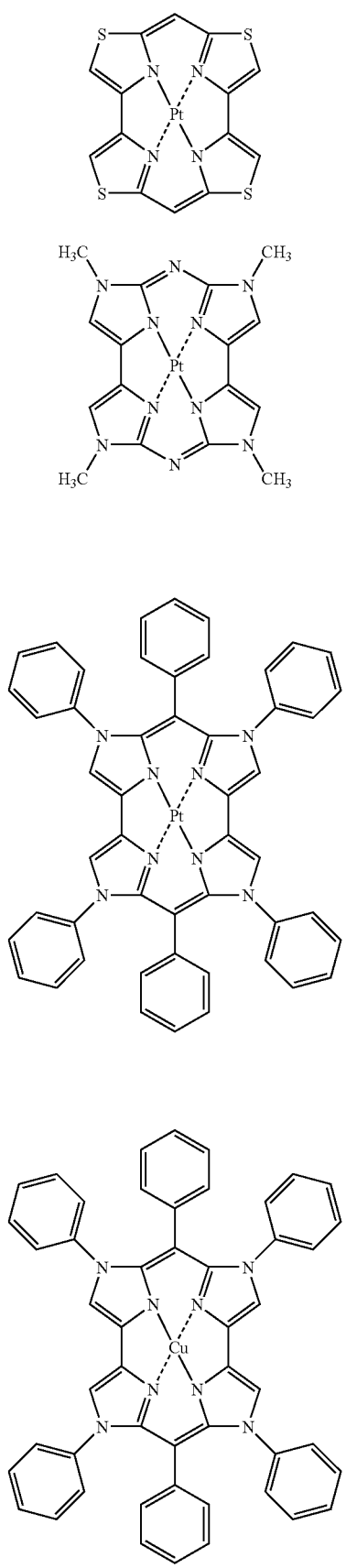
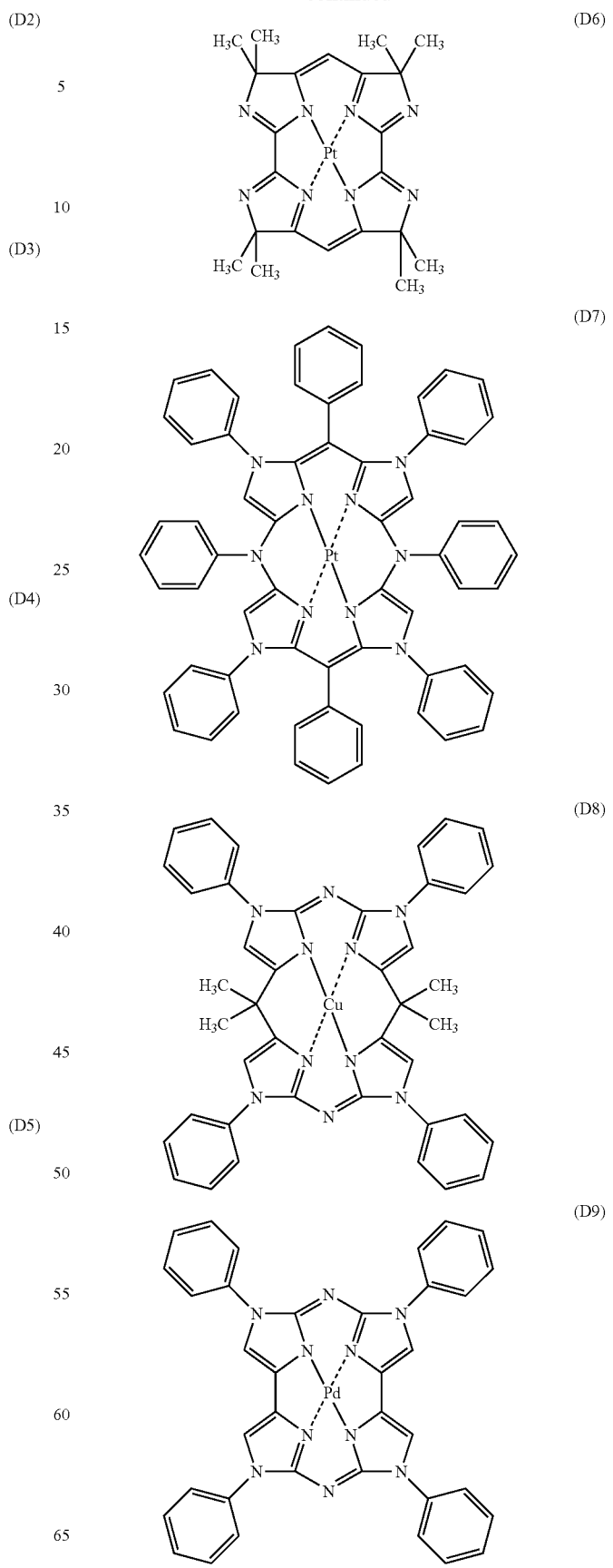

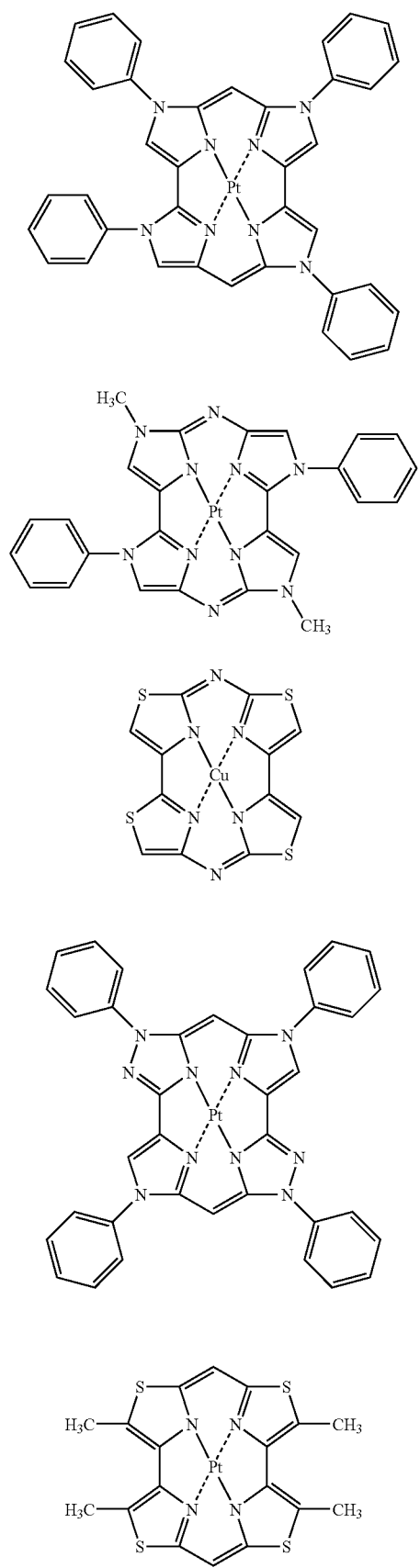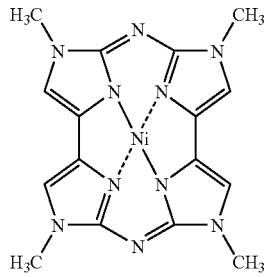

(D19)
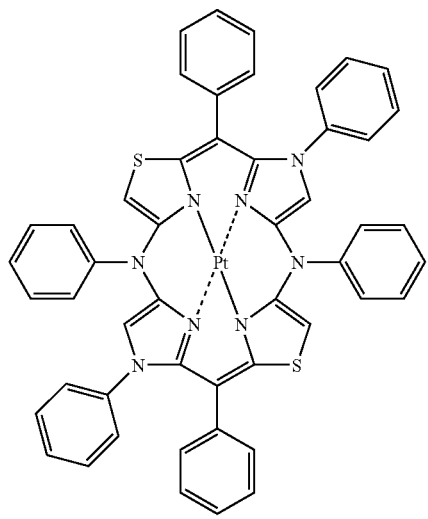

(D20)
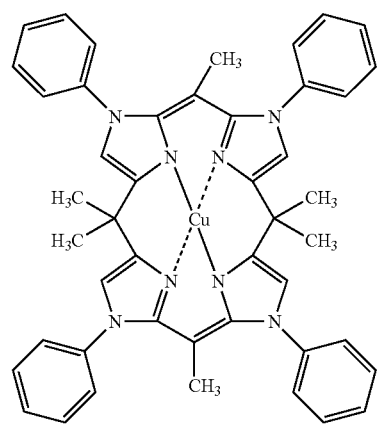

(D21)
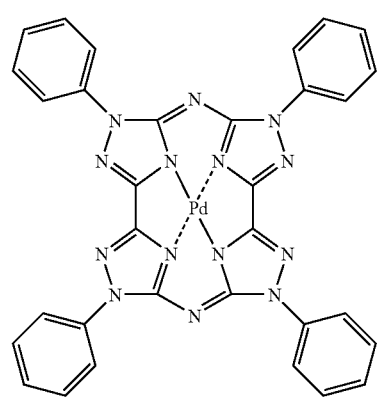

(D22)
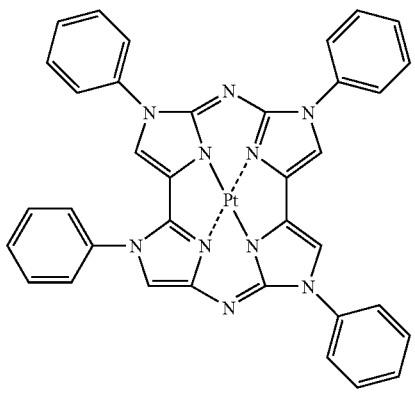

(D23)
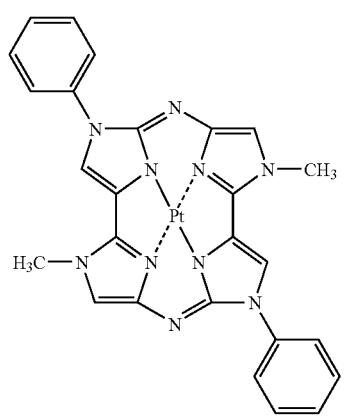

(D24)
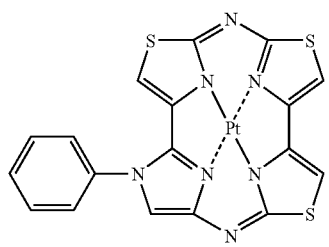

An example of preferable metal complexes usable in the invention is a compound represented by the following Formula (E-1).

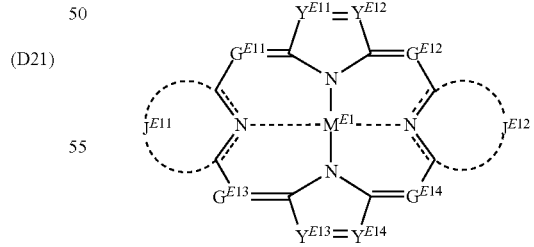

Formula (E-1)

In Formula (E-1), $M^{E1}$ represents a metal ion. $J^{E11}$ and $J^{E12}$ each independently represent an atomic group necessary for forming a 5-membered ring. $G^{E11}$, $G^{E12}$, $G^{E13}$ and $G^{E14}$ each independently represent a nitrogen atom or a substituted or unsubstituted carbon atom. $Y^{E11}$, $Y^{E12}$, $Y^{E13}$ and $Y^{E14}$ each independently represent a nitrogen atom or a substituted or unsubstituted carbon atom.

Formula (E-1) will be described in detail.

$M^{E1}$ has the same definition as $M^{A1}$ in Formula (A-1), and its preferable examples are also the same. $G^{E11}$, $G^{E12}$, $G^{E13}$ and $G^{E14}$ have the same definition as $G^{C11}$ and $G^{C12}$ in Formula (C-1), and their preferable examples are also the same. $J^{E11}$ and $J^{E12}$ have the same definition as $J^{D11}$ to $J^{D14}$ in Formula (D-1), and their preferable examples are also the same. $Y^{E11}$, $Y^{E12}$, $Y^{E13}$ and $Y^{E14}$ have the same definitions as corresponding $Y^{C21}$ to $Y^{C24}$ in Formula (C-2) respectively, and their preferable examples are also the same.

The compound represented by Formula (E-1) is more preferably a compound represented by the following Formula (E-2) or (E-3).

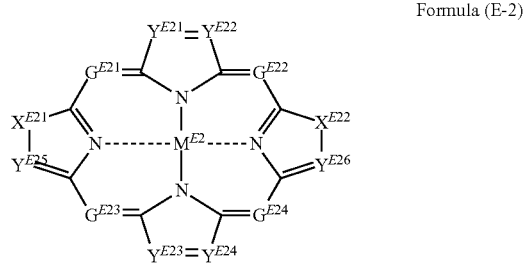

Formula (E-2)

In Formula (E-2), $M^{E2}$ represents a metal ion. $G^{E21}$, $G^{E22}$, $G^{E23}$ and $G^{E24}$ each independently represent a nitrogen atom or a substituted or unsubstituted carbon atom. $Y^{E21}$, $Y^{E22}$, $Y^{E23}$, $Y^{E24}$, $Y^{E25}$ and $Y^{E26}$ each independently represent a nitrogen atom or a substituted or unsubstituted carbon atom. $X^{E21}$ and $X^{E22}$ each independently represent an oxygen atom, a sulfur atom, $-NR^{E21}-$ or $-(R^{E22})R^{E23}-$, $R^{E21}$, $R^{E22}$ and $R^{E23}$ each independently represent a hydrogen atom or a substituent.

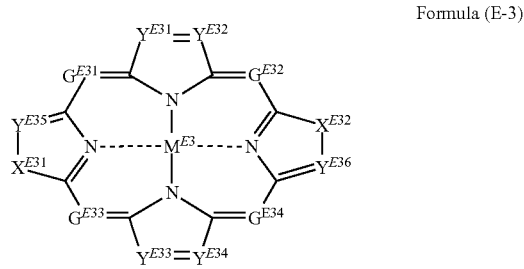

Formula (E-3)

In Formula (E-3), $M^{E3}$ represents a metal ion. $G^{E31}$, $G^{E32}$, $G^{E33}$ and $G^{E34}$ each independently represent a nitrogen atom or a substituted or unsubstituted carbon atom. $Y^{E31}$, $Y^{E32}$, $Y^{E33}$, $Y^{E34}$, $Y^{E35}$ and $Y^{E36}$ each independently represent a nitrogen atom or a substituted or unsubstituted carbon atom. $X^{E31}$ and $X^{E32}$ each independently represent an oxygen atom, a sulfur atom, $-NR^{E31}-$ or $-C(R^{E32})R^{E33}-$. $R^{E31}$, $R^{E32}$ and $R^{E33}$ each independently represent a hydrogen atom or a substituent.

Formula (E-2) will be described in detail.

In Formula (E-2), $M^{E2}$, $G^{E21}$, $G^{E22}$, $G^{E23}$, $G^{E24}$, $Y^{E21}$, $Y^{E22}$, $Y^{E23}$ and $Y^{E24}$ have the same definitions as corresponding $M^{E1}$, $G^{E11}$, $G^{E12}$, $G^{E13}$, $G^{E14}$, $Y^{E11}$, $Y^{E12}$, $Y^{E13}$ and $Y^{E14}$ in Formula (E-1) respectively, and their preferable examples are also the same. $Y^{E25}$ and $Y^{E26}$ have the same definition corresponding $Y^{E11}$ and $Y^{E12}$ in Formula (E-1) respectively, and their preferable examples are also the same. $X^{E21}$ and $X^{E22}$ have the same definitions corresponding $X^{D21}$ and $X^{D22}$ in Formula (D-2) respectively, and their preferable examples are also the same.

Formula (E-3) will be described in detail.

In Formula (E-3), $M^{E3}$, $G^{E31}$, $G^{E32}$, $G^{E33}$, $G^{E34}$, $Y^{E31}$, $Y^{E32}$, $Y^{E33}$ and $Y^{E34}$ have the same definitions as corresponding $M^{E1}$, $G^{E11}$, $G^{E12}$, $G^{E13}$, $G^{E14}$, $Y^{E11}$, $Y^{E12}$, $Y^{E13}$ and $Y^{E14}$ in Formula (E-1) respectively, and their preferable examples are also the same. $Y^{E35}$ and $Y^{E36}$ have the same definition corresponding $Y^{E11}$ and $Y^{E12}$ in Formula (E-1) respectively, and their preferable examples are also the same. $X^{E31}$ and $X^{E32}$ have the same definitions as corresponding $X^{E21}$ and $X^{E22}$ in Formula (E-2) respectively, and their preferable examples are also the same.

Specific examples of the compounds represented by Formula (E-1) are illustrated below, but the invention is not limited thereto.

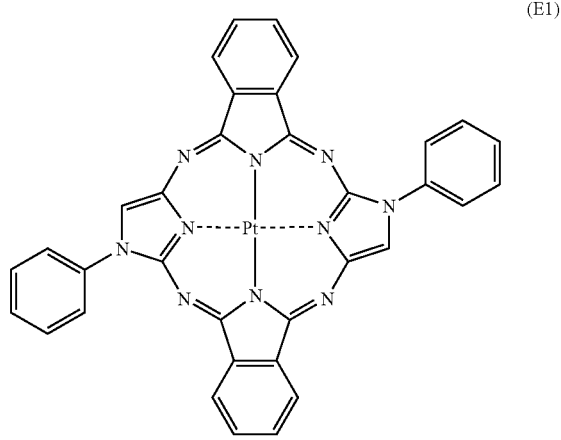

(E1)

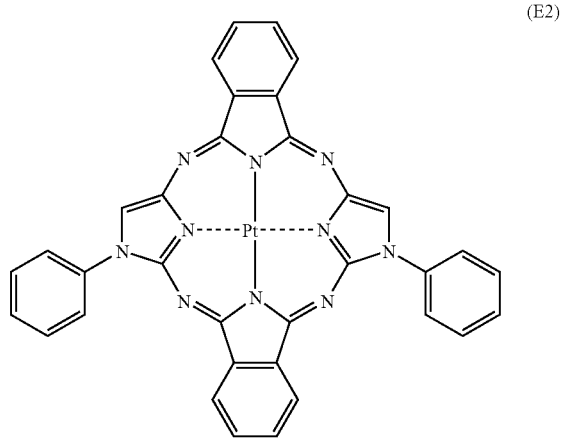

(E2)

(E3)
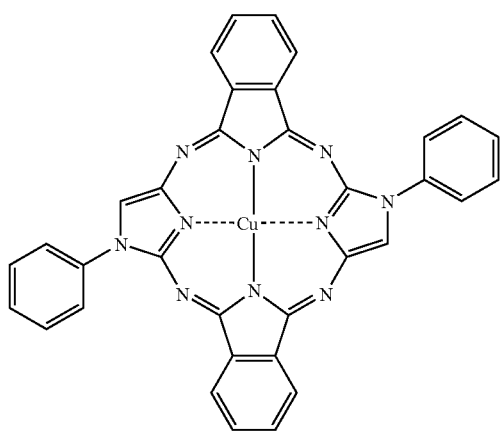
(E4)
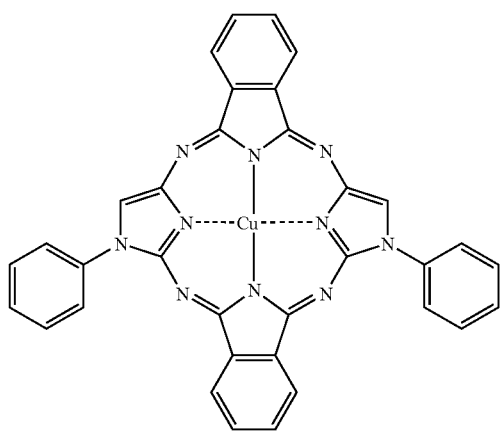
(E5)
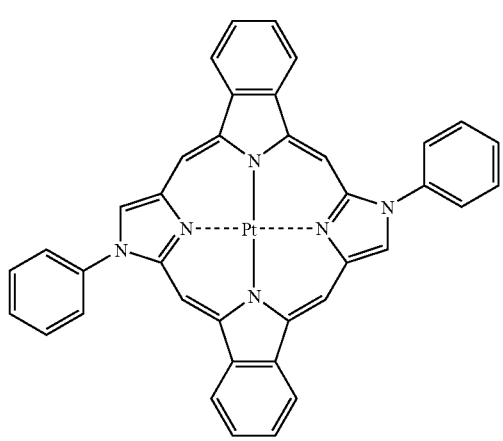
(E6)
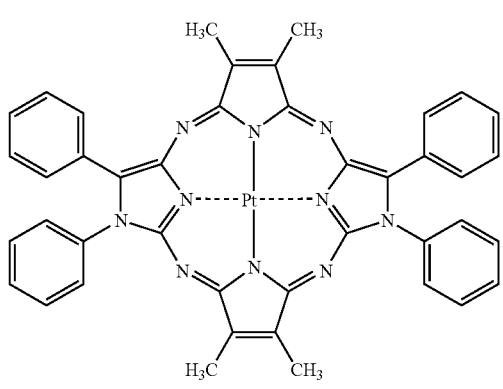
(E7)
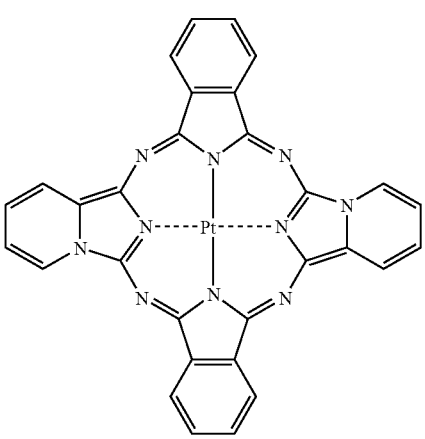
(E8)
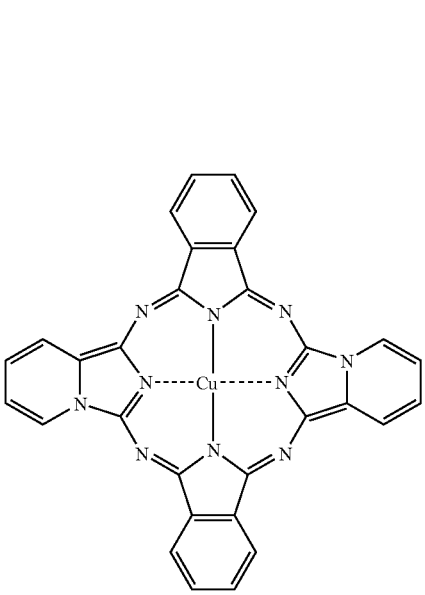
(E9)
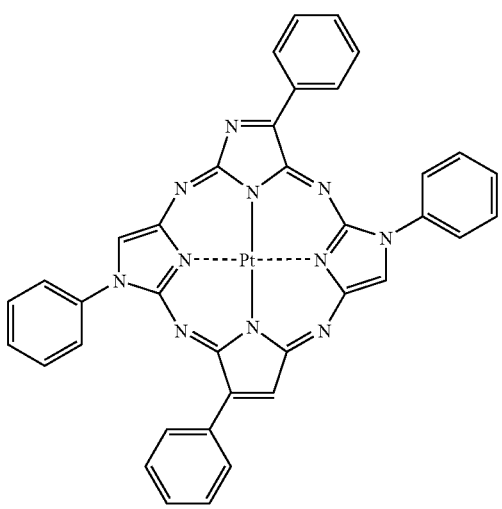

(E10)
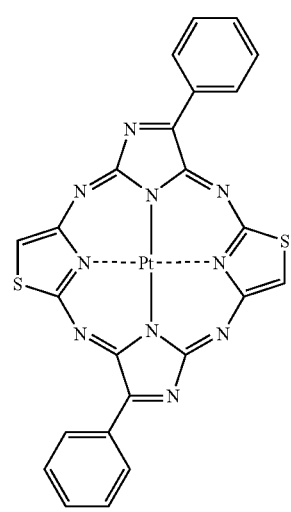
(E11)
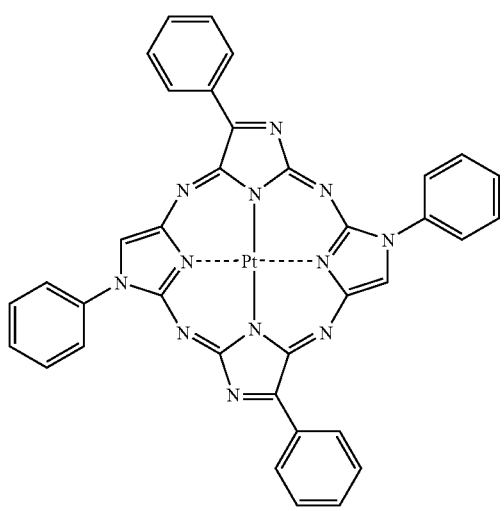
(E12)
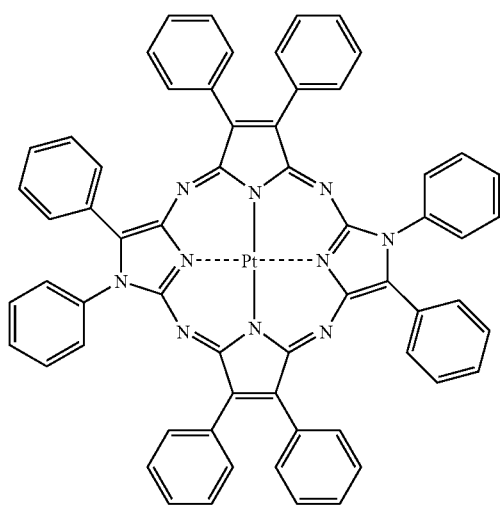
(E13)
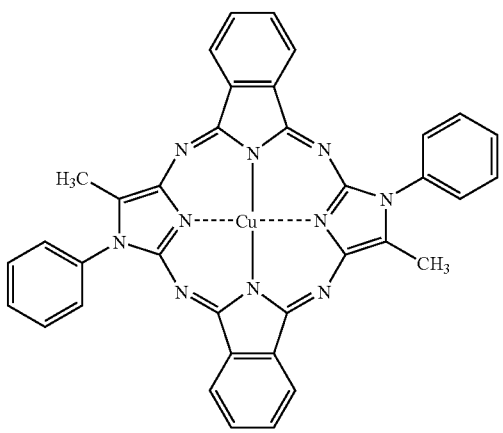
(E14)
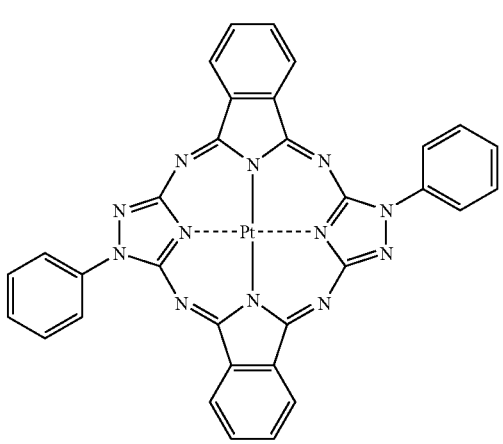
(E15)
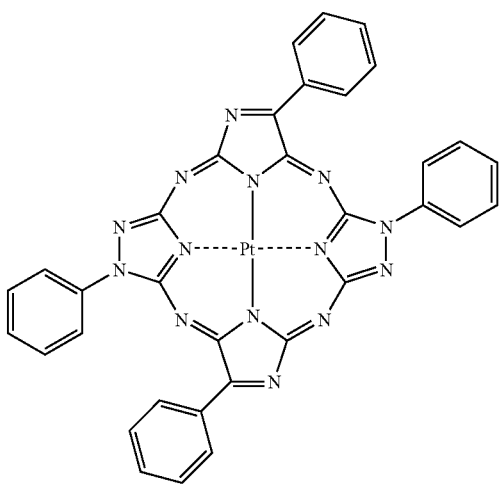

An example of metal complexes usable in the invention is a compound represented by the following Formula (F-1).

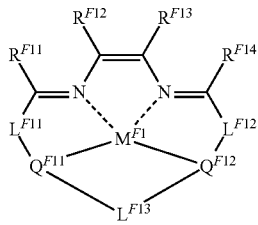

Formula (F-1)

In Formula (F-1), $M^{F1}$ represents a metal ion. $L^{F11}$, $L^{F12}$ and $L^{F13}$ each independently represent a connecting group. $R^{F11}$, $R^{F12}$, $R^{F13}$ and $R^{F14}$ each independently represent a hydrogen atom or a substituent. $R^{F11}$ and $R^{F12}$ may, if possible, be bonded to each other to form a 5-membered ring. $R^{F12}$ and $R^{F13}$ may, if possible, be bonded to each other to form a ring. $R^{F13}$ and $R^{F14}$ may, if possible, be bonded to each other to form a 5-membered ring. $Q^{F11}$ and $Q^{F12}$ each independently represent a partial structure containing an atom covalently bonded to $M^{F1}$.

The compound represented by Formula (F-1) will be described in detail.

In Formula (F-1), $M^{F1}$, $L^{F11}$, $L^{F12}$, $L^{F13}$, $Q^{F11}$ and $Q^{F12}$ have the same definitions as corresponding $M^{A1}$, $L^{A11}$, $L^{A12}$, $L^{A13}$, $Q^{A11}$ and $Q^{A12}$ in Formula (A-1) respectively, and their preferable examples are also the same. $R^{F11}$, $R^{F12}$, $R^{F13}$ and $R^{F14}$ each independently represent a hydrogen atom or a substituent. $R^{F11}$ and $R^{F12}$ may, if possible, be bonded to each other to form a 5-membered ring. $R^{F12}$ and $R^{F13}$ may, if possible, be bonded to each other to form a ring. $R^{F13}$ and $R^{F14}$ may, if possible, be bonded to each other to form a 5-membered ring. The substituent represented by $R^{F11}$, $R^{F12}$, $R^{F13}$ or $R^{F14}$ may be selected from the above-mentioned examples of the substituent represented by $R^{C11}$ to $R^{C14}$ in Formula (C-1). In a preferable embodiment, $R^{F11}$ and $R^{F12}$ are bonded to each other to form a 5-membered ring, and $R^{F13}$ and $R^{F14}$ are bonded to each other to form a 5-membered ring. In another preferable embodiment, $R^{F12}$ and $R^{F13}$ are bonded to each other to form an aromatic ring.

The compound represented by Formula (F-1) is more preferably a compound represented by Formula (F-2), (F-3) or (F-4).

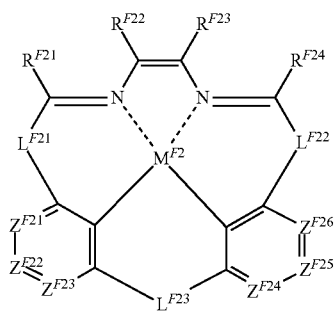

Formula (F-2)

In Formula (F-2), $M^{F2}$ represents a metal ion. $L^{F21}$, $L^{F22}$ and $L^{F23}$ each independently represent a connecting group. $R^{F21}$, $R^{F22}$, $R^{F23}$ and $R^{F24}$ each independently represent a substituent. $R^{F21}$ and $R^{F22}$ may, if possible, be bonded to each other to form a 5-membered ring. $R^{F22}$ and $R^{F23}$ may, if possible, be bonded to each other to form a ring. $R^{F23}$ and $R^{F24}$ may, if possible, be bonded to each other to form a 5-membered ring. $Z^{F21}$, $Z^{F22}$, $Z^{F23}$, $Z^{F24}$, $Z^{F25}$ and $Z^{F26}$ each independently represent a nitrogen atom or a substituted or unsubstituted carbon atom.

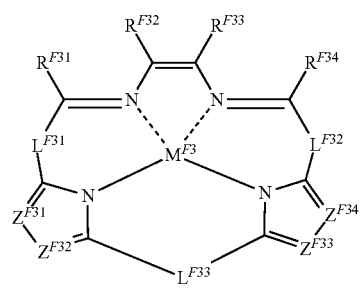

Formula (F-3)

In Formula (F-3), $M^{F3}$ represents a metal ion. $L^{F31}$, $L^{F32}$ and $L^{F33}$ each independently represent a connecting group. $R^{F31}$, $R^{F32}$, $R^{F33}$ and $R^{F34}$ each independently represent a substituent. $R^{F31}$ and $R^{F32}$ may, if possible, be bonded to each other to form a 5-membered ring. $R^{F32}$ and $R^{F33}$ may, if possible, be bonded to each other to form a ring. $R^{F33}$ and $R^{F34}$ may, if possible, be bonded to each other to form a 5-membered ring. $Z^{F31}$, $Z^{F32}$, $Z^{F33}$ and $Z^{F34}$ each independently represent a nitrogen atom or a substituted or unsubstituted carbon atom.

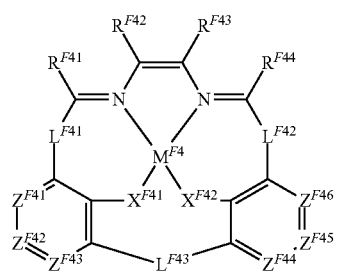

Formula (F-4)

In Formula (F-4), $M^{F4}$ represents a metal ion. $L^{F41}$, $L^{F42}$ and $L^{F43}$ each independently represent a connecting group. $R^{F41}$, $R^{F42}$, $R^{F43}$ and $R^{F44}$ each independently represent a substituent. $R^{F41}$ and $R^{F42}$ may, if possible, be bonded to each other to form a 5-membered ring. $R^{F42}$ and $R^{F43}$ may, if possible, be bonded to each other to form a ring. $R^{F43}$ and $R^{F44}$ may, if possible, be bonded to each other to form a 5-membered ring. $Z^{F41}$, $Z^{F42}$, $Z^{F43}$, $Z^{F44}$, $Z^{F45}$ and $Z^{F46}$ each independently represent a nitrogen atom or a substituted or unsubstituted carbon atom. $X^{F41}$ and $X^{F42}$ each independently represent an oxygen atom, a sulfur atom or a substituted or unsubstituted nitrogen atom.

The compound represented by Formula (F-2) will be described in detail.

$M^{F2}$, $L^{F21}$, $L^{F22}$, $L^{F23}$, $R^{F21}$, $R^{F22}$, $R^{F23}$ and $R^{F24}$ have the same definitions as corresponding $M^{F1}$, $L^{F11}$, $L^{F12}$, $L^{F13}$, $R^{F11}$, $R^{F12}$, $R^{F13}$ and $R^{F14}$ in Formula (F-1) respectively, and their preferable examples are also the same.

$Z^{F21}$, $Z^{F22}$, $Z^{F23}$, $Z^{F24}$, $Z^{F25}$ and $Z^{F26}$ each independently represent a nitrogen atom or a substituted or unsubstituted carbon atom. Each of $Z^{F21}$, $Z^{F22}$, $Z^{F23}$, $Z^{F24}$, $Z^{F25}$ and $Z^{F26}$ is preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

The compound represented by Formula (F-3) will be described in detail.

In Formula (F-3), $M^{F3}$, $L^{F31}$, $L^{F32}$, $L^{F33}$, $R^{F31}$, $R^{F32}$, $R^{F33}$ and $R^{F34}$ have the same definitions as corresponding $M^{F1}$, $L^{F11}$, $L^{F12}$, $L^{F13}$, $R^{F11}$, $R^{F12}$, $R^{F13}$ and $R^{F14}$ in Formula (F-1) respectively, and their preferable examples are also the same. $Z^{F31}$, $Z^{F32}$, $Z^{F33}$ and $Z^{F34}$ each independently represent a nitrogen atom or a substituted or unsubstituted carbon atom. Each of $Z^{F31}$, $Z^{F32}$, $Z^{F33}$ and $Z^{F34}$ is preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

The compound represented by Formula (F-4) will be described in detail.

In Formula (F-4), $M^{F4}$, $L^{F41}$, $L^{F42}$, $L^{F43}$, $R^{F41}$, $R^{F42}$, $R^{F43}$ and $R^{F44}$ have the same definitions as corresponding $M^{F1}$, $L^{F11}$, $L^{F12}$, $L^{F13}$, $R^{F11}$, $R^{F12}$, $R^{F13}$ and $R^{F14}$ in Formula (F-1) respectively, and their preferable examples are also the same. $Z^{F41}$, $Z^{F42}$, $Z^{F43}$, $Z^{F44}$, $Z^{F45}$ and $Z^{F46}$ each independently represent a nitrogen atom or a substituted or unsubstituted carbon atom. Each of $Z^{F41}$, $Z^{F42}$, $Z^{F43}$, $Z^{F44}$, $Z^{F45}$ and $Z^{F46}$ is preferably a substituted or unsubstituted carbon atom, and more preferably an unsubstituted carbon atom. When the carbon atom is substituted, the substituent may be selected from the above-mentioned examples of the substituent on the divalent connecting group represented by $L^{A11}$, $L^{A12}$, $L^{A13}$ or $L^{A14}$ in Formula (A-1).

$X^{F41}$ and $X^{F42}$ each independently represent an oxygen atom, a sulfur atom or a substituted or unsubstituted nitrogen atom. Each of $X^{F41}$ and $X^{F42}$ is preferably an oxygen atom or a sulfur atom, and more preferably an oxygen atom.

Specific examples of the compounds represented by Formula (F-1) are illustrated below, but the invention is not limited thereto.

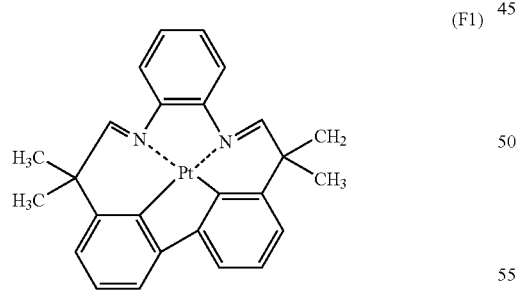

(F1)

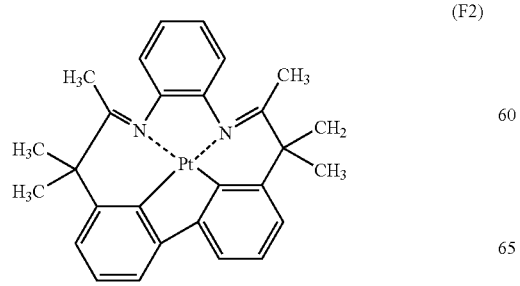

(F2)

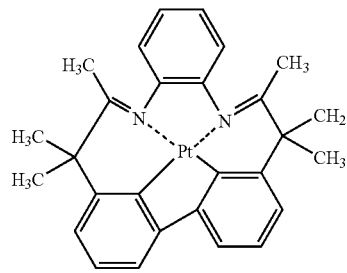

(F3)

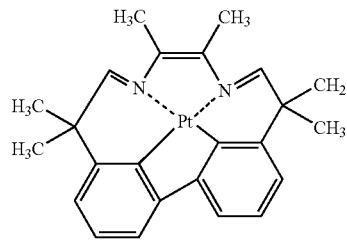

(F4)

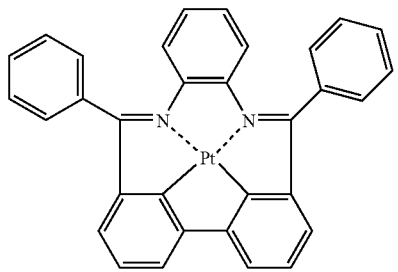

(F5)

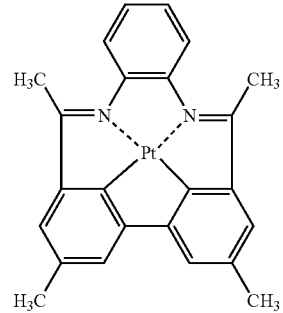

(F6)

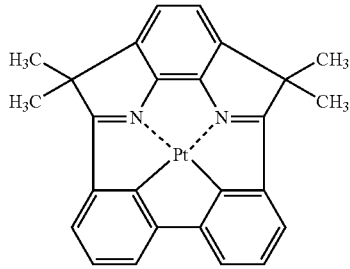

(F7)

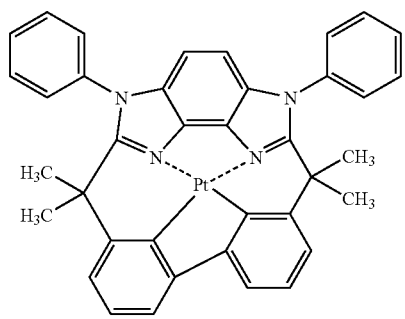
(F8)
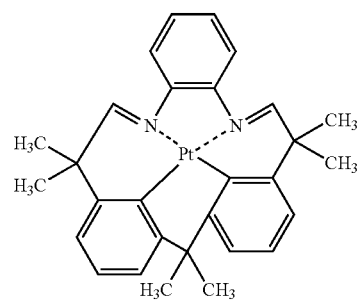
(F9)
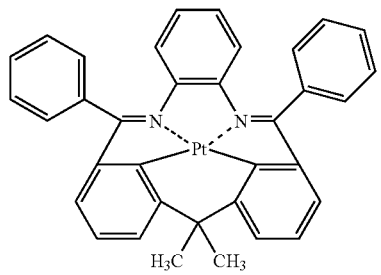
(F10)
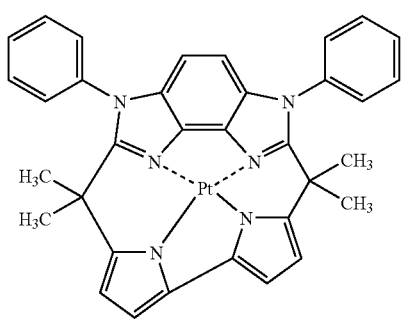
(F11)
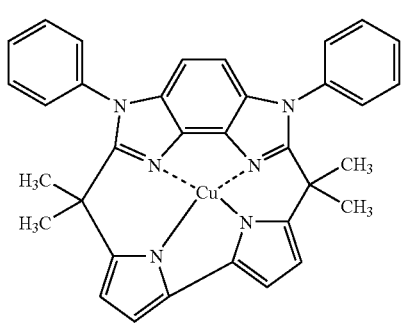
(F12)
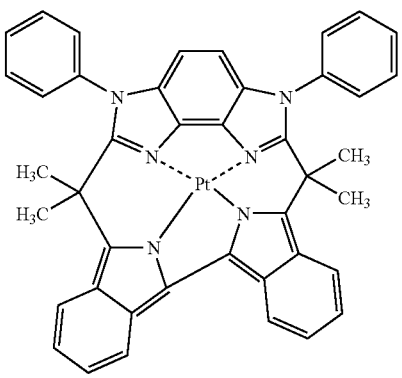
(F13)
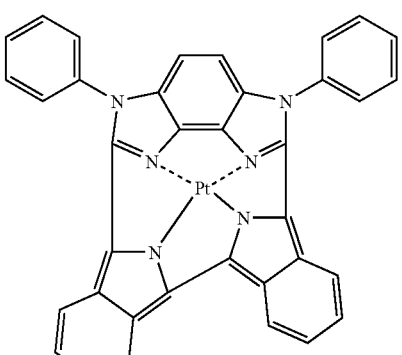
(F14)
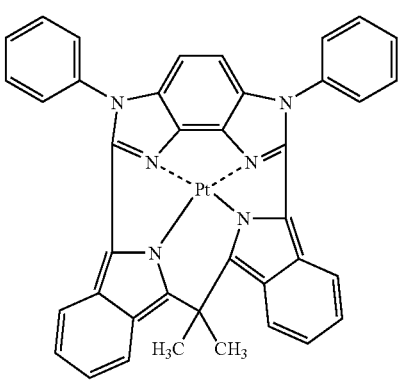
(F15)
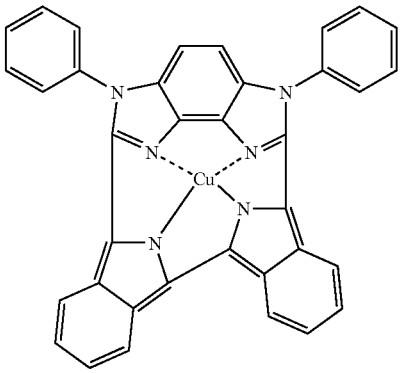
(F16)

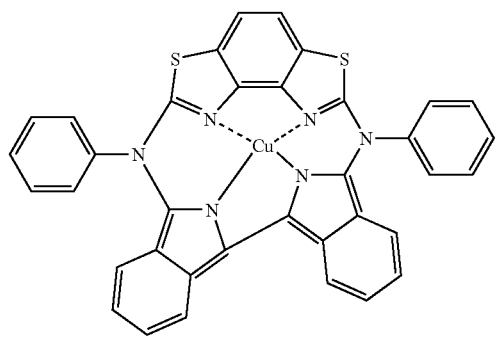
(F17)
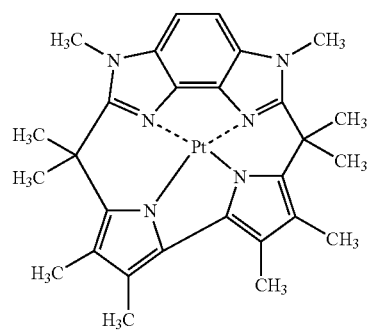
(F18)
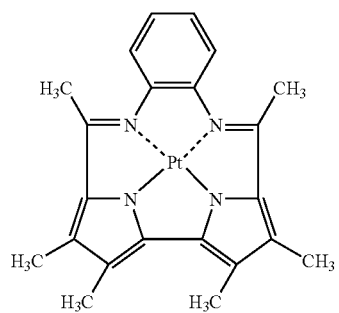
(F19)
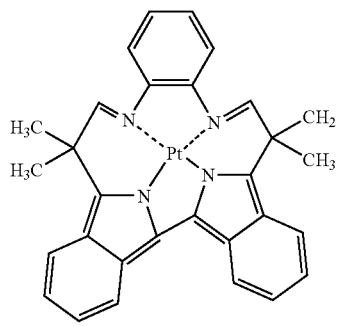
(F20)
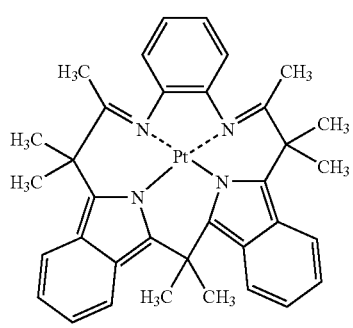
(F21)
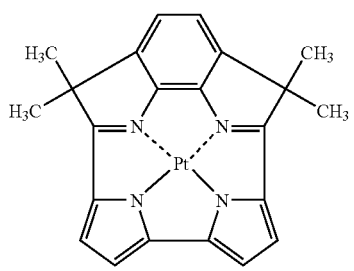
(F22)
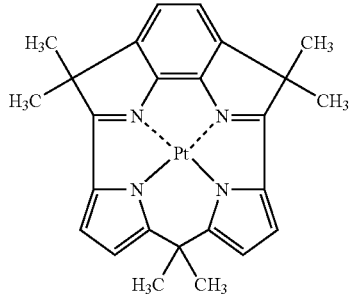
(F23)
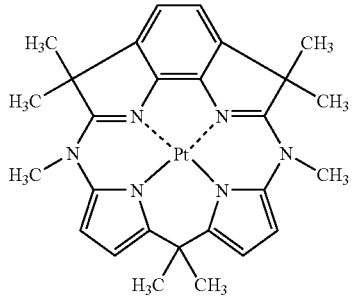
(F24)
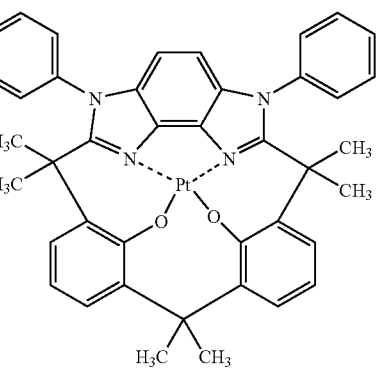
(F25)
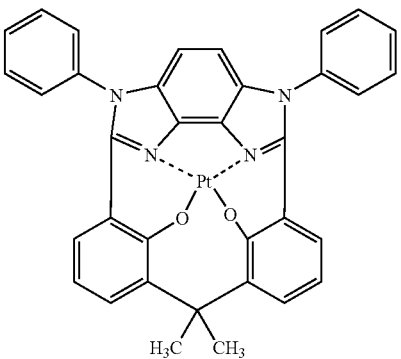
(F26)

-continued
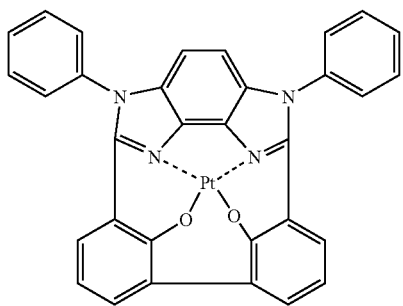
(F27)
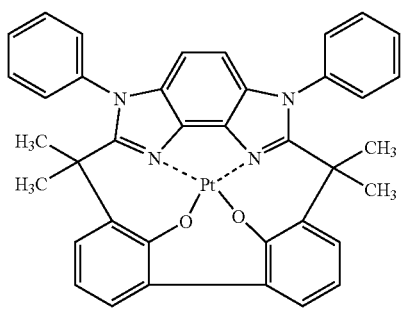
(F28)
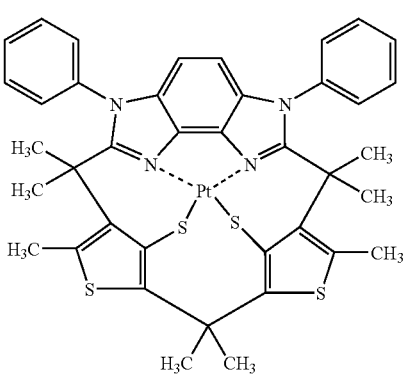
(F29)
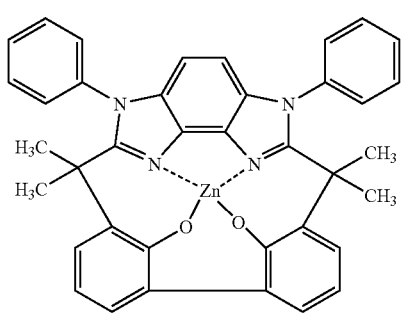
(F30)
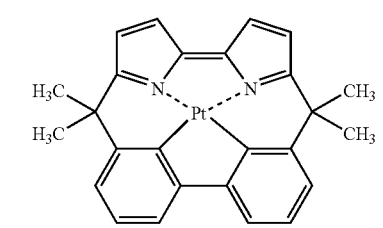
(F31)
-continued
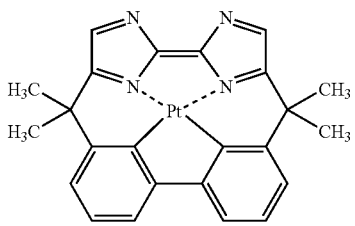
(F32)
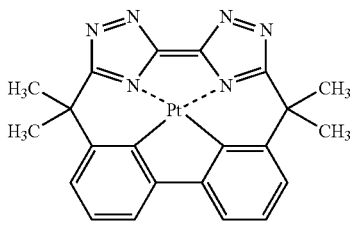
(F33)
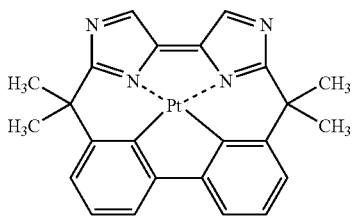
(F34)
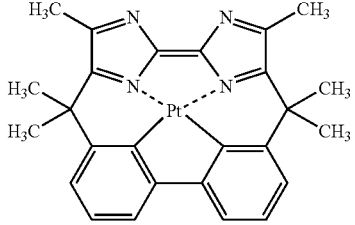
(F35)
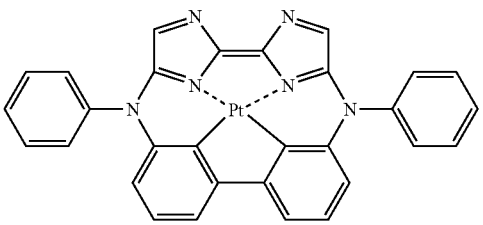
(F36)
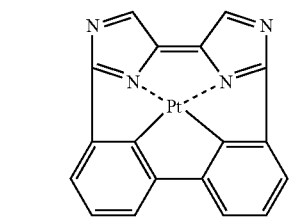
(F37)
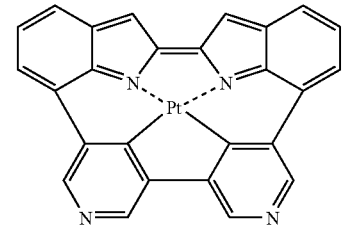
(F38)

(F39)
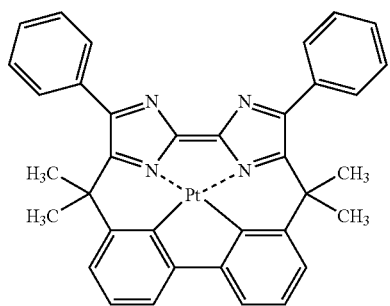
(F40)
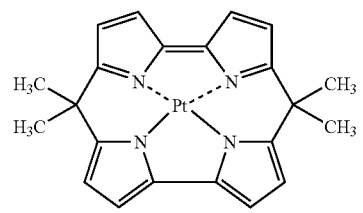
(F41)
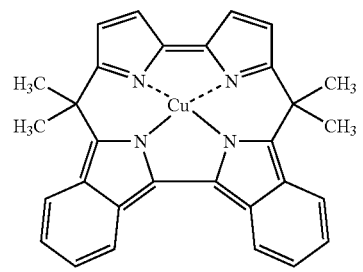
(F42)
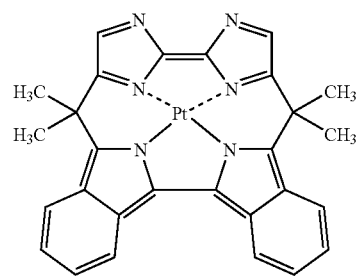
(F43)
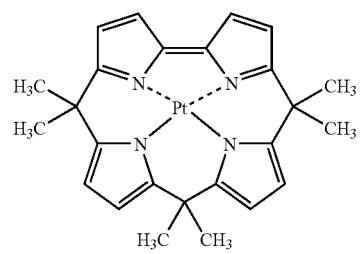
(F44)
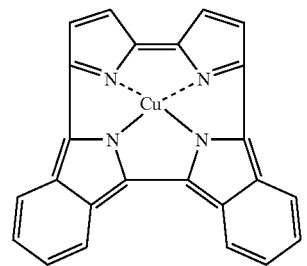
(F45)
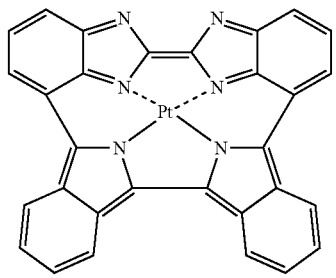
(F46)
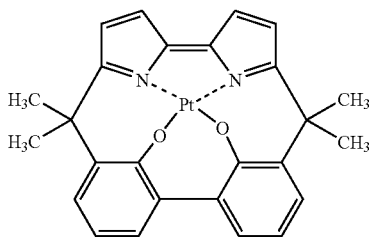
(F47)
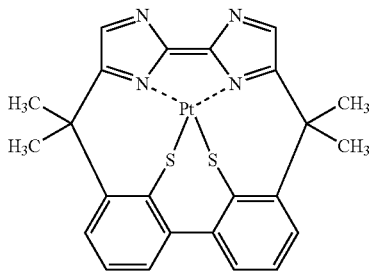
(F48)
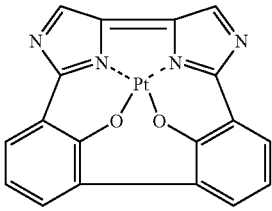
(F49)
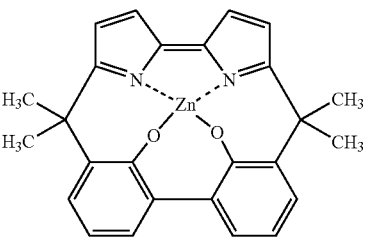
(F50)
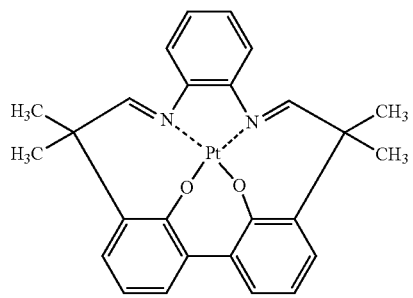

(F51)

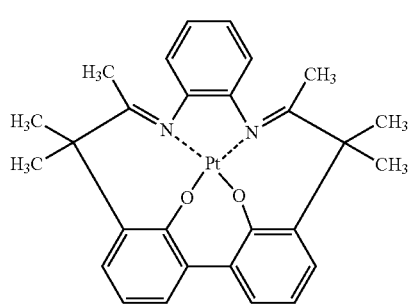

(F52)

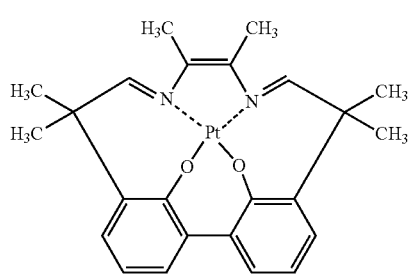

The metal complex is preferably the one represented by Formula (1), more preferably the one represented by any one of Formulae (2), (3) and (4), further preferably the one represented by Formula (3), particularly preferably the one represented by Formula (3-B), and most preferably the one represented by Formula (3-C).

Compounds represented by any one of Formulae (A-1) to (F-1) can be synthesized by conventionally-known methods.

2. Polymer having Metal Complex

The polymer that comprises the metal complex and is used in the invention is herein explained.

The polymer used in the invention may comprise the metal complex in either its main chain or a side chain thereof. The polymer used in the invention may be either a homopolymer or an copolymer. In a case where the polymer is a copolymer, it may be either a random copolymer, an alternating copolymer or a block copolymer. Preferable examples of a monomer unit which is used in combination with the metal complex include those which has a portion having an electron-transporting property and/or a hole-transporting property.

Examples of a skeleton having the portion having the electron-transporting property include those exemplified as materials which can be included in the electron transport layer described below. Further, examples of a skeleton having the portion having the hole-transporting property include those exemplified as materials which can be included in the hole transport layer described below.

A preferable polymer used in the invention is the compound represented by the following Formula (P-1).

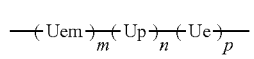

Formula (P-1)

In Formula (P-1), $U_{em}$ represents a unit comprising a metal complex having a tri- or higher-dentate ligand; $U_p$ represents a unit comprising a hole transporting moiety; $U_e$ represents a unit comprising an electron transporting moiety; m represents a positive number; and each of n and p represents a number equal to or larger than 0. Each of m, n and p represents a mol percentage (mol %) that satisfies the equation of m+n+p=100 mol % so as to constitute the polymer represented by Formula (P-1).

Hereinafter, Formula (P-1) will be described in detail.

The metal complex that is represented by $U_{em}$ in Formula (P-1) and constitutes the unit including a metal complex with a tri- or higher-dentate ligand may be selected from those listed as the above-described metal complex, and their preferable ranges are also the same. The Metal complex represented by $U_{em}$ preferably emits phosphorescence in view of luminous efficiency.

$U_{em}$ may include the metal complex moiety with a tri- or higher-dentate ligand on its polymer principal chain or its side chain.

Examples of a hole transporting material which constitutes the unit that comprises the hole transporting moiety and is represented by $U_p$ may include materials for a hole injection layer and a hole transportation layer described below. Preferable examples of the hole transporting materials include a carbazole compound, an azacarbazole compound, an arylamine compound and a thiophene compound. More preferable examples among these include a carbazole compound, an azacarbazole compound and an arylamine compound.

Specific examples of the hole transporting moiety include the followings ("*" represents a site at which the hole transporting moiety bonds to a polymer chain).

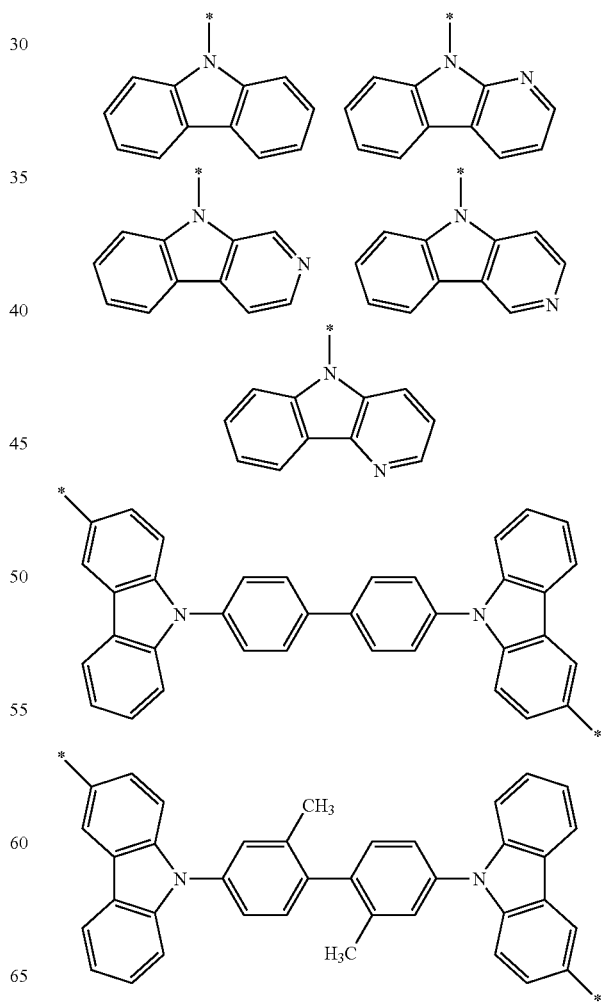

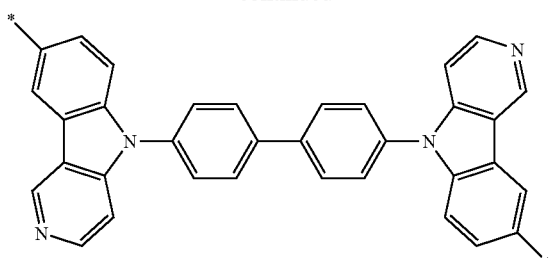

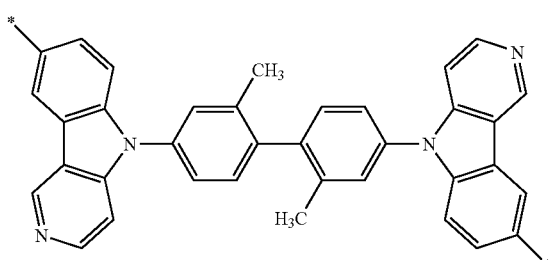

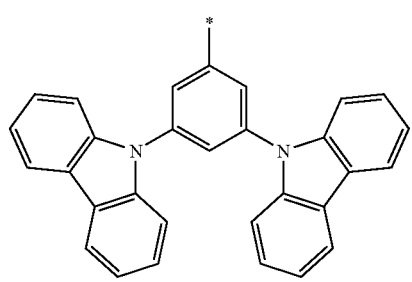

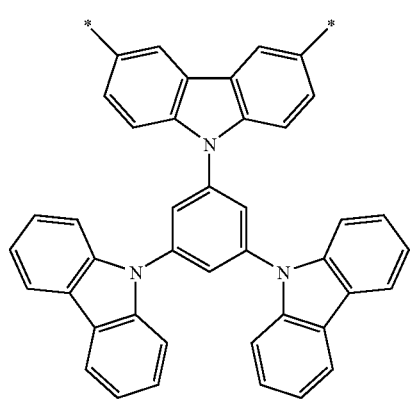

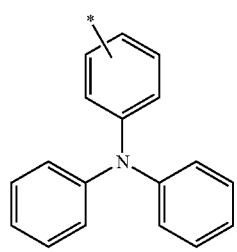

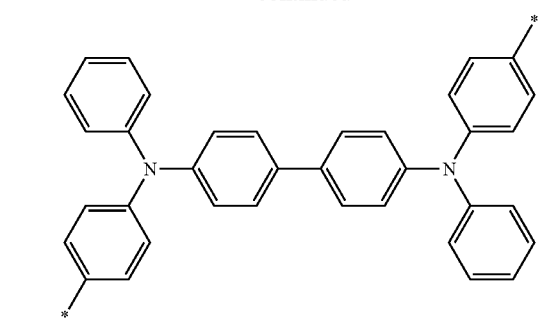

The above-listed hole transporting moieties may respectively have a substituent. Examples of the substituent include the substituents described as those which are applicable to $R^{21}$ to $R^{24}$ in Formula (1).

Examples of a electron transporting material which constitutes the unit that comprises the electron transporting moiety and is represented by $U_e$ may include materials for a electron injection layer and a electron transportation layer described below. Examples of the electron transporting materials which constitute a unit containing an electron transporting moiety represented by Ue may include materials for an electron injection layer and an electron transportation layer described later. Preferable examples of the electron transporting materials include a pyridine compound, a quinoline compound, a phenanthroline compound, a silole compound, a triazole compound, an oxadiazole compound, an imidazole compound, a benzimidazole compound, and an azabenzimidazole compound. More preferable examples among these include a phenanthroline compound, a silole compound, a triazole compound, an oxadiazole compound, an imidazole compound, a benzimidazole compound and an azabenzimidazole compound.

Specific examples of the electron transporting moiety include the followings ("*" represents a site at which the hole transporting moiety bonds to a polymer chain).

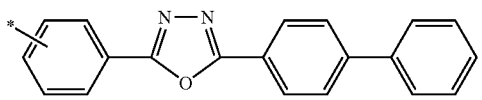

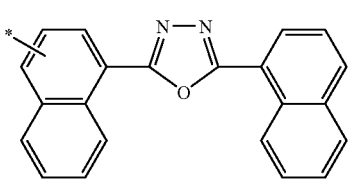

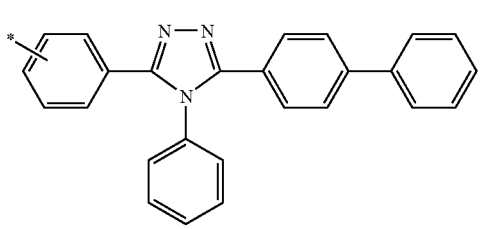

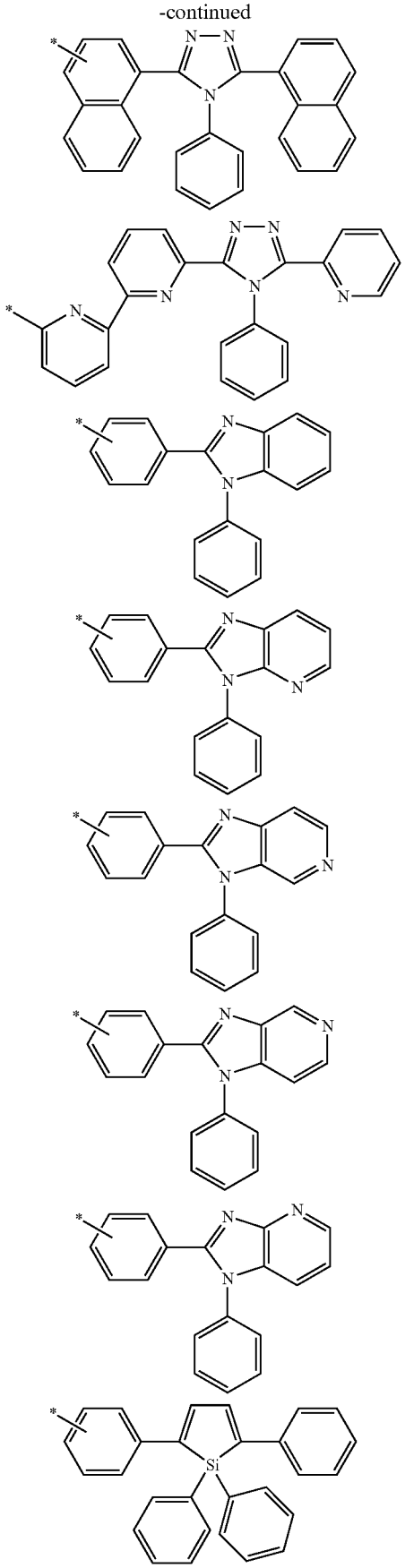

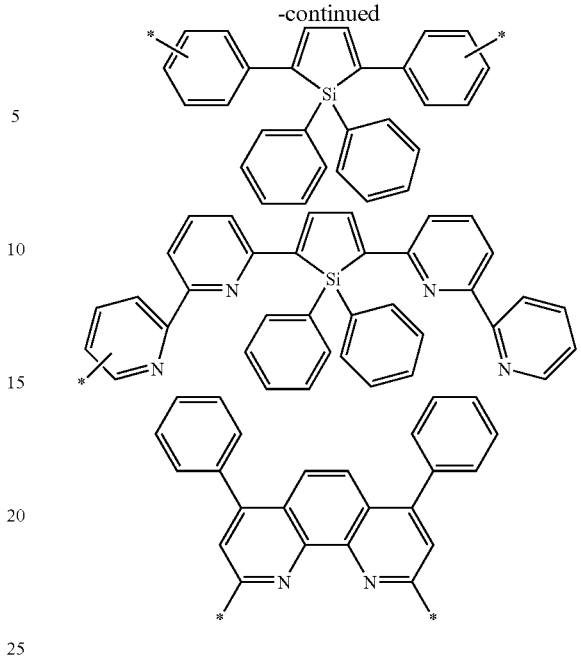

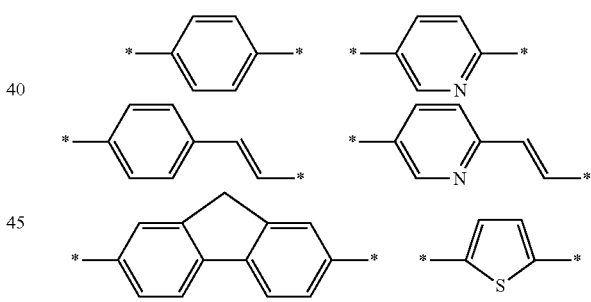

The above-listed electron transporting moieties may respectively have a substituent. Examples of the substituent include the substituents described as those which are applicable to $R^{21}$ to $R^{24}$ in Formula (1).

The hole transporting moiety and the electron transporting moiety may be a conjugated polymer. Typical examples of the conjugated polymers include the followings ("*" represents a site at which the hole transporting moiety or the electron transporting moiety bonds to a polymer chain).

The conjugated polymers shown above may respectively have a substituent. Examples of the substituent include the substituents described as those which are applicable to $R^{21}$ to $R^{24}$ in Formula (1). Preferable examples of the substituent include an alkyl group (preferably having 1 to 30 carbon atoms, more preferably having 1 to 20 atoms, and even more preferably having 1 to 10 carbon atoms, and specific examples thereof include a methyl group, an ethyl group, an isopropyl group, a tert-butyl group, a n-octyl group, a n-decyl group, a n-hexadexyl group, a cyclopropyl group, a cyclopentyl group, and a cyclohexyl group); an aryl group (preferably having 6 to 30 carbon atoms, more preferably having 6 to 20 carbon atoms, and even more preferably having 6 to 12 carbon atoms, and specific examples thereof include a phenyl group, a p-methylphenyl group, a naphthyl group and an anthranyl group); an alkoxyl group (preferably having 1 to 30 carbon atoms, more preferably having 1 to 20 carbon atoms, and even more preferably having 1 to 10 carbon atoms, and specific examples thereof include a methoxy group, an ethoxy group, a buthoxy group, and a 2-ethylhexyloxy group); an aryloxy group (preferably having 6 to 30 carbon atoms, more preferably having 6 to 20 carbon atoms, and even more preferably having 6 to 12 carbon atoms, and specific examples thereof include a phenyloxy group, a 1-naphthyloxy group and a 2-naphthyloxy group); a heterocyclicoxy group (preferably having 1 to 30 carbon atoms, more preferably having 1 to 20 carbon atoms, and even more preferably having 1 to 12 carbon atoms, and specific examples thereof include a pyridyloxy group, a pyradyloxy group, a pyrimidyloxy group and a quinolyloxy group); an acyl group (preferably having 1 to 30 carbon atoms, more preferably having 1 to 20 carbon atoms, and even more preferably having 1 to 12 carbon atoms, and specific examples thereof include an acetyl group, a benzoyl group, a formyl group and a pivaloyl group);

an alkylthio group (preferably having 1 to 30 carbon atoms, more preferably having 1 to 20 carbon atoms, and even more preferably having 1 to 12 carbon atoms, and specific examples thereof include a methylthio group and an ethylthio group); an arylthio group (preferably having 6 to 30 carbon atoms, more preferably having 6 to 20 carbon atoms, and even more preferably having 6 to 12 carbon atoms, and specific examples thereof include a phenylthio group); a heterocyclicthio group (preferably having 1 to 30 carbon atoms, more preferably having 1 to 20 carbon atoms, and even more preferably having 1 to 12 carbon atoms, and specific examples thereof include a pyridylthio group, a 2-benzimizolylthio group, a 2-benzoxazolylthio group and a 2-benzthiazolylthio group); a cyano group; a heterocyclic group (preferably having 1 to 30 carbon atoms, and more preferably having 1 to 12 carbon atoms, and examples of a hetero atom contained therein include a nitrogen atom, an oxygen atom and a sulfur atom; specific examples of the heterocyclic group include an imidazolyl group, a pyridyl group, a quinolyl group, a furyl group, a thienyl group, a piperidyl group, a morpholino group, a benzoxazolyl group, a benzimidazolyl group, a benzthiazolyl group, a carbazolyl group and an azepinyl group); a silyl group (preferably having 3 to 40 carbon atoms, more preferably having 3 to 30 carbon atoms, and even more preferably having 3 to 24 carbon atoms, and specific examples thereof include a trimethylsilyl group and a triphenylsilyl group); and a silyloxy group (preferably having 3 to 40 carbon atoms, more preferably having 3 to 30 carbon atoms, and even more preferably having 3 to 24 carbon atoms, and specific examples thereof include a trimethylsilyloxy group and a triphenylsilyloxy group). More preferable examples among these include an alkyl group, an aryl group, an alkoxy group, an aryloxy group, a heterocyclicoxy group, a cyano group, a heterocyclic group, a silyl group and a silyloxy group, and further preferable examples among these include an alkyl group, an aryl group, an alkoxy group, an aryloxy group and a cyano group.

m represents a positive number; and each of n and p represents a number equal to or larger than 0. Each of m, n and p represents a mol percentage (mol %) that satisfies the equation of $m+n+p=100$ mol % so as to constitute the polymer represented by Formula (P-1). In view of high luminescence efficiency, low-voltage driving property and high durability, the inequality of $0.0001 \leq m/(m+n+p) \leq 0.5$ is preferably satisfied, $0.001 \leq m/(m+n+p) \leq 0.4$ is more preferably satisfied, $0.01 \leq m/(m+n+p) \leq 0.3$ is even more preferably satisfied, and $0.05 \leq m/(m+n+p) \leq 0.2$ is particularly preferably satisfied.

When two or more kinds of the polymers which are respectively represented by Formula (P-1) are used, the polymer represented by Formula (P-1) in which n represents 0 and the polymer represented by Formula (P-1) in which p represents 0 may be mixed or laminated. When a luminescent polymer and a hole transporting polymer and/or an electron transporting polymer are used in combination, the amount of the luminescent polymer relative to the total amount of the polymers is preferably in a range of 0.01% to 50% by mass, more preferably in a range of 0.1% to 40% by mass, even more preferably in a range of 1% to 30% by mass, and particularly preferably in a range of 5% to 20% by mass.

The weight average molecular weight (in terms of polystyrene) is preferably in the range of 1,000 to 5,000,000, more preferably in the range of 2,000 to 1,000,000, and still more preferably in the range of 3,000 to 100,000. The polymer having the weight average molecular weight within the preferable range has superiority in film formability, light emission efficiency and durability.

Examples of the polymer which can be used in the invention are shown below, while the invention is not limited thereto.

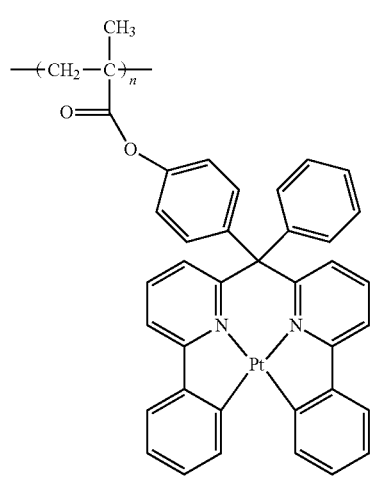

P1

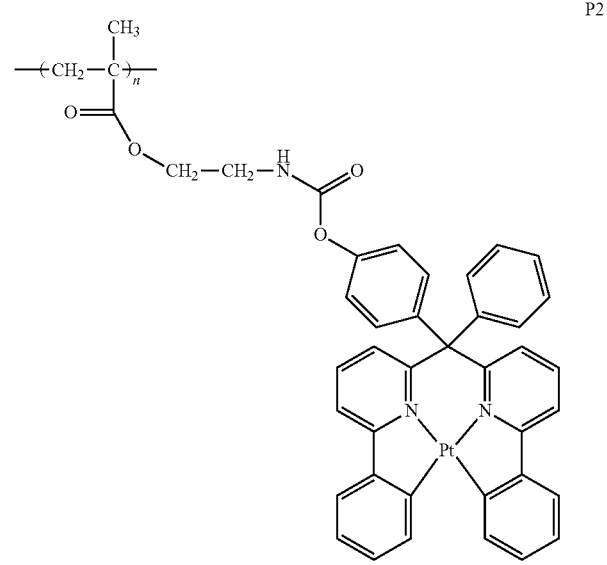

P2

-continued
P3
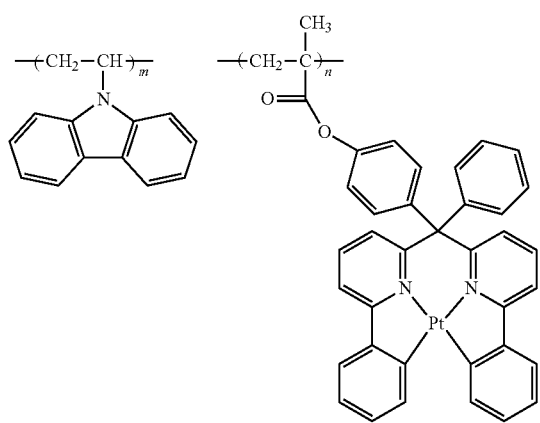
(mol % ratio of m:n = 90:10)
P4
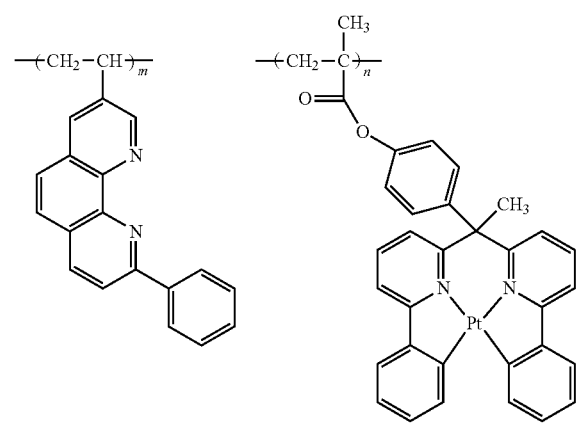
(mol % ratio of m:n = 85:15)
P5
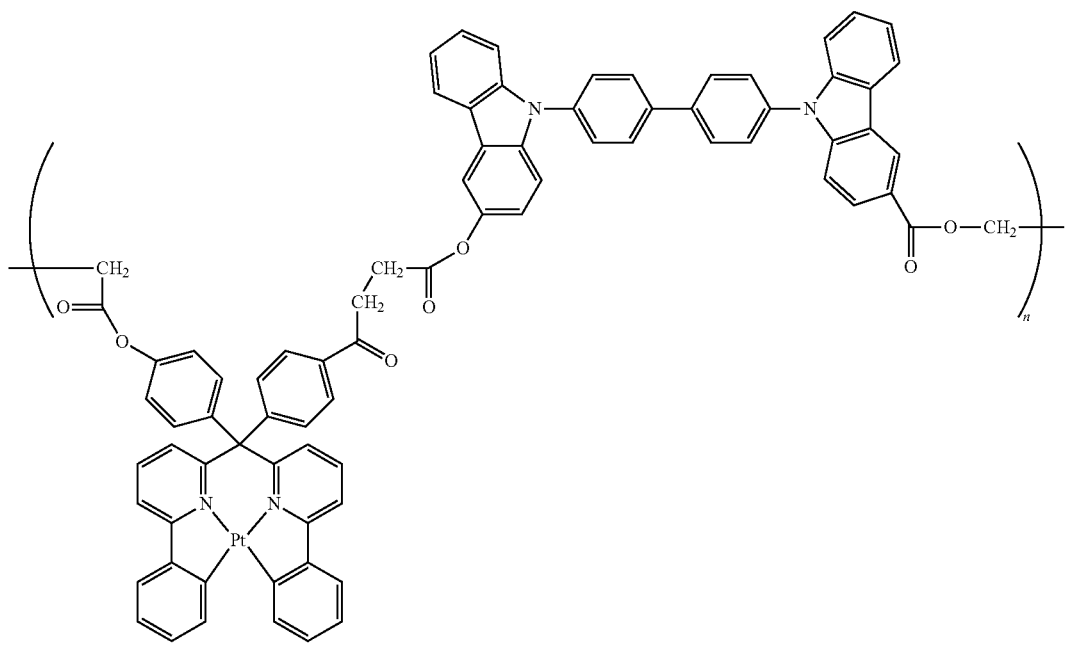
P6
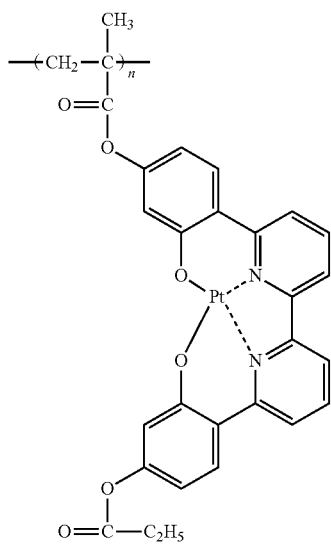
P7
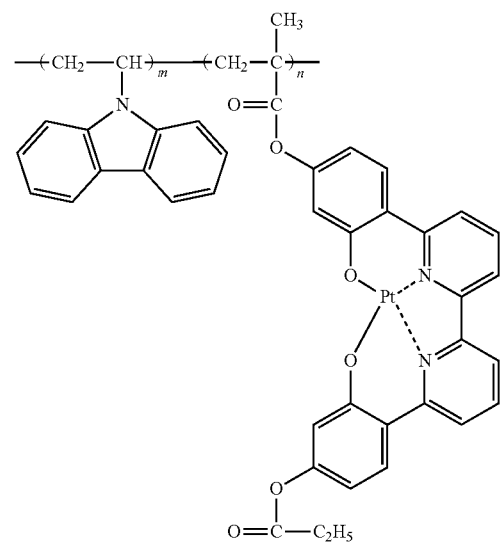
(mol % ratio of m:n = 88:12)

-continued
P8
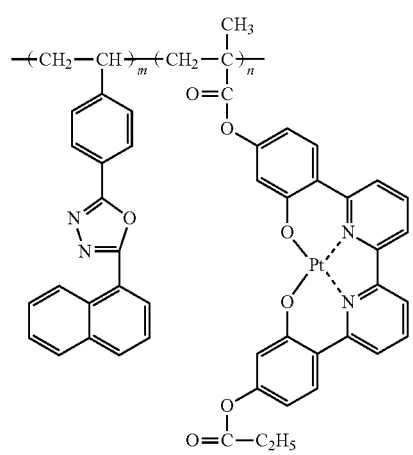
(mol % ratio of m:n = 85:15)
P9
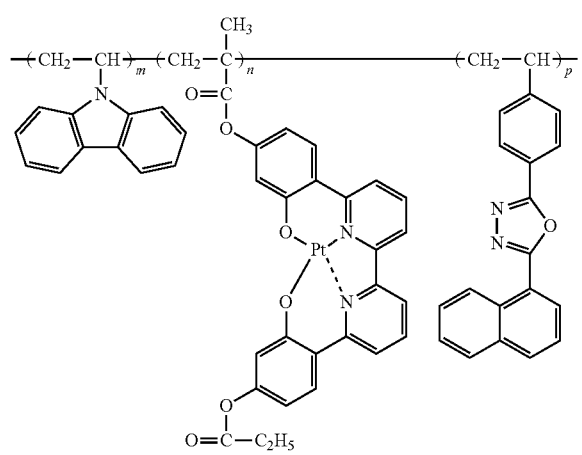
(mol % ratio of m:n:p = 65:15:20)
P10
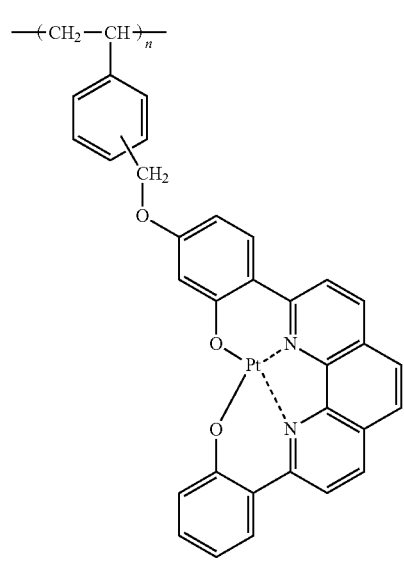
P11
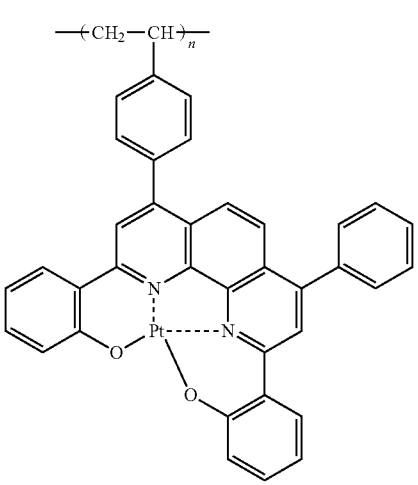
(mol % ratio of m:n = 85:15)
P12
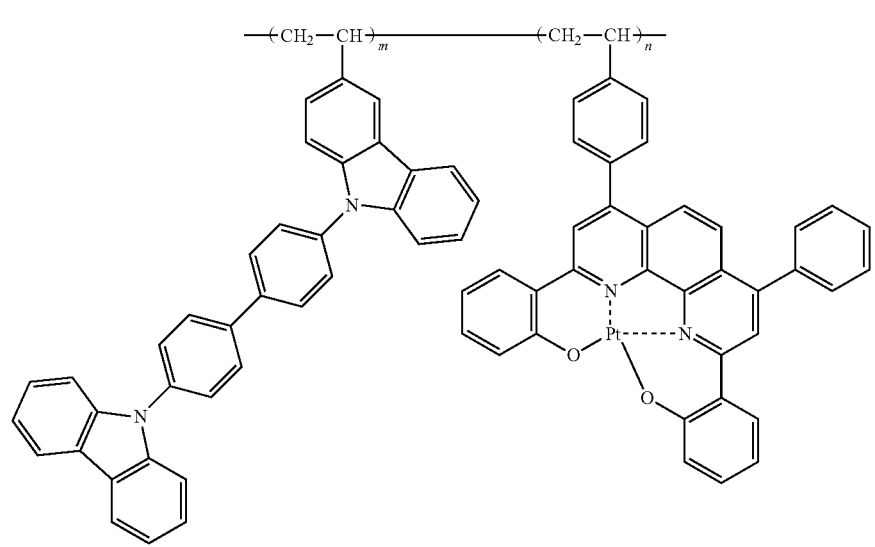
(mol % ratio of m:n = 90:10)

211                                                                                                 212
-continued
P13                                                    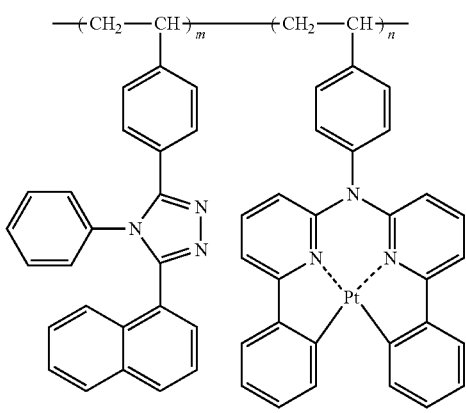                          P14
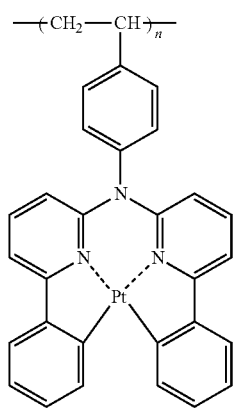
P15                                                    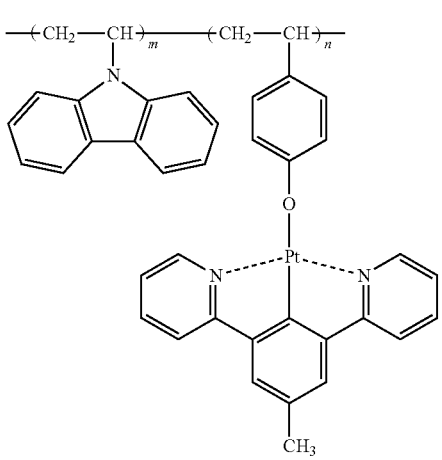                          P16
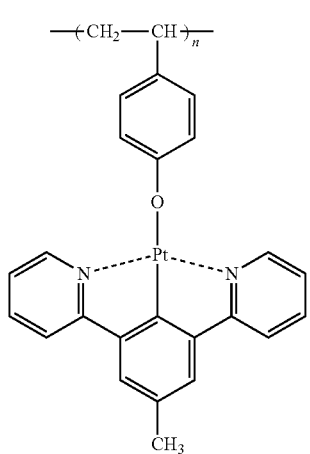
(mol % ratio of m:n = 90:10)
P17                                                    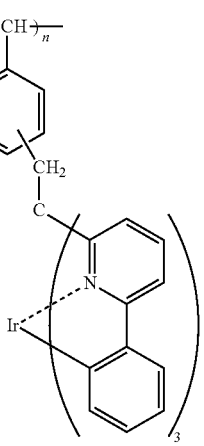                          P18
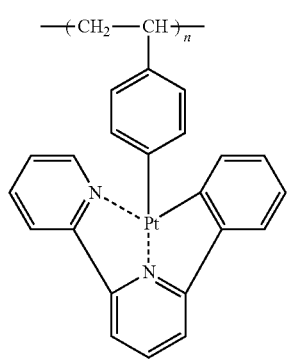

-continued
P19
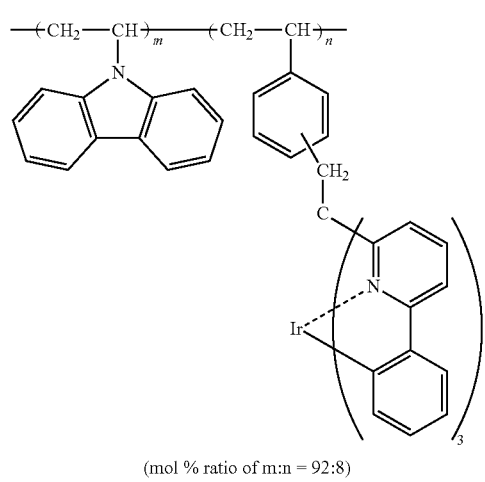
(mol % ratio of m:n = 92:8)
P20
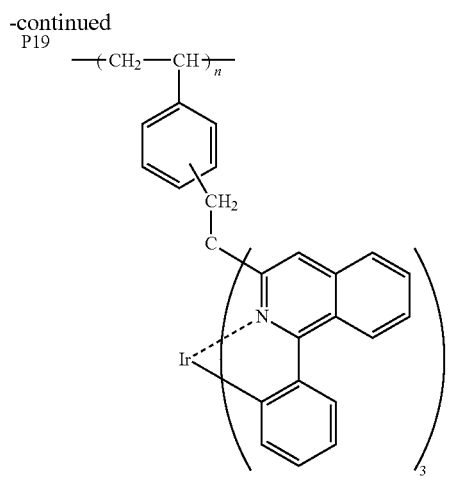
P21
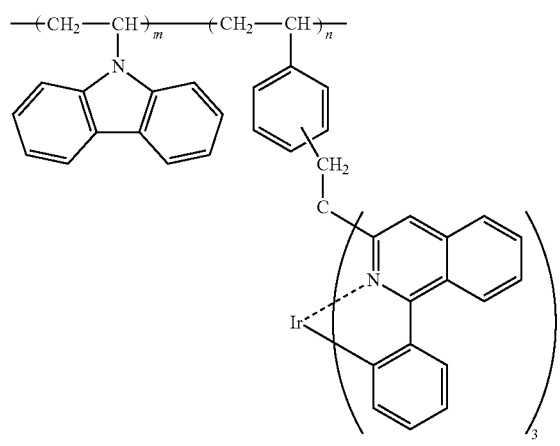
(mol % ratio of m:n = 92:8)
P22
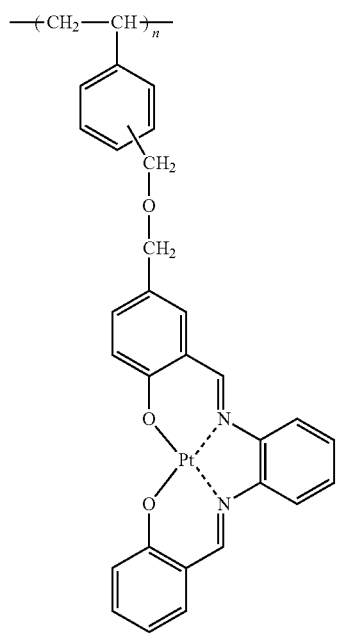
P23
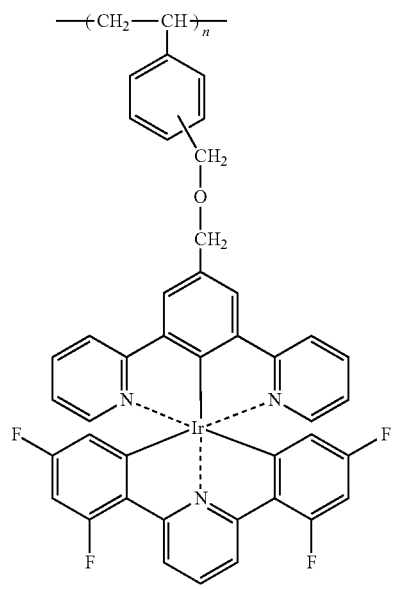

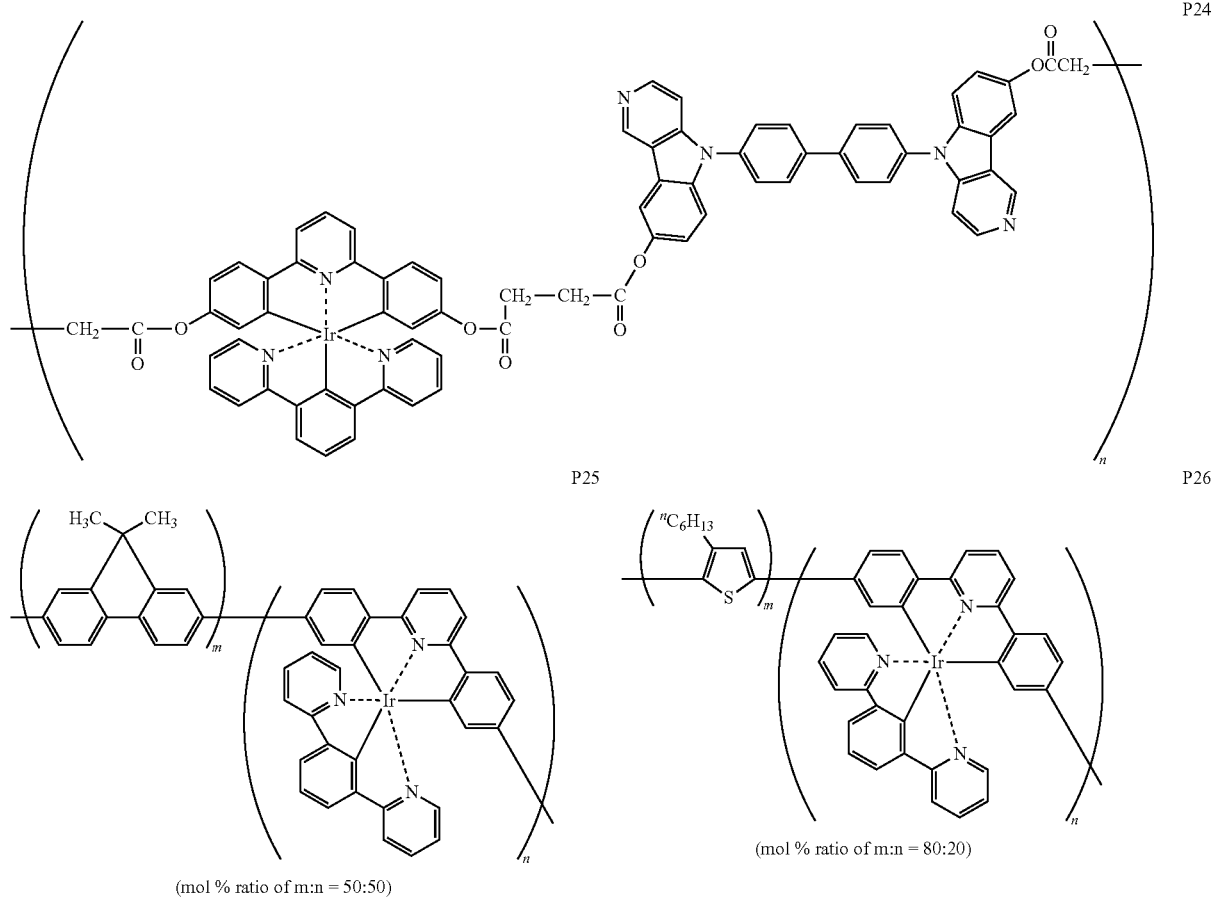

(mol % ratio of m:n = 50:50)   (mol % ratio of m:n = 80:20)

3. Configuration Elements of Organic Electroluminescent Device

Further, the configuration elements of the organic electroluminescent device of the invention are hereinafter explained in detail.

Substrate

The substrate to be used in the invention is preferably a substrate that does not scatter or attenuate light emitted from an organic compound layer. Specific examples of the substrate include inorganic materials such as Yttria-stabilized Zirconia (YSZ) and glass; polyesters such as polyethylene terephthalate, polybutylene phthalate, and polyethylene naphthalate; and organic materials such as polystyrene, polycarbonate, polyether sulfone, polyallylate, polyimides, polycycloolefins, norbornene resin, and poly(chlorotrifluoroethylene).

When the substrate is made of glass, the glass is preferably alkali-free glass in order to reduce ions deriving from the glass. When the substrate is made of soda lime glass, the substrate is preferably coated with a barrier coating such as silica. When an organic material is used, the material is preferably excellent in heat resistance, dimension stability, solvent resistance, electric insulation and processability.

A shape, structure, size and the like of the substrate are not particularly limited and can be selected as appropriate depending on the applications, purposes and the like of a luminescent device. In general, the shape is preferably plate-shaped. The structure of the substrate may be a single-layer structure or may also be a laminated structure. The substrate may be fabricated with a single member or may also be formed with two or more members.

The substrate may be colorless transparent or may be colored transparent, and is preferably colorless transparent in terms of no scattering or attenuation of the light emitted from the luminescent layer.

A moisture penetration prevention layer (gas barrier layer) can be formed on a surface or a back (the aforementioned transparent electrode side) of the substrate. Materials for the moisture penetration prevention layer (gas barrier layer) that are suitably used include inorganic substances such as silicon nitrate or silicon oxide. The moisture penetration prevention layer (gas barrier layer) can be formed by, for example, a radio-frequency (high-frequency) sputtering process or the like.

When a thermoplastic substrate is used as the substrate, the substrate may be further equipped with a hard coat layer or an undercoat layer in accordance with necessity.

Anode

The anode may usually serve as an electrode that supplies holes to the organic compound layer. A shape, structure, size and the like thereof are not particularly limited and can be appropriately selected from well known electrodes depending on the applications and purposes of the luminescent device. As mentioned supra, the anode is usually formed as a transparent anode.

Preferable examples of the material of the anode that are suitable include metals, alloys, metal oxides, electric conductive organic compounds and mixtures thereof. Specific examples the material of the anode include electric conductive metal oxides such as tin oxides doped with antimony or fluorine (ATO, FTO), tin oxide, zinc oxide, indium oxide, indium tin oxide (ITO), and indium zinc oxide (IZO); metals such as gold, silver, chromium, and nickel; mixtures or laminates of these metals and electric conductive metal oxides; electric conductive inorganic substances such as copper iodide and copper sulfate; electric conductive organic materials such as polyaniline, polythiophene, and polypyrrole; laminates and the like of these and ITO. Among them, the material of the anode is preferably an electric conductive metal oxide, and more preferably ITO from the viewpoint of productivity, high electric conductivity, transparency and the like.

An anode can be formed on the above-described substrate in accordance with a method selected, as appropriate, in consideration of its suitability to the materials constituting the above-described anode, from wet methods such as the printing method and the coating method, physical methods such as the vacuum deposition method, the sputtering method and the ion plating method, chemical methods such as CVD and the plasma CVD method, and the like. For instance, when ITO is selected as the material of the anode, the formation of the anode can be carried out according to the direct current or high-frequency sputtering method, the vacuum deposition method, the ion plating method or the like.

In the organic electroluminescent device of the invention, while the position of the anode to be formed is not particularly limited and can be appropriately selected depending on the applications or purposes of the luminescent device, it is preferable that the is formed anode is formed on the substrate. The anode may be formed on the entire surface of one side of the substrate, or may also be formed on a portion thereof.

Patterning for forming the anode may be carried out by chemical etching such as photolithography, or may also be carried out by physical etching such as by means of a laser, or may also be carried out by vacuum deposition or sputtering after placing a mask, or may also be carried out by a lift-off method or a printing method.

A thickness of the anode can be appropriately selected depending on the material constituting the above-described anode. It is usually from 10 nm to 50 μm, and is preferably from 50 nm to 20 μm.

A resistance value of the anode is preferably $10^3$ Ω/sq or less, and more preferably $10^2$ Ω/sq or less. When the anode is a transparent anode, the anode may be colorless transparent or may also be colored transparent. In view of extracting light emission from a transparent anode side, the transmittance is preferably 60% or more, and more preferably 70% or more.

Additionally, transparent anodes which can be applied to the invention are described in detail in "Tohmeidodenmaku No Shintenkai (Developments of Transparent Conductive Films)" edited by Yutaka Sawada, published by CMC (1999). When a plastic substrate of low heat resistance is used, and a transparent anode that employs ITO or IZO and is film formed at a low temperature of 150° C. or less is preferably used.

Cathode

The cathode may usually serve as an electrode that injects an electron to an organic compound layer. A shape, structure, size and the like are not particularly limited and can be appropriately selected from well known electrodes depending on the applications and purposes of the luminescent device.

Examples of the material of the cathode include metals, alloys, metal oxides, electric conductive compounds and mixtures thereof. Specific examples thereof include alkali metals (e.g., Li, Na, K, Cs and the like), alkali earth metals (e.g., Mg, Ca, and the like), gold, silver, lead, aluminum, sodium-potassium alloy, lithium-aluminum alloy, magnesium-silver alloy, indium, rare earth metals such as ytterbium, and the like. These may be used singly and can be used in combination of two or more kinds from the standpoint of compatibility between stability and electron injection properties.

Among them, preferable examples of the material of the cathode include alkali metals and alkali earth metals in terms of electron injection properties. Specifically, a material primarily made of aluminum is preferable in terms of excellent shelf life.

The scope of the material primarily made of aluminum as used herein includes aluminum alone, an alloy of aluminum and a 0.01 to 10% by mass alkali metal or alkali earth metal, and a mixture thereof (e.g., lithium-aluminum alloy, magnesium-aluminum alloy, and the like).

In addition, details of materials of the cathode are described in JP-A Nos. 2-15595 and 5-121172, the disclosures of which are incorporated by reference herein, and the materials described in these gazettes can also be applied to the invention.

Methods for forming the cathode are not particularly limited and can be carried out in accordance with well known methods. For example, a cathode can be formed in accordance with a method selected, as appropriate, in consideration of its suitability to the materials constituting the above-described cathode, from wet methods such as the printing method and the coating method; physical methods such as the vacuum deposition method, the sputtering method and the ion plating method; chemical methods such as CVD and the plasma CVD method; and the like. For example, when metals and the like are selected as materials of the cathode, the formation can be carried out with one kind thereof or two or more kinds thereof at the same time or one by one in accordance with the sputtering method or the like.

The patterning for forming the cathode may be carried out by chemical etching such as photolithography, or may also be carried out by physical etching such as by means of a laser, or may also be carried out by vacuum deposition or sputtering after placing a mask, or may also be carried out by the lift-off method or the printing method.

In the invention, the position of a cathode to be formed is not particularly limited and may be formed on the entire organic compound layer, or may also be formed on a portion thereof.

Also, a dielectric layer with a thickness of 0.1 nm to 5 nm made of a fluoride or an oxide of an alkali metal or an alkali earth metal, or the like, may be inserted between the cathode and the organic compound layer. This dielectric layer can be considered to be a kind of electron injecting layer. The dielectric layer can be formed by, for example, a vacuum deposition method, a sputtering method, an ion plating method or the like.

The thickness of a cathode can be selected, as appropriate, depending on the material constituting the above-described cathode, cannot be unconditionally specified, while it may be normally from 10 nm to 5 μm, and is preferably from 50 nm to 1 μm.

The cathode may be transparent or may be opaque. A transparent cathode can be formed by a process that involves thinly film-forming the material constituting the above-described cathode to a thickness of from 1 to 10 nm, and then laminating thereon a transparent, electric conductive material of the aforementioned ITO, IZO, or the like.

Organic Compound Layer

Explanations for the organic compound layer in the organic electroluminescent device of the invention are hereinafter provided.

The organic electroluminescent device of the invention includes at least one organic compound layer including at least one organic luminescent layer. Examples of organic compound layer other than the organic luminescent layer include the hole transporting layer, the electron transporting layer, the charge blocking layer, the hole injecting layer, and the electron injecting layer as described above.

Formation of Organic Compound Layer

In the organic electroluminescent device of the invention, each layers constituting the organic compound layer(s) can be appropriately formed by any of a dry film forming method (e.g., vapor-deposition, sputtering), a transfer method, a printing method or the like.

Organic Luminescent Layer

The organic luminescent layer is a layer having a function of receiving a hole from the anode, hole injecting layer or hole transporting layer when an electric field is applied, and receiving an electron from the cathode, electron injecting layer or electron transporting layer, thereby providing a site for the recombination of a hole and an electron to emit light.

An organic luminescent layer in the invention may be constituted of either a luminescent material alone or a mixed layer of a host material and a luminescent material. The luminescent material may be either a fluorescent material or a phosphorescent material, and for dopant a single kind or two or more kinds may be used. For host material an electron transport material is preferably. The host material may be a single kind or two or more kinds. For instance, a constitution where an electron transporting host material and a hole transporting host material are blended can be cited. Furthermore, the organic luminescent layer may contain materials that neither have electron transportability nor emit light.

Furthermore, the organic luminescent layer may be made of either a single layer or two or more layers. Respective layers may emit light of colors different from each other.

As luminescent materials that can be used in the invention, fluorescent materials and phosphorescent materials other than the polymer compounds according to the invention can be used. Luminescent materials used in combination may be low molecular weight compounds or high molecular weight compounds.

Examples of the fluorescent materials that can be used in the invention include a benzoxazole compound, a benzimidazole compound, a benzothiazole compound, a styrylbenzene compound, a polyphenyl compound, a diphenylbutadiene compound, a tetraphenylbutadiene compound, a naphthalimide compound, a coumarin compound, a condensed aromatic compound, a perinone compound, an oxadiazole compound, an oxazine compound, an aldazine compound, a pyralidine compound, a cyclopentadiene compound, a bisstyrylanthracene compound, a quinacridone compound, a pyrrolopyridine compound, a thiadiazolopyridine compound, a cyclopentadiene compound, a styrylamine compound, a diketopyrrolopyrole compound, an aromatic dimethylidene compound, various kinds of metal complexes as typified by a metal complex of 8-quinolinol compound and a metal complex of a pyrromethene compound, polymer compounds such as polythiophene, polyphenylene and polyphenylene vinylene, and compounds such as an organic silane compound.

Examples of the phosphorescent luminescent material include complexes containing a transition metal atom or a lanthanoid atom.

The transition metal atom is not particularly limited. Preferable examples thereof include a ruthenium atom, a rhodium atom, a palladium atom, a tungsten atom, a rhenium atom, an osmium atom, an iridium atom and a platinum atom. Among these, a rhenium atom, an iridium atom and a platinum atom are more preferable.

Examples of the lanthanoid atom include a lanthanum atom, a cerium atom, a praseodymium atom, a neodymium atom, a samarium atom, a europium atom, a gadolinium atom, a terbium atom, a dysprosium atom, a holmium atom, an erbium atom, a thulium atom, a ytterbium atom and a lutecium atom. Among these lanthanoid atoms, a neodymium atom, a europium atom and a gadolinium atom are preferable.

Examples of the ligand of the complex include ligands described in G. Wilkinson et al., Comprehensive Coordination Chemistry, Pergamon Press (1987), H. Yersin, Photochemistry and Photophysics of Coordination Compounds, Springer-Verlag (1987), and Akio Yamamoto, Yuki Kinzoku Kagaku—Kiso to Oyo— (Organic Metal Chemistry—Basics and Applications—), Shokabo (1982), the disclosures of which are incorporated by reference herein.

Specific examples of the ligand include a halogen ligand (preferably chlorine ligand), a nitrogen-containing heterocyclic ligand (e.g., phenylpyridine, benzoquinoline, quinolinol, bipyridyl, phenanthroline), a diketone ligand (e.g., acetylacetone), a carboxylic acid ligand (e.g., acetic acid ligand), a carbon monoxide ligand, an isonitrile ligand and a cyano ligand, and more preferable specific examples thereof include a nitrogen-containing heterocyclic ligand.

The complex may contain one transition metal atom in the compound or may be a so-called binuclear complex having two or more transition metal atoms. Also, different metal atoms may be contained therein at the same time.

The amount of the phosphorescent luminescent material contained in the organic luminescent layer is preferably in a range of 0.1 to 40 mass %, and is more preferably in a range of 0.5 to 20 mass %.

Examples of the host material contained in the organic luminescent layer in the invention include host materials having a carbazole skeleton, host materials having a diarylamine skeleton, host materials having a pyridine skeleton, host materials having a pyrazine skeleton, host materials having a triazine skeleton, host materials having an arylsilane skeleton, and materials exemplified in the following descriptions regarding the hole injecting layer, the hole transporting layer, the electron injecting layer, and the electron transporting layer.

The organic luminescent layer is not particularly limited in its thickness. In general, the thickness is preferably in a range from 1 nm to 500 nm, more preferably in a range from 5 nm to 200 nm, and still more preferably in a range from 10 nm to 100 nm.

Positive Hole Injection Layer, Positive Hole Transport Layer

A positive hole injection layer and a positive hole transport layer are layers with the function of receiving positive holes from the positive electrode, or the positive electrode side, and transporting them toward a negative electrode side.

In view of reducing necessary voltage and increasing driving durability, the positive hole injection layer and the positive hole transport layer preferably contain an electron-acceptive dopant.

Any materials such as an organic compound or an inorganic compound can be used as the electron-acceptive dopant as long as it is electron-acceptive and capable of oxidizing organic compounds, and specific preferable examples thereof among inorganic compounds include Lewis acid compounds such as ferric chloride, aluminum chloride, gallium chloride, indium chloride, antimony pentachloride or the like.

Preferable examples thereof among organic compounds include a compound having a nitro group, a halogen, a cyano group, a trifluoromethyl group or the like as a substituent thereof, a quinone compound, an acid anhydride compound, and fullerene.

Specific examples thereof include hexacyanobutadiene, hexacyanobenzene, tetracyanoethylene, tetracyanoquinodimethane, tetrafluorotetracyanoquinodimethane, p-fluoranyl, p-chloranyl, p-bromanyl, p-benzoquinone, 2,6-dichlorobenzoquinone, 2,5-dichlorobenzoquinone, tetramethylbenzoquinone, 1,2,4,5-tetracyanobenzene, o-dicyanobenzene, p-dicyanobenzene, 1,4-dicyanotetrafluorobenzene, 2,3-dichloro-5,6-dicyanobenzoquinone, p-dinitrobenzene, m-dinitrobenzene, o-dinitrobenzene, p-cyanonitrobenzene, m-cyanonitrobenzene, o-cyanonitrobenzene, 1,4-naphtoquinone, 2,3-dichloronaphtoquinone, 1-nitronaphthalene, 2-nitronaphthalene, 1,3-dinitronaphthalene, 1,5-dinitronaphthalene, 9-cyanoanthracene, 9-nitroanthracene, 9,10-anthraquinone, 1,3,6,8-tetranitrocarbazole, 2,4,7-trinitro-9-fluorenone, 2,3,5,6-tetracyanopyridine, maleic acid anhydride, phthalic acid anhydride, fullerrene C60, fullerrene C70 and the like, and compounds described in JP-A Nos. 6-212153, 11-111463, 11-251067, 2000-196140, 2000-286054, 2000-315580, 2001-102175, 2001-160493, 2002-252085, 2002-56985, 2003-157981, 2003-271862, 2003-229278, 2004-342614, 2005-72012, 2005-166637, 2005-209643 or the like can be preferably used.

Preferable examples among these include hexacyanobutadiene, hexacyanobenzene, tetracyanoethylene, tetracyanoquinodimethane, tetrafluorotetracyanoquinodimethane, p-fluoranyl, p-chloranyl, p-bromanyl, p-benzoquinone, 2,6-dichlorobenzoquinone, 2,5-dichlorobenzoquinone, tetramethylbenzoquinone, 1,2,4,5-tetracyanobenzene, 1,4-dicyanotetrafluorobenzene, 2,3-dichloro-5,6-dicyanobenzoquinone, p-dinitrobenzene, m-dinitrobenzene, o-dinitrobenzene, 1,4-naphtoquinone, 2,3-dichloronaphtoquinone, 1,3-dinitronaphthalene, 1,5-dinitronaphthalene, 9,10-anthraquinone, 1,3,6,8-tetranitrocarbazole, 2,4,7-trinitro-9-fluorenone, 2,3,5,6-tetracyanopyridine, and fullerrene C60. More preferable examples among these include hexacyanobutadiene, hexacyanobenzene, tetracyanoethylene, tetracyanoquinodimethane, tetrafluorotetracyanoquinodimethane, p-fluoranyl, p-chloranyl, p-bromanyl, 2,6-dichlorobenzoquinone, 2,5-dichlorobenzoquinone, 2,3-dichloronaphtoquinone, 1,2,4,5-tetracyanobenzene, 2,3-dichloro-5,6-dicyanobenzoquinone, and 2,3,5,6-tetracyanopyridine. Particularly preferable examples among these is tetrafluorotetracyanoquinodimethane.

These electron-acceptive dopant may be used singly or in combination of two or more thereof. An amount of the electron-acceptive dopant used in the hole injecting layer or the hole transporting layer may vary depending on a material thereof. It is preferably in a range of 0.01 to 50% by mass, more preferably in a range of 0.05 to 20% by mass, and further preferably in a range of 0.1 to 10% by mass relative to materials constituting the hole transporting layer. In a case where the amount of the electron-acceptive dopant is smaller than 0.01% by mass, the effects of the invention become insufficient and thus it is not preferable, and in a case where the amount of the electron-acceptive dopant exceeds 50% by mass, the hole transporting property is deteriorated and thus it is not preferable.

The positive hole injection layer and the positive hole transport layer, specifically, preferably contain a carbazole compound, an azacarbazole compound, a triazole compound, an oxazole compound, an oxadiazole compound, an imidazole compound, a thiophene compound, a polyarylalkane compound, a pyrazoline compound, a pyrazolone compound, a phenylenediamine compound, an arylamine compound, an amino-substituted chalcone compound, a styrylanthracene compound, a fluorenone compound, a hydrazone compound, a stilbene compound, a silazane compound, an aromatic tertiary amine compound, a styrylamine compound, an aromatic dimethylidyne compound, a porphyrin compound, an organic silane compound or carbon.

The thicknesses of the positive hole injection layer and the positive hole transport layer are respectively, from a viewpoint of lowering the driving voltage, preferably 500 nm or less.

The thickness of the positive hole transport layer is preferably in the range of 1 to 500 nm, more preferably in the range of 5 to 200 nm and still more preferably in the range of 10 to 100 nm. Furthermore, a thickness of the positive hole injection layer is preferably in the range of 0.1 to 200 nm, more preferably in the range of 0.5 to 100 nm and still more preferably in the range of 1 to 100 nm The positive hole injection layer and the positive hole transport layer may have a single layer structure made of a single kind, or more than one kind, of the above-mentioned materials, or may have a multi-layer structure made of plural layers having the same composition or differing in composition.

Electron Injection Layer and Electron Transport Layer

An electron injection layer and an electron transport layer are layers with the function of receiving electrons from the negative electrode, or the negative electrode side, and transporting toward the positive electrode side.

In view of reducing necessary voltage and increasing driving durability, the electron injection layer and the electron transport layer preferably contain an electron-donative dopant.

Any materials can be used as the electron-donative dopant as long as it is electron-donative and capable of reducing organic compounds, and preferable examples thereof include alkali metals such as Li, alkali earth metals such as Mg, transition metals including rare earth metals, reductive organic materials and the like.

Preferable examples of a metal which can be used as the electron-donative dopant include those having work function of 4.2 eV or less, and specific examples thereof include Li, Na, K, Be, Mg, Ca, Sr, Ba, Y, Cs, La, Sm, Gd and Yb. Examples of the reductive organic compound include a nitrogen-containing compound, a calcogen-containing compound (such as a sulfur-containing compound, a selenium-containing compound, or a tellurium-containing compound), and a phosphor-containing compound. Examples of the electron-donative dopant further include materials described in JP-A Nos. 6-212153, 2000-196140, 2003-68468, 2003-229278, 2004-342614 or the like.

These electron-donative dopant may be used singly or in combination of two or more thereof. An amount of the electron-donative dopant used in the electron injecting layer or the electron transporting layer may vary depending on a material thereof. It is preferably in a range of 0.1 to 99% by mass, more preferably in a range of 1.0 to 80% by mass, and further preferably in a range of 2.0 to 70% by mass relative to materials constituting the electron transporting layer. In a case where the amount of the electron-acceptive dopant is smaller than 0.1% by mass, the effects of the invention become insufficient and thus it is not preferable, and in a case where the amount of the electron-acceptive dopant exceeds 99% by mass, the electron transporting property is deteriorated and thus it is not preferable.

The electron injection layer and the electron transport layer, specifically, preferably contain a pyridine compound, a quinoline compound, a phenanthroline compound, a silole compound, a triazole compound, an oxazole compound, an oxadiazole compound, an imidazole compound, a benzimidazole compound and an azabenzimidazole compound, a fluorenone compound, an anthraquinodimethane compound, an anthrone compound, a diphenylquinone compound, a thiopyran dioxide compound, a carbodimide compound, a fluorenylidenemethane compound, a distyrylpyrazine compound, aromatic cyclic tetracarboxylic anhydride of naphthalene and perylene and the like, a phthalocyanine compound, various kinds of metal complexes typified by a metal complex of a 8-quinolinol compound, metallophthalocyanine, and a metal complex having benzoxazole or benzothiazole as a ligand, or an organic silane compound.

The respective thicknesses of the electron injection layer and the electron transport layer are, from a viewpoint of lowering a driving voltage, preferably 500 nm or less.

The thickness of the electron transport layer is preferably in the range of 1 to 500 nm, more preferably in the range of 5 to 200 nm and still more preferably in the range of 10 to 100 nm. Furthermore, the thickness of the electron injection layer is preferably in the range of 0.1 to 200 nm, more preferably in the range of 0.2 to 100 nm and still more preferably in the range of 0.5 to 50 nm.

The electron injection layer and the electron transport layer may have a single layer structure made of a single kind, or of more than 1 kind, of the above-mentioned materials, or may have a multi-layer structure made of plural layers having the same composition or differing in composition.

Positive Hole Blocking Layer

The positive hole blocking layer is a layer with the function of inhibiting positive holes transported from the positive electrode side to the luminescent layer from passing through to the negative electrode side. In the invention, the positive hole blocking layer can be disposed as an organic compound layer that is adjacent to the luminescent layer on the negative electrode side.

Examples of organic compounds that constitutes a positive hole blocking layer include aluminum complexes such as BAlq, triazole compounds and phenanthroline compounds such as BCP.

The thickness of the positive hole blocking layer is preferably in the range of 1 to 500 nm, more preferably in the range of 5 to 200 nm and still more preferably in the range of 10 to 100 nm.

The positive hole blocking layer may have a single layer structure made of a single kind, or more than one kind, of the above-mentioned materials, or may have a multi-layer structure made of plural layers having the same composition or differing in composition.

Protective Layer

In the invention, the whole organic electroluminescent device may be protected by a protective layer.

Any material may be contained in the protective layer insofar as it has the ability to prevent intrusions of materials which promote the deterioration of the element, such as water or oxygen, into the device.

Specific examples of the material of the protective layer include metals such as In, Sn, Pb, Au, Cu, Ag, Al, Ti or Ni; metal oxides such as MgO, SiO, $SiO_2$, $Al_2O_3$, GeO, NiO, CaO, BaO, $Fe_2O_3$, $Y_2O_3$, or $TiO_2$; metal nitrates such as $SiN_x$ or $SiN_xO_y$; metal fluorides such as $MgF_2$, LiF, $AlF_3$ or $CaF_2$; polyethylene, polypropylene, polymethylmethacrylate, a polyimide, polyurea, polytetrafluoroethylene, polychlorotrifluoroethylene, polydichlorodifluoroethylene and copolymers of chlorotrifluoroethylene and dichlorodifluoroethylene; copolymers obtained by copolymerization of a monomer mixture including tetrafluoroethylene and at least one kind of comonomer; fluorine-containing copolymers having a ring structure on the copolymer backbone thereof; water absorptive materials having a water absorption of 1% or more; moisture-proof materials having a water absorption of 0.1% or less; and the like.

A process for forming the protective layer is not particularly limited. Examples of a method that can be used include a vacuum deposition process, a sputtering process, a reactive sputtering process, a MBE (molecular beam epitaxy) process, a cluster ion beam process, a ion plating process, a plasma polymerization process (the high-frequency excited ion plating process), a plasma CVD process, a laser CVD process, a thermal CVD process, a gas source CVD process, a coating process, a printing process, and a transfer process.

Sealing

Furthermore, in the organic electroluminescent device of the invention, the entire device may be sealed by a sealing container.

Also, a space between the sealing container and the luminescent device may be filled with a moisture absorbent or an inert liquid. The moisture absorbent is not particularly limited. Specific examples of the moisture absorbent include barium oxide, sodium oxide, potassium oxide, calcium oxide, sodium sulfate, calcium sulfate, magnesium sulfate, phosphorus pentaoxide, calcium chloride, magnesium chloride, copper chloride, cesium fluoride, niobium fluoride, calcium bromide, vanadium bromide, a molecular sieve, zeolite, magnesium oxide, and the like. An inert liquid is not particularly limited and the examples include paraffins, liquid paraffins, fluorine-based solvents such as perfluoroalkanes, perfluoroamines or perfluoroethers, chlorine-based solvents, and silicone oils.

Driving

In the organic electroluminescent device of the invention, a direct current (which, if desired, may contain an alternating current component) voltage (usually in a range of 2 to 15 V) or a direct current is applied between the anode and the cathode, whereby light emission can be obtained.

Examples of a method for driving the organic electroluminescent device of the invention include those described in JP-A Nos. 2-148687, 6-301355, 5-29080, 7-134558, 8-234685 and 8-241047, Japanese Patent No. 2784615, U.S. Pat. Nos. 5,828,429 and 6,023,308 and the like.

The efficiency of emitted light of the organic electroluminescent device of the invention can be raised by various conventionally-known schemes such as a processing of a surface shape of a substrate (for example, forming a pattern having fine irregularities), controlling of refractive index of a substrate, an ITO layer and/or an organic layer, controlling of film thickness of a substrate, an ITO layer and/or an organic layer or the like so as to raise the external quantum efficiency.

The organic electroluminescent device of the invention may use what is called the "top emission electroluminescent device" in which light is emitted from anode side.

The organic electroluminescent device of the invention can be suitably used in the fields of display devices, displays, backlights, electrophotography, light sources for illumination, light sources for recording, light sources for exposure, light sources for reading, signs, sign boards, interiors, optical communications, and the like.

EXAMPLES

Hereinafter, the organic EL device of the present invention is specifically described with reference to Examples. However, the Examples should not be construed as limiting the invention.

Comparative Example 1

A glass substrate (25 mm×25 mm×0.7 mm) with ITO deposited at a thickness of 150 nm (manufactured by Tokyo Sanyo Vacuum Industries Co., Ltd.) was used as a transparent substrate. The transparent substrate was etched and cleaned. On the ITO glass substrate, BAYTRON® P (trade name, PEDOT-PSS solution (polyethylenedioxythiophene-polystyrene sulfonic acid doped material), manufactured by Bayer A.G.) was spin-coated, dried at 100° C. in a vacuum for 1 hour, thereby obtaining a positive hole injection and transport layer (a film thickness: about 100 nm). Thereon, a solution where 40 mg of a compound P-A (a compound described in JP-A No. 2003-77675) was dissolved in 3 mL of 1,2-dichloroethane was spin-coated to form a luminescent layer (a film thickness: about 50 nm). Next, electron transport materials BAlq and Alq were sequentially deposited so as to be 20 nm and 30 nm, respectively, in the film thickness, and thereby an electron transport layer was formed. Further thereon, LiF was deposited at a film thickness of about 3 nm. The deposition was carried out in a vacuum of $10^{-3}$ to $10^{-4}$ Pa under a substrate temperature of room temperature. Thereon, a patterned mask (a mask to give a luminescence area of 2 mm×2 mm) was disposed and aluminum was deposited at a film thickness of about 400 nm to form an element. The prepared element was sealed in a dry glove box.

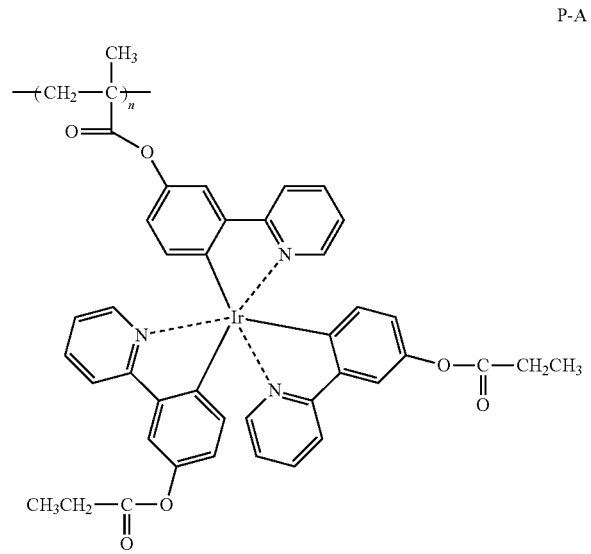

P-A

Comparative Example 2

The EL device of Comparative example 2 was formed in the same manner as that of Comparative example 1, except that a compound P-B (, that is disclosed in Japanese patent No. 2003-77675,) was used in place of the compound P-A.

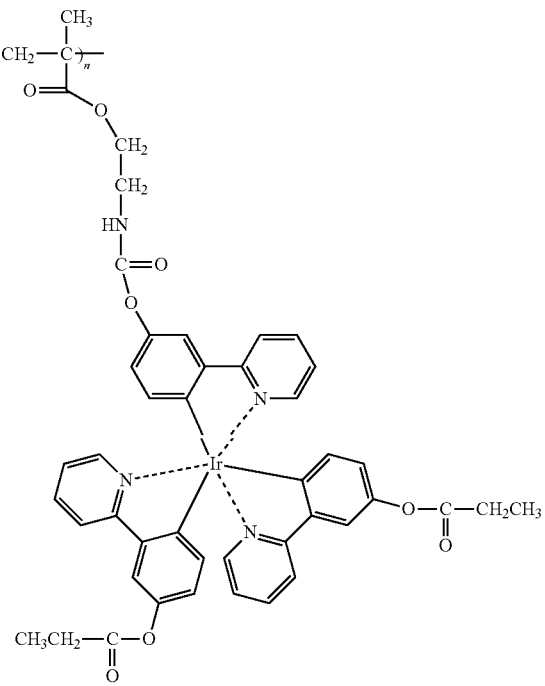

P-B

Example 1

The EL device of Example 1 was formed in the same manner as that of Comparative example 1, except that a compound P1 (shown above) was used in place of the compound P-A.

Example 2

The EL device of Example 2 was formed in the same manner as that of Comparative example 1, except that a compound P3 (shown above) was used in place of the compound P-A.

(1) External Quantum Efficiency

Application of a direct current voltage to each of the electroluminescent device of the above Examples and Comparative examples to cause light emission by using a source measure unit (trade name: MODEL 2400, manufactured by Toyo Corporation). The brightness of the light emission was measured by a brightness meter (trade name: BM-8, manufactured by Topcon Corporation). The waveform of the light emission spectrum of the produced luminescent device was measured by using a multi-channel analyzer (trade name: PMA-11, manufactured by Hamamatsu Photonics K.K). Based on the measured data, the external quantum efficiency in the range of around 1,000 cd/m² was calculated according to the brightness conversion method.

(2) Driving Durability: Brightness Half-Life Time

A continuous driving test was conducted by applying a direct current voltage to the electroluminescent device to cause light emission so that an initial brightness thereof becomes 1,000 cd/cm², and the time period until the brightness decreases to 500 cd/m² was determined as a brightness half-life time. The brightness half-life time was used as an index of the driving durability of each of the devices in the Examples and Comparative examples.

(3) External Quantum Efficiency and Brightness Half-Life when Storing Metal Complex Solution In the manufacture of each element, elements of Examples 1' and 2' and Comparative Examples 1' and 2' were prepared in exactly the same manner as in Examples 1 and 2 and Comparative Examples 1 and 2, respectively, except that solutions obtained by dissolving the metal complex polymers according to the invention and comparative metal complexes in 1,2-dichloroethane were stored for 5 hours before spin-coating. The external quantum efficiency and the brightness half-life of each of thus prepared elements were measured according to methods similar to (1) and (2).

Obtained results are summarized in Tables 1 and 2 below.

TABLE 1

| EL device | Color of emitted light | External quauntum efficiency | Brightness half-life time |
|---|---|---|---|
| Comparative example 1 | Green | 4% | 450 hr |
| Comparative example 2 | Green | 5% | 480 hr |
| Example 1 | Green | 8% | 2,810 hr |
| Example 2 | Green | 12% | 3,120 hr |

TABLE 2

| EL device | Color of emitted light | External quantum efficiency (using coating solution after time passage) | Brightness half-life time (using coating solution after time passage) |
|---|---|---|---|
| Comparative example 1 | Green | 2% | 220 hr |
| Comparative example 2 | Green | 4% | 260 hr |
| Example 1 | Green | 7% | 2,730 hr |
| Example 2 | Green | 11% | 3,070 hr |

As is clear from the above results, the elements according to the invention were superior to the comparative elements in luminescence efficiency and driving durability. Furthermore, the deterioration in the performance with elapse of time of the solution was small and the variation of the performance due to variations in manufacturing factors could be suppressed.

What is claimed is:

1. An organic electroluminescent device comprising an organic compound layer provided between a pair of electrodes, which comprises a polymer represented by the formula

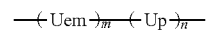

wherein Uem represents a unit comprising a metal complex represented by the following Formula (3-C):

Formula (3-C)

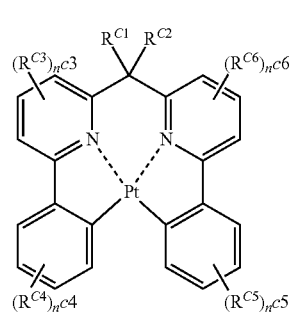

wherein $R^{C1}$ and $R^{C2}$ each independently represent an alkyl group or an aryl group; $R^{C3}$, $R^{C4}$, $R^{C5}$, and $R^{C6}$ each independently represent a hydrogen atom, an alkyl group, an aryl group, a heteroaryl group, a halogen atom, or a cyano group; each of $n^{C3}$ and $n^{C6}$ represents an integer of 0 to 3; each of $n^{C4}$ and $n^{C5}$ represents an integer of 0 to 4; when there are plural $R^{C3}$s, $R^{C4}$s, $R^{C5}$s, or $R^{C6}$s, the plural $R^{C3}$s, $R^{C4}$s, $R^{C5}$s, or $R^{C6}$s may be the same as each other or different from each other, the metal complex being linked to the polymer via $R^{C1}$;

wherein Up represents a unit comprising a hole transporting moiety having the following structure:

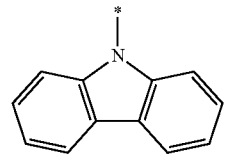

wherein the asterisk * represents a site at which the hole transporting moiety bonds to the polymer; and each of m and n represents a mole percentage that satisfies the equation of m+n=100 mol %, with the mole percent ratio of m:n being in the range of from 5:95 to 20:80.

* * * * *